(12) United States Patent
Chowdhury et al.

(10) Patent No.: US 8,049,016 B2
(45) Date of Patent: Nov. 1, 2011

(54) THIAZOLE DERIVATIVES WHICH INHIBIT STEAROYL-COA DESATURASE ENZYMES

(75) Inventors: Sultan Chowdhury, Surrey (CA); Natalie Dales, Arlington, MA (US); Julia Fonarev, Richmond (CA); Jianmin Fu, Coquitlam (CA); Duanjie Hou, Burnaby (CA); Qi Jia, Burnaby (CA); Vishnumurthy Kodumuru, Burnaby (CA); Natalia Pokrovskaia, New Westminster (CA); Shaoyi Sun, Coquitlam (CA); Zaihui Zhang, Vancouver (CA)

(73) Assignees: Novartis AG, Basel (CH); Xenon Pharmaceuticals Inc, Burnaby (CA)

( * ) Notice: Subject to any disclaimer, the term of this patent is extended or adjusted under 35 U.S.C. 154(b) by 0 days.

(21) Appl. No.: 12/378,997

(22) Filed: Feb. 20, 2009

(65) Prior Publication Data

US 2009/0264444 A1    Oct. 22, 2009

Related U.S. Application Data

(60) Provisional application No. 61/030,137, filed on Feb. 20, 2008.

(51) Int. Cl.
| | |
|---|---|
| *C07D 277/20* | (2006.01) |
| *C07D 417/14* | (2006.01) |
| *C07D 401/04* | (2006.01) |
| *A61K 31/501* | (2006.01) |
| *A61K 31/4965* | (2006.01) |
| *A61K 31/4402* | (2006.01) |
| *A61K 31/4406* | (2006.01) |
| *A61K 31/4409* | (2006.01) |
| *A61K 31/4436* | (2006.01) |
| *A61K 31/427* | (2006.01) |

(52) U.S. Cl. ............ 548/196; 548/268.7; 544/405; 544/333; 544/238; 514/252.05; 514/255.05; 514/256; 514/341; 514/371

(58) Field of Classification Search .......... None
See application file for complete search history.

(56) References Cited

U.S. PATENT DOCUMENTS

| | | | |
|---|---|---|---|
| 3,998,952 | A | 12/1976 | Ilvespaa |
| 4,058,617 | A | 11/1977 | Ilvespaa |
| 2009/0156615 | A1 | 6/2009 | Dales et al. |
| 2010/0029718 | A1 | 2/2010 | Dales et al. |
| 2010/0029722 | A1 | 2/2010 | Dales et al. |
| 2010/0233116 | A1 | 9/2010 | Dales et al. |

FOREIGN PATENT DOCUMENTS

| | | |
|---|---|---|
| EP | 1621539 | 2/2006 |
| IL | 44282 | 1/1979 |
| WO | 9921555 | 5/1999 |
| WO | 0110865 | 2/2001 |
| WO | 0174811 | 10/2001 |
| WO | 02051442 | 7/2002 |
| WO | 02100433 | 12/2002 |
| WO | 2005077937 | 8/2005 |
| WO | 2006/034440 | 3/2006 |
| WO | 2006/034440 A | 3/2006 |
| WO | 2007/130075 A | 11/2007 |
| WO | 2007/143597 | 12/2007 |
| WO | 2008/024390 | 2/2008 |
| WO | 2008/024390 A | 2/2008 |
| WO | 2008/036715 | 3/2008 |
| WO | 2008/074835 | 6/2008 |
| WO | 2008/127349 A | 10/2008 |
| WO | 2008127349 | 10/2008 |
| WO | 2009103739 | 8/2009 |
| WO | 2009/156484 | 12/2009 |
| WO | 2009156484 | 12/2009 |

OTHER PUBLICATIONS

Robert, et al., "Synthesis and antileishmanial activity of new imidazolidin-2-one derivatives" European Journal of Medicinal Chemistry (2003), 38(7-8), 711-718.
Alvarez, et al., "Inhibition of Parasite Protein Kinase C by New Antileishmanial Imidazolidin-2-one Compounds" Journal of Enzyme Inhibition and Medicinal Chemistry (2002), 17(6), 443-447.
Kosary, et al., "Synthesis of thiazole derivatives with positive inotropic effect" Pharmazie (1987), 42(6), 373-5.

*Primary Examiner* — Kamal Saeed
*Assistant Examiner* — Nyeemah A Grazier
(74) *Attorney, Agent, or Firm* — Theresa Devlin

(57) ABSTRACT

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

19 Claims, No Drawings

THIAZOLE DERIVATIVES WHICH INHIBIT STEAROYL-COA DESATURASE ENZYMES

This application claims benefit under 35 U.S.C. §119(e) of U.S. Provisional Application No. 61/030,137, filed Feb. 20, 2008, the contents of which are incorporated herein by reference in their entirety.

The present invention relates generally to the field of inhibitors of stearoyl-CoA desaturase, such as heterocyclic derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome, dermatological disorders and the like.

Acyl desaturase enzymes catalyze the formation of a double bond in fatty acids derived from either dietary sources or de novo synthesis in the liver. In mammals, at least three fatty acid desaturases exists, each with differing specificity: delta-9, delta-6, and delta-5, which introduce a double bond at the 9-10, 6-7, and 5-6 positions respectively.

Stearoyl-CoA desaturases (SCDs) act with cofactors (other agents) such as NADPH, cytochrome b5, cytochrome b5 reductase, Fe, and molecular $O_2$ to introduce a double bond into the C9-C10 position (delta 9) of saturated fatty acids, when conjugated to Coenzyme A (CoA). The preferred substrates are palmitoyl-CoA (16:0) and stearoyl-CoA (18:0), which are converted to palmitoleoyl-CoA (16:1) and oleyl-CoA (18:1), respectively. The resulting mono-unsaturated fatty acids are substrates for further metabolism by fatty acid elongases or incorporation into phospholipids, triglycerides, and cholesterol esters. A number of mammalian SCD genes have been cloned. For example, two genes have been identified in humans (hSCD1 and hSCD5) and four SCD genes have been isolated from mouse (SCD1, SCD2, SCD3, and SCD4). While the basic biochemical role of SCD has been known in rats and mice since the 1970s (Jeffcoat, R. et al., *Eur. J. Biochem.* (1979), Vol. 101, No. 2, pp. 439-445; de Antueno, R. et al., *Lipids* (1993), Vol. 28, No. 4, pp. 285-290), it has only recently been directly implicated in human disease processes.

The two human SCD genes have been previously described: hSCD1 by Brownlie et. al., PCT published patent application, WO 01/62954, and hSCD2 by Brownlie, PCT published patent application, WO 02/26944.

The present invention solves this problem by presenting new drug-like classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of Formula (I):

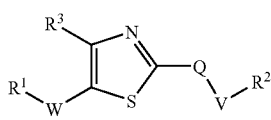
(I)

wherein,
Q is

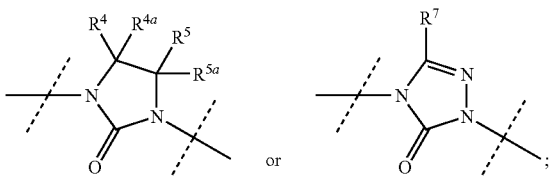

W is —N($R^6$)C(O)—, —$R^8$—C(O)N($R^6$)—, —$R^8$—OC(O)N($R^6$)—, —N($R^6$)C(O)O—, —N($R^6$)C(O)N($R^6$)—, —O—, —S—, —N($R^6$)—, —S(O)$_t$—, —N($R^6$)S(O)$_t$—, —S(O)$_t$N($R^6$)—, —OS(O)$_t$N($R^6$)—, —$R^8$—C(O)—, —OC(O)—, —C(O)O—, —N($R^6$)C(=N($R^{6a}$))N($R^6$)—, —N($R^6$)(($R^{6a}$)N=)C—, —C(=N($R^{6a}$))N($R^6$)—, or a direct bond;

V is —C(O)N($R^6$)—, —S(O)$_t$—, —S(O)$_2$N($R^6$)—, —C(O)—, —$R^8$—C(O)O—, —$R^8$—OC(O)N($R^6$)—, —$R^8$—C(O)N($R^6$)—, —$R^8$—C(O)—, —C(=N($R^{6a}$))N($R^6$)—, or a direct bond;

t is 1 or 2;

$R^1$ is halo, hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, or heteroarylalkyl;

or $R^1$ is a multi-ring structure having 2 to 4 rings wherein the rings are independently cycloalkyl, heterocyclyl, aryl or heteroaryl and where some or all of the rings may be fused to each other;

$R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl;

or $R^2$ is a multi-ring structure having 2 to 4 rings wherein the rings are independently cycloalkyl, heterocyclyl, aryl or heteroaryl and where some or all of the rings may be fused to each other;

$R^3$ is hydrogen or alkyl;

$R^4$ and $R^{4a}$ are independently hydrogen, alkyl, haloalkyl, hydroxyl, hydroxyalkyl, alkoxy, cycloalkylalkyl or aralkyl;

or $R^4$ and $R^{4a}$ are taken together to form an oxo (=O) group, cycloalkyl or heterocyclyl;

$R^5$ and $R^{5a}$ are independently hydrogen, alkyl or haloalkyl;

or $R^4$ and $R^5$ are taken to form a cycloalkyl, aryl, heteroaryl or heterocyclyl, and the remaining $R^{4a}$ and $R^{5a}$ are as described above;

$R^6$ is independently hydrogen, alkyl, hydroxyalkyl, cycloalkylalkyl, aryl, heteroaryl, heterocyclyl or aralkyl;

$R^{6a}$ is independently hydrogen, alkyl, cycloalkylalkyl, or cyano;

$R^7$ is hydrogen, alkyl, trifluoromethyl, aryl, cycloalkyl, heteroaryl, heterocyclyl, hydroxyalkyl, cycloalkylalkyl or aralkyl; and $R^8$ is independently a direct bond, an optionally substituted straight or branched alkylene chain, an optionally substituted straight or branched alkenylene chain or an optionally substituted straight or branched alkynylene chain;

as a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism and/or lipid homeostasis utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

DEFINITIONS

Certain chemical groups named herein are preceded by a shorthand notation indicating the total number of carbon atoms that are to be found in the indicated chemical group. For example, $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Cyano" refers to the —CN radical;
"Hydroxy" refers to the —OH radical;
"Nitro" refers to the —$NO_2$ radical;
"Amino" refers to the —$NR^{14}$ or $NR^{15}$ radical;
"Mercapto" refers to the —SR radical;
"Acid" refers to the —COOH radical;
"Trifluoromethyl" refers to the —$CF_3$ radical;

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, (R)-methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one or more of the following groups: alkyl, alkenyl, halo, haloalkyl, cyano, aryl, cycloalkyl, heterocyclyl, heteroaryl, silyloxy, —$OR^{14}$, —OC(O)—$R^{14}$, —$N(R^{14})_2$, —C(O)$R^{14}$, —C(O)O$R^{14}$, —C(O)N($R^{14})_2$, —$N(R^{14})$C(O)O$R^{16}$, —$N(R^{14})$C(O)$R^{16}$, —$N(R^{14})$S(O)$_t$$R^{16}$), —S(O)$_t$O$R^{16}$, —S$R^{16}$, —S(O)$_t$$R^{16}$, —O—S(O)$_2$$R^{16}$, —O—Si($R^{16})_3$ and —S(O)$_t$N($R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl cycloalkyl, cycloalkylalkyl, aryl, aralkyl (e.g. tolyl), heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms or two to six carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one or more of the following groups: alkyl, alkenyl, halo, haloalkyl, aryl, aralkyl, cycloalkyl, cycloalkylalkyl, heterocyclyl, heterocylylalkyl, heteroaryl, heteroarylalkyl, —$OR^{14}$, —OC(O)—$R^{14}$N($R^{14})_2$, —C(O)$R^{14}$, —C(O)O$R^{14}$, —C(O)N($R^{14})_2$, —$N(R^{14})$C(O)O$R^{16}$, —$N(R^{14})$C(O)$R^{16}$, —$N(R^{14})$S(O)$_t$$R^{16}$), —S$R^{16}$, —S(O)$_t$O$R^{16}$, —S(O)$_t$$R^{16}$, and —S(O)$_t$N($R^{14})_2$, where each $R^{14}$ is independently hydrogen, alkyl, haloalkyl, cycloalkyl, cycloalkylalkyl, aryl aralkyl, heterocyclyl, heterocyclylalkyl, heteroaryl, or heteroarylalkyl; and each $R^{16}$ is alkyl, cycloalkyl, cycloalkylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one triple bond, having from two to twelve carbon atoms, preferably two to eight carbon atoms or two to six carbon atoms and which is attached to the rest of the molecule by a single bond. Unless stated otherwise specifically in the specification, an alkynyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —$OR^{14}$, —OC(O)—$R^{14}$N($R^{14})_2$, —C(O)$R^{14}$, —C(O)O$R^{14}$, —C(O)N($R^{14})_2$, —$N(R^{14})$C(O)O$R^{16}$, —$N(R^{14})$C(O)O$R^{16}$, —$N(R^{14})$(S(O)$_t$$R^{16})$, —S$R^{16}$, —S(O)$_t$O$R^{16}$, —S(O)$_t$$R^{16}$, and —S(O)$_t$N($R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each $R^{16}$ is alkyl, cycloalkyl, cycloalkylalkyl, aryl, aralkyl, heterocyclyl, heterocyclylalkyl, heteroaryl or heteroarylalkyl.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms or two to six carbon atoms, e.g., ethenylene, propenylene, n-butenylene, and the like. Unless stated otherwise specifically in the specification, an alkenylene chain may be optionally substituted by one or more of the following groups: alkyl, alkenyl, halo, cyano, aryl, cycloalkyl, heterocyclyl, heteroaryl, —$OR^{14}$, —OC(O)—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$, —S—, $S(O)_tOR^{16}$, —$S(O)_tR^{16}$, and —$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, cycloalkyl, cycloalkylalkyl, aryl, aralkyl, heterocyclyl, heterocyclylalkyl, heteroaryl or heteroarylalkyl.

"Alkynylene" and "Alkynylene chain" refer to a straight or branched divalent hydrocarbon chain linking the rest of the molecule to a radical group, consisting solely of carbon and hydrogen, containing at least one triple bond and having from two to twelve carbon atoms or two to six carbon atoms, e.g. propynylene, n butenylene, and the like. Unless stated otherwise specifically in the specification, an alkynylene chain may be optionally substituted by one or more of the following groups: alkyl, alkenyl, halo, cyano, aryl, cycloalkyl, heterocyclyl, heteroaryl, —$OR^{14}$, —OC(O)—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})(S(O)_tR^{16})$, —S—, —$S(O)_tOR^{16}$, —$S(O)_tR^{16}$, and —$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, cycloalkyl, cycloalkylalkyl, aryl, aralkyl, heterocyclyl, heterocyclylalkyl, heteroaryl or heteroarylalkyl.

"Alkoxy" refers to a radical of the formula —$OR_a$ where $R_a$ is an alkyl radical as generally defined above. The alkyl part of the alkoxy radical may be optionally substituted as defined above for an alkyl radical.

"Alkoxyalkyl" refers to a radical of the formula —$R_a$—O—$R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from six to nineteen carbon atoms, preferably six to ten carbon atoms, where the ring system may be partially saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$—$R^{15}N(R^{14})C(O)R^{16}$, —$R^{15}$—$N(R^{14})(S(O)_tR^{16})$, —$R^{15}$—$SR^{16}$, —$R^{15}$—$S(O)_tOR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aralkyl" refers to a radical of the formula —$R_aR_b$ where $R_a$ is an alkylene chain as defined above and $R_b$ is one or more aryl radicals as defined above, e.g., benzyl, diphenylmethyl and the like. The aryl part of the aralkyl radical may be optionally substituted as described above for an aryl group. The alkylene chain part of the aralkyl radical may be optionally substituted as defined above for an alkyl group.

"Aralkenyl" refers to a radical of the formula —$R_aR_b$ where $R_a$ is an alkenylene chain as defined above and $R_b$ is one or more aryl radicals as defined above, which may be optionally substituted as described above. The aryl part of the aralkenyl radical may be optionally substituted as described above for an aryl group. The alkenylene chain of the aralkenyl radical may be optionally substituted as defined above for an alkenyl group.

"Aryloxy" refers to a radical of the formula —$OR_b$ where $R_b$ is an aryl group as defined above. The aryl part of the aryloxy radical may be optionally substituted as defined above.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms or from three to seven atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, alkynyl, halo, haloalkyl, cyano, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$, —$R^{15}$—$SR^{16}$, —$R^{15}$—$S(O)_tOR^{16}$, —$R^{15}$—$S(O)_tR^{16}$, and —$R^{15}$—$S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Cycloalkylalkyl" refers to a radical of the formula —$R_aR_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems, which may be partially unsaturated; and the nitrogen, carbon or sulfur atoms in the heterocyclyl radical may be optionally oxidized; the nitrogen atom may be optionally alkylated/substituted; and the heterocyclyl radical may be partially or fully saturated. Examples of such heterocyclyl radicals include, but are not limited to, azetidinyl, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl, homopiperidinyl, homopiperazinyl, and quinuclidinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, cyano, oxo, thioxo, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$ $R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$), $R^{15}$—S$R^{16}$, —$R^{15}$—S(O)$_t$O$R^{16}$, —$R^{15}$—S(O)$R^{16}$, and —$R^{15}$—S(O)$_t$N($R^{14}$)$_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl, and where each of the above substituents is unsubstituted.

"Heterocyclylalkyl" refers to a radical of the formula —$R_a R_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic or tricyclic ring system, which may include fused or bridged ring systems, which may be partially saturated; and the nitrogen, carbon or sulfur atoms in the heteroaryl radical may be optionally oxidized; the nitrogen atom may be optionally alkylated/substituted. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl, benzo[b]thiophenyl, benzothiophenyl, benzotriazolyl, benzo[4,6]imidazo[1,2-a]pyridinyl, benzo[c][1,2,5]oxadiazolyl, benzo[c][1,2,5]thiadiazolyl, carbazolyl, cinnolinyl, dibenzofuranyl, 6,7-dihydro-5H-pyrrolo[2,1-c][1,2,4]triazole, furanyl, furanonyl, isoquinolinyl, isothiazolyl, imidazolyl, imidazo[1,2-a]pyridinyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyridinyl 1-oxide, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, alkynyl, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$—$R^{15}$—N($R^{14}$)C(O)$R^{16}$, —$R^{15}$—N($R^{14}$)(S(O)$_t$$R^{16}$), $R^{15}$—S$R^{16}$, —$R^{15}$—S(O)$_t$O$R^{16}$, —$R^{15}$—S(O)$_t$$R^{16}$, and —$R^{15}$—S(O)$_t$N($R^{14}$)$_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Heteroarylalkyl" refers to a radical of the formula —$R_a R_f$ where $R_a$ is an alkylene chain as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to each other through direct bonds or some or all of the rings may be fused to each other.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto or acid group is bonded to any group that, when the prodrug of the compound of the invention is administered to a mammalian subject, cleaves to form a free hydroxy, free amino or free mercapto or acid group, respectively. Examples of prodrugs include, but are not limited to, acetate, formate and benzoate derivatives of alcohol or amides of amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent. A skilled artisan will recognize unstable combinations of substituents.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients thereof.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age and body weight of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes: (i) preventing the disease or condition from occurring in a mammal, in particular, when such mammal is predisposed to the condition but has not yet been diagnosed as having it; (ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

The invention includes pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of formula (I), for example, those incorporating a radioactive isotope, are useful in drug and/or substrate tissue distribution studies. The radioactive isotopes $^3$H and $^{14}$C are particularly useful for this purpose in view of their ease of incorporation and ready means of detection. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described herein using an appropriate isotopically-labelled reagent in place of the non-labelled reagent previously employed.

The chemical naming protocol and structure diagrams used herein employ and rely on the chemical naming features as utilized by Chemdraw version 10.0 (available from Cambridgesoft Corp., Cambridge, Mass.) or ISIS draw version 2.5 (available from MDL information systems).

EMBODIMENTS OF THE INVENTION

Various embodiments of the invention are described herein. It will be recognised that features specified in each embodiment may be combined with other specified features to provide further embodiments.

One embodiment of the invention is the compounds of Formula (I)

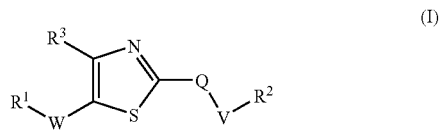

wherein,
Q is

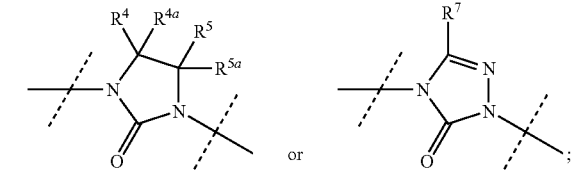

W is —N(R$^6$)C(O)—, —R$^8$—C(O)N(R$^6$)—, —R$^8$—OC(O)N(R$^6$)—, —N(R$^6$)C(O)O—, —N(R$^6$)C(O)N(R$^6$)—, —O—, —S—, —N(R$^6$)—, —S(O)$_t$—, —N(R$^6$)S(O)$_t$—, —S(O)$_t$N(R$^6$)—, —OS(O)$_t$N(R$^6$)—, —R$^8$—C(O)—, —OC(O)—, —C(O)O—, —N(R$^6$)C(═N(R$^{6a}$))N(R$^6$)—, —N(R$^6$)((R$^{6a}$)N═)C—C(═N(R$^{6a}$))N(R$^6$)—, or a direct bond;

V is —C(O)N(R$^6$)—, —S(O)$_t$—, —S(O)$_2$N(R$^6$)—, —C(O)—, —R$^8$—C(O)O—, —R$^8$—C(O)N(R$^6$)—, —R$^8$—C(O)—, —C(═N(R$^{6a}$))N(R$^6$)—, or a direct bond;

t is 1 or 2;

R$^1$ is halo, hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, or heteroarylalkyl;

or R$^1$ is a multi-ring structure having 2 to 4 rings wherein the rings are independently cycloalkyl, heterocyclyl, aryl or heteroaryl and where some or all of the rings may be fused to each other;

R$^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl;

or R$^2$ is a multi-ring structure having 2 to 4 rings wherein the rings are independently cycloalkyl, heterocyclyl, aryl or heteroaryl and where some or all of the rings may be fused to each other;

R$^3$ is hydrogen or alkyl;

R$^4$ and R$^{4a}$ are independently hydrogen, alkyl, haloalkyl, hydroxyl, hydroxyalkyl, alkoxy, cycloalkylalkyl or aralkyl;

or R$^4$ and R$^{4a}$ are taken together to form a cycloalkyl or heterocyclyl;

R$^5$ and R$^{5a}$ are independently hydrogen, alkyl or haloalkyl;

or R$^4$ and R$^5$ are taken to form a cycloalkyl, aryl, heteroaryl or heterocyclyl, and the remaining R$^{4a}$ and R$^{5a}$ are as described above;

$R^6$ is independently hydrogen, alkyl, hydroxyalkyl, cycloalkylalkyl, aryl, heteroaryl, heterocyclyl or aralkyl;

$R^{6a}$ is independently hydrogen, alkyl, cycloalkylalkyl, or cyano;

$R^7$ is hydrogen, alkyl, trifluoromethyl, aryl, cycloalkyl, heteroaryl, heterocyclyl, hydroxyalkyl, cycloalkylalkyl or aralkyl; and $R^8$ is independently a direct bond, an optionally substituted straight or branched alkylene chain, an optionally substituted straight or branched alkenylene chain or an optionally substituted straight or branched alkynylene chain;

as a stereoisomer, enantiomer or tautomer thereof, a pharmaceutically acceptable salt thereof, a pharmaceutical composition thereof or a prodrug thereof.

Another embodiment of Formula (I) wherein, $R^1$ is halo, hydrogen, $C_{1-4}$alkyl, $C_{2-6}$alkenyl, $C_{2-6}$alkynyl, $C_{1-4}$alkoxy, hydroxy$C_{1-4}$alkyl, $C_{1-4}$alkoxy$C_{1-4}$alkyl, $C_{3-6}$cycloalkyl, $C_{3-6}$cycloalkyl$C_{1-4}$alkyl, $C_{5-10}$aryl, aralkyl, $C_{1-5}$heterocyclyl, $C_{1-5}$heterocyclyl$C_{1-4}$alkyl, $C_{1-9}$heteroaryl, or $C_{1-9}$heteroaryl$C_{1-4}$alkyl;

or $R^1$ is a multi-ring structure having 2 to 4 rings wherein the rings are independently $C_{3-6}$cycloalkyl, $C_{1-5}$heterocyclyl, $C_{5-10}$aryl, or $C_{1-9}$heteroaryl and where some or all of the rings may be fused to each other;

$R^2$ is hydrogen, $C_{1-4}$alkyl, $C_{2-6}$alkenyl, $C_{2-6}$alkynyl, $C_{1-4}$alkoxy, hydroxy$C_{1-4}$alkyl, $C_{1-4}$alkoxy$C_{1-4}$alkyl, $C_{3-6}$cycloalkyl, $C_{3-6}$cycloalkyl$C_{1-4}$alkyl, $C_{5-10}$aryl, aralkyl, $C_{1-5}$heterocyclyl, $C_{1-5}$heterocyclyl$C_{1-4}$alkyl, $C_{1-9}$heteroaryl, or $C_{1-9}$heteroaryl$C_{1-4}$alkyl;

or $R^2$ is a multi-ring structure having 2 to 4 rings wherein the rings are independently $C_{3-6}$cycloalkyl, $C_{1-5}$heterocyclyl, $C_{5-10}$aryl or $C_{1-9}$heteroaryl and where some or all of the rings may be fused to each other;

$R^3$ is hydrogen or $C_{1-4}$alkyl;

$R^4$ and $R^{4a}$ are independently hydrogen, $C_{1-4}$alkyl, halo$C_{1-4}$alkyl, hydroxyl, hydroxy$C_{1-4}$alkyl, alkoxy, $C_{3-6}$cycloalkyl$C_{1-4}$alkyl or aralkyl;

or $R^4$ and $R^{4a}$ are taken together to form a $C_{3-6}$cycloalkyl or $C_{1-5}$heterocyclyl;

$R^5$ and $R^{5a}$ are independently hydrogen, $C_{1-4}$alkyl or halo$C_{1-4}$alkyl;

or $R^4$ and $R^5$ are taken to form a $C_{3-6}$cycloalkyl, $C_{5-10}$aryl, $C_{1-9}$heteroaryl or $C_{1-5}$heterocyclyl, while the remaining $R^{4a}$ and $R^{5a}$ are as described above;

$R^6$ is independently hydrogen, $C_{1-4}$alkyl, hydroxy$C_{1-4}$alkyl, $C_{3-6}$cycloalkyl$C_{1-4}$alkyl, $C_{5-10}$aryl, $C_{1-9}$heteroaryl, $C_{1-5}$heterocyclyl or aralkyl;

$R^{6a}$ is independently hydrogen, $C_{1-4}$alkyl, $C_{3-6}$cycloalkyl$C_{1-4}$alkyl, or cyano;

$R^7$ is hydrogen, $C_{1-4}$alkyl, trifluoromethyl, $C_{5-10}$aryl, $C_{3-6}$cycloalkyl, $C_{1-9}$heteroaryl, $C_{1-5}$heterocyclyl, hydroxy$C_{1-4}$alkyl, $C_{3-6}$cycloalkyl$C_{1-4}$alkyl or aralkyl; and $R^8$ is independently a direct bond, an optionally substituted straight or branched alkylene chain, an optionally substituted straight or branched alkenylene chain or an optionally substituted straight or branched alkynylene chain;

One embodiment of the compounds of Formula (I) is that embodiment wherein, Q is

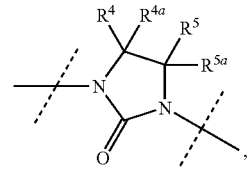

i.e., compound having the following Formula (II):

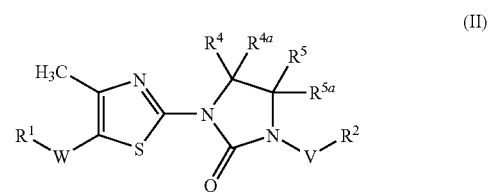

where V, W, $R^1$, $R^2$, $R^4$, $R^{4a}$, $R^5$ and $R^{5a}$ are as defined above.

Of this group of compounds, a subgroup of compounds are those compounds wherein W is —N($R^6$)C(O)—, —C(O)—, —OC(O)— or a direct bond; V is —$R^8$—C(O)—, —$R^8$—C(O)O—, —$R^8$—C(O)N($R^6$)— or a direct bond; $R^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; each of $R^4$ and $R^{4a}$ is independently hydrogen, hydroxyl or alkoxy; or $R^4$ and $R^{4a}$ are together to form an oxo (=O) group; $R^5$ and $R^{5a}$ are hydrogen or $C_{1-4}$alkyl; each $R^6$ is independently hydrogen, alkyl, hydroxyalkyl, cycloalkylalkyl, aryl, heteroaryl, heterocyclyl or aralkyl; and each $R^8$ is a direct bond, an optionally substituted straight or branched alkylene chain, an optionally substituted straight or branched alkenylene chain or an optionally substituted straight or branched alkynylene chain.

Of this subgroup, a set of compounds are those compounds where W is —N($R^6$)C(O)—; V is —$R^8$—C(O)—, —$R^8$—C(O)O—, —$R^8$—C(O)N($R^6$)— or a direct bond; each of $R^4$ and $R^{4a}$ is hydrogen; each $R^5$ and $R^{5a}$ are hydrogen or $C_{1-4}$alkyl; each $R^6$ is hydrogen or alkyl; and each $R^8$ is a direct bond or an optionally substituted straight or branched alkylene chain.

Of this set of compounds, a subset of compounds are those compounds where W is —N(H)C(O)—; and V is —$R^8$—C(O)N($R^6$)—, or a direct bond.

Of this subset $R^1$ is preferably hydrogen, aralkyl or heteroarylalkyl.

Of this subset $R^2$ is preferably $C_{1-4}$ alkyl, haloalkyl, cycloalkylalkyl, aralkyl or haloalkyl.

Of the above subgroup, another set of compounds are those compounds where W is a direct bond; V is —$R^8$—C(O)—, —$R^8$—C(O)O—, —$R^8$—C(O)N($R^6$)— or a direct bond; each of $R^4$ and $R^{4a}$ are hydrogen; each $R^5$ and $R^{5a}$ is hydrogen or $C_{1-4}$ alkyl; each $R^6$ is hydrogen or alkyl; and each $R^8$ is a direct bond or an optionally substituted straight or branched alkylene chain.

Of this set of compounds, a subset of compounds are those compounds where W is a direct bond and V is —$R^8$—C(O)N($R^6$)— or a direct bond.

Of this subset $R^1$ is preferably heteroaryl, or heteroarylalkyl.

Of this subset $R^2$ is preferably haloalkyl, cycloalkylalkyl, or aralkyl.

Another embodiment is represented by Formula (II):

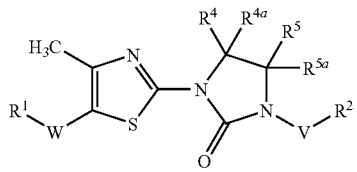
(II)

wherein:

V is a direct bond; W is selected from —N($R^6$)C(O)—, —$R^8$—C(O)N($R^6$)—, —C(O)O— or a direct bond; $R^1$ is hydrogen, alkyl, aryl, aralkyl, cycloalkyl, cycloalkylalkyl, heterocyclyl, heterocyclylalkyl, heteroaryl, or heteroarylalkyl; $R^2$ is selected from the group consisting of $C_{1-4}$alkyl, cycloalkylalkyl, aryl, aralkyl, haloalkyl, heteroaryl and heteroarylalkyl; $R^4$ is hydrogen or $C_{1-4}$ alkyl; $R^{4a}$ is hydrogen; $R^5$ is hydrogen or $C_{1-4}$ alkyl; $R^{5a}$ is hydrogen; $R^6$ is hydrogen or $C_{1-4}$alkyl; and $R^8$ is a direct bond, an optionally substituted straight alkylene chain or an optionally substituted branched alkylene chain.

An embodiment of the invention is represented by Formula (III):

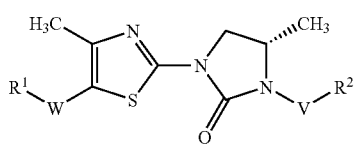
(III)

wherein, V is a direct bond; W is selected from —N($R^6$)C(O)—, or —C(O)O—; $R^1$ is hydrogen, aralkyl, or heteroarylalkyl; $R^2$ is $C_{1-4}$ alkyl, cycloalkylalkyl, aryl, haloalkyl or aralkyl; and $R^6$ is hydrogen.

An embodiment of the present invention is wherein V is a direct bond; W is —N($R^6$)C(O)—; $R^1$ is selected from hydrogen, aralkyl or heteroarylalkyl; $R^6$ is hydrogen; and $R^2$ is $C_{1-4}$ alkyl, cycloalkylalkyl, haloalkyl or aralkyl;

wherein the cycloalkylalkyl is

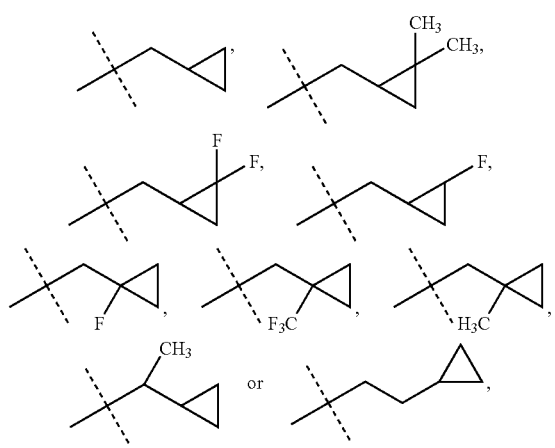

wherein the aralkyl is

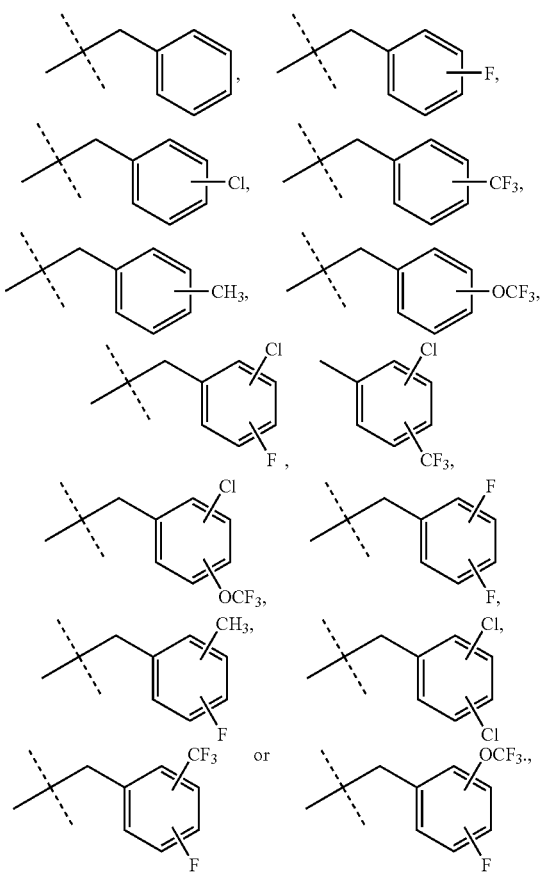

wherein the $C_{1-4}$ alkyl is

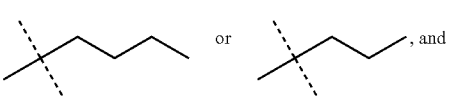

wherein haloalkyl is

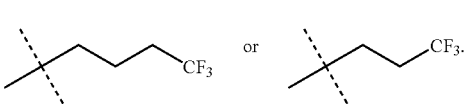

An embodiment of the invention is represented by Formula (IV):

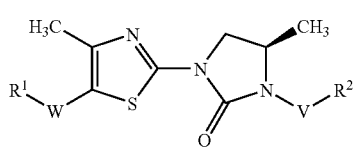
(IV)

wherein, V is a direct bond; W is selected from —N($R^6$)C(O)—, or —C(O)O—; $R^1$ is hydrogen, aralkyl, or heteroarylalkyl; $R^2$ is $C_{1-4}$ alkyl, cycloalkylalkyl, aryl, haloalkyl or aralkyl; and $R^6$ is hydrogen.

An embodiment of the present invention is wherein V is a direct bond; W is —N(R⁶)C(O)—; R¹ is selected from hydrogen, aralkyl or heteroarylalkyl; R⁶ is hydrogen; and R² is $C_{1-4}$ alkyl, cycloalkylalkyl, haloalkyl or aralkyl;

wherein the cycloalkylalkyl is

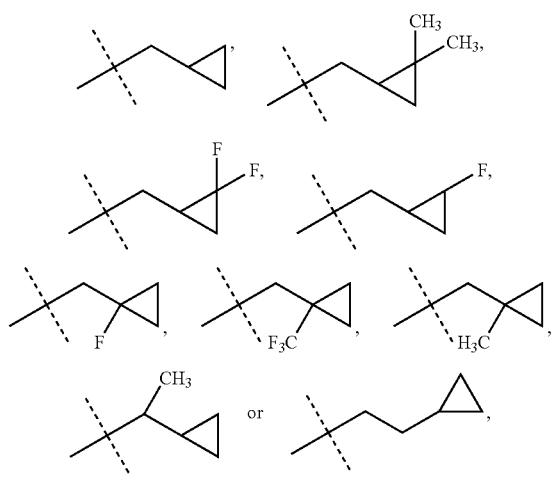

wherein the aralkyl is

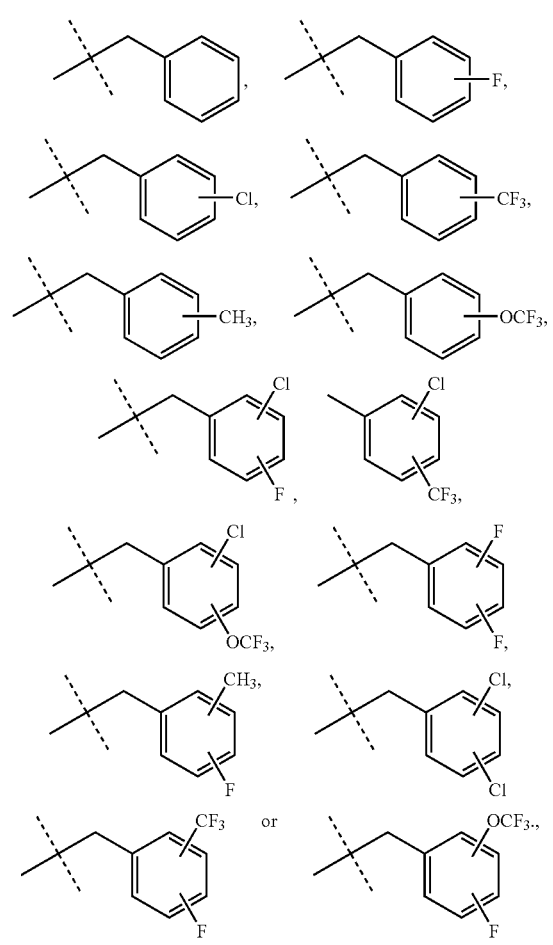

wherein the $C_{1-4}$ alkyl is

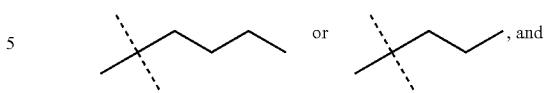, and wherein haloalkyl is

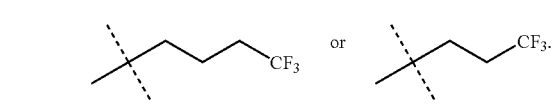

An embodiment of the invention is represented by Formula (V):

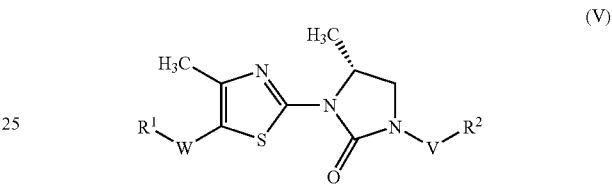

wherein, V is a direct bond; W is selected from —N(R⁶)C(O)—, or —C(O)O—; R¹ is hydrogen, aralkyl, or heteroarylalkyl; R² is $C_{1-4}$ alkyl, cycloalkylalkyl, aryl, haloalkyl or aralkyl; and R⁶ is hydrogen.

An embodiment of the present invention is wherein V is a direct bond; W is —N(R⁶)C(O)—; R¹ is select hydrogen, aralkyl or heteroarylalkyl; R⁶ is hydrogen; and R² is $C_{1-4}$ alkyl, cycloalkylalkyl, haloalkyl or aralkyl;

wherein the cycloalkylalkyl is

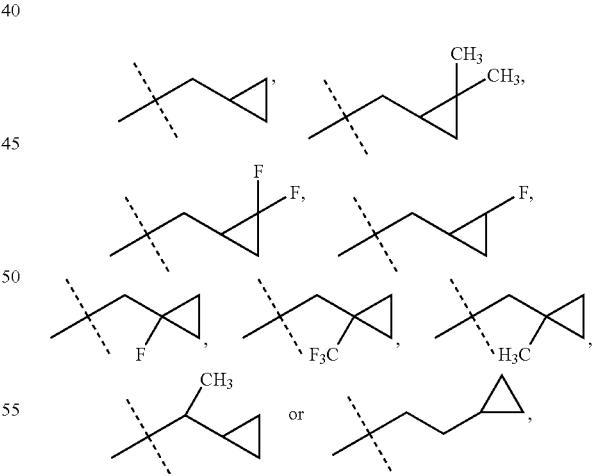

wherein the aralkyl is

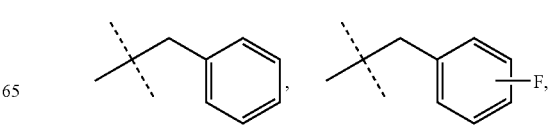

-continued

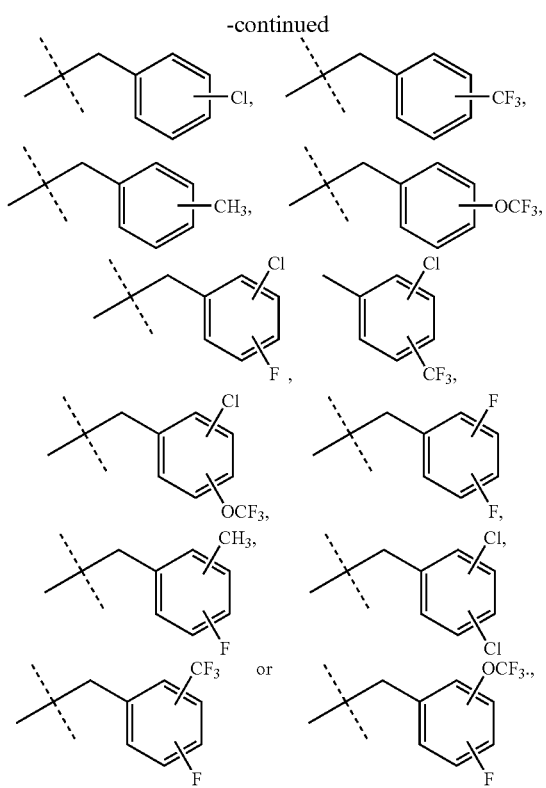

wherein the C$_{1-4}$ alkyl is

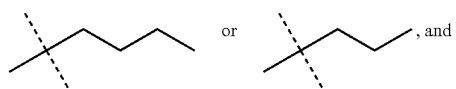

wherein haloalkyl is

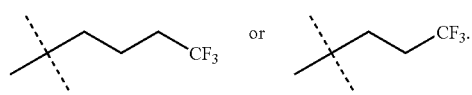

An embodiment of the invention is represented by Formula (VI):

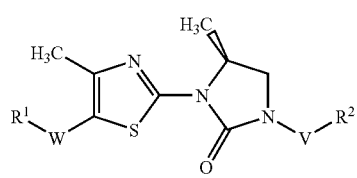

wherein, V is a direct bond; W is selected from —N(R$^6$)C(O)—, or —C(O)O—; R$^1$ is hydrogen, aralkyl, or heteroarylalkyl; R$^2$ is C$_{1-4}$alkyl, cycloalkylalkyl, aryl, haloalkyl or aralkyl; and R$^6$ is hydrogen.

An embodiment of the present invention is wherein V is a direct bond; W is —N(R$^6$)C(O)—; R$^1$ is hydrogen, aralkyl or heteroarylalkyl; R$^6$ is hydrogen; and R$^2$ is C$_{1-4}$ alkyl, cycloalkylalkyl, haloalkyl or aralkyl;

wherein the cycloalkylalkyl is

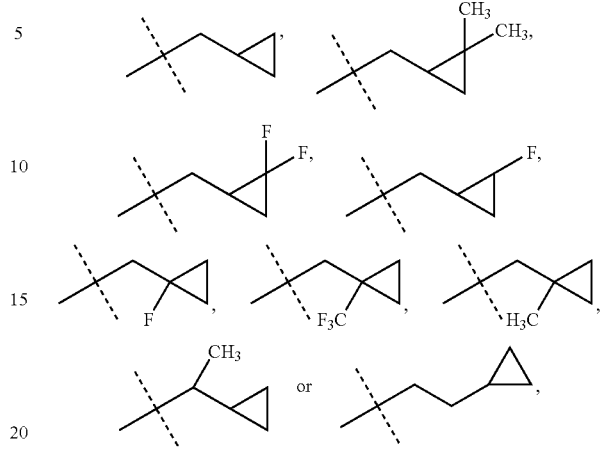

wherein the aralkyl is

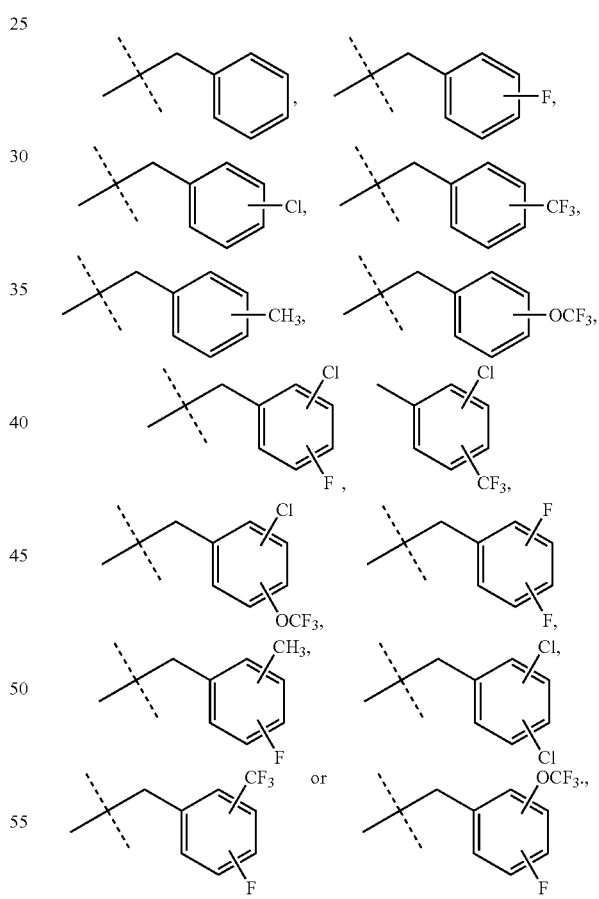

wherein the C$_{1-4}$ alkyl is

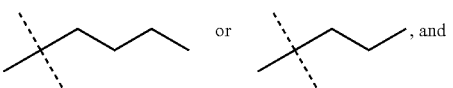

wherein haloalkyl is

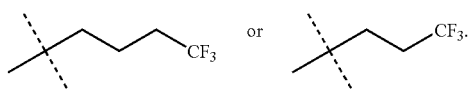

An embodiment of the invention is represented by Formula (VII):

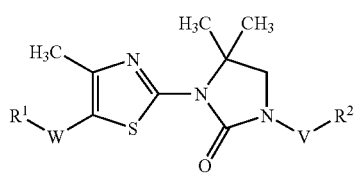

(VII)

wherein, V is a direct bond; W is —N(R$^6$)C(O)—, or —C(O)O—; R$^1$ is hydrogen, aralkyl, or heteroarylalkyl; R$^2$ is C$_{1-4}$ alkyl, cycloalkylalkyl, aryl, haloalkyl or aralkyl; and R$^6$ is hydrogen.

An embodiment of the present invention is V is a direct bond; W is —N(R$^6$)C(O)—; R$^1$ is hydrogen, aralkyl or heteroarylalkyl; R$^6$ is hydrogen; and R$^2$ is C$_{1-4}$ alkyl, cycloalkylalkyl, haloalkyl or aralkyl;

wherein the cycloalkylalkyl is

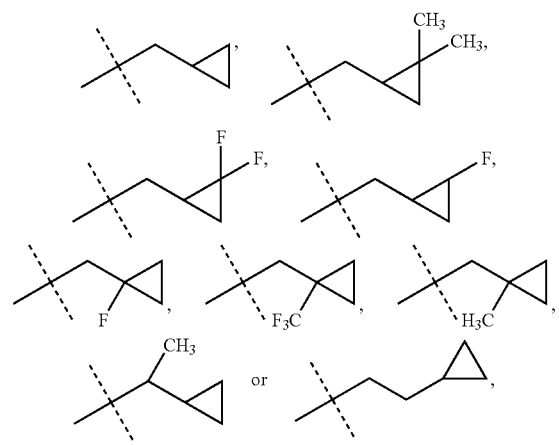

wherein the aralkyl is

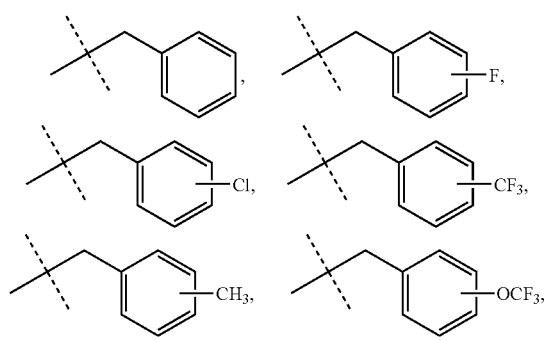

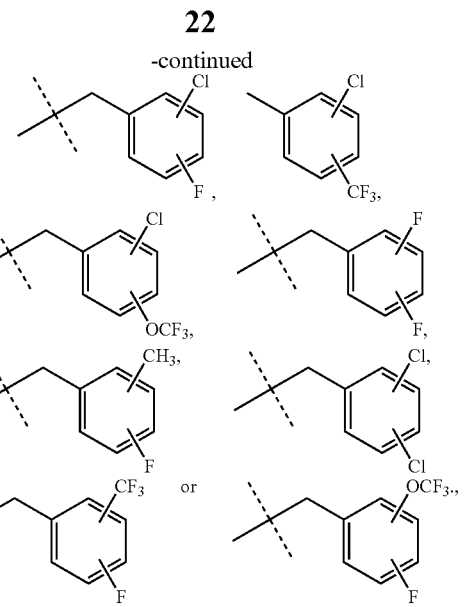

wherein the C$_{1-4}$ alkyl is

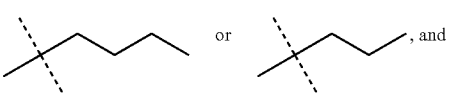

wherein haloalkyl is

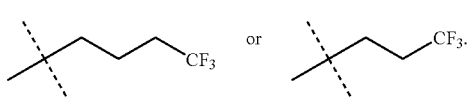

An embodiment of the invention is represented by Formula (VIII):

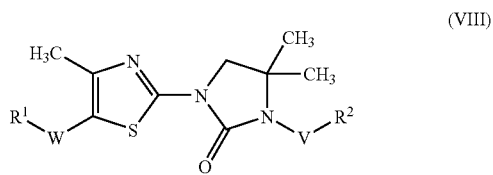

(VIII)

wherein, V is a direct bond; W is —N(R$^6$)C(O)—, or —C(O)O—; R$^1$ is hydrogen, aralkyl, or heteroarylalkyl; R$^2$ is C$_{1-4}$ alkyl, cycloalkylalkyl, aryl, haloalkyl or aralkyl; and R$^6$ is hydrogen.

A preferred embodiment of the present invention is V is a direct bond; W is —N(R$^6$)C(O)—; R$^1$ is hydrogen, aralkyl or heteroarylalkyl; R$^6$ is hydrogen; and R$^2$ is C$_{1-4}$ alkyl, cycloalkylalkyl, haloalkyl or aralkyl;

wherein the cycloalkylalkyl is

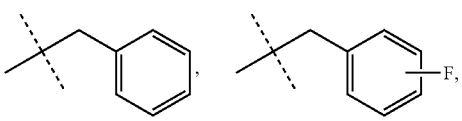

-continued

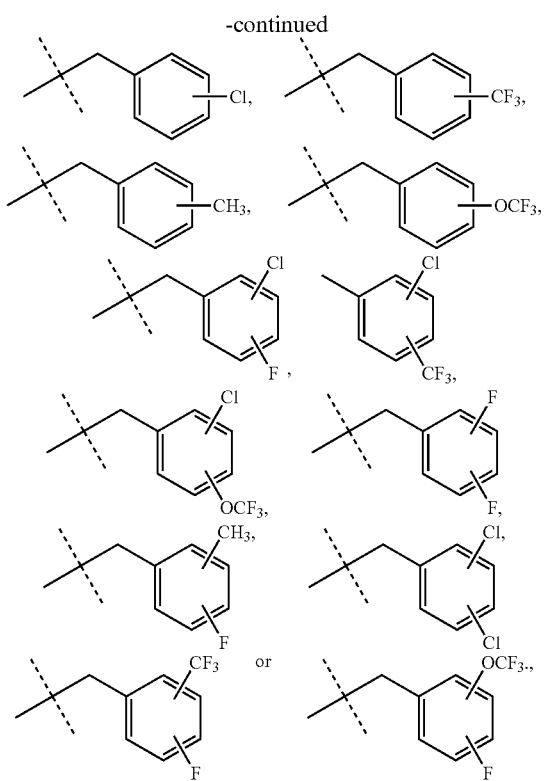

wherein the aralkyl is

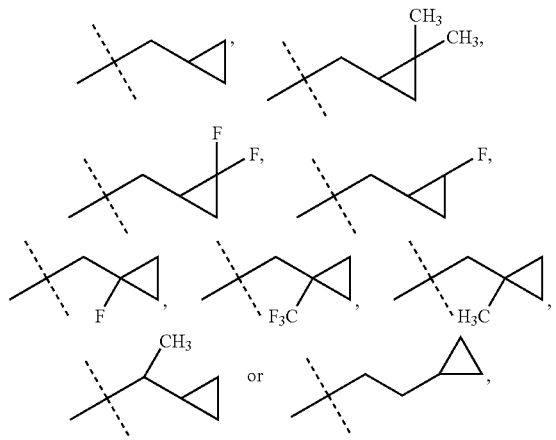

wherein the $C_{1-4}$ alkyl is

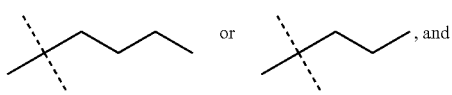

wherein haloalkyl is

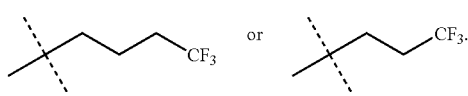

In yet another embodiment of the invention, a group of compounds of Formula (I) is directed to compounds wherein Q is

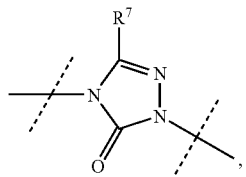

i.e., compounds having the following Formula (IX):

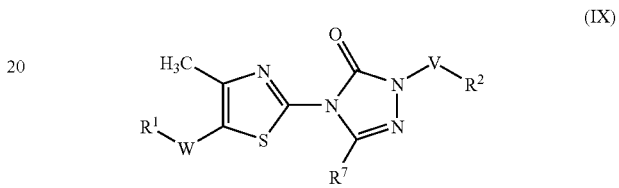

(IX)

wherein V, W, $R^1$, $R^2$, and $R^7$ are as defined above.

Of this group of compounds, a subgroup of compounds are those compounds wherein W is —N($R^6$)C(O)— or —OC(O)—; V is —$R^8$—OC(O)N($R^6$)—, —$R^8$—C(O)N($R^6$)—, or a direct bond; $R^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; each $R^6$ is independently hydrogen or alkyl; and each $R^7$ is independently hydrogen, alkyl, trifluoromethyl or aryl.

Of this subgroup of compounds, a set of compounds are those compounds where W is —N($R^6$)C(O)—; V is a direct bond; $R^1$ is hydrogen, aralkyl or heteroarylalkyl; $R^2$ is hydrogen, alkyl, cycloalkylalkyl, haloalkyl, aralkyl or heteroarylalkyl; and $R^7$ is hydrogen.

Another embodiment of the invention is represented by Formula (X):

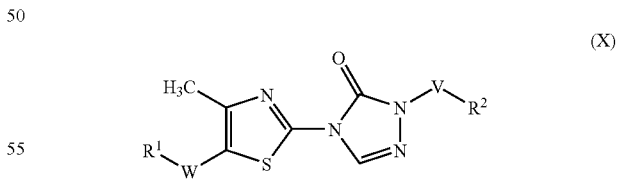

(X)

wherein, V is a direct bond; W is selected from —N($R^6$)C(O)—, —$R^8$—C(O)N($R^6$)—, —OC(O)—, —C(O)O—, or a direct bond; $R^1$ is hydrogen, alkyl, aryl, aralkyl, cycloalkyl, cycloalkylalkyl, heterocyclyl, heterocyclylalkyl, heteroaryl, or heteroarylalkyl; $R^2$ is selected from the group consisting of $C_{1-4}$ alkyl, cycloalkylalkyl, haloalkyl, aryl, aralkyl, heteroaryl and heteroarylalkyl; $R^6$ is hydrogen or $C_{1-4}$ alkyl; and $R^8$ is a direct bond, an optionally substituted straight alkylene chain or an optionally substituted branched alkylene chain.

Another embodiment of the invention is represented by Formula (X):

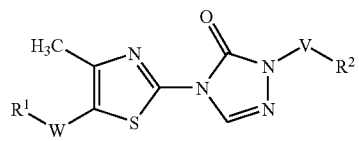

wherein, V is a direct bond; W is selected from —N(R⁶)C(O)—, or —C(O)O—; t is 1 or 2; R¹ is hydrogen, aralkyl, or heteroarylalkyl; R² is $C_{1-4}$alkyl, cycloalkylalkyl, haloalkyl, aryl or aralkyl; and R⁶ is hydrogen.

The preferred R² for the compounds represented by Formula (X) is $C_{1-4}$ alkyl, cycloalkylalkyl, or aralkyl;

wherein the cycloalkylalkyl is

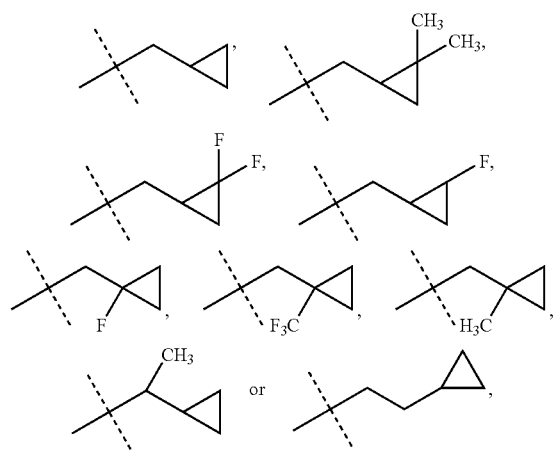

wherein the aralkyl is

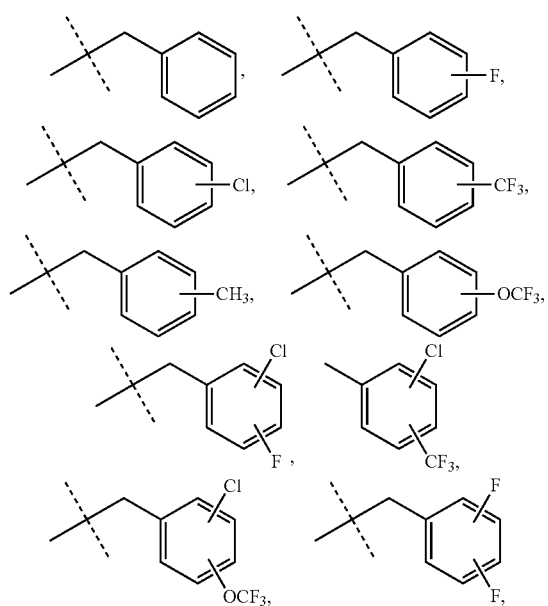

wherein the $C_{1-4}$ alkyl is

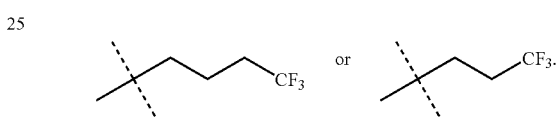

wherein haloalkyl is

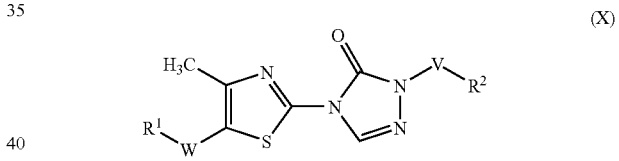

Another embodiment of the invention is represented by Formula (X):

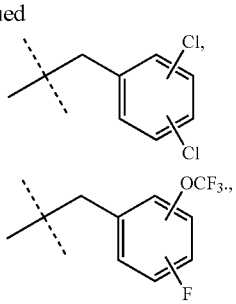

wherein, W is a direct bond; V is a direct bond; R¹ is hydrogen, aralkyl, heteroaryl or heteroarylalkyl; and R² is $C_{1-4}$alkyl, cycloalkylalkyl, haloalkyl, aryl or aralkyl.

The embodiment of the compounds represented Formulae (I, II, III, IV, V, VI, VII, VIII, IX and X), wherein W is —N(R⁶)C(O)—, and R¹ is hydrogen,

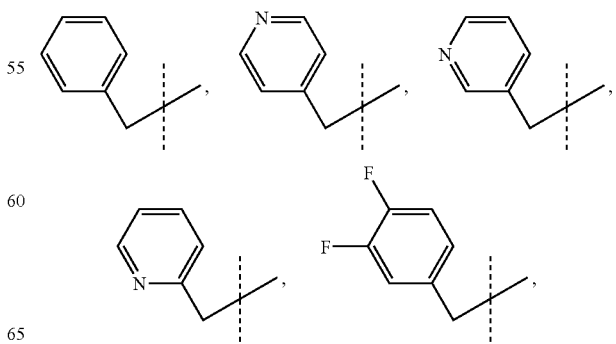

-continued

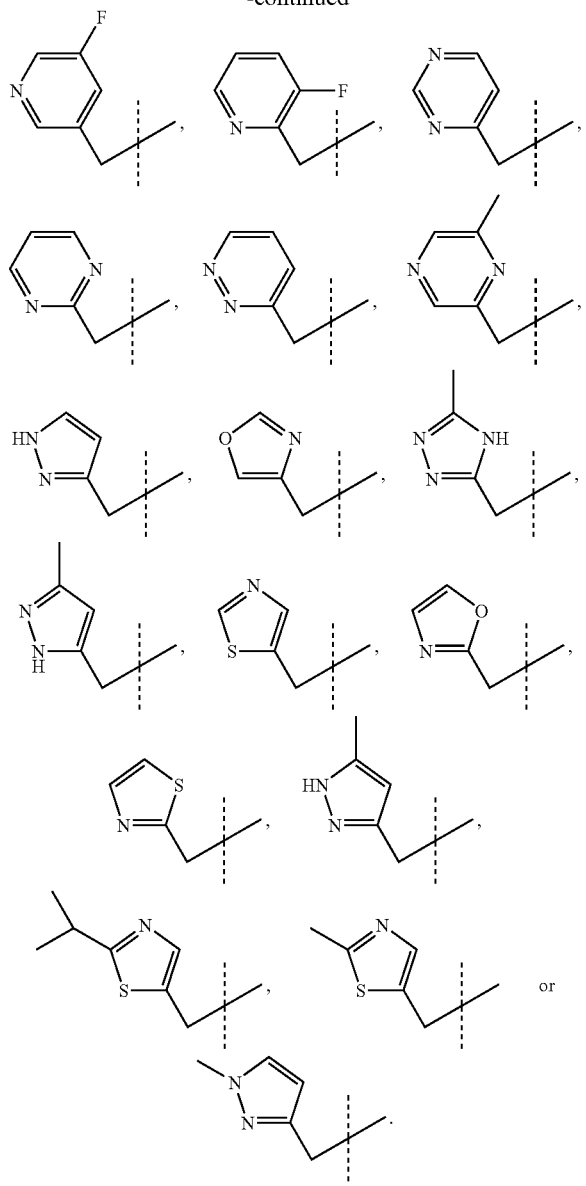

The embodiment of the compounds represented Formulae (I, II, III, IV, V, VI, VII, VIII, IX and X), wherein W is a direct bond and
R¹ is

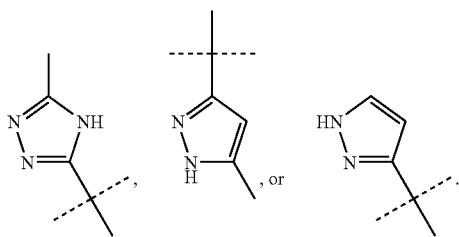

In another aspect of the invention, there is provided:
2-(3-(2-(4-fluorobenzylamino)-2-oxoethyl)-2-oxoimidazolidin-1-yl)-4-methyl-N-(pyridin-3-ylmethyl)thiazole-5-carboxamide;
4-methyl-2-(3-(2-(methylamino)-2-oxoethyl)-2-oxoimidazolidin-1-yl)-N-(pyridin-3-ylmethyl)thiazole-5-carboxamide;
4-methyl-2-(2-oxo-3-(2-oxo-2-(pyrrolidin-1-yl)ethyl)imidazolidin-1-yl)-N-(pyridin-3-ylmethyl)thiazole-5-carboxamide;
N-benzyl-2-(3-(4-fluorobenzyl)-2-oxo-2,3-dihydro-1H-benzo[d]imidazol-1-yl)-4-methylthiazole-5-carboxamide;
2-(1-(2-cyclopropylethyl)-5-oxo-1H-1,2,4-triazol-4(5H)-yl)-4-methyl-N-(pyridin-3-ylmethyl)thiazole-5-carboxamide;
2-(1-(cyclopropylmethyl)-5-oxo-1H-1,2,4-triazol-4(5H)-yl)-4-methyl-N-(pyridin-4-ylmethyl)thiazole-5-carboxamide;
(1-(cyclopropylmethyl)-5-oxo-1H-1,2,4-triazol-4(5H)-yl)-4-methyl-N-(pyridin-4-ylmethyl)thiazole-5-carboxamide;
N-((1H-pyrazol-3-yl)methyl)-2-(1-(cyclopropylmethyl)-5-oxo-1H-1,2,4-triazol-4(5H)-yl)-4-methylthiazole-5-carboxamide;
2-(1-(cyclopropylmethyl)-5-oxo-1H-1,2,4-triazol-4(5H)-yl)-4-methyl-N-(oxazol-4-ylmethyl)thiazole-5-carboxamide;
2-(1-(cyclopropylmethyl)-5-oxo-1H-1,2,4-triazol-4(5H)-yl)-4-methyl-N-(pyridin-2-ylmethyl)thiazole-5-carboxamide;
2-(1-((2,2-difluorocyclopropyl)methyl)-5-oxo-1H-1,2,4-triazol-4(5H)-yl)-4-methyl-N-(pyridin-3-ylmethyl)thiazole-5-carboxamide;
2-(1-(4-fluorobenzyl)-5-oxo-1H-1,2,4-triazol-4(5H)-yl)-4-methylthiazole-5-carboxamide;
2-[1-(cyclopropylmethyl)-5-oxo-1H-1,2,4-triazol-4(5H)-yl]-4-methylthiazole-5-carboxamide;
2-(3-(but-3-enyl)-2-oxoimidazolidin-1-yl)-4-methyl-N-(pyridin-3-ylmethyl)thiazole-5-carboxamide;
4-methyl-2-{2-oxo-3-[4-(trifluoromethyl)benzyl]imidazolidin-1-yl}thiazole-5-carboxamide;
1-(4-fluorobenzyl)-3-[4-methyl-5-(5-methyl-4H-1,2,4-triazol-3-yl)thiazol-2-yl]imidazolidin-2-one;
2-(3-(4-fluorobenzyl)-2-oxoimidazolidin-1-yl)-4-methyl-N-((3-methyl-1H-pyrazol-5-yl)methyl)thiazole-5-carboxamide;
2-(1-(4-fluorobenzyl)-5-oxo-1H-1,2,4-triazol-4(5H)-yl)-4-methyl-N-((3-methyl-1H-pyrazol-5-yl)methyl)thiazole-5-carboxamide;
(S)-2-(3-(4-fluorobenzyl)-4-methyl-2-oxoimidazolidin-1-yl)-4-methyl-N-(pyridin-3-ylmethyl)thiazole-5-carboxamide;
(S)—N-(3,4-difluorobenzyl)-2-(3-(4-fluorobenzyl)-4-methyl-2-oxoimidazolidin-1-yl)-4-methylthiazole-5-carboxamide;
(S)-2-(3-(4-fluorobenzyl)-4-methyl-2-oxoimidazolidin-1-yl)-4-methylthiazole-5-carboxamide;
1-(4-methyl-5-(5-methyl-4H-1,2,4-triazol-3-yl)thiazol-2-yl)-3-(4-(trifluoromethyl)benzyl)imidazolidin-2-one;
N-(3-(dimethylamino)benzyl)-2-(1-(4-fluorobenzyl)-5-oxo-1H-1,2,4-triazol-4(5H)-yl)-4-methylthiazole-5-carboxamide;
2-(3-((2,2-difluorocyclopropyl)methyl)-2-oxoimidazolidin-1-yl)-4-methyl-N-(pyridin-3-ylmethyl)thiazole-5-carboxamide;
2-(3-((2,2-difluorocyclopropyl)methyl)-2-oxoimidazolidin-1-yl)-4-methyl-N-(thiazol-5-ylmethyl)thiazole-5-carboxamide;

2-(3-((2,2-difluorocyclopropyl)methyl)-2-oxoimidazolidin-1-yl)-4-methyl-N-(oxazol-2-ylmethyl)thiazole-5-carboxamide;

2-(3-((2,2-difluorocyclopropyl)methyl)-2-oxoimidazolidin-1-yl)-4-methyl-N-((4-methylthiazol-2-yl)methyl)thiazole-5-carboxamide;

1-(cyclopropylmethyl)-3-(4-methyl-5-(5-methyl-1H-pyrazol-3-yl)thiazol-2-yl)imidazolidin-2-one;

1-(4-fluorobenzyl)-3-(4-methyl-5-(1H-pyrazol-3-yl)thiazol-2-yl)imidazolidin-2-one;

2-(3-benzyl-2-oxoimidazolidin-1-yl)-4-methylthiazole-5-carboxamide;

1-benzyl-3-(4-methyl-5-(5-methyl-4H-1,2,4-triazol-3-yl)thiazol-2-yl)imidazolidin-2-one;

2-(3-(cyclopropylmethyl)-2-oxoimidazolidin-1-yl)-N-((5-fluoropyridin-3-yl)methyl)-4-methylthiazole-5-carboxamide, 1-(cyclopropylmethyl)-3-(4-methyl-5-(1H-pyrazol-3-yl)thiazol-2-yl)imidazolidin-2-one;

1-(2-cyclopropylethyl)-3-(4-methyl-5-(1H-pyrazol-3-yl)thiazol-2-yl)imidazolidin-2-one;

1-(4-fluorobenzyl)-3-(4-methyl-5-(1H-pyrazol-3-yl)thiazol-2-yl)imidazolidin-2-one;

2-(3-(cyclopropylmethyl)-2-oxoimidazolidin-1-yl)-N-((5-fluoropyridin-3-yl)methyl)-4-methylthiazole-5-carboxamide;

2-(3-(cyclopropylmethyl)-2-oxoimidazolidin-1-yl)-N-((3-fluoropyridin-2-yl)methyl)-4-methylthiazole-5-carboxamide;

2-(3-(cyclopropylmethyl)-2-oxoimidazolidin-1-yl)-4-methyl-N-(pyrimidin-4-ylmethyl)thiazole-5-carboxamide;

2-(3-(cyclopropylmethyl)-2-oxoimidazolidin-1-yl)-4-methyl-N-(pyrimidin-2-ylmethyl)thiazole-5-carboxamide;

2-(3-(cyclopropylmethyl)-2-oxoimidazolidin-1-yl)-4-methyl-N-(pyridazin-3-ylmethyl)thiazole-5-carboxamide;

2-(3-(cyclopropylmethyl)-2-oxoimidazolidin-1-yl)-4-methylthiazole-5-carboxamide;

2-(3-isobutyl-2-oxoimidazolidin-1-yl)-4-methylthiazole-5-carboxamide;

2-(3-(cyclopropylmethyl)-2-oxoimidazolidin-1-yl)-4-methyl-N-(pyridin-4-ylmethyl)thiazole-5-carboxamide;

2-(3-(cyclopropylmethyl)-2-oxoimidazolidin-1-yl)-4-methyl-N-((2-methylthiazol-5-yl)methyl)thiazole-5-carboxamide;

2-(3-(cyclopropylmethyl)-2-oxoimidazolidin-1-yl)-4-methyl-N-(oxazol-2-ylmethyl)thiazole-5-carboxamide;

4-methyl-2-(2-oxo-3-(4,4,4-trifluorobutyl)imidazolidin-1-yl)thiazole-5-carboxylic acid;

2-(3-(4-fluorobenzyl)-2-oxoimidazolidin-1-yl)-4-methyl-N-(oxazol-4-ylmethyl)thiazole-5-carboxamide;

(Duplicate) 4-methyl-2-(2-oxo-3-(4,4,4-trifluorobutyl)imidazolidin-1-yl)-N-(pyridin-2-ylmethyl)thiazole-5-carboxamide;

4-methyl-2-(2-oxo-3-(4,4,4-trifluorobutyl)imidazolidin-1-yl)thiazole-5-carboxamide;

4-methyl-N-(oxazol-4-ylmethyl)-2-(2-oxo-3-(4,4,4-trifluorobutyl)imidazolidin-1-yl)thiazole-5-carboxamide;

4-methyl-N-(oxazol-2-ylmethyl)-2-(2-oxo-3-(4,4,4-trifluorobutyl)imidazolidin-1-yl)thiazole-5-carboxamide;

4-methyl-N-((6-methylpyrazin-2-yl)methyl)-2-(2-oxo-3-(4,4,4-trifluorobutyl)imidazolidin-1-yl)thiazole-5-carboxamide;

4-methyl-2-(2-oxo-3-(4,4,4-trifluorobutyl)imidazolidin-1-yl)-N-(pyridin-4-ylmethyl)thiazole-5-carboxamide;

4-methyl-N-((1-methyl-1H-pyrazol-4-yl)methyl)-2-(2-oxo-3-(4,4,4-trifluorobutyl)imidazolidin-1-yl)thiazole-5-carboxamide;

1-(4-methyl-5-(5-methyl-1H-pyrazol-3-yl)thiazol-2-yl)-3-(3-(trifluoromethyl)benzyl)imidazolidin-2-one;

4-methyl-2-(2-oxo-3-(4,4,4-trifluorobutyl)imidazolidin-1-yl)-N-(pyridin-3-ylmethyl)thiazole-5-carboxamide;

N-((1H-pyrazol-4-yl)methyl)-4-methyl-2-(2-oxo-3-(4,4,4-trifluorobutyl)imidazolidin-1-yl)thiazole-5-carboxamide;

2-(3-(cyclopropylmethyl)-2-oxoimidazolidin-1-yl)-4-methyl-N-(pyridin-4-ylmethyl)thiazole-5-carboxamide;

2-(3-isobutyl-2-oxoimidazolidin-1-yl)-4-methyl-N-(pyridin-4-ylmethyl)thiazole-5-carboxamide;

2-(3-isobutyl-2-oxoimidazolidin-1-yl)-4-methyl-N-(pyridin-3-ylmethyl)thiazole-5-carboxamide;

2-(3-isobutyl-2-oxoimidazolidin-1-yl)-4-methyl-N-(pyridin-2-ylmethyl)thiazole-5-carboxamide;

2-(3-isobutyl-2-oxoimidazolidin-1-yl)-4-methyl-N-((6-methylpyrazin-2-yl)methyl)thiazole-5-carboxamide;

2-(3-isobutyl-2-oxoimidazolidin-1-yl)-4-methyl-N-((1-methyl-1H-pyrazol-4-yl)methyl)thiazole-5-carboxamide;

2-(3-isobutyl-2-oxoimidazolidin-1-yl)-4-methyl-N-((1-methyl-1H-pyrazol-3-yl)methyl)thiazole-5-carboxamide;

2-(3-isobutyl-2-oxoimidazolidin-1-yl)-4-methyl-N-(oxazol-4-ylmethyl)thiazole-5-carboxamide;

1-(4-methyl-5-(1H-pyrazol-3-yl)thiazol-2-yl)-3-(3-(trifluoromethyl)benzyl) imidazolidin-2-one;

1-(4-fluorobenzyl)-3-(4-methyl-5-(2H-tetrazol-5-yl)thiazol-2-yl)imidazolidin-2-one;

1-(4-fluorobenzyl)-4-(4-methyl-5-(2H-tetrazol-5-yl)thiazol-2-yl)-1H-1,2,4-triazol-5(4H)-one;

2-(4-(4-fluorobenzyl)-3-oxo-2,4-diazabicyclo[3.1.0]hexan-2-yl)-4-methyl-N-(pyridin-3-ylmethyl)thiazole-5-carboxamide;

4-methyl-2-[3-(1-methyl-cyclopropylmethyl)-2-oxo-imidazolidin-1-yl]-thiazole-5-carboxylic acid (oxazol-4-ylmethyl)-amide;

2-(1-(3,5-difluorobenzyl)-5-oxo-1H-1,2,4-triazol-4(5H)-yl)-4-methyl-N-((1-methyl-1H-pyrazol-3-yl)methyl)thiazole-5-carboxamide;

4-methyl-2-(5-oxo-1-(1-phenylethyl)-1H-1,2,4-triazol-4(5H)-yl)-N-(pyridin-3-ylmethyl)thiazole-5-carboxamide;

4-methyl-2-(5-oxo-1-(1-phenylethyl)-1H-1,2,4-triazol-4(5H)-yl)thiazole-5-carboxamide;

4-methyl-N-((3-methyl-1H-pyrazol-4-yl)methyl)-2-(5-oxo-1-(1-phenylethyl)-1H-1,2,4-triazol-4(5H)-yl)thiazole-5-carboxamide;

2-(1-(4-fluorobenzyl)-5-oxo-1H-1,2,4-triazol-4(5H)-yl)-4-methyl-N-((6-(trifluoromethyl)pyridin-3-yl)methyl)thiazole-5-carboxamide;

2-(3-(cyclopropylmethyl)-2-oxoimidazolidin-1-yl)-N-(3,5-difluorobenzyl)-4-methylthiazole-5-carboxamide;

4-methyl-2-(5-oxo-1-(1-phenylethyl)-1H-1,2,4-triazol-4(5H)-yl)-N-(thiazol-5-ylmethyl)thiazole-5-carboxamide;

N-((3-chloro-5-(trifluoromethyl)pyridin-2-yl)methyl)-2-(1-(4-fluorobenzyl)-5-oxo-1H-1,2,4-triazol-4(5H)-yl)-4-methylthiazole-5-carboxamide;

2-(1-((2,2-difluorocyclopropyl)methyl)-5-oxo-1H-1,2,4-triazol-4(5H)-yl)-4-methyl-N-(thiazol-5-ylmethyl)thiazole-5-carboxamide;

2-(1-((2,2-difluorocyclopropyl)methyl)-5-oxo-1H-1,2,4-triazol-4(5H)-yl)-4-methyl-N-(thiazol-2-ylmethyl)thiazole-5-carboxamide;

2-(1-((2,2-difluorocyclopropyl)methyl)-5-oxo-1H-1,2,4-triazol-4(5H)-yl)-4-methyl-N-(oxazol-4-ylmethyl)thiazole-5-carboxamide;

2-(3-(3,4-difluorobenzyl)-2-oxoimidazolidin-1-yl)-4-methylthiazole-5-carboxamide;

2-(1-((2,2-difluorocyclopropyl)methyl)-5-oxo-1H-1,2,4-triazol-4(5H)-yl)-4-methyl-N-((2-(trifluoromethyl)thiazol-4-yl)methyl)thiazole-5-carboxamide;

4-methyl-2-(5-oxo-1-(1-phenylethyl)-1H-1,2,4-triazol-4(5H)-yl)-N-((2-(trifluoromethyl)thiazol-4-yl)methyl)thiazole-5-carboxamide;

1-(4-fluorobenzyl)-4-(4-methyl-5-(5-methyl-1H-1,2,4-triazol-3-yl)thiazol-2-yl)-1H-1,2,4-triazol-5(4H)-one;

2-(3-(2,5-difluorobenzyl)-2-oxoimidazolidin-1-yl)-4-methylthiazole-5-carboxamide;

2-(3-(2,4-difluorobenzyl)-2-oxoimidazolidin-1-yl)-4-methylthiazole-5-carboxamide;

2-(3-((2,2-difluorocyclopropyl)methyl)-2-oxoimidazolidin-1-yl)-4-methyl-N-((6-(trifluoromethyl)pyridin-3-yl)methyl)thiazole-5-carboxamide;

N-(imidazo[1,2-a]pyridin-6-ylmethyl)-4-methyl-2-(2-oxo-3-(4-(trifluoromethyl)benzyl)imidazolidin-1-yl)thiazole-5-carboxamide;

(R)—N-(3,4-difluorobenzyl)-2-(3-(4-fluorobenzyl)-4-methyl-2-oxoimidazolidin-1-yl)-4-methylthiazole-5-carboxamide;

(R)-2-(3-(4-Fluorobenzyl)-4-methyl-2-oxoimidazolidin-1-yl)-4-methyl-N-(pyridin-3-ylmethyl)thiazole-5-carboxamide;

4-methyl-2-(2-oxo-3-(4-(trifluoromethyl)benzyl)imidazolidin-1-yl)-N-((2-(trifluoromethyl)thiazol-4-yl)methyl)thiazole-5-carboxamide;

2-(3-(3-fluorobenzyl)-2-oxoimidazolidin-1-yl)-4-methylthiazole-5-carboxamide;

4-methyl-2-(2-oxo-3-(1-phenylethyl)imidazolidin-1-yl)-N-(pyridin-3-ylmethyl)thiazole-5-carboxamide;

4-methyl-2-(2-oxo-3-(1-phenylethyl)imidazolidin-1-yl)-N-(thiazol-5-ylmethyl)thiazole-5-carboxamide;

2-(3-(2-fluorobenzyl)-2-oxoimidazolidin-1-yl)-4-methylthiazole-5-carboxamide;

2-(1-((2,2-difluorocyclopropyl)methyl)-5-oxo-1H-1,2,4-triazol-4(5H)-yl)-4-methyl-N-(pyridin-2-ylmethyl)thiazole-5-carboxamide;

4-methyl-2-(2-oxo-3-(1-phenylethyl)imidazolidin-1-yl)thiazole-5-carboxamide;

4-methyl-2-(2-oxo-3-(4-(trifluoromethyl)benzyl)imidazolidin-1-yl)-N-(pyridin-2-ylmethyl)thiazole-5-carboxamide;

2-(1-(4-fluorobenzyl)-5-oxo-1H-1,2,4-triazol-4(5H)-yl)-N-((4-fluoropyridin-2-yl)methyl)-4-methylthiazole-5-carboxamide;

2-(3-(2,6-difluorobenzyl)-2-oxoimidazolidin-1-yl)-4-methylthiazole-5-carboxamide;

2-(1-(1-(4-fluorophenyl)ethyl)-5-oxo-1H-1,2,4-triazol-4(5H)-yl)-4-methyl-N-(pyridin-2-ylmethyl)thiazole-5-carboxamide;

2-(1-(1-(4-fluorophenyl)ethyl)-5-oxo-1H-1,2,4-triazol-4(5H)-yl)-4-methyl-N-(thiazol-5-ylmethyl)thiazole-5-carboxamide;

2-(1-(1-(4-fluorophenyl)ethyl)-5-oxo-1H-1,2,4-triazol-4(5H)-yl)-4-methylthiazole-5-carboxamide;

2-(3-(3,5-difluorobenzyl)-2-oxoimidazolidin-1-yl)-4-methylthiazole-5-carboxamide;

(R)-2-(3-(4-fluorobenzyl)-4-methyl-2-oxoimidazolidin-1-yl)-4-methyl-N-(thiazol-5-ylmethyl)thiazole-5-carboxamide;

(R)-2-(3-(4-fluorobenzyl)-4-methyl-2-oxoimidazolidin-1-yl)-4-methyl-N-((3-methyl-1H-pyrazol-5-yl)methyl)thiazole-5-carboxamide;

(R)—N-(3,5-difluorobenzyl)-2-(3-(4-fluorobenzyl)-4-methyl-2-oxoimidazolidin-1-yl)-4-methylthiazole-5-carboxamide;

2-(3-(2,3-difluorobenzyl)-2-oxoimidazolidin-1-yl)-4-methylthiazole-5-carboxamide;

4-methyl-2-(2-oxo-3-(4-(trifluoromethyl)benzyl)imidazolidin-1-yl)-N-(thiazol-2-ylmethyl)thiazole-5-carboxamide;

2-(1-((2,2-difluorocyclopropyl)methyl)-5-oxo-1H-1,2,4-triazol-4(5H)-yl)-4-methyl-N-((5-methylisoxazol-3-yl)methyl)thiazole-5-carboxamide;

2-(3-((2,2-difluorocyclopropyl)methyl)-2-oxoimidazolidin-1-yl)-4-methyl-N-((5-methylisoxazol-3-yl)methyl)thiazole-5-carboxamide;

2-(1-(1-(4-fluorophenyl)ethyl)-5-oxo-1H-1,2,4-triazol-4(5H)-yl)-4-methyl-N-((5-methylisoxazol-3-yl)methyl)thiazole-5-carboxamide;

(R)-2-(3-(4-fluorobenzyl)-4-methyl-2-oxoimidazolidin-1-yl)-4-methyl-N-(pyridin-2-ylmethyl)thiazole-5-carboxamide;

2-(1-(3-fluorobenzyl)-5-oxo-1H-1,2,4-triazol-4(5H)-yl)-4-methylthiazole-5-carboxamide;

2-(1-(4-fluorobenzyl)-5-oxo-1H-1,2,4-triazol-4(5H)-yl)-4-methyl-N-((5-(trifluoromethyl)-1,2,4-oxadiazol-3-yl)methyl)thiazole-5-carboxamide, 2-(3-(3,4-difluorobenzyl)-2-oxoimidazolidin-1-yl)-4-methyl-N-((6-methylpyrazin-2-yl)methyl)thiazole-5-carboxamide;

2-(3-(3,4-difluorobenzyl)-2-oxoimidazolidin-1-yl)-4-methyl-N-(pyridin-2-ylmethyl)thiazole-5-carboxamide;

2-(1-(4-fluorobenzyl)-5-oxo-1H-1,2,4-triazol-4(5H)-yl)-4-methyl-N-(pyridin-2-ylmethyl)thiazole-5-carboxamide;

2-(3-(4-fluorobenzyl)-2-oxoimidazolidin-1-yl)-4-methyl-N-((5-methylisoxazol-3-yl)methyl)thiazole-5-carboxamide;

2-(1-(4-fluorobenzyl)-5-oxo-1H-1,2,4-triazol-4(5H)-yl)-4-methyl-N-((5-methylisoxazol-3-yl)methyl)thiazole-5-carboxamide;

2-(3-(3,4-difluorobenzyl)-2-oxoimidazolidin-1-yl)-4-methyl-N-(oxazol-4-ylmethyl)thiazole-5-carboxamide;

2-(1-(3,4-difluorobenzyl)-5-oxo-1H-1,2,4-triazol-4(5H)-yl)-4-methylthiazole-5-carboxamide;

2-(1-(3,4-difluorobenzyl)-5-oxo-1H-1,2,4-triazol-4(5H)-yl)-4-methyl-N-(pyridin-2-ylmethyl)thiazole-5-carboxamide;

2-(3-(3,4-difluorobenzyl)-2-oxoimidazolidin-1-yl)-4-methyl-N-((1-methyl-1H-pyrazol-4-yl)methyl)thiazole-5-carboxamide;

2-(1-(3,5-difluorobenzyl)-5-oxo-1H-1,2,4-triazol-4(5H)-yl)-4-methyl-N-(pyridin-2-ylmethyl)thiazole-5-carboxamide;

2-(1-(3,5-difluorobenzyl)-5-oxo-1H-1,2,4-triazol-4(5H)-yl)-4-methylthiazole-5-carboxamide;

4-methyl-2-(5-oxo-1-(4-(trifluoromethoxy)benzyl)-1H-1,2,4-triazol-4(5H)-yl)-N-(pyridin-2-ylmethyl)thiazole-5-carboxamide;

4-methyl-2-(2-oxo-3-(4-(trifluoromethoxy)benzyl)imidazolidin-1-yl)-N-(pyridin-2-ylmethyl)thiazole-5-carboxamide;

4-methyl-2-(2-oxo-3-(4-(trifluoromethoxy)benzyl)imidazolidin-1-yl)thiazole-5-carboxamide;

4-methyl-N-((5-methylisoxazol-3-yl)methyl)-2-(2-oxo-3-(4-(trifluoromethoxy)benzyl)imidazolidin-1-yl)thiazole-5-carboxamide;

1-(4-methyl-5-(5-methyl-1H-1,2,4-triazol-3-yl)thiazol-2-yl)-3-(4-(trifluoromethoxy)benzyl)imidazolidin-2-one;

2-(3-((2,2-difluorocyclopropyl)methyl)-2-oxoimidazolidin-1-yl)-4-methyl-N-(thiazol-2-ylmethyl)thiazole-5-carboxamide;

4-methyl-2-(5-oxo-1-(4-(trifluoromethoxy)benzyl)-1H-1,2,4-triazol-4(5H)-yl)-N-(thiazol-5-ylmethyl)thiazole-5-carboxamide;

4-methyl-N-((5-methylisoxazol-3-yl)methyl)-2-(5-oxo-1-(4-(trifluoromethoxy)benzyl)-1H-1,2,4-triazol-4(5H)-yl)thiazole-5-carboxamide;
4-methyl-2-(5-oxo-1-(4-(trifluoromethoxy)benzyl)-1H-1,2,4-triazol-4(5H)-yl)-N-(thiazol-2-ylmethyl)thiazole-5-carboxamide;
4-methyl-N-((5-methylisoxazol-3-yl)methyl)-2-(5-oxo-1-(4-(trifluoromethyl)benzyl)-1H-1,2,4-triazol-4(5H)-yl)thiazole-5-carboxamide;
4-methyl-2-(5-oxo-1-(4-(trifluoromethyl)benzyl)-1H-1,2,4-triazol-4(5H)-yl)-N-(thiazol-2-ylmethyl)thiazole-5-carboxamide;
4-methyl-2-(5-oxo-1-(4-(trifluoromethyl)benzyl)-1H-1,2,4-triazol-4(5H)-yl)thiazole-5-carboxamide;
2-(3-(4-fluorobenzyl)-2-oxoimidazolidin-1-yl)-4-methyl-N-((2-methylthiazol-4-yl)methyl)thiazole-5-carboxamide;
2-(3-(4-methoxybenzyl)-2-oxoimidazolidin-1-yl)-4-methylthiazole-5-carboxamide;
2-(1-(3-fluoro-4-(trifluoromethoxy)benzyl)-5-oxo-1H-1,2,4-triazol-4(5H)-yl)-4-methylthiazole-5-carboxamide;
2-(3-(3-fluoro-4-methoxybenzyl)-2-oxoimidazolidin-1-yl)-4-methyl-N-(pyridin-2-ylmethyl)thiazole-5-carboxamide;
4-methyl-2-(2-oxo-3-((6-(trifluoromethyl)pyridin-3-yl)methyl)imidazolidin-1-yl)-N-(pyridin-2-ylmethyl)thiazole-5-carboxamide;
4-methyl-N-((5-methylisoxazol-3-yl)methyl)-2-(2-oxo-3-((6-(trifluoromethyl)pyridin-3-yl)methyl)imidazolidin-1-yl)thiazole-5-carboxamide;
4-methyl-2-(5-oxo-1-(4-(trifluoromethyl)benzyl)-1H-1,2,4-triazol-4(5H)-yl)-N-(pyridin-2-ylmethyl)thiazole-5-carboxamide;
2-(3-(3-fluoro-4-methoxybenzyl)-2-oxoimidazolidin-1-yl)-4-methylthiazole-5-carboxamide;
4-methyl-N-((1-methyl-1H-pyrazol-3-yl)methyl)-2-(2-oxo-3-(4-(trifluoromethyl)benzyl)imidazolidin-1-yl)thiazole-5-carboxamide;
4-methyl-N-((5-methylisoxazol-3-yl)methyl)-2-(2-oxo-3-(4-(trifluoromethyl)benzyl)imidazolidin-1-yl)thiazole-5-carboxamide;
2-(3-(3-fluoro-4-methoxybenzyl)-2-oxoimidazolidin-1-yl)-4-methyl-N-((5-methylisoxazol-3-yl)methyl)thiazole-5-carboxamide;
2-(1-((2,2-difluorocyclopropyl)methyl)-5-oxo-1H-1,2,4-triazol-4(5H)-yl)-4-methyl-N-((1-methyl-1H-pyrazol-3-yl)methyl)thiazole-5-carboxamide;
2-(3-((2,2-difluorocyclopropyl)methyl)-2-oxoimidazolidin-1-yl)-4-methyl-N-((1-methyl-1H-pyrazol-3-yl)methyl)thiazole-5-carboxamide;
4-methyl-2-(2-oxo-3-(1-phenylethyl)imidazolidin-1-yl)-N-(pyridin-2-ylmethyl)thiazole-5-carboxamide;
N-(isoxazol-3-ylmethyl)-4-methyl-2-(2-oxo-3-((6-(trifluoromethyl)pyridin-3-yl)methyl)imidazolidin-1-yl)thiazole-5-carboxamide;
2-(3-(cyclopropylmethyl)-2-oxoimidazolidin-1-yl)-4-methyl-N-((1-methyl-1H-pyrazol-4-yl)methyl)thiazole-5-carboxamide;
4-methyl-N-((1-methyl-1H-pyrazol-4-yl)methyl)-2-(2-oxo-3-(4-(trifluoromethyl)benzyl)imidazolidin-1-yl)thiazole-5-carboxamide;
N-(isoxazol-3-ylmethyl)-4-methyl-2-(2-oxo-3-(4-(trifluoromethyl)benzyl)imidazolidin-1-yl)thiazole-5-carboxamide;
2-(3-(cyclopropylmethyl)-2-oxoimidazolidin-1-yl)-4-methyl-N-((5-methylisoxazol-3-yl)methyl)thiazole-5-carboxamide;
2-(3-(3-fluoro-4-(trifluoromethoxy)benzyl)-2-oxoimidazolidin-1-yl)-4-methyl-N-((5-methylisoxazol-3-yl)methyl)thiazole-5-carboxamide;
2-(3-(3-fluoro-4-(trifluoromethoxy)benzyl)-2-oxoimidazolidin-1-yl)-4-methyl-N-((1-methyl-1H-pyrazol-4-yl)methyl)thiazole-5-carboxamide;
2-(3-(3-fluoro-4-(trifluoromethoxy)benzyl)-2-oxoimidazolidin-1-yl)-4-methyl-N-(pyridin-2-ylmethyl)thiazole-5-carboxamide;
2-(3-(4-methoxybenzyl)-2-oxoimidazolidin-1-yl)-4-methyl-N-(pyridin-2-ylmethyl)thiazole-5-carboxamide;
(S)-2-(3-(4-fluorobenzyl)-5-methyl-2-oxoimidazolidin-1-yl)-4-methyl-N-(pyridin-2-ylmethyl)thiazole-5-carboxamide;
(S)-2-(3-(4-fluorobenzyl)-5-methyl-2-oxoimidazolidin-1-yl)-4-methyl-N-((1-methyl-1H-pyrazol-4-yl)methyl)thiazole-5-carboxamide;
(S)-2-(3-(4-fluorobenzyl)-5-methyl-2-oxoimidazolidin-1-yl)-4-methyl-N-((5-methylisoxazol-3-yl)methyl)thiazole-5-carboxamide;
(S)-2-(3-(4-fluorobenzyl)-5-methyl-2-oxoimidazolidin-1-yl)-4-methylthiazole-5-carboxamide;
2-(3-(4-chlorobenzyl)-2-oxoimidazolidin-1-yl)-4-methyl-N-(pyridin-2-ylmethyl)thiazole-5-carboxamide;
2-(3-(4-chlorobenzyl)-2-oxoimidazolidin-1-yl)-4-methylthiazole-5-carboxamide;
2-(3-(3,5-dichlorobenzyl)-2-oxoimidazolidin-1-yl)-4-methyl-N-(pyridin-2-ylmethyl)thiazole-5-carboxamide;
(R)-2-(3-(4-fluorobenzyl)-4-methyl-2-oxoimidazolidin-1-yl)-4-methyl-N-((5-methylisoxazol-3-yl)methyl)thiazole-5-carboxamide;
(R)-2-(3-(3,5-difluorobenzyl)-4-methyl-2-oxoimidazolidin-1-yl)-4-methyl-N-(pyridin-2-ylmethyl)thiazole-5-carboxamide;
(R)-2-(3-(3,5-difluorobenzyl)-4-methyl-2-oxoimidazolidin-1-yl)-4-methylthiazole-5-carboxamide;
2-(3-(4-chlorobenzyl)-2-oxoimidazolidin-1-yl)-4-methyl-N-((5-methylpyrazin-2-yl)methyl)thiazole-5-carboxamide;
2-(3-((6-(4-fluorophenyl)pyridin-3-yl)methyl)-2-oxoimidazolidin-1-yl)-4-methyl-N-(thiazol-2-ylmethyl)thiazole-5-carboxamide;
2-(3-((6-(4-fluorophenyl)pyridin-3-yl)methyl)-2-oxoimidazolidin-1-yl)-4-methyl-N-((5-methylisoxazol-3-yl)methyl)thiazole-5-carboxamide;
2-(3-(3,5-difluorobenzyl)-2-oxoimidazolidin-1-yl)-4-methyl-N-(pyridin-2-ylmethyl)thiazole-5-carboxamide;
2-(3-(3,5-difluorobenzyl)-2-oxoimidazolidin-1-yl)-4-methyl-N-((5-methylisoxazol-3-yl)methyl)thiazole-5-carboxamide;
(R)-2-(3-(3,5-difluorobenzyl)-4-methyl-2-oxoimidazolidin-1-yl)-4-methyl-N-((5-methylpyrazin-2-yl)methyl)thiazole-5-carboxamide;
2-(3-(4-chlorobenzyl)-2-oxoimidazolidin-1-yl)-4-methyl-N-((1-methyl-1H-pyrazol-4-yl)methyl)thiazole-5-carboxamide;
2-(3-(3,5-difluorobenzyl)-2-oxoimidazolidin-1-yl)-4-methyl-N-((5-methylpyrazin-2-yl)methyl)thiazole-5-carboxamide;
2-(3-(3,5-difluorobenzyl)-2-oxoimidazolidin-1-yl)-4-methyl-N-(thiazol-2-ylmethyl)thiazole-5-carboxamide;
2-(3-(3,5-dichlorobenzyl)-2-oxoimidazolidin-1-yl)-4-methyl-N-((1-methyl-1H-pyrazol-4-yl)methyl)thiazole-5-carboxamide;
(R)-2-(3-(4-fluorobenzyl)-4-methyl-2-oxoimidazolidin-1-yl)-4-methylthiazole-5-carboxamide;

2-(3-(2-cyclopropylethyl)-2-oxoimidazolidin-1-yl)-4-methyl-N-(pyridin-2-ylmethyl)thiazole-5-carboxamide;
4-methyl-N-((5-methylpyrazin-2-yl)methyl)-2-(2-oxo-3-(4-(trifluoromethoxy)benzyl)imidazolidin-1-yl)thiazole-5-carboxamide;
2-(3-(3-fluoro-4-methoxybenzyl)-2-oxoimidazolidin-1-yl)-4-methyl-N-((5-methylpyrazin-2-yl)methyl)thiazole-5-carboxamide;
2-(3-(3,4-dichlorobenzyl)-2-oxoimidazolidin-1-yl)-4-methyl-N-((5-methylpyrazin-2-yl)methyl)thiazole-5-carboxamide;
2-(3-(3,4-dichlorobenzyl)-2-oxoimidazolidin-1-yl)-4-methyl-N-(pyridin-2-ylmethyl)thiazole-5-carboxamide;
2-(3-(3-fluoro-4-(trifluoromethoxy)benzyl)-2-oxoimidazolidin-1-yl)-4-methyl-N-((5-methylpyrazin-2-yl)methyl)thiazole-5-carboxamide;
2-(3-((2,2-difluorocyclopropyl)methyl)-2-oxoimidazolidin-1-yl)-4-methyl-N-((5-methylpyrazin-2-yl)methyl)thiazole-5-carboxamide;
2-(3-(2-cyclopropylethyl)-2-oxoimidazolidin-1-yl)-4-methyl-N-((5-methylpyrazin-2-yl)methyl)thiazole-5-carboxamide;
2-(3-(2-cyclopropylethyl)-2-oxoimidazolidin-1-yl)-4-methylthiazole-5-carboxamide;
(R)-2-(3-(3,5-difluorobenzyl)-4-methyl-2-oxoimidazolidin-1-yl)-4-methyl-N-((5-methylisoxazol-3-yl)methyl)thiazole-5-carboxamide;
4-methyl-N-((5-methylpyrazin-2-yl)methyl)-2-(2-oxo-3-((6-(trifluoromethyl)pyridin-3-yl)methyl)imidazolidin-1-yl)thiazole-5-carboxamide;
2-(3-(3,4-dichlorobenzyl)-2-oxoimidazolidin-1-yl)-4-methyl-N-((1-methyl-1H-pyrazol-4-yl)methyl)thiazole-5-carboxamide;
2-(3-(2-cyclopropylethyl)-2-oxoimidazolidin-1-yl)-4-methyl-N-((5-methylisoxazol-3-yl)methyl)thiazole-5-carboxamide;
2-(3-(2-cyclopropylethyl)-2-oxoimidazolidin-1-yl)-4-methyl-N-((1-methyl-1H-pyrazol-4-yl)methyl)thiazole-5-carboxamide;
2-(3-(3-fluorobenzyl)-2-oxoimidazolidin-1-yl)-4-methyl-N-((1-methyl-1H-pyrazol-4-yl)methyl)thiazole-5-carboxamide;
2-(3-((6-chloropyridin-3-yl)methyl)-2-oxoimidazolidin-1-yl)-4-methyl-N-(pyridin-2-ylmethyl)thiazole-5-carboxamide;
2-(3-(3-fluorobenzyl)-2-oxoimidazolidin-1-yl)-4-methyl-N-(pyridin-2-ylmethyl)thiazole-5-carboxamide;
2-(3-(3-fluorobenzyl)-2-oxoimidazolidin-1-yl)-4-methyl-N-((5-methylpyrazin-2-yl)methyl)thiazole-5-carboxamide;
2-(1-(3,5-difluorobenzyl)-5-oxo-1H-1,2,4-triazol-4(5H)-yl)-4-methyl-N-((5-methylisoxazol-3-yl)methyl)thiazole-5-carboxamide;
2-(1-(3,5-difluorobenzyl)-5-oxo-1H-1,2,4-triazol-4(5H)-yl)-4-methyl-N-((5-methyl-1H-pyrazol-3-yl)methyl)thiazole-5-carboxamide;
2-(1-(3,5-difluorobenzyl)-5-oxo-1H-1,2,4-triazol-4(5H)-yl)-4-methyl-N-(pyridin-3-ylmethyl)thiazole-5-carboxamide;
2-(1-(3,5-difluorobenzyl)-5-oxo-1H-1,2,4-triazol-4(5H)-yl)-4-methyl-N-(oxazol-4-ylmethyl)thiazole-5-carboxamide;
2-(1-(3,5-difluorobenzyl)-5-oxo-1H-1,2,4-triazol-4(5H)-yl)-4-methyl-N-(thiazol-2-ylmethyl)thiazole-5-carboxamide;
2-(3-(3-chlorobenzyl)-2-oxoimidazolidin-1-yl)-4-methyl-N-(pyridin-2-ylmethyl)thiazole-5-carboxamide;
2-(3-(3-chlorobenzyl)-2-oxoimidazolidin-1-yl)-4-methyl-N-((5-methylpyrazin-2-yl)methyl)thiazole-5-carboxamide;
2-(3-(3-chlorobenzyl)-2-oxoimidazolidin-1-yl)-4-methyl-N-((1-methyl-1H-pyrazol-4-yl)methyl)thiazole-5-carboxamide;
N-((1H-pyrazol-4-yl)methyl)-2-(3-(4-fluorobenzyl)-2-oxoimidazolidin-1-yl)-4-methylthiazole-5-carboxamide;
4-methyl-2-(2-oxo-3-((6-(trifluoromethyl)pyridin-3-yl)methyl)imidazolidin-1-yl)-N-(thiazol-2-ylmethyl)thiazole-5-carboxamide;
4-methyl-N-(oxazol-2-ylmethyl)-2-(2-oxo-3-((6-(trifluoromethyl)pyridin-3-yl)methyl)imidazolidin-1-yl)thiazole-5-carboxamide;
4-methyl-2-(3-(4-(methylsulfonyl)benzyl)-2-oxoimidazolidin-1-yl)-N-(pyridin-2-ylmethyl)thiazole-5-carboxamide;
4-methyl-2-(3-(4-(methylsulfonyl)benzyl)-2-oxoimidazolidin-1-yl)thiazole-5-carboxamide;
(R)-4-methyl-2-(4-methyl-2-oxo-3-(4-(trifluoromethyl)benzyl)imidazolidin-1-yl)thiazole-5-carboxamide;
(R)-4-methyl-2-(4-methyl-2-oxo-3-(4-(trifluoromethyl)benzyl)imidazolidin-1-yl)-N-(pyridin-2-ylmethyl)thiazole-5-carboxamide;
(R)-2-(3-(4-fluorobenzyl)-5-methyl-2-oxoimidazolidin-1-yl)-4-methyl-N-(pyridin-2-ylmethyl)thiazole-5-carboxamide;
(R)-2-(3-(4-fluorobenzyl)-5-methyl-2-oxoimidazolidin-1-yl)-4-methyl-N-(thiazol-5-ylmethyl)thiazole-5-carboxamide;
2-(1-(1-(4-fluorophenyl)ethyl)-5-oxo-1H-1,2,4-triazol-4(5H)-yl)-N-(isoxazol-3-ylmethyl)-4-methylthiazole-5-carboxamide;
2-(1-(1-(4-fluorophenyl)ethyl)-5-oxo-1H-1,2,4-triazol-4(5H)-yl)-4-methyl-N-((5-methylpyrazin-2-yl)methyl)thiazole-5-carboxamide;
1-(4-methyl-5-(1H-pyrazol-3-yl)thiazol-2-yl)-3-(4,4,4-trifluorobutyl)-imidazolidin-2-one;
1-((2,2-difluorocyclopropyl)methyl)-3-(4-methyl-5-(1H-pyrazol-3-yl)thiazol-2-yl)imidazolidin-2-one;
1-(4-methyl-5-(1H-pyrazol-3-yl)thiazol-2-yl)-3-(4,4,4-trifluorobutyl)imidazolidin-2-one;
N-((2-isopropylthiazol-4-yl)methyl)-4-methyl-2-(1-(4-methylbenzyl)-5-oxo-1H-1,2,4-triazol-4(5H)-yl)thiazole-5-carboxamide;
2-(3-(4-fluorobenzyl)-2-oxoimidazolidin-1-yl)-N-((2-isopropylthiazol-4-yl)methyl)-4-methylthiazole-5-carboxamide; and
2-(1-((2,2-difluorocyclopropyl)methyl)-5-oxo-1H-1,2,4-triazol-4(5H)-yl)-4-methylthiazole-5-carboxamide.

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome, dermatological disorders and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome, dermatological disorders and the like, by administering to a patient in need of such treatment an effective amount of an SCD modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1. The general value of the compounds of the invention in modulating, especially inhibiting, the activity of SCD can be determined using the assay described below in Example 21.

Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)), and Sprague Dawley rats (Charles Rivers), as used in models for diet-induced obesity (Ghibaudi, L. et al., (2002), *Obes. Res.* Vol. 10, pp. 956-963). Similar models have also been developed for mice and Lewis rat.

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition is defined as any disease or condition in which the activity of SCD is elevated and/or where inhibition of SCD activity can be demonstrated to bring about symptomatic improvements for the individual so treated. As defined herein, an SCD-mediated disease or condition includes, but is not limited to, a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport)), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy.

An SCD-mediated disease or condition also includes metabolic syndrome (including but not limited to dyslipidemia, obesity and insulin resistance, hypertension, microalbuminemia, hyperuricaemia, and hypercoaguability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin-related diseases. In a preferred embodiment, compounds of the invention will be used to treat diabetes mellitus and/or obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoaguability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids, wax esters, and the like. Preferably, the compounds of the invention will prevent or attenuate keloid scar formation by reduction of excessive sebum production that typically results in their formation. The investigation of the role of SCD inhibitors in the treatment of acne was advanced by the discovery that rodents lacking a functional SCD1 gene had changes to the condition of their eyes, skin, coat (Zheng Y., et al. "SCD1 is expressed in sebaceous glands and is disrupted in the asebia mouse", *Nat. Genet.* (1999) 23:268-270. Miyazaki, M., "Targeted Disruption of Stearoyl-CoA Desaturase1 Gene in Mice Causes Atrophy of Sebaceous and Meibomian Glands and Depletion of Wax Esters in the Eyelid", *J. Nutr.* (2001), Vol. 131, pp 2260-68., Binczek, E. et al., "Obesity resistance of the stearoyl-CoA desaturase-deficient mouse results from disruption of the epidermal lipid barrier and adaptive thermoregulation", *Biol. Chem.* (2007) Vol. 388 No. 4, pp 405-18).

An SCD-mediated disease or condition also includes inflammation, sinusitis, asthma, pancreatitis, osteoarthritis, rheumatoid arthritis, cystic fibrosis, and premenstrual syndrome. An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition that is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calcivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, ITheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POCYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA), which is accomplished by delta-9 desaturases, such as stearoyl-CoA desaturase 1 (SCD1). As such, these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 20 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ ("Inhibitory Concentration of 50%") in a 15 minute microsomal assay of preferably less than 10 mM, less than 5 □M, less than 2.5 □M, less than 1 □M, less than 750 nM, less than 500 nM, less than 250 nM, less than 100 nM, less than 50 nM, and most preferably less than 20 nM. Compounds of the invention may show reversible inhibition (i.e., competitive inhibition) and preferably do not inhibit other iron binding proteins.

The identification of compounds of the invention as SCD inhibitors was readily accomplished using the SCD enzyme and microsomal assay procedure described in Shanklin J. and Summerville C., *Proc. Natl. Acad. Sci. USA* (1991), Vol. 88, pp. 2510-2514. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain-groups tend to provide more potent inhibitory compounds. SAR analysis is one of the tools those skilled in the art may employ to identify preferred embodiments of the compounds of the invention for use as therapeutic agents. Other methods of testing the compounds disclosed herein are also readily available to those skilled in the art. Thus, in addition, the determination of the ability of a compound to inhibit SCD may be accomplished in vivo. In one such embodiment this is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (-TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase or other enzymes containing iron at the active site.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available. Rabbits and hamsters are also useful as animal models, especially those expressing CETP (cholesterol ester transfer protein).

Another suitable method for determining the in vivo efficacy of the compounds of the invention is to indirectly measure their impact on inhibition of SCD enzyme by measuring a subject's Desaturation Index after administration of the compound. "Desaturation Index" as employed in this specification means the ratio of the product over the substrate for the SCD enzyme as measured from a given tissue sample. This may be calculated using three different equations 18:1n–9/18:0 (oleic acid over stearic acid); 16:1n–7/16:0 (palmitoleic acid over palmitic acid); and/or 16:1n–7+18:1n–7/16:0 (measuring all reaction products of 16:0 desaturation over 16:0 substrate). Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, with a subsequent modulation of the activity of multiple enzymes present within the membrane, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented.

For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Alternatively, another format can be used to measure the effect of SCD inhibition on sebaceous gland function. In a typical study using ridnets, oral, intravenous or topical formulations of the SCD inhibitor are administered to a rodent for a period of 1 to 8 days. Skin samples are taken and prepared for histological assessment to determine sebaceous gland number, size, or lipid content. A reduction of sebaceous gland size, number or function would indicate that the SCD inhibitor would have a beneficial impact on acne vulgaris, (Clark, S. B. et al. "Pharmacological modulation of sebaceous gland activity: mechanisms and clinical applications", *Dermatol. Clin.* (2007) Vol. 25, No. 2, pp 137-46. Geiger, J. M., "Retinoids and sebaceous gland activity" *Dermatology* (1995), Vol. 191, No. 4, pp 305-10).

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are familiar with how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side effects for the patient. The preferred dosage range for an animal is 0.001 mg/Kg to 10,000 mg/Kg, including 0.5 mg/Kg, 1.0 mg/Kg, 2.0 mg/Kg 5.0 mg/Kg, 10 mg/Kg and 20 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, transdermal, topical, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

The pharmaceutical compositions according to the invention are those suitable for enteral, such as oral or rectal, transdermal and parenteral administration to mammals, including man, to inhibit stearoyl-CoA desaturase, and for the treatment of conditions associated with stearoyl desaturase activity. In general, the pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. For enteral or parenteral application, it is preferred to administer an effective amount of a pharmaceutical composition according to the invention as tablets or gelatin capsules. Such pharmaceutical compositions may comprise, for example, the active ingredient together with diluents (e.g., lactose, dextrose, sucrose, mannitol, sorbitol, cellulose and/or glycine), lubricants (e.g., silica, talcum, stearic acid, its magnesium or calcium salt and/or polyethyleneglycol), and for tablets also comprises binders (e.g., magnesium aluminum silicate, starch paste, gelatin, tragacanth, methylcellulose, sodium carboxymethylcellulose and/or polyvinylpyrrolidone) and disintegrants (e.g., starches, agar, alginic acid or its sodium salt) or effervescent mixtures and absorbants, colorants, flavors and sweeteners.

In another aspect of the present invention the compounds may be in the form of injectable compositions, e.g. preferably aqueous isotonic solutions or suspensions, and suppositories, which can be advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions may be prepared according to conventional mixing, granulating or coating methods, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate-controlling barrier to deliver the compound of the skin of the host at a controlled and pre-determined rate over a prolonged period of time, and means to secure the device to the skin.

The most suitable route will depend on the nature and severity of the condition being treated. Those skilled in the art are also familiar with determining administration methods, dosage forms, suitable pharmaceutical excipients and other matters relevant to the delivery of the compounds to a subject in need thereof.

The compounds of the invention may be usefully combined with one or more other therapeutic agents for the treatment of SCD-mediated diseases and conditions. Preferably, the other therapeutic agent is selected from antidiabetics, hypolipidemic agents, anti-obesity agents, anti-hypertensive agents or inotropic agents.

Thus, an additional aspect of the present invention concerns a pharmaceutical composition comprising a therapeutically effective amount of a compound of the invention in combination with one or more other therapeutic agents. For example, the composition can be formulated to comprise a therapeutically effective amount of a compound of the invention as defined above, in combination with another therapeutic agent, each at an effective therapeutic dose as reported in the art. Such therapeutic agents may, for example, include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARγ and/or PPARα (peroxisome proliferator-activated receptor) ligands such as MCC-555, MK767, L-165041, GW7282 or thiazolidinediones such as rosiglitazone, pioglitazone, troglitazone; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441, N,N-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237 (Vildagliptin); hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na-K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; □-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (*Expert Opin Investig Drugs*. (2003) April; 12(4):623-33) in the FIGS. 1 to 7. A compound of the present invention may be administered either simultaneously, before or after the other active ingredient, either separately by the same or different route of administration or together in the same pharmaceutical formulation.

The structure of the active agents identified by code numbers (nos.), generic or trade names may be taken from the actual edition of the standard compendium "The Merck Index" or from databases, e.g. Patents International (e.g. IMS World Publications).

In another aspect is the use of the pharmaceutical composition as described above for production of a medicament for the treatment of SCD-mediated disease or conditions. In another aspect is the use of a pharmaceutical composition or combination as described above for the preparation of a medicament for the treatment of conditions associated with stearoyl-CoA desatruase activity. A pharmaceutical composition as described above for the treatment of conditions associated with the inhibition of stearoyl-CoA desaturase.

Preparations of Compounds

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in Green, T. W. and P. G. M. Wuts, *Protective Groups in Organic Synthesis* (2006), 4th Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. $R^1$, $R^2$, $R^3$, $R^4$, $R^{4a}$, $R^5$, $R^{5a}$, X, W and V are defined as in the Specification unless specifically defined. $R^1$ is a protecting group.

In general, the cyclized urea compounds of Formula (I) of this invention can be synthesized following the general procedure as described in Scheme 1 where $R^2$ is alkyl, or aralkyl, or aryl, or heteroaryl, Q is

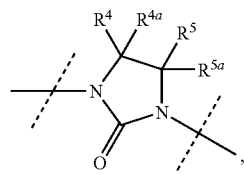

$R^4$, $R^{4a}$, $R^5$ and $R^{5a}$ are hydrogen, W is —N($R^6$)C(O)— and V is a direct bond.

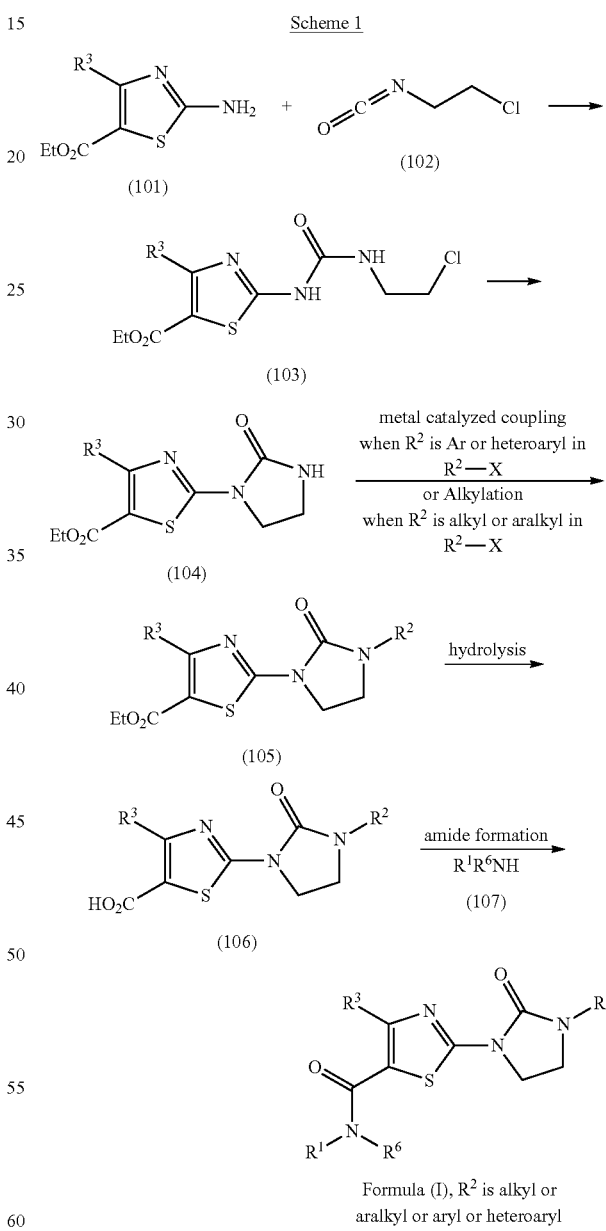

Formula (I), $R^2$ is alkyl or aralkyl or aryl or heteroaryl

The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (101) reacts isocyanate (102) to generate compound (103) which undergoes intramolecular cyclization in the presence of a base, such as, but not limited to, potassium carbonate, to afford the cyclized compound (104). Compound (104) reacts with an aryl halide or heteroaryl halide compound under metal catalyzed coupling reaction conditions to afford compound (105) where $R^2$ is an aryl or heteroaryl. Alternatively, compound (104) reacts with an alkyl halide or aralkyl halide under alkylation conditions to generate compound (105) where $R^2$ is an alkyl or aralkyl. Compound (105) undergoes standard hydrolysis known to one skilled in the art to generate compound (106). Compound (106) then undergoes a standard amide formation reaction with an amine compound (107) to afford compounds of Formula (I) of the invention where $R^2$ is alkyl, aralkyl, aryl, or heteroaryl, Q is

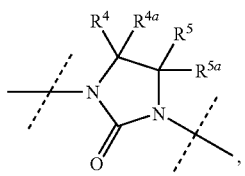

$R^4$, $R^{4a}R^5$ and $R^{5a}$ are hydrogen, W is —N($R^6$)C(O)— and V is a direct bond.

Alternatively, the cyclized urea compounds of Formula (I) of this invention can be synthesized following the general procedure as described in Scheme 2 where $R^2$ is aryl or heteroaryl, Q is

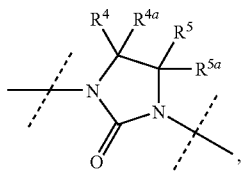

$R^4$, $R^{4a}$, $R^5$ and $R^{5a}$ are hydrogen, W is —N($R^6$)C(O)— and V is a direct bond.

Scheme 2

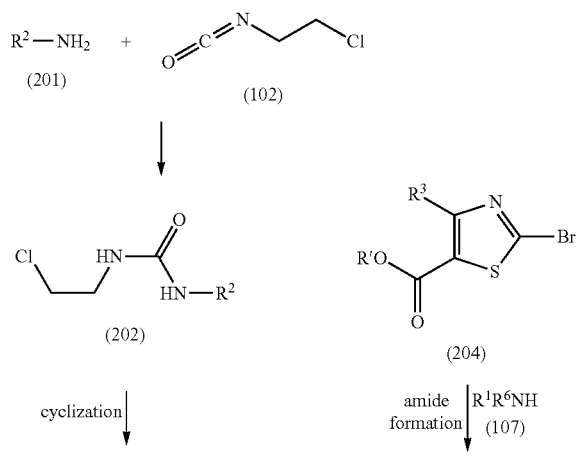

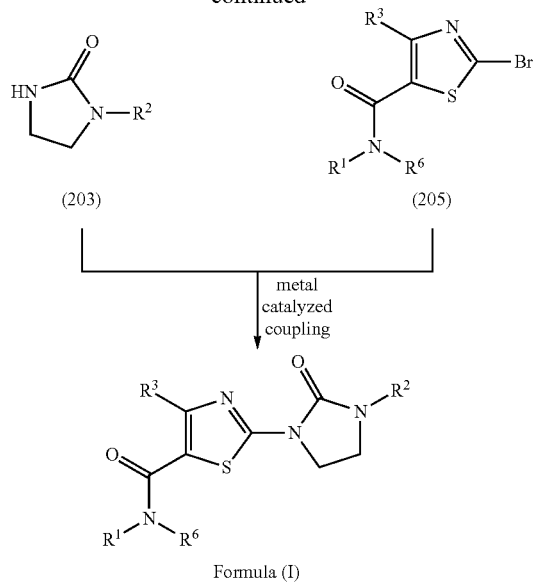

The starting materials for the above reaction scheme are commercially available or can be prepared according to methods known to one skilled in the art or by methods disclosed herein. In general, the compounds of the invention are prepared in the above reaction scheme as follows:

The amine compound (201) reacts with isocyanate (102) to generate compound (202) which undergoes intramolecular cyclization in the presence of a base, such as, but not limited to, potassium carbonate, to afford the cyclized compound (203). In parallel, the bromo compound (204) is coupled with the amine compound (107) under standard amide formation conditions to generate compound (205). Compound (203) is coupled with compound (205) under metal catalyzed coupling reaction conditions to afford compounds of Formula (I) of the invention where $R^2$ is aryl or heteroaryl, Q is

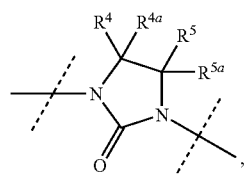

$R^4$, $R^{4a}$, $R^5$ and $R^{5a}$ are hydrogen, W is —N($R^6$)C(O)— and V is a direct bond.

Alternatively, the cyclized urea compounds of Formula (III) of this invention can be synthesized following the general procedure as described in Scheme 3 where $R^2$ is alkyl, aralkyl, aryl or heteroaryl, W is —N($R^6$)C(O)— and V is a direct bond.

Scheme 3

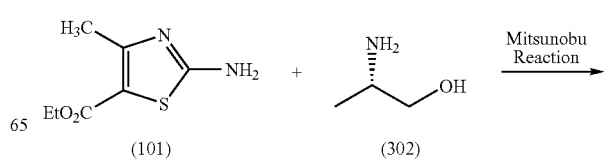

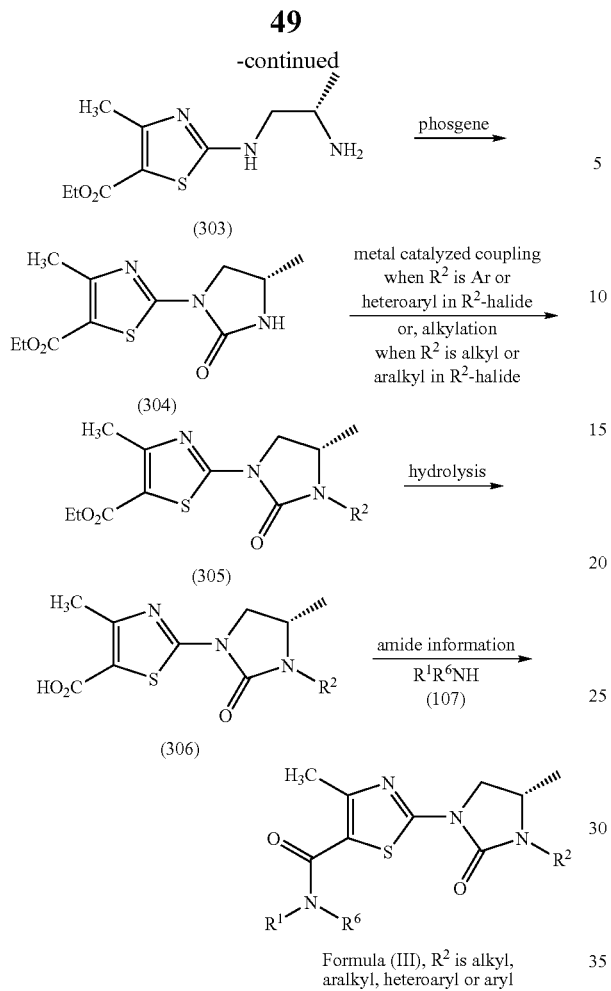

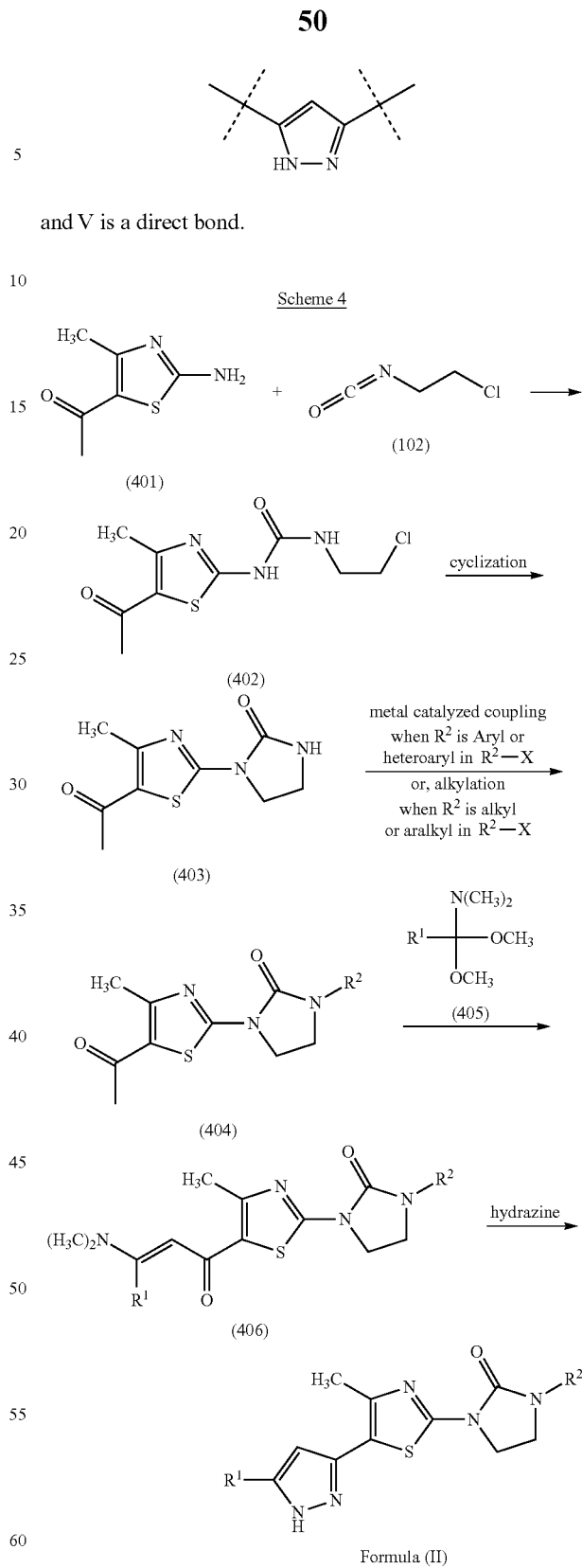

and V is a direct bond.

The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (101) reacts with (S)-(+)-2-amino-1-propanol (302) under standard Mitsunobu reaction conditions to generate compound (303) which is cyclized with phosgene to afford the cyclized compound (304). Compound (304) reacts with an aryl halide or heteroaryl halide compound under metal catalyzed coupling reaction conditions to afford compound (305) where $R^2$ is an aryl or heteroaryl. Alternatively, compound (304) reacts with an alkyl halide or aralkyl halide under alkylation conditions to generate compound (305) where $R^2$ is an alkyl or aralkyl. Compound (305) undergoes standard hydrolysis known to one skilled in the art to generate compound (306). Compound (306) then undergoes a standard amide formation reaction with an amine compound (107) to afford compounds of Formula (III) of the invention where $R^2$ is alkyl, aralkyl, aryl or heteroaryl, W is —N($R^6$)C(O)— and V is a direct bond.

Similarly, the cyclized urea compounds of Formula (IV), (V), (VI), (VII) and (VIII) of this invention can be synthesized following the general procedure as described in Scheme 3 using different starting material to replace (S)-(+)-2-amino-1-propanol (102) where $R^2$ is alkyl, aralkyl, aryl or heteroaryl, W is —N($R^6$)C(O)— and V is a direct bond.

Alternatively, the cyclized urea compounds of Formula (II) of this invention can be synthesized following the general procedure as described in Scheme 4 where $R^4$, $R^{4a}$, $R^5$ and $R^{5a}$ are hydrogen, W is The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (401) reacts with isocyanate (102) to generate compound (402) which undergoes intramolecular cyclization in the presence of a base, such as, but not limited to, potassium carbonate, to afford the cyclized compound (403). Compound (403) reacts with an aryl halide or heteroaryl halide compound under metal catalyzed coupling reaction conditions to afford compound (404) where $R^2$ is an aryl or heteroaryl. Alternatively, compound (403) reacts with an alkyl halide or aralkyl halide under alkylation conditions to generate compound (404) where $R^2$ is an alkyl or aralkyl. Compound (404) reacts with dimethyl acetal of formula (405) under heating to generate compound (406) which is cyclized with hydrazine to afford the compound of formula (II) where $R^4$, $R^{4a}$, $R^5$ and $R^{5a}$ are hydrogen, W is

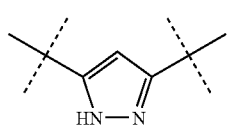

and V is a direct bond.

Alternatively, the cyclized urea compounds of Formula (II) of this invention can be synthesized following the general procedure as described in Scheme 5 where $R^4$, $R^{4a}$, $R^5$ and $R^{5a}$ are hydrogen, and V is a direct bond.

The starting materials for the above reaction scheme are commercially available or can be prepared according to methods known to one skilled in the art or by methods disclosed herein. In general, the compounds of the invention are prepared in the above reaction scheme as follows:

The carboxylic acid (106) is coupled with either ammonia or ammonium chloride under amide formation conditions known to one skilled in the art to generate the amide compound (501). Compound (501) is then treated with dimethyl acetal of formula (405) under heating and subsequent cyclization with hydrazine to afford the compound of formula (II) of the invention where $R^4$, $R^{4a}$, $R^5$ and $R^{5a}$ are hydrogen, W is

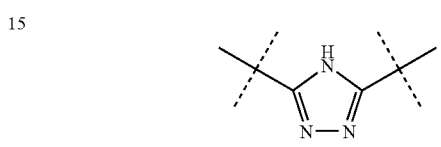

and V is a direct bond. Alternatively, compound (501) is treated with trifluoroacetic anhydride in the presence of pyridine to generate the nitrile compound (502) which is cyclized with an azide compound to afford the compound of formula (II) of the invention where $R^1$ is

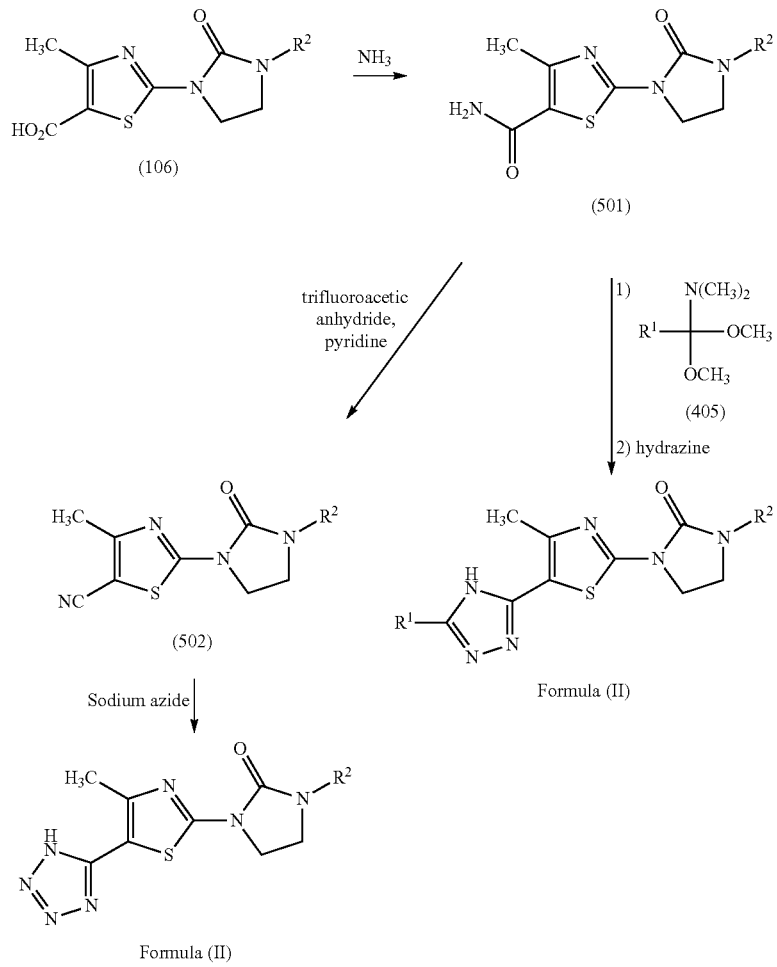

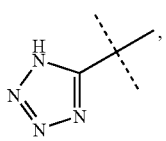

$R^4$, $R^{4a}$, $R^5$ and $R^{5a}$ are hydrogen, W and V are direct bonds.

Alternatively, the triazolone compounds of Formula (IX) of this invention can be synthesized following the general procedure as described in Scheme 6 where $R^7$ is hydrogen, W is —N($R^6$)C(O)— and V is a direct bond.

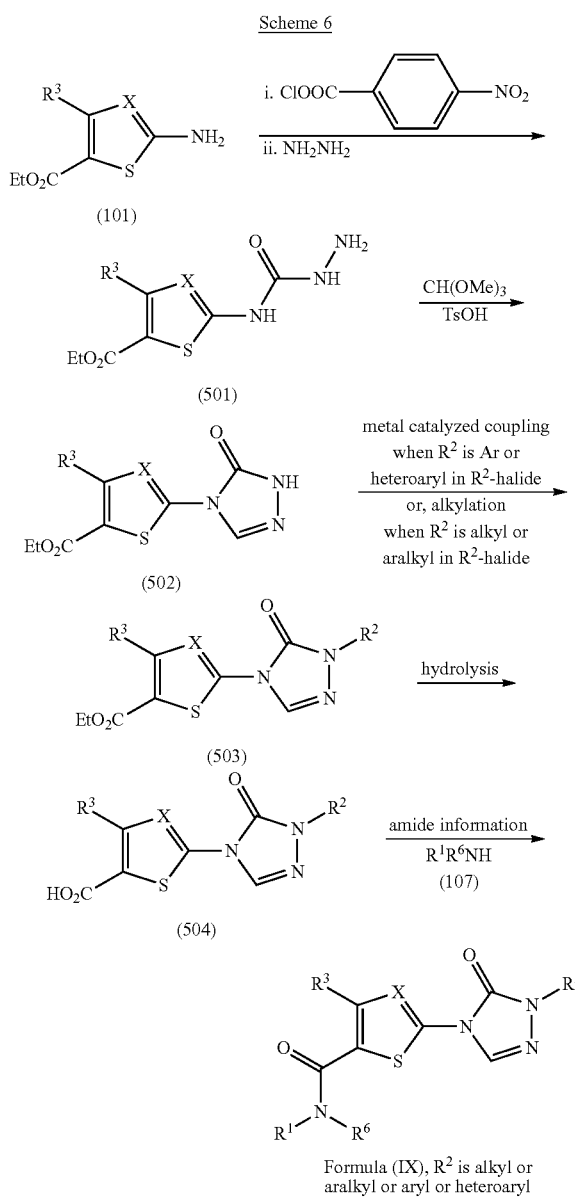

The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (101) reacts with chloroformate and then hydrazine to generate compound (601) which is cyclized using trimethyl orthoformate in the presence of p-toluenesulfonic acid to afford the cyclized compound (602). Compound (602) reacts with an aryl halide or heteroaryl halide compound under metal catalyzed coupling reaction conditions to afford compound (603) where $R^2$ is an aryl or heteroaryl. Alternatively, compound (602) reacts with an alkyl halide under alkylation conditions to generate compound (603) where $R^2$ is an alkyl or aralkyl. Compound (603) undergoes standard hydrolysis known to one skilled in the art to generate compound (604). Compound (604) then undergoes a standard amide formation reaction with an amine compound to afford compounds of Formula (IX) of the invention where $R^7$ is hydrogen, W is —N($R^6$)C(O)— and V is a direct bond.

Alternatively, the triazolone compounds of Formula (IX) of this invention can be synthesized following the general procedure as described in Scheme 7 where $R^7$ is hydrogen, W is

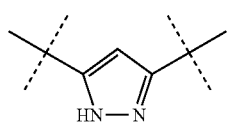

and V is a direct bond.

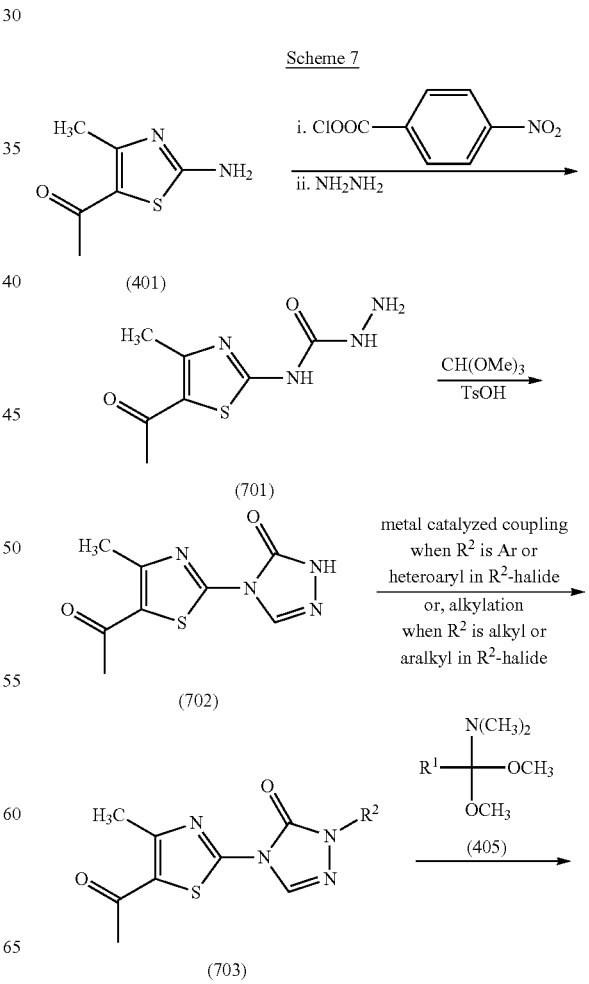

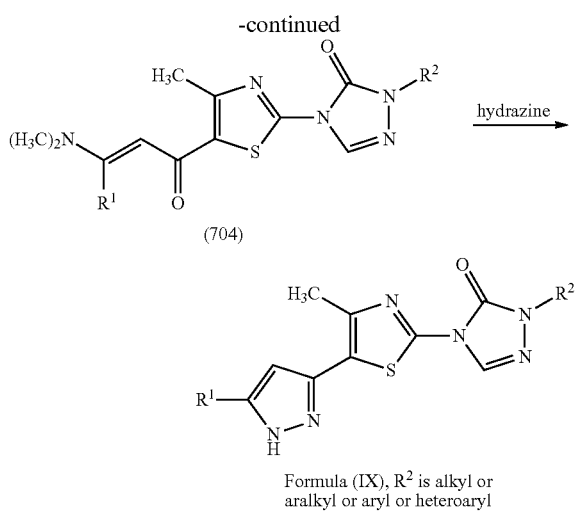

(704)

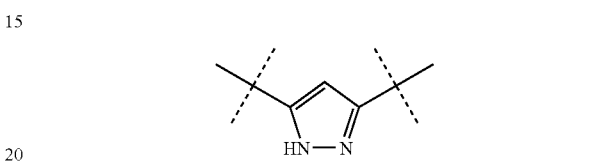

Formula (IX), $R^2$ is alkyl or aralkyl or aryl or heteroaryl

The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (101) reacts with chloroformate and then hydrazine to generate compound (601) which is cyclized using trimethyl orthoformate in the presence of p-toluenesulfonic acid to afford the cyclized compound (602). Compound (602) reacts with an aryl halide or heteroaryl halide compound under metal catalyzed coupling reaction conditions to afford compound (603) where $R^2$ is an aryl or heteroaryl. Alternatively, compound (602) reacts with an alkyl halide or aralkyl halide under alkylation conditions to generate compound (603) where $R^2$ is an alkyl or aralkyl. Compound (603) reacts with dimethyl acetal of formula (405) under heating to generate compound (604) which is cyclized with hydrazine to afford the compound of formula (IX) of the invention where $R^7$ is hydrogen, W is and V is a direct bond.

Alternatively, the triazolone compounds of Formula (IX) of this invention can be synthesized following the general procedure as described in Scheme 8 where $R^7$ is hydrogen, W and V are direct bonds.

Scheme 8

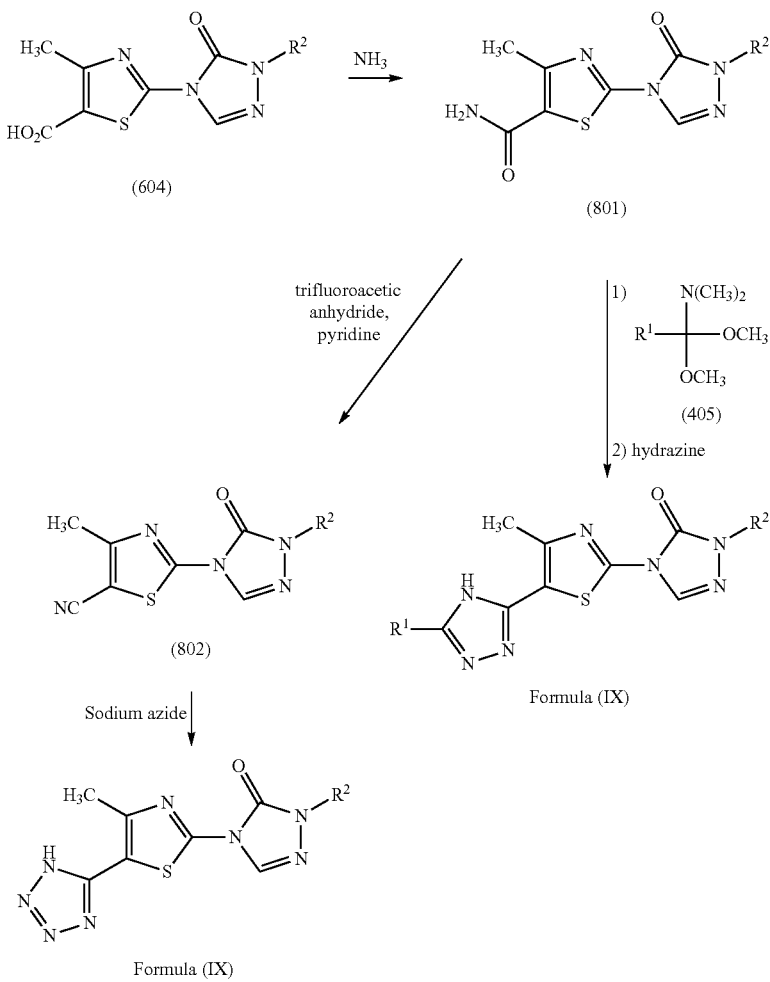

The starting materials for the above reaction scheme are commercially available or can be prepared according to methods known to one skilled in the art or by methods disclosed herein. In general, the compounds of the invention are prepared in the above reaction scheme as follows:

The carboxylic acid (604) is coupled with either ammonia or ammonium chloride under amide formation conditions known to one skilled in the art to generate the amide compound (801). Compound (801) is then treated with dimethyl acetal of formula (405) under heating and subsequent cyclization with hydrazine to afford the compound of formula (IX) of the invention where $R^7$ is hydrogen, W is

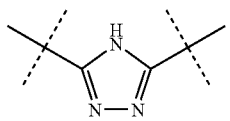

and V is a direct bond. Alternatively, compound (801) is treated with trifluoroacetic anhydride in the presence of pyridine to generate the nitrile compound (802) which is cyclized with an azide compound to afford the compound of formula (IX) of the invention where $R^1$ is

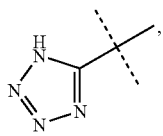

$R^7$ is hydrogen, W and V are direct bonds.

Preparation 1

Preparation of ethyl 2-(tert-butoxycarbonylamino)-4-methylthiazole-5-carboxylate

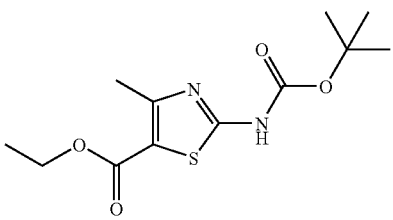

To a mixture of ethyl 2-amino-4-methylthiazole-5-carboxylate (5.00 g, 26.80 mmol) and di-tert-butyl dicarbonate (6.44 g, 29.50 mmol) in anhydrous tetrahydrofuran (200.0 mL) was added triethylamine (2.99 g, 29.50 mmol) and N,N-dimethyl-4-aminopyridine (0.30 g, 2.46 mmol) at 0° C. The resulting solution was stirred at ambient temperature for 16 h, acidified to pH ~2 with 1 N hydrochloric acid solution and extracted with ethyl acetate (3×300 mL). The organic layer was washed with saturated aqueous ammonium chloride solution (250 mL), dried over anhydrous sodium sulphate and filtered. The filtrate was concentrated in vacuo to afford the title compound as an off-white solid (6.10 g, 79%): $^1$H NMR (300 MHz, DMSO-d$_6$) δ 11.87 (s, 1H), 4.21 (q, J=7.1 Hz, 2H), 2.49 (s, 3H), 1.48 (s, 9H), 1.26 (t, J=7.1 Hz, 2H).

Preparation 2

Preparation of (S)-ethyl 2-(tert-butoxycarbonyl(2-(tert-butoxycarbonylamino)propyl)amino)-4-methylthiazole-5-carboxylate

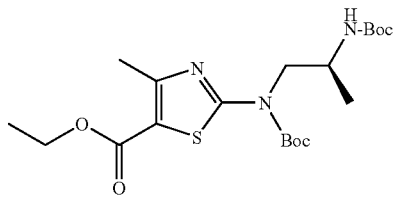

To a mixture of ethyl 2-(tert-butoxycarbonylamino)-4-methylthiazole-5-carboxylate (0.29 g, 1.00 mmol), (S)-(+)-2-amino-1-propanol (0.18 g, 1.00 mmol) and diphenyl-2-pyridinylphosphine (0.40 g, 1.50 mmol) in anhydrous tetrahydrofuran (20.0 mL) was added diethyl azodicarboxylate (0.26 g, 1.50 mmol) at 0° C. The resulting solution was stirred at ambient temperature for 0.5 h. Additional diphenyl-2-pyridinylphosphine (0.13 g, 0.50 mmol) and diethyl azodicarboxylate (0.096 g, 0.50 mmol) were added to the reaction mixture and stirred at ambient temperature for 4 h. The reaction mixture was diluted with ethyl acetate (80 mL) and washed with 25% aqueous ammonium chloride solution (3×20 mL). The organic layer was dried over anhydrous sodium sulphate and filtered. The filtrate was concentrated in vacuo and the residue was purified by column chromatography eluted with 15-45% ethyl acetate in hexanes to afford the title compound as a colorless oil (0.35 g, 78%): $^1$H NMR (300 MHz, CDCl$_3$) δ 5.30 (s, 1H), 4.26 (q, J=7.1 Hz, 2H), 4.18-3.95 (m, 3H), 2.59 (s, 3H), 1.58 (s, 9H), 1.33-1.28 (m, 12H), 1.17 (d, J=6.3 Hz, 3H); MS (ES+) m/z 244 (M−2Boc+1).

Preparation 2.1

Preparation of (R)-ethyl 2-(tert-butoxycarbonyl(2-(tert-butoxycarbonylamino)propyl)amino)-4-methylthiazole-5-carboxylate

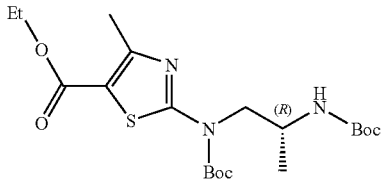

Following the procedure as described in Preparation 2, making variations as required to replace (S)-(+)-2-amino-1-propanol with (R)-(−)-2-amino-1-propanol, the title compound was obtained as colorless oil (74%): $^1$H NMR (300 MHz, CDCl$_3$) δ 5.24 (d, J=6.9 Hz, 1H), 4.24-3.90 (m, 5H), 2.54 (s, 3H), 1.53 (s, 9H), 1.28-1.18 (m, 12H), 1.12 (d, J=6.1 Hz, 3H); MS (ES+) m/z 465.8 (M+23).

Preparation 2.2

Preparation of (R)-ethyl 2-(tert-butoxycarbonyl(1-(tert-butoxycarbonylamino)propan-2-yl)amino)-4-methylthiazole-5-carboxylate

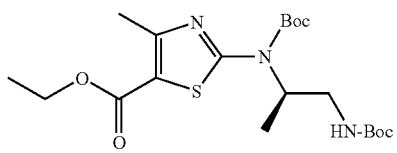

Following the procedure as described in Preparation 2, making variations as required to replace (S)-(+)-2-amino-1-propanol with N-Boc-(S)-1-amino-2-propanol, the title compound was obtained as colorless oil (66%): $^1$H NMR (300 MHz, DMSO-$d_6$) δ 5.35-5.23 (m, 1H), 4.87 (br s, 1H), 4.25 (q, J=7.1 Hz, 2H), 3.78-3.68 (m, 1H), 3.41-3.33 (m, 1H), 2.56 (s, 3H), 1.56 (s, 9H), 1.39 (d, J=7.1 Hz, 3H), 1.35 (s, 9H), 1.30 (t, J=7.1 Hz, 3H); MS (ES+) m/z 465.9 (M+23).

Preparation 2.3

Preparation of (S)-ethyl 2-(tert-butoxycarbonyl(1-(tert-butoxycarbonylamino)propan-2-yl)amino)-4-methylthiazole-5-carboxylate

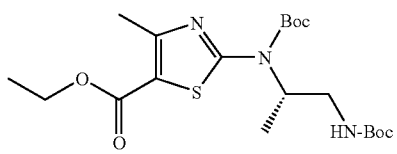

Following the procedure as described in Preparation 2, making variations as required to replace (S)-(+)-2-amino-1-propanol with N-Boc-(R)-1-amino-2-propanol, the title compound was obtained as colorless oil (23%): MS (ES+) m/z 465.8 (M+23).

Preparation 3

Preparation of (S)-ethyl 2-(2-aminopropylamino)-4-methylthiazole-5-carboxylate

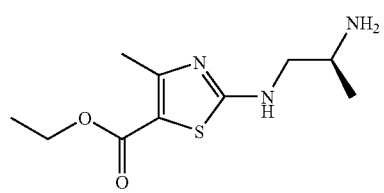

To a solution of ethyl (S)-ethyl 2-(tert-butoxycarbonyl(2-(tert-butoxycarbonylamino)propyl)amino)-4-methylthiazole-5-carboxylate (3.70 g, 8.34 mmol), in anhydrous dichloromethane (30.0 mL) was added trifluoroacetic acid (20 mL). The resulting mixture was stirred at ambient temperature for 4 h and concentrated in vacuo. The residue was diluted with ethyl acetate (200 mL) and extracted with 1 N aqueous hydrochloric acid solution (3×70 mL). The aqueous layer was basified to pH ~11 with 20% aqueous sodium hydroxide solution and extracted with dichloromethane (3×70 mL). The organic layer was dried over anhydrous sodium sulphate and filtered. The filtrate was concentrated in vacuo and the residue was purified by column chromatography eluted with 5-12% methanol (contains 0.2% aqueous ammonia) in dichloromethane to afford the title compound as a colorless solid (1.30 g, 70%): MS (ES+) m/z 244.0 (M+1).

Preparation 3.1

Preparation of (R)-ethyl 2-(2-aminopropylamino)-4-methylthiazole-5-carboxylate

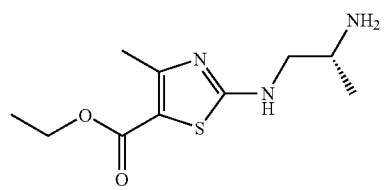

Following the procedure as described in Preparation 3, making variations as required to replace ethyl (S)-ethyl 2-(tert-butoxycarbonyl(2-(tert-butoxycarbonylamino)-propyl)amino)-4-methylthiazole-5-carboxylate with ethyl (R)-ethyl 2-(tert-butoxycarbonyl-(2-(tert-butoxycarbonylamino)propyl)amino)-4-methylthiazole-5-carboxylate, the title compound was obtained as a colorless solid (91%): MS (ES+) m/z 243.8 (M+1).

Preparation 3.2

Preparation of (R)-ethyl 2-(1-aminopropan-2-ylamino)-4-methylthiazole-5-carboxylate

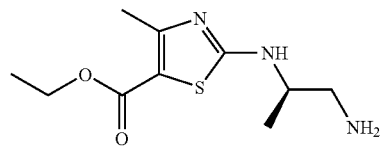

Following the procedure as described in Preparation 3, making variations as required to replace ethyl (S)-ethyl 2-(tert-butoxycarbonyl(2-(tert-butoxycarbonylamino)-propyl)amino)-4-methylthiazole-5-carboxylate with (R)-ethyl 2-(tert-butoxycarbonyl(1-(tert-butoxycarbonylamino)propan-2-yl)amino)-4-methylthiazole-5-carboxylate, the title compound was obtained as a colorless solid (98%): MS (ES+) m/z 243.8 (M+1).

Preparation 3.3

Preparation of (S)-ethyl 2-(1-aminopropan-2-ylamino)-4-methylthiazole-5-carboxylate

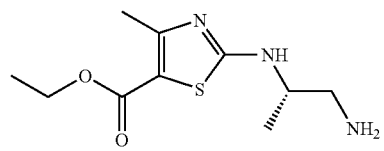

Following the procedure as described in Preparation 3, making variations as required to replace ethyl (S)-ethyl 2-(tert-butoxycarbonyl(2-(tert-butoxycarbonylamino)-propyl)amino)-4-methylthiazole-5-carboxylate with (S)-ethyl 2-(tert-butoxycarbonyl(1-(tert-butoxycarbonylamino)propan-2-yl)amino)-4-methylthiazole-5-carboxylate, the title compound was obtained as a light yellow oil: MS (ES+) m/z 243.8 (M+1).

Preparation 4

Preparation of (S)-ethyl 4-methyl-2-(4-methyl-2-oxoimidazolidin-1-yl)thiazole-5-carboxylate

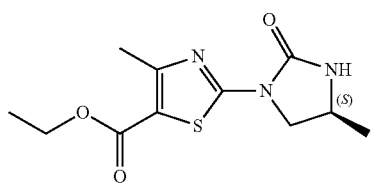

To a solution of ethyl (S)-ethyl 2-(2-aminopropylamino)-4-methylthiazole-5-carboxylate (0.95 g, 3.90 mmol) in anhydrous dichloromethane (40.0 mL) was added 20% phosgene in toluene solution (2.26 mL, 4.30 mmol). The resulting mixture was stirred at ambient temperature for 16 h and followed by the addition of saturated aqueous sodium bicarbonate solution (30 mL). The mixture was extracted with dichloromethane (2×50 mL). The organic layer was dried over anhydrous sodium sulphate and filtered. The filtrate was concentrated in vacuo to yield a colorless solid, which was purified by crystallization in diethyl ether to afford the title compound as a colorless solid (0.83 g, 79%): $^1$H NMR (300 MHz, CDCl$_3$) δ 5.53 (s, 1H), 4.35-4.25 (m, 3H), 4.12-4.00 (m, 1H), 3.76 (dd, J=10.4, 5.9 Hz, 1H), 2.62 (s, 3H), 1.38 (d, J=5.9 Hz, 3H), 1.34 (t, J=7.1 Hz, 3H); MS (ES+) m/z 270.0 (M+1).

Preparation 4.1

Preparation of (R)-ethyl 4-methyl-2-(4-methyl-2-oxoimidazolidin-1-yl)thiazole-5-carboxylate

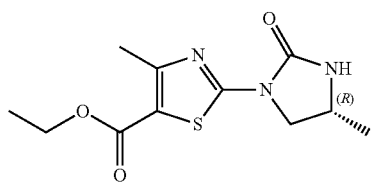

Following the procedure as described in Preparation 4, making variations as required to replace (S)-ethyl 2-(2-aminopropylamino)-4-methylthiazole-5-carboxylate with (R)-ethyl 2-(2-aminopropylamino)-4-methylthiazole-5-carboxylate, the title compound was obtained as a colorless solid (74%): MS (ES+) m/z 269.7 (M+1).

Preparation 4.2

Preparation of (R)-ethyl 4-methyl-2-(5-methyl-2-oxoimidazolidin-1-yl)thiazole-5-carboxylate

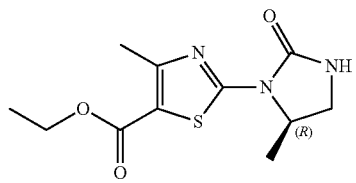

Following the procedure as described in Preparation 4, making variations as required to replace (S)-ethyl 2-(2-aminopropylamino)-4-methylthiazole-5-carboxylate with (R)-ethyl 2-(1-aminopropan-2-ylamino)-4-methylthiazole-5-carboxylate, the title compound was obtained as a colorless solid (86%): MS (ES+) m/z 269.7 (M+1).

Preparation 4.3

Preparation of (S)-ethyl 4-methyl-2-(5-methyl-2-oxoimidazolidin-1-yl)thiazole-5-carboxylate

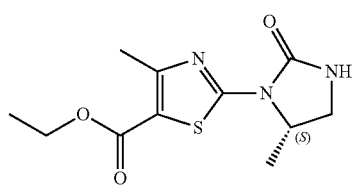

Following the procedure as described in Preparation 4, making variations as required to replace (S)-ethyl 2-(2-aminopropylamino)-4-methylthiazole-5-carboxylate with (S)-ethyl 2-(1-aminopropan-2-ylamino)-4-methylthiazole-5-carboxylate, the title compound was obtained as a colorless solid (52%): MS (ES+) m/z 269.7 (M+1).

Preparation 5

Preparation of (S)-ethyl 2-(3-(4-fluorobenzyl)-4-methyl-2-oxoimidazolidin-1-yl)-4-methylthiazole-5-carboxylate

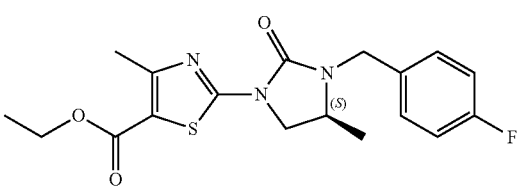

To a solution of (S)-ethyl 4-methyl-2-(4-methyl-2-oxoimidazolidin-1-yl)thiazole-5-carboxylate (0.45 g, 1.67 mmol) in 2-butanone (20.0 mL) was added cesium carbonate (1.09 g, 3.34 mmol) and 4-fluorobenzyl bromide (0.40 g, 2.09 mmol).

The reaction mixture was refluxed for 16 h, filtered and washed with acetone (150 mL). The filtrate was concentrated in vacuo and the residue was purified by column chromatography eluted with 2-5% methanol in dichloromethane to afford the title compound as a colorless solid (0.55 g, 87%): $^1$H NMR (300 MHz, CDCl$_3$) δ 7.40-7.35 (m, 2H), 7.21-7.15 (m, 2H), 4.60 (d, J=15.6 Hz, 1H), 4.31 (d, J=15.6 Hz, 1H), 4.26-4.17 (m, 3H), 3.79-3.72 (m, 1H), 3.57 (dd, J=10.3, 6.7 Hz, 1H), 2.52 (s, 3H), 1.27 (t, J=7.1 Hz, 3H), 1.22 (d, J=6.2 Hz, 3H); MS (ES+) m/z 377.9 (M+1).

Preparation 5.1

Preparation of (R)-ethyl 2-(3-(4-fluorobenzyl)-4-methyl-2-oxoimidazolidin-1-yl)-4-methylthiazole-5-carboxylate

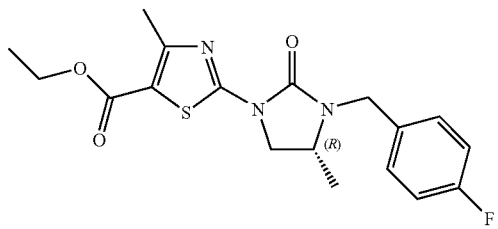

Following the procedure as described in Preparation 5, making variations as required to replace (S)-ethyl 4-methyl-2-(4-methyl-2-oxoimidazolidin-1-yl)thiazole-5-carboxylate with (R)-ethyl 4-methyl-2-(4-methyl-2-oxoimidazolidin-1-yl)thiazole-5-carboxylate, the title compound was obtained as a colorless solid (98%): MS (ES+) m/z 378.1 (M+1).

Preparation 5.2

Preparation of (R)-ethyl 2-(3-(4-fluorobenzyl)-5-methyl-2-oxoimidazolidin-1-yl)-4-methylthiazole-5-carboxylate

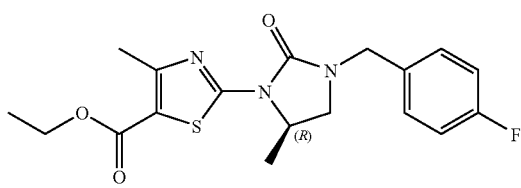

Following the procedure as described in Preparation 5, making variations as required to replace (S)-ethyl 4-methyl-2-(4-methyl-2-oxoimidazolidin-1-yl)thiazole-5-carboxylate with (R)-ethyl 4-methyl-2-(5-methyl-2-oxoimidazolidin-1-yl)thiazole-5-carboxylate, the title compound was obtained as a colorless solid (98%): $^1$H NMR (300 MHz, CDCl$_3$) δ 7.25-7.21 (m, 2H), 7.03-6.97 (m, 2H), 4.61-4.55 (m, 1H), 4.47 (d, J=14.9 Hz, 1H), 4.38 (d, J=14.9 Hz, 1H), 4.25 (q, J=7.1 Hz, 2H), 3.54 (t, J=8.9 Hz, 1H), 2.96 (dd, J=9.0, 3.3 Hz, 1H), 2.57 (s, 3H), 1.43 (d, J=6.3 Hz, 3H), 1.30 (t, J=7.1 Hz, 3H); MS (ES+) m/z 378.0 (M+1).

Preparation 5.3

Preparation of (S)-ethyl 2-(3-(4-fluorobenzyl)-5-methyl-2-oxoimidazolidin-1-yl)-4-methylthiazole-5-carboxylate

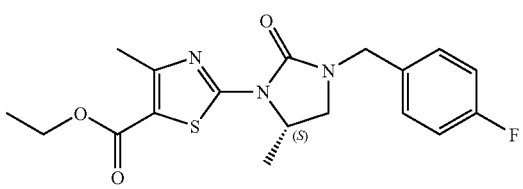

Following the procedure as described in Preparation 5, making variations as required to replace (S)-ethyl 4-methyl-2-(4-methyl-2-oxoimidazolidin-1-yl)thiazole-5-carboxylate with (S)-ethyl 4-methyl-2-(5-methyl-2-oxoimidazolidin-1-yl)thiazole-5-carboxylate, the title compound was obtained as a colorless solid (98%): $^1$H NMR (300 MHz, CDCl$_3$) δ 7.30-7.26 (m, 2H), 7.08-7.03 (m, 2H), 4.65-4.60 (m 1H), 4.52 (d, J=14.9 Hz, 1H), 4.38 (d, J=14.9 Hz, 1H), 4.30 (q, J=7.1 Hz, 2H), 3.59 (t, J=8.9 Hz, 1H), 3.01 (dd, J=9.0, 3.3 Hz, 1H), 2.63 (s, 3H), 1.48 (d, J=6.3 Hz, 3H), 1.35 (t, J=7.1 Hz, 3H); MS (ES+) m/z 378.0 (M+1).

Preparation 5.4

Preparation of ethyl 2-(3-(but-3-enyl)-2-oxoimidazolidin-1-yl)-4-methylthiazole-5-carboxylate

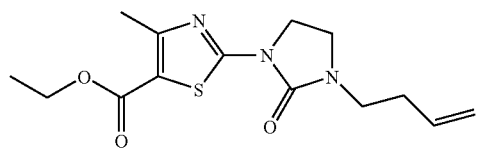

Following the procedure as described in Preparation 5, making variations as required to replace (S)-ethyl 4-methyl-2-(4-methyl-2-oxoimidazolidin-1-yl)thiazole-5-carboxylate and with ethyl 4-methyl-2-(2-oxoimidazolidin-1-yl)thiazole-5-carboxylate to react with 4-bromobut-1-ene, the title compound was obtained as an off-white solid (2.05 g, 85%): mp 97-98° C. (diethyl ether); $^1$H NMR (300 MHz, DMSO-d$_6$) δ 5.86-5.72 (m, 1H), 5.16-5.02 (m, 2H), 4.22 (q, J=7.1 Hz, 2H), 4.02-3.79 (m, 2H), 3.60-3.55 (m, 2H), 3.34-3.29 (m, 2H), 2.51 (s, 3H), 2.33-2.26 (m, 2H), 1.27 (t, J=7.1 Hz, 3H); MS (ES+) m/z 309.8 (M+1).

Preparation 6

Preparation of (S)-2-(3-(4-fluorobenzyl)-4-methyl-2-oxoimidazolidin-1-yl)-4-methylthiazole-5-carboxylic acid

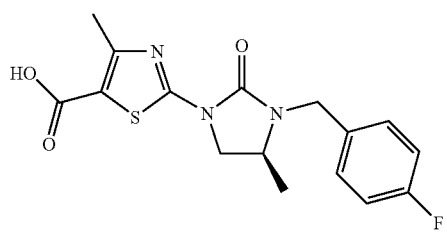

To a solution of (S)-ethyl 2-(3-(4-fluorobenzyl)-4-methyl-2-oxoimidazolidin-1-yl)-4-methylthiazole-5-carboxylate (0.50 g, 1.32 mmol) in tetrahydrofuran (20.0 mL) was added a solution of lithium hydroxide (0.16 g, 6.62 mmol) in water (15 mL). The reaction mixture was refluxed for 16 h and followed by the addition of 1 N aqueous hydrochloric acid solution to adjust pH to 2. The mixture was extracted with ethyl acetate (3×40 mL). The organic layer was washed with saturated aqueous sodium chloride solution (30 mL), dried over anhydrous sodium sulphate and filtered. The filtrate was concentrated in vacuo and the residue was purified by crystallized in ethyl acetate to afford the title compound as a colorless solid (0.32 g, 69%): mp 208-210° C. (ethyl acetate); $^1$H NMR (300 MHz, CDCl$_3$) δ 7.31-7.26 (m, 2H), 7.04 (dd, J=8.6, 8.6 Hz, 2H), 4.83 (d, J=15.3 Hz, 1H), 4.29-4.14 (m, 2H), 3.78-3.65 (m, 2H), 2.65 (s, 3H), 1.31 (d, J=5.9 Hz, 3H); MS (ES−) m/z 347.9 (M−1).

Preparation 6.1

Synthesis of 2-(3-(but-3-enyl)-2-oxoimidazolidin-1-yl)-4-methylthiazole-5-carboxylic acid

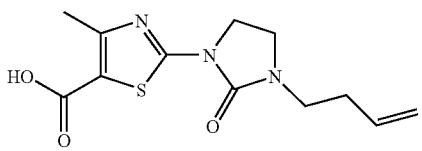

Following the procedure as described in Preparation 6, making variations as required to replace (S)-ethyl 2-(3-(4-fluorobenzyl)-4-methyl-2-oxoimidazolidin-1-yl)-4-methylthiazole-5-carboxylate with ethyl 2-(3-(but-3-enyl)-2-oxoimidazolidin-1-yl)-4-methylthiazole-5-carboxylate, the title compound was obtained as a colourless solid (85%): mp 205-207° C.; $^1$H NMR (300 MHz, DMSO-d$_6$) δ 12.70 (s, 1H), 5.86-5.72 (m, 1H), 5.16-5.02 (m, 2H), 4.01-3.96 (m, 2H), 3.60-3.54 (m, 2H), 3.31 (t, J=7.1 Hz, 2H), 2.50 (s, 3H), 2.32-2.26 (m, 2H); MS (ES+) m/z 281.8 (M+1).

Preparation 6.2

Preparation of (R)-2-(3-(4-fluorobenzyl)-4-methyl-2-oxoimidazolidin-1-yl)-4-methylthiazole-5-carboxylic acid

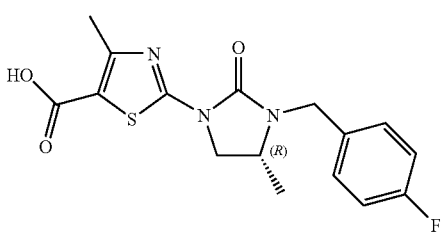

Following the procedure as described in Preparation 6, making variations as required to replace (S)-ethyl 2-(3-(4-fluorobenzyl)-4-methyl-2-oxoimidazolidin-1-yl)-4-methylthiazole-5-carboxylate with (R)-ethyl 2-(3-(4-fluorobenzyl)-4-methyl-2-oxoimidazolidin-1-yl)-4-methylthiazole-5-carboxylate, the title compound was obtained as a colorless solid (87%): $^1$H NMR (300 MHz, DMSO-d$_6$) δ 12.85 (s, 1H), 7.40-7.35 (m, 2H), 7.21-7.15 (m, 2H), 4.59 (d, J=15.6 Hz, 1H), 4.30 (d, J=15.6 Hz, 1H), 4.19 (t, J=9.6 Hz, 1H), 4.29-4.14 (m, 1H), 3.78-3.71 (m, 1H), 3.56 (dd, J=10.6, 6.3 Hz, 1H), 2.50 (s, 3H), 1.22 (d, J=6.2 Hz, 3H); MS (ES+) m/z 349.9 (M+1).

Preparation 6.3

Preparation of (R)-2-(3-(4-fluorobenzyl)-5-methyl-2-oxoimidazolidin-1-yl)-4-methylthiazole-5-carboxylic acid

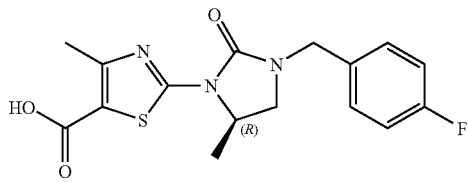

Following the procedure as described in Preparation 6, making variations as required to replace (S)-ethyl 2-(3-(4-fluorobenzyl)-4-methyl-2-oxoimidazolidin-1-yl)-4-methylthiazole-5-carboxylate with (R)-ethyl 2-(3-(4-fluorobenzyl)-5-methyl-2-oxoimidazolidin-1-yl)-4-methylthiazole-5-carboxylate, the title compound was obtained as a colorless solid (73%): mp 184-186° C.; $^1$H NMR (300 MHz, DMSO-d$_6$) δ 12.83 (s, 1H), 7.37-7.32 (m, 2H), 7.22-7.16 (m, 2H), 4.58-4.51 (m 1H), 4.46 (d, J=15.2 Hz, 1H), 4.38 (d, J=15.2 Hz, 1H), 3.61 (t, J=9.0 Hz, 1H), 3.03 (dd, J=9.0, 3.3 Hz, 1H), 2.50 (s, 3H), 1.38 (d, J=6.2 Hz, 3H); (ES+) m/z 349.7 (M+1).

Preparation 6.4

Preparation of (S)-2-(3-(4-fluorobenzyl)-5-methyl-2-oxoimidazolidin-1-yl)-4-methylthiazole-5-carboxylic acid

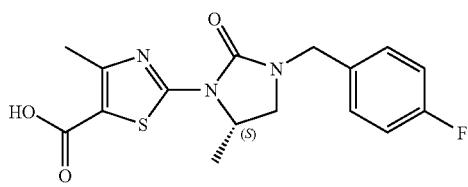

Following the procedure as described in Preparation 6, making variations as required to replace (S)-ethyl 2-(3-(4-fluorobenzyl)-4-methyl-2-oxoimidazolidin-1-yl)-4-methylthiazole-5-carboxylate with (S)-ethyl 2-(3-(4-fluorobenzyl)-5-methyl-2-oxoimidazolidin-1-yl)-4-methylthiazole-5-carboxylate, the title compound was obtained as a colorless solid (91%): $^1$H NMR (300 MHz, CDCl$_3$) δ 7.29-7.25 (m, 2H), 7.08-7.02 (m, 2H), 4.67-4.62 (m 1H), 4.55 (d, J=14.9 Hz, 1H), 4.44 (d, J=14.9 Hz, 1H), 3.58 (t, J=9.0 Hz, 1H), 3.00 (dd, J=9.0, 3.1 Hz, 1H), 2.64 (s, 3H), 1.48 (d, J=6.2 Hz, 3H); (ES+) m/z 349.9 (M+1).

Preparation 7

Preparation of ethyl 2-(3-(2-ethoxy-2-oxoethyl)-2-oxoimidazolidin-1-yl)-4-methylthiazole-5-carboxylate

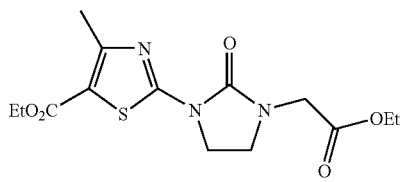

A mixture of ethyl 4-methyl-2-(2-oxoimidazolidin-1-yl)thiazole-5-carboxylate (2.00 g, 7.83 mmol), ethyl bromoacetate (1.30 mL, 11.75 mmol) and potassium carbonate (1.62 g, 11.75 mmol) in N,N-dimethylformamide (20 mL) was stirred at 80° C. for 2 h. The reaction mixture was allowed to cool to ambient temperature, and then partitioned between ethyl acetate (75 mL) and water (50 mL). The aqueous layer was extracted with ethyl acetate (75 mL), and the combined organic layer was dried over sodium sulfate, filtered and concentrated in vacuo. The residue was triturated with ethyl acetate in hexanes to afford the title compound as a colorless solid (2.03 g, 76%): $^1$H NMR (300 MHz, CDCl$_3$) δ 4.33-4.13 (m, 6H), 4.09 (s, 2H), 3.76-3.69 (m, 2H), 2.62 (s, 3H), 1.37-1.26 (m, 6H); MS (ES+) m/z 342.3 (M+1).

Preparation 8

Preparation of ethyl 2-(3-(2-(4-fluorobenzylamino)-2-oxoethyl)-2-oxoimidazolidin-1-yl)-4-methylthiazole-5-carboxylate

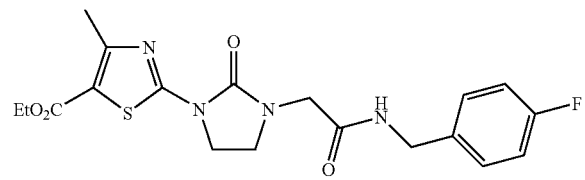

A mixture of ethyl 2-(3-(2-ethoxy-2-oxoethyl)-2-oxoimidazolidin-1-yl)-4-methylthiazole-5-carboxylate (0.43 g, 1.25 mmol), 4-fluorobenzylamine (3 mL) and catalytic amount of sodium cyanide was stirred at 80° C. for 16 h. The reaction mixture was allowed to cool to ambient temperature, diluted with dichloromethane (25 mL) and filtered. The solid was washed with dichloromethane and hexanes on the filter. The filtrate was filtered again, and the solid was washed with hexanes. The combined material was dried to afford the title compound as a colorless solid (0.45 g, 86%): $^1$H NMR (300 MHz, CDCl$_3$) δ 7.28-7.20 (m, 2H), 7.05-6.97 (m, 2H), 6.42 (br s, 1H), 4.42 (d, J=5.7 Hz, 2H), 4.29 (q, J=7.1 Hz, 2H), 4.19-4.10 (m, 2H), 3.99 (s, 2H), 3.77-3.70 (m, 2H), 2.62 (s, 3H), 1.34 (t, J=7.1 Hz, 3H); MS (ES+) m/z 421.2 (M+1).

Preparation 8.1

Preparation of ethyl 4-methyl-2-(3-(2-(methylamino)-2-oxoethyl)-2-oxoimidazolidin-1-yl)thiazole-5-carboxylate

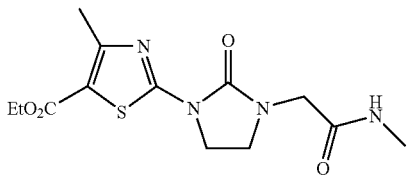

Following the procedure as described in Preparation 8, making variation as required to replace 4-fluorobenzylamine with methylamine, the title compound was obtained as a white solid in 74% yield: $^1$H NMR (300 MHz, DMSO-d$_6$) δ 8.04 (br s, 1H), 4.22 (q, J=6.8 Hz, 2H), 4.08-3.99 (m, 2H), 3.84 (s, 2H), 3.65-3.55 (m, 2H), 2.61 (d, J=3.1 Hz, 3H), 2.53 (s, 3H), 1.27 (t, J=6.8 Hz, 3H); MS (ES+) m/z 349.2 (M+23).

Preparation 8.2

Preparation of ethyl 4-methyl-2-(2-oxo-3-(2-oxo-2-(pyrrolidin-1-yl)ethyl)imidazolidin-1-yl)thiazole-5-carboxylate

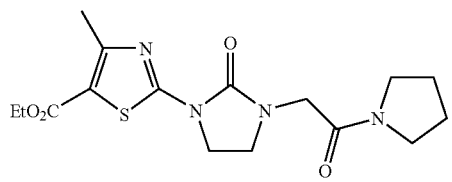

Following the procedure as described in Preparation 8, making variation as required to replace 4-fluorobenzylamine with pyrrolidine, the title compound was obtained as a white solid in 80% yield: $^1$H NMR (300 MHz, CDCl$_3$) δ 4.27 (q, J=7.1 Hz, 2H), 4.20-4.12 (m, 2H), 4.05 (s, 2H), 3.85-3.74 (m, 2H), 3.52-3.43 (m, 4H), 2.62 (s, 3H), 2.06-1.95 (m, 2H), 1.93-1.81 (m, 2H), 1.32 (t, J=7.1 Hz, 2H); MS (ES+) m/z 367.2 (M+1).

Preparation 9

Preparation of 2-(3-(2-(4-fluorobenzylamino)-2-oxoethyl)-2-oxoimidazolidin-1-yl)-4-methylthiazole-5-carboxylic acid

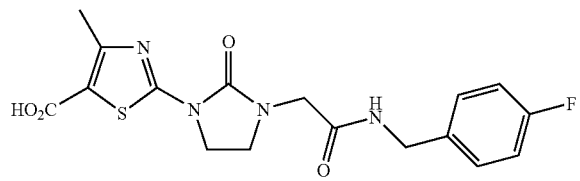

A mixture of ethyl 2-(3-(2-(4-fluorobenzylamino)-2-oxoethyl)-2-oxoimidazolidin-1-yl)-4-methylthiazole-5-carboxylate (0.20 g, 0.48 mmol) and 1 N aqueous sodium hydroxide solution (1.0 mL, 1.0 mmol) in ethanol (2 mL) was stirred at reflux for 1 h, cooled to 0° C. and acidified with 10% aqueous hydrochloric acid to pH ~2. The mixture was diluted with water (25 mL), and the aqueous layer was extracted with dichloromethane (2×50 mL). The aqueous layer was concentrated to dryness in vacuo to afford the crude title compound as an off-white foamy solid (0.18 g): MS (ES+) m/z 393.2 (M+1).

Preparation 9.1

Preparation of 4-methyl-2-(3-(2-(methylamino)-2-oxoethyl)-2-oxoimidazolidin-1-yl)thiazole-5-carboxylic acid

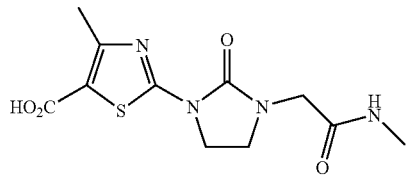

Following the procedure as described in Preparation 9, making variations as required to replace ethyl 2-(3-(2-(4-fluorobenzylamino)-2-oxoethyl)-2-oxoimidazolidin-1-yl)-4-methylthiazole-5-carboxylate with ethyl 4-methyl-2-(3-(2-(methylamino)-2-oxoethyl)-2-oxoimidazolidin-1-yl)thiazole-5-carboxylate, the crude title compound was obtained.

Preparation 9.2

Preparation of 4-methyl-2-(2-oxo-3-(2-oxo-2-(pyrrolidin-1-yl)ethyl)imidazolidin-1-yl)thiazole-5-carboxylic acid

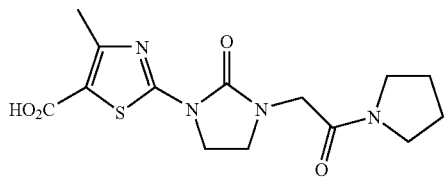

Following the procedure as described in Preparation 9, making variations as required to replace ethyl 2-(3-(2-(4-fluorobenzylamino)-2-oxoethyl)-2-oxoimidazolidin-1-yl)-4-methylthiazole-5-carboxylate with ethyl 4-methyl-2-(2-oxo-3-(2-oxo-2-(pyrrolidin-1-yl)ethyl)imidazolidin-1-yl) thiazole-5-carboxylate, the crude title compound was obtained as a colorless solid in 85% yield: $^1$H NMR (300 MHz, DMSO-$d_6$) δ 12.84 (br s, 1H), 4.09-4.00 (m, 4H), 3.84 (s, 2H), 3.65-3.57 (m, 2H), 3.42 (t, J=6.7 Hz, 2H), 3.30 (t, J=6.7 Hz, 2H), 2.51 (s, 3H), 1.95-1.84 (m, 2H), 1.83-1.71 (m, 2H); MS (ES+) m/z 339.3 (M+1).

Preparation 10

Preparation of ethyl 2-(3-(4-fluorobenzyl)-2-oxo-2,3-dihydro-1H-benzo[d]imidazol-1-yl)-4-methylthiazole-5-carboxylate

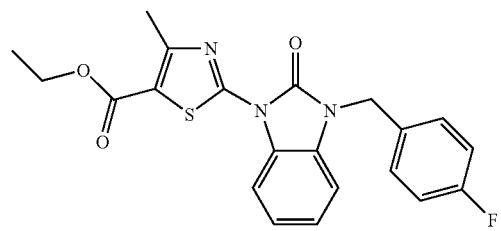

A. To a stirred cold (0° C.) solution of 1-fluoro-2-nitrobenzene (1.00 g, 7.13 mmol) in N,N-dimethylformamide was added ethyl 2-amino-4-methylthiazole-5-carboxylate (2.00 g, 10.7 mmol). The cold bath was removed after 1 h, and the mixture was stirred at ambient temperature for 17 h. The mixture was concentrated in vacuo. The residue was diluted with dichloromethane (150 mL) and washed with saturated aqueous ammonium chloride (2×25 mL), water (3×20 mL), dried over sodium sulfate, and filtered. The filtrate was concentrated and purified by column chromatography eluted with hexanes/ethyl acetate to give 4-methyl-2-(2-nitrophenylamino)thiazole-5-carboxylate as an orange solid (1.45 g, yield 67%): $^1$H NMR (300 MHz, CDCl$_3$) δ 8.66-8.63 (m, 1H), 8.27-8.24 (m, 1H), 7.70-7.64 (m, 1H), 7.13-7.07 (m, 1H), 4.30 (q, J=7.2 Hz, 2H), 2.65 (s, 3H), 1.34 (t, J=7.2 Hz, 3H); MS (ES+) m/z 308.0 (M+1).

B. 4-Methyl-2-(2-nitrophenylamino)thiazole-5-carboxylate (0.45 g, 1.46 mmol), tin(II) chloride dehydrate (1.66 g, 7.34 mmol) and tetrahydrofuran (25 mL) was added to a 100-mL round bottom flask. The mixture was refluxed at 75-85° C. for 3 h, cooled down to 0° C. and followed by the addition of saturated aqueous sodium carbonate solution (16 mL). The mixture was filtered through a celite cake and the filtrate was washed with saturated aqueous sodium carbonate solution (18 mL), water (2×15 mL) and brine (15 mL), dried over sodium sulfate, filtered and concentrated in vacuo to a small volume and triturated with diethyl ether. The solid was collected by filtration, washed with hexanes and dried in vacuo to afford ethyl 2-(2-aminophenylamino)-4-methylthiazole-5-carboxylate as a white solid (0.31 g, 77% yield): $^1$H NMR (300 MHz, CDCl$_3$) δ 7.31-7.24 (m, 1H), 7.17-7.12 (m, 1H), 6.84-6.77 (m, 2H), 4.45-4.06 (m, 5H), 2.48 (s, 3H), 1.25 (t, J=7.05 Hz, 3H); MS (ES+) m/z 278.0 (M+1).

C. To a suspension of ethyl 2-(2-aminophenylamino)-4-methylthiazole-5-carboxylate (0.24 g, 0.87 mmol) in dichloromethane (12 mL) was added phosgene solution (purum, ~20% in toluene, 0.48 mL, 0.91 mmol) at ambient temperature. The mixture was stirred at ambient temperature for 16 h followed by the addition of saturated aqueous sodium bicarbonate solution. The mixture was extracted with dichloromethane (30 mL), washed with water and brine, dried over sodium sulfate, filtered, concentrated to small volume, and triturated with diethyl ether (5 mL) to precipitate the product. The solid was collected by filtration, washed with water (3×5 mL) and hexanes (5 mL), and dried in vacuo to afford ethyl 4-methyl-2-(2-oxo-2,3-dihydro-1H-benzo[d]imidazol-1-yl) thiazole-5-carboxylate as a white solid (0.21 g, 80% yield): MS (ES+) m/z 304.2 (M+1).

D. To a 25-mL round bottom flask was added 4-methyl-2-(2-oxo-2,3-dihydro-1H-benzo[d]imidazol-1-yl)thiazole-5-carboxylate (0.10 g, 0.33 mmol), tetrahydrofuran (95 mL), 4-fluorobenzyl bromide (0.08 g, 0.43 mmol) and potassium carbonate (0.10 g, 0.73 mmol) at ambient temperature. The reaction mixture was stirred at ambient temperature for 16 h and refluxed for 3 h. The second portion of 4-fluorobenzyl bromide (0.08 g, 0.43 mmol) was added and stirred at ambient temperature for 17 h. The third portion of 4-fluorobenzyl bromide (0.08 g, 0.43 mmol) and second portion of potassium carbonate (0.10 g, 0.73 mmol) were added at ambient temperature. The mixture was stirred for an additional 3 h at ambient temperature, filtered and washed with tetrahydrofuran. The filtrate was concentrated and the residue was purified by column chromatography to afford the title compound as a white solid (0.08 g, 59% yield): mp 192-193° C.; $^1$H NMR (300 MHz, CDCl$_3$) δ 8.58-8.55 (m, 1H), 7.38-7.31 (m, 2H), 7.26-7.16 (m, 2H), 7.05-6.95 (m, 3H), 5.09 (s, 2H), 4.32 (q, J=7.2 Hz, 2H), 2.76 (s, 3H), 1.36 (t, J=7.2 Hz, 3H); $^{13}$C NMR (75 MHz, CDCl$_3$) δ 162.8, 157.1, 157.0, 151.9, 131.0, 131.0, 129.5, 129.4, 128.9, 126.3, 124.2, 122.9, 116.8, 116.1, 115.8, 115.0, 108.4, 61.0, 44.5, 17.5, 14.3; MS (ES+) m/z 412.0 (M+1).

Preparation 11

Preparation of 2-(3-(4-fluorobenzyl)-2-oxo-2,3-dihydro-1H-benzo[d]imidazol-1-yl)-4-methylthiazole-5-carboxylic acid

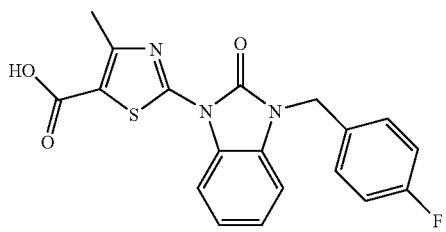

A suspension of 2-(3-(4-fluorobenzyl)-2-oxo-2,3-dihydro-1H-benzo[d]imidazol-1-yl)-4-methylthiazole-5-carboxylate in a mixture of tetrahydrofuran and water (2/1) is added lithium hydroxide monohydrate (6.9 equivalents) at ambient temperature. The reaction mixture is stirred at ambient temperature for 17 h and concentrated in vacuo. The residue is acidified by the addition of 4 M hydrochloric acid solution to pH ~3. The solid is collected by filtration, washed with water and hexane, and dried in vacuo to afford the title compound.

Preparation 12

Preparation of ethyl 4-methyl-2-(2-oxoimidazolidin-1-yl)thiazole-5-carboxylate

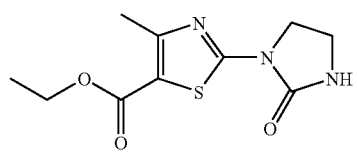

To a solution of ethyl 2-amino-4-methylthiazole-5-carboxylate (9.31 g, 49.99 mmol) in tetrahydrofuran (200 mL) was added 2-chloroethyl isocyanate (5.50 mL, 64.0 mmol) at ambient temperature. The resulting reaction mixture was heated to reflux for 7 hours, followed by the addition of potassium carbonate (8.30 g, 60.0 mmol) and tetra-n-butylammonium iodide (0.50 g, 1.35 mmol) and the resulting mixture was heated to reflux for 23 hours. The solvent was removed in vacuo, and the residue was washed with water (200 mL) and ethyl acetate (50 mL) to afford the title compound in 71% yield (9.10 g): mp 197-199° C.; $^1$H NMR (300 MHz, DMSO-d$_6$) δ 7.83 (s, 1H), 4.20-3.93 (m, 4H), 3.49-3.43 (m, 2H), 2.46 (s, 3H), 1.20 (t, J=6.9 Hz, 3H); MS (ES+) m/z 256.3 (M+1).

Preparation 13

Preparation of ethyl 2-(3-((2,2-difluorocyclopropyl)methyl)-2-oxoimidazolidin-1-yl)-4-methylthiazole-5-carboxylate

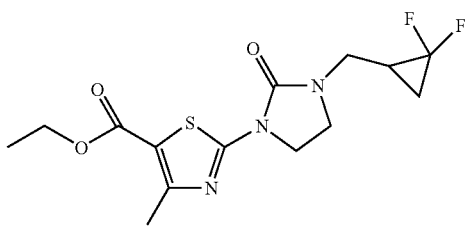

To a solution of ethyl 4-methyl-2-(2-oxoimidazolidin-1-yl)thiazole-5-carboxylate (1.19 g, 4.68 mmol) in anhydrous dioxane (50.0 mL) was added potassium carbonate (1.29 g, 9.36 mmol) and bromomethyl-2,2-difluorocyclopropane (1.00 g, 5.85 mmol). The reaction mixture was heated at 80° C. for 16 h, filtered and the solid was washed with ethyl acetate (100 mL). The filtrate was concentrated in vacuo and the residue was recrystallized from ethyl acetate in hexane to afford the title compound as a yellow solid (0.87 g, 54%): mp 146-148° C.; $^1$H NMR (300 MHz, CDCl$_3$) δ 4.18 (q, J=7.1 Hz, 2H), 3.99 (t, J=8.4 Hz, 2H), 3.65-3.44 (m, 3H), 3.20-3.12 (m, 1H), 2.48 (s, 3H), 2.02-1.88 (m, 1H), 1.68-1.55 (m, 1H), 1.38-1.28 (m, 1H), 1.23 (t, J=7.1 Hz, 3H); $^{13}$C NMR (75 MHz, CDCl$_3$) δ 162.5, 160.1, 156.8, 155.2, 114.9 (t), 113.8, 60.8, 42.4, 42.1, 41.1 (d), 20.3 (t, $^2J_{C-F}$=43 Hz), 17.5, 14.9 (t, $^2J_{C-F}$=43 Hz), 14.6; MS (ES+) m/z 399.0 (M+1).

Preparation 13.1

Preparation of ethyl 2-(3-benzyl-2-oxoimidazolidin-1-yl)-4-methylthiazole-5-carboxylate

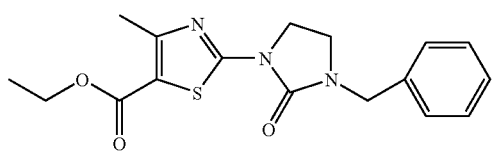

Following the procedure as described in Preparation 13, making variations as required to replace bromomethyl-2,2-difluorocyclopropane with benzyl bromide to react with ethyl 4-methyl-2-(2-oxoimidazolidin-1-yl)thiazole-5-carboxylate, the title compound was obtained in 93% yield: mp 122-124° C.; $^1$H NMR (300 MHz, DMSO-d$_6$) δ 7.35-7.26 (m, 5H), 4.40 (s, 2H), 4.19 (q, J=7.2 Hz, 2H), 3.97 (t, J=7.5 Hz, 2H), 3.42 (t, J=7.5 Hz, 2H), 2.48 (s, 3H), 1.23 (t, J=7.2 Hz, 3H); MS (ES+) m/z 346.0 (M+1).

Preparation 13.2

Preparation of ethyl 2-(3-(cyclopropylmethyl)-2-oxoimidazolidin-1-yl)-4-methylthiazole-5-carboxylate

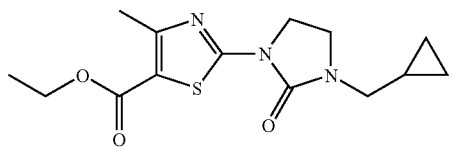

Following the procedure as described in Preparation 13, making variations as required to replace bromomethyl-2,2-difluorocyclopropane with cyclopropylmethyl bromide to react with ethyl 4-methyl-2-(2-oxoimidazolidin-1-yl)thiazole-5-carboxylate, the title compound was obtained in 96% yield: $^1$H NMR (300 MHz, CDCl$_3$) δ 4.23 (q, J=7.2 Hz, 2H), 4.07 (t, J=7.8 Hz, 2H), 3.67 (t, J=7.8 Hz, 2H), 3.16 (d, J=6.9 Hz, 2H), 2.58 (s, 3H), 1.28 (t, J=7.2 Hz, 3H), 0.97-0.88 (m, 1H), 0.59-0.42 (m, 2H), 0.25-0.12 (m, 2H); MS (ES+) m/z 310.3 (M+1).

Preparation 13.3

Preparation of ethyl 2-(1-(4-fluorobenzyl)-5-oxo-1H-1,2,4-triazol-4(5H)-yl)-4-methylthiazole-5-carboxylate

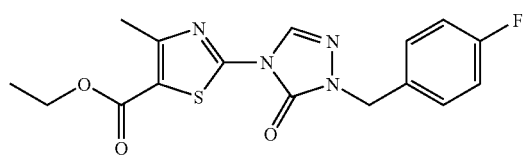

Following the procedure as described in Preparation 13, making variation as required to replace bromomethyl-2,2-difluorocyclopropane with 1-(bromomethyl)-4-fluorobenzene to react with ethyl 4-methyl-2-(5-oxo-1H-1,2,4-triazol-4(5H)-yl)thiazole-5-carboxylate in place of ethyl 4-methyl-2-(2-oxoimidazolidin-1-yl)thiazole-5-carboxylate, the title compound was obtained as a white solid in 84% yield: $^1$H NMR (300 MHz, CDCl$_3$) δ 8.27 (s, 1H), 7.47-7.30 (m, 2H), 7.11-6.97 (m, 2H), 4.98 (s, 2H), 4.32 (q, J=7.1 Hz, 2H), 2.65 (s, 3H), 1.34 (t, J=7.1 Hz, 3H); MS (ES+) m/z 363.1 (M+1).

Preparation 13.4

Preparation of ethyl 2-(1-(cyclopropylmethyl)-5-oxo-1H-1,2,4-triazol-4(5H)-yl)-4-methylthiazole-5-carboxylate

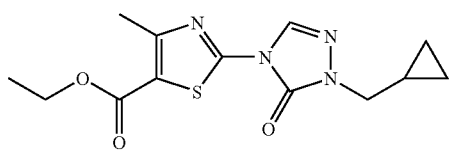

Following the procedure as described in Preparation 13, making variation as required to replace bromomethyl-2,2-difluorocyclopropane with (bromomethyl)cyclopropane to react with ethyl 4-methyl-2-(5-oxo-1H-1,2,4-triazol-4(5H)-yl)thiazole-5-carboxylate in place of ethyl 4-methyl-2-(2-oxoimidazolidin-1-yl)thiazole-5-carboxylate, the title compound was obtained as a white solid in 83% yield: $^1$H NMR (300 MHz, CDCl$_3$) δ 8.27 (s, 1H), 4.31 (q, J=7.1 Hz, 2H), 3.63 (d, J=7.1 Hz, 2H), 2.64 (s, 3H), 1.35 (t, J=7.1 Hz, 3H), 1.19-1.04 (m, 1H), 0.53-0.42 (m, 2H), 0.36-0.27 (m, 2H); MS (ES+) m/z 309.2 (M+1).

Preparation 13.5

Preparation of ethyl 4-methyl-2-(2-oxo-3-(4-(trifluoromethyl)benzyl)imidazolidin-1-yl)thiazole-5-carboxylate

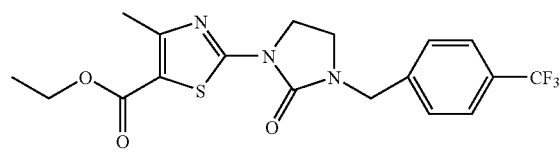

Following the procedure as described in Preparation 13, making variations to replace bromomethyl-2,2-difluorocyclopropane with 4-(trifluoromethyl)benzyl bromide to react with ethyl 4-methyl-2-(2-oxoimidazolidin-1-yl)thiazole-5-carboxylate, the title compound was obtained in 92% yield: mp 126-127° C.; $^1$H NMR (300 MHz, DMSO-d$_6$) δ 7.70 (d, J=8.1 Hz, 2H), 7.51 (d, J=8.1 Hz, 2H), 4.51 (s, 2H), 4.17 (q, J=6.9 Hz, 2H), 4.00 (t, J=8.1 Hz, 2H), 3.47 (t, J=8.1 Hz, 2H), 2.49 (s, 3H), 1.23 (t, J=6.9 Hz, 3H); MS (ES+) m/z 414.1 (M+1).

Preparation 13.6

Preparation of ethyl 2-(3-(4-fluorobenzyl)-2-oxoimidazolidin-1-yl)-4-methylthiazole-5-carboxylate

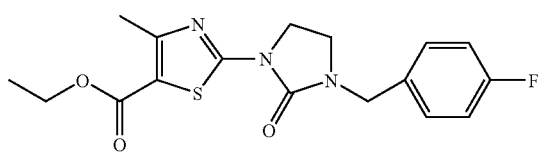

Following the procedure as described in Preparation 13, making variations to replace bromomethyl-2,2-difluorocyclopropane with 4-fluorobenzyl bromide to react with ethyl 4-methyl-2-(2-oxoimidazolidin-1-yl)thiazole-5-carboxylate, the title compound was obtained in 98% yield: MS (ES+) m/z 364.2 (M+1).

Preparation 13.7

Preparation of ethyl 4-methyl-2-(2-oxo-3-(4,4,4-trifluorobutyl)imidazolidin-1-yl)thiazole-5-carboxylate

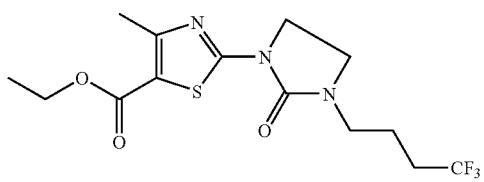

Following the procedure as described in Preparation 13, making variations to replace bromomethyl-2,2-difluorocyclopropane with 4-bromo-1,1,1-trifluorobutane to react with ethyl 4-methyl-2-(2-oxoimidazolidin-1-yl)thiazole-5-carboxylate, the title compound was obtained in 98% yield: MS (ES+) m/z 366.1 (M+1).

Preparation 13.8

Preparation of ethyl 2-(3-isobutyl-2-oxoimidazolidin-1-yl)-4-methylthiazole-5-carboxylate

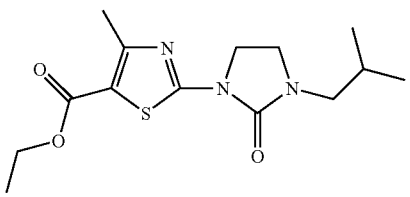

Following the procedure as described in Preparation 13, making variations to replace bromomethyl-2,2-difluorocyclopropane with 1-bromo-2-methylpropane to react with ethyl 4-methyl-2-(2-oxoimidazolidin-1-yl)thiazole-5-carboxylate, the title compound was obtained in 98% yield: MS (ES+) m/z 311.8 (M+1).

Preparation 14

Preparation of 2-(3-((2,2-difluorocyclopropyl)methyl)-2-oxoimidazolidin-1-yl)-4-methylthiazole-5-carboxylic acid

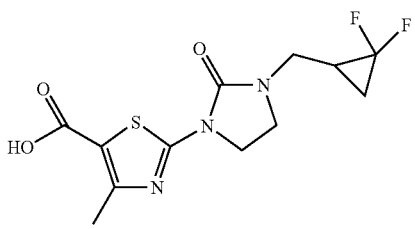

To a solution of ethyl 2-(3-((2,2-difluorocyclopropyl)methyl)-2-oxoimidazolidin-1-yl)-4-methylthiazole-5-carboxylate (0.77 g, 2.24 mmol) in tetrahydrofuran (40.0 mL) was added lithium hydroxide monohydrate (0.27 g, 11.2 mmol) in water (2.0 mL). The reaction mixture was heated at reflux for 16 h, cooled to an ambient temperature, then acidified with a solution of hydrochloric acid (3.0 N, 10.0 mL). The solvent was removed in vacuo to dryness and the precipitate was filtered, dried to afford the title compound as a colourless solid (0.49 g, 68%): mp 210-215° C.; $^1$H NMR (300 MHz, DMSO-$d_6$) δ 12.79 (br, 1H), 3.99 (t, J=9.0 Hz, 2H), 3.64-3.48 (m, 3H), 3.19-3.12 (m, 1H), 2.46 (s, 3H), 2.02-1.88 (m, 1H), 1.67-1.55 (m, 1H), 1.37-1.26 (m, 1H); $^{13}$C NMR (75 MHz, DMSO-$d_6$) δ 164.0, 159.8, 156.0, 155.2, 115.2, 114.9 (t), 42.4, 42.1, 41.1 (d), 20.3 (t, $^2J_{C-F}$=43 Hz), 17.4, 14.9 (t, $^2J_{C-F}$=43 Hz); MS (ES+) m/z 318.0 (M+1).

Preparation 14.1

Synthesis of 2-(1-((2,2-difluorocyclopropyl)methyl)-5-oxo-1H-1,2,4-triazol-4(5H)-yl)-4-methylthiazole-5-carboxylic acid

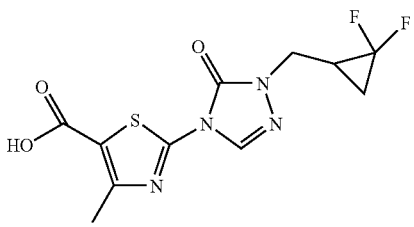

Following the procedure as describe in Preparation 14, making variations as required to replace ethyl 2-(3-((2,2-difluorocyclopropyl)methyl)-2-oxoimidazolidin-1-yl)-4-methylthiazole-5-carboxylate with ethyl 2-(1-((2,2-difluorocyclopropyl)methyl)-5-oxo-1H-1,2,4-triazol-4(5H)-yl)-4-methylthiazole-5-carboxylate, the title compound was obtained as a colourless solid in 18% yield: mp 220-222° C.; $^1$H NMR (300 MHz, DMSO-$d_6$) δ 13.59 (br, 1H), 7.35 (dd, J=13.9, 7.7 Hz, 1H), 7.17 (d, J=7.7 Hz, 1H), 7.07 (dd, J=18.9, 9.0 Hz, 2H), 5.14 (s, 2H); $^{13}$C NMR (75 MHz, DMSO-$d_6$) δ 162.9 (d), 153.2, 136.3 (d), 130.7 (d), 123.9 (d), 115.8 (d), 115.3 (d), 47.7 (d); MS (ES+) m/z 317.1 (M+1).

Preparation 14.2

Preparation of 2-(3-(cyclopropylmethyl)-2-oxoimidazolidin-1-yl)-4-methylthiazole-5-carboxylic acid

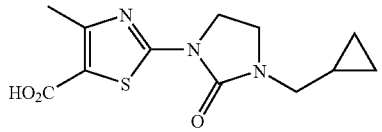

Following the procedure as describe in Preparation 14, making variations as required to replace ethyl 2-(3-((2,2-difluorocyclopropyl)methyl)-2-oxoimidazolidin-1-yl)-4-methylthiazole-5-carboxylate with ethyl 2-(3-(cyclopropylmethyl)-2-oxoimidazolidin-1-yl)-4-methylthiazole-5-carboxylate, the title compound was obtained as a colourless solid in 82% yield: $^1$H NMR (300 MHz, DMSO-$d_6$) δ 3.96 (t, J=7.8 Hz, 2H), 3.67 (t, J=7.8 Hz, 2H), 3.06 (d, J=6.9 Hz, 2H), 2.52 (s, 3H), 0.97-0.84 (m, 1H), 0.53-0.37 (m, 2H), 0.20-0.11 (m, 2H); MS (ES+) m/z 282.2 (M+1).

Preparation 14.3

Preparation of 2-(1-(4-fluorobenzyl)-5-oxo-1H-1,2,4-triazol-4(5H)-yl)-4-methylthiazole-5-carboxylic acid

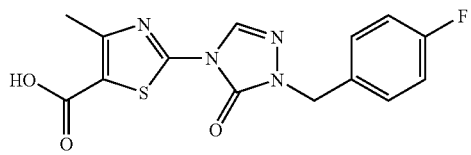

Following the procedure as described in Preparation 14, making variations as required to replace ethyl 2-(3-((2,2-difluorocyclopropyl)methyl)-2-oxoimidazolidin-1-yl)-4-methylthiazole-5-carboxylate with ethyl 2-(1-(4-fluorobenzyl)-5-oxo-1H-1,2,4-triazol-4(5H)-yl)-4-methylthiazole-5-carboxylate, the title compound was obtained as a white solid in 99% yield: $^1$H NMR (300 MHz, DMSO-$d_6$) δ 13.40 (br s, 1H), 8.74 (s, 1H), 7.37-7.31 (m, 2H), 7.19-7.11 (m, 2H), 4.96 (s, 2H), 2.57 (s, 3H); MS (ES−) m/z 333.0 (M−1).

Preparation 14.4

Synthesis of 2-(1-(cyclopropylmethyl)-5-oxo-1H-1,2,4-triazol-4(5H)-yl)-4-methylthiazole-5-carboxylic acid

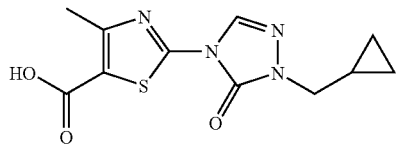

Following the procedure as described in Preparation 14, making variations as required to replace ethyl 2-(3-((2,2-difluorocyclopropyl)methyl)-2-oxoimidazolidin-1-yl)-4-methylthiazole-5-carboxylate with ethyl 2-(1-(cyclopropylmethyl)-5-oxo-1H-1,2,4-triazol-4(5H)-yl)-4-methylthiazole-5-carboxylate, the title compound was obtained as a white solid in 92% yield: $^1$H NMR (300 MHz, DMSO-$d_6$) δ 13.39 (br s, 1H), 8.72 (s, 1H), 3.63 (d, J=7.1 Hz, 2H), 2.57 (s, 3H), 1.19-1.04 (m, 1H), 0.53-0.42 (m, 2H), 0.36-0.27 (m, 2H); MS (ES−) m/z 279.0 (M−1).

Preparation 14.5

Preparation of 4-methyl-2-(2-oxo-3-(4-(trifluoromethyl)benzyl)imidazolidin-1-yl)thiazole-5-carboxylic acid

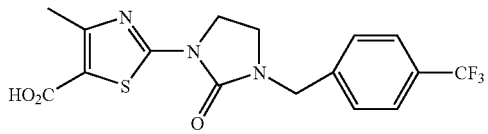

Following the procedure as described in Preparation 14, making variations as required to replace ethyl 2-(3-((2,2-difluorocyclopropyl)methyl)-2-oxoimidazolidin-1-yl)-4-methylthiazole-5-carboxylate with ethyl 4-methyl-2-(2-oxo-3-(4-(trifluoromethyl)benzyl)-imidazolidin-1-yl)thiazole-5-carboxylate, the title compound was obtained in 85% yield: mp 195-197° C.; $^1$H NMR (300 MHz, DMSO-$d_6$) δ 7.74 (d, J=11.4 Hz, 2H), 7.60 (d, J=11.4 Hz, 2H), 4.51 (s, 2H), 4.00 (t, J=8.1 Hz, 2H), 3.47 (t, J=8.1 Hz, 2H), 2.47 (s, 3H); MS (ES+) m/z 386.2 (M+1).

Preparation 14.6

Preparation of 2-(3-(4-fluorobenzyl)-2-oxoimidazolidin-1-yl)-4-methylthiazole-5-carboxylic acid

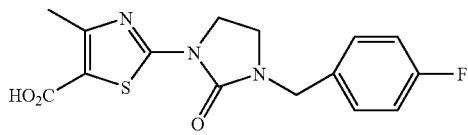

Following the procedure as described in Preparation 14, making variations as required to replace ethyl 2-(3-((2,2-difluorocyclopropyl)methyl)-2-oxoimidazolidin-1-yl)-4-methylthiazole-5-carboxylate with ethyl 2-(3-(4-fluorobenzyl)-2-oxoimidazolidin-1-yl)-4-methylthiazole-5-carboxylate, the title compound was obtained in 97% yield: $^1$H NMR (300 MHz, DMSO-$d_6$) δ 7.84-7.07 (m, 4H), 4.32 (s, 2H), 3.93 (t, J=8.1 Hz, 2H), 3.22 (t, J=8.1 Hz, 2H), 2.46 (s, 3H); MS (ES+) m/z 336.2 (M+1).

Preparation 14.7

Preparation of 2-(3-benzyl-2-oxoimidazolidin-1-yl)-4-methylthiazole-5-carboxylic acid

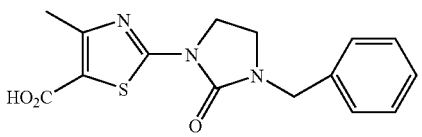

Following the procedure as described in Preparation 14, making variations as required to replace ethyl 2-(3-((2,2-difluorocyclopropyl)methyl)-2-oxoimidazolidin-1-yl)-4-methylthiazole-5-carboxylate with ethyl 2-(3-benzyl-2-oxoimidazolidin-1-yl)-4-methylthiazole-5-carboxylate, the title compound was obtained in 84% yield: mp 248-249° C.; $^1$H NMR (300 MHz, DMSO-$d_6$) δ 7.36-7.22 (m, 5H), 4.47 (s, 2H), 3.97 (t, J=7.5 Hz, 2H), 3.42 (t, J=7.5 Hz, 2H), 2.49 (s, 3H); MS (ES+) m/z 318.3 (M+1).

Preparation 14.8

Preparation of 4-methyl-2-(2-oxo-3-(4,4,4-trifluorobutyl)imidazolidin-1-yl)thiazole-5-carboxylic acid

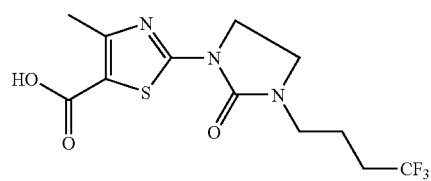

Following the procedure as described in Preparation 14, making variations as required to replace ethyl 2-(3-((2,2-difluorocyclopropyl)methyl)-2-oxoimidazolidin-1-yl)-4-methylthiazole-5-carboxylate with ethyl 4-methyl-2-(2-oxo-3-(4,4,4-trifluorobutyl)imidazolidin-1-yl)thiazole-5-carboxylate, the title compound was obtained as a colourless solid in 87% yield: $^1$H NMR (300 MHz, DMSO-d$_6$) δ 12.8 (s, 1H), 4.02-3.97 (m, 2H), 3.59-3.54 (m, 2H), 3.33-3.29 (m, 2H), 2.50 (s, 3H), 2.35-2.26 (m, 2H), 1.79-1.69 (m 2H); MS (ES+) m/z 338.1 (M+1).

Preparation 14.9

Preparation of 2-(3-isobutyl-2-oxoimidazolidin-1-yl)-4-methylthiazole-5-carboxylic acid

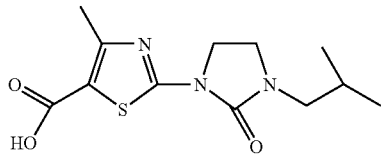

Following the procedure as described in Preparation 14, making variations as required to replace ethyl 2-(3-((2,2-difluorocyclopropyl)methyl)-2-oxoimidazolidin-1-yl)-4-methylthiazole-5-carboxylate with ethyl 2-(3-isobutyl-2-oxoimidazolidin-1-yl)-4-methylthiazole-5-carboxylate, the title compound was obtained as a colourless solid in 96% yield: $^1$H NMR (300 MHz, DMSO-d$_6$) δ 4.04-3.98 (m, 2H), 3.58-3.53 (m, 2H), 3.03 (d, J=7.4 Hz, 2H), 2.50 (s, 3H), 1.94-1.85 (m, 1H), 0.87 (d, J=6.6 Hz, 6H); MS (ES+) m/z 283.8 (M+1).

Preparation 15

Preparation of ethyl 4-methyl-2-(5-oxo-1H-1,2,4-triazol-4(5H)-yl)thiazole-5-carboxylate

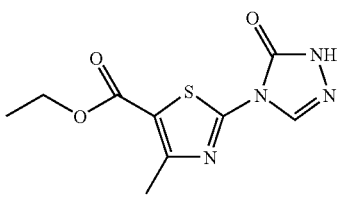

A. To a 2-neck round bottom flask (1 L) equipped with a mechanical stirrer was added ethyl 2-amino-4-methylthiazole-5-carboxylate (30.00 g, 161.00 mmol) in anhydrous tetrahydrofuran (750 mL) and pyridine (191.10 g, 242.00 mmol), followed by the dropwise addition of 4-nitrophenyl chloroformate (40.60 g, 202.00 mmol) in anhydrous dichloromethane (100 mL) at 0° C. The yellow reaction mixture was stirred at 0° C. for 2 h, followed by the addition of hydrazine monohydrate (25.50 g, 796.00 mmol). The resulting mixture was stirred at ambient temperature for 16 h. The yellow solid was collected by filtration and washed with cold methanol (100 mL) and diethyl ether (100 mL) to afford ethyl 2-(hydrazinecarboxamido)-4-methylthiazole-5-carboxylate as a yellow solid in quantitative yield (42.00 g): mp 225-230° C.; $^1$H NMR (300 MHz, DMSO-d$_6$) δ 7.24 (br s, 4H), 4.21 (t, J=7.1 Hz, 2H), 2.48 (s, 3H), 1.26 (t, J=7.1 Hz, 3H); $^{13}$C NMR (75 MHz, DMSO-d$_6$) δ 162.6, 156.8, 156.3, 156.3, 60.7, 17.5, 14.7; MS (ES+) m/z 245.0 (M+1).

B. To a 2-neck round bottom flask (1 L) equipped with a mechanical stirrer was added ethyl 2-(hydrazinecarboxamido)-4-methylthiazole-5-carboxylate (42.00 g, 172.00 mmol) in anhydrous triethyl orthoformate (393 mL). The yellow reaction mixture was heated at 95° C. for 2 h, and then cooled to ambient temperature. The precipitate was filtered and washed with cold methanol (100 mL) to afford the title compound as a colourless solid (34.9 g, 80%): mp 165-167° C.; $^1$H NMR (300 MHz, DMSO-d$_6$) δ 12.94 (br, 1H), 9.09 (s, 1H), 4.64 (t, J=7.1 Hz, 2H), 2.98 (s, 3H), 1.67 (t, J=7.1 Hz, 3H); $^{13}$C NMR (75 MHz, DMSO-d$_6$) δ 162.3, 157.1, 154.5, 152.3, 133.6, 118.4, 61.9, 17.7, 14.9; MS (ES+) m/z 255.0 (M+1).

Preparation 16

Preparation of ethyl 2-(1-((2,2-difluorocyclopropyl)methyl)-5-oxo-1H-1,2,4-triazol-4(5H)-yl)-4-methylthiazole-5-carboxylate

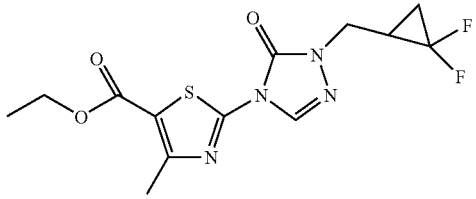

To a solution of ethyl 4-methyl-2-(5-oxo-1H-1,2,4-triazol-4(5H)-yl)thiazole-5-carboxylate (9.36 g, 36.8 mmol) in anhydrous N,N-dimethylformamide (150 mL) was added cesium carbonate (23.90 g, 73.70 mmol). The reaction mixture was stirred at ambient temperature for 30 min, followed by the addition of bromomethyl-2,2-difluorocyclopropane (6.00 g, 35.10 mmol) in N,N-dimethylformamide (50 mL). The reaction mixture was heated at 40° C. for 3 h and filtered. The solid was washed with ethyl acetate (100 mL). The filtrate was concentrated in vacuo to dryness. The residue was triturated with ethyl acetate (50 mL) to afford the title compound as a yellow solid (10.8 g, 98%): mp 146-148° C.; $^1$H NMR (300 MHz, DMSO-d$_6$) δ 8.74 (s, 1H), 4.23 (t, J=7.1 Hz, 2H), 3.97-3.77 (m, 2H), 2.54 (s, 3H), 2.20-2.04 (m, 1H), 1.73-1.60 (m, 1H), 1.48-1.37 (m, 1H), 1.26 (t, J=7.1 Hz, 3H); $^{13}$C NMR (75 MHz, DMSO-d$_6$) δ 161.8, 156.6, 154.0, 149.9, 132.2, 118.2, 114.4 (t), 61.6, 42.8 (d), 20.7 (t), 17.2, 14.9 (t), 14.5; MS (ES+) m/z 345.9 (M+1).

Preparation 16.1

Preparation of 1-(5-acetyl-4-methylthiazol-2-yl)-3-(4,4,4-trifluorobutyl)imidazolidin-2-one

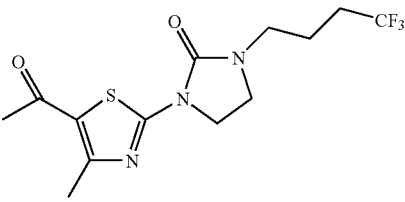

Following the procedure as describe in Preparation 16, making variations as required to replace ethyl 4-methyl-2-(5-oxo-1H-1,2,4-triazol-4(5H)-yl)thiazole-5-carboxylate with 1-(5-acetyl-4-methylthiazol-2-yl)imidazolidin-2-one to react with 4-bromo-1,1,1-trifluorobutane instead of bromomethyl-2,2-difluorocyclopropane, the title compound was obtained as a yellow solid in 60% yield: mp 108-110° C.; $^1$H NMR (300 MHz, DMSO-d$_6$) δ 3.97 (t, J=9.0 Hz, 2H), 3.57-3.47 (m, 2H), 3.28 (t, J=9.0 Hz, 2H), 2.50 (s, 3H), 2.40 (s, 3H), 2.32-2.19 (m, 2H), 1.76-1.62 (m, 2H); $^{13}$C NMR (75 MHz, DMSO-d$_6$) δ 155.9, 155.8, MS (ES+) m/z 336.9 (M+1).

Preparation 16.2

Preparation of -(5-acetyl-4-methylthiazol-2-yl)-3-((2,2-difluorocyclopropyl)methyl) imidazolidin-2-one

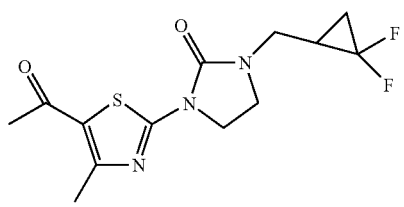

Following the procedure as describe in Preparation 16, making variations as required to replace ethyl 4-methyl-2-(5-oxo-1H-1,2,4-triazol-4(5H)-yl)thiazole-5-carboxylate with 1-(5-acetyl-4-methylthiazol-2-yl)imidazolidin-2-one to react with bromomethyl-2,2-difluorocyclopropane, the title compound was obtained as a yellow solid in 49% yield: mp 146-148° C.; $^1$H NMR (300 MHz, DMSO-d$_6$) δ 4.00 (t, J=9.0 Hz, 2H), 3.65-3.48 (m, 2H), 3.20-3.13 (m, 2H), 2.51 (s, 3H), 2.41 (s, 3H), 2.05-2.18 (m, 1H), 1.68-1.56 (m, 1H), 1.38-1.27 (m, 1H); $^{13}$C NMR (75 MHz, DMSO-d$_6$) δ 190.8, 160.1, 155.1, 154.9, 125.8, 114.8 (t), 42.4, 42.1, 41.1 (d), 30.4, 20.2 (t), 18.6, 14.9 (t); MS (ES+) m/z 316.9 (M+1).

Preparation 16.3

Preparation of 1-(5-acetyl-4-methylthiazol-2-yl)-3-(4-fluorobenzyl)imidazolidin-2-one

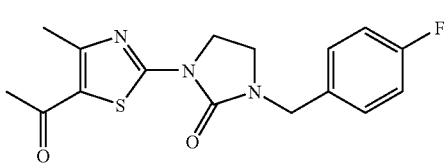

Following the procedure as described in Preparation 16, making variations as required to replace ethyl 4-methyl-2-(5-oxo-1H-1,2,4-triazol-4(5H)-yl)thiazole-5-carboxylate with 1-(5-acetyl-4-methylthiazol-2-yl)imidazolidin-2-one to react with 4-fluorobenzyl bromide, the title compound was obtained as a yellow solid in 98% yield: $^1$H NMR (300 MHz, CDCl$_3$) δ 7.32-7.22 (m, 2H), 7.07-6.97 (m, 2H), 4.45 (s, 2H), 4.10-4.04 (m, 2H), 3.48-3.37 (m, 2H), 2.67 (s, 3H), 2.38 (s, 3H); MS (ES+) m/z 334.1 (M+1).

Preparation 16.4

Preparation of 1-(5-acetyl-4-methylthiazol-2-yl)-3-(3-(trifluoromethyl)benzyl)imidazolidin-2-one

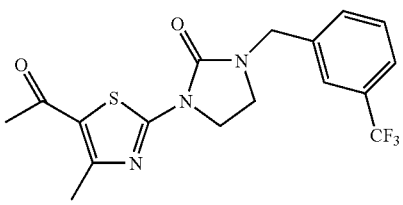

Following the procedure as describe in Preparation 16, making variations as required to replace ethyl 4-methyl-2-(5-oxo-1H-1,2,4-triazol-4(5H)-yl)thiazole-5-carboxylate with 1-(5-acetyl-4-methylthiazol-2-yl)imidazolidin-2-one to react with 3-(trifluoromethyl)benzyl bromide, the title compound was obtained as a yellow solid in 50% yield: mp 149-151° C.; $^1$H NMR (300 MHz, DMSO-d$_6$) δ 7.70-7.58 (m, 4H), 4.55 (s, 2H), 4.04 (t, J=6.0 Hz, 2H), 3.51 (t, J=6.0 Hz, 2H), 2.51 (s, 3H), 2.45 (s, 3H); $^{13}$C NMR (75 MHz, DMSO-d$_6$) δ 190.9, 160.4, 155.6, 155.1, 138.5, 132.5, 130.4, 129.9 (q, $^3J_{C-F}$=38 Hz), 126.6, 125.9, 125.1-124.8 (m), 122.9, 47.1, 42.6, 42.4, 30.5, 18.8; MS (ES+) m/z 384.2 (M+1).

Preparation 17

Preparation of 1-(4-fluorobenzyl)-4-(5-(hydroxymethyl)-4-methylthiazol-2-yl)-1H-1,2,4-triazol-5(4H)-one

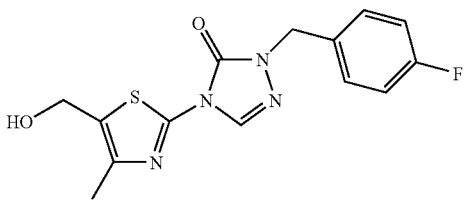

To a solution of ethyl 2-(1-(4-fluorobenzyl)-5-oxo-1H-1,2,4-triazol-4(5H)-yl)-4-methylthiazole-5-carboxylate (2.26 g, 6.23 mmol) in anhydrous tetrahydrofuran (60.0 mL) was added lithium aluminium hydride (0.35 g, 9.33 mmol) at 0° C. The reaction mixture was stirred at ambient temperature for 4 h, then quenched with 10% aqueous hydrochloric acid solution (3 mL) and extracted with ethyl acetate (3×50 mL). The combined organic layers were dried over anhydrous sodium sulfate and filtered. The filtrate was concentrated in vacuo and the residue was triturated with ether to the title compound: mp 164-166° C.; $^1$H NMR (300 MHz, DMSO-d$_6$) δ 8.64 (s, 1H), 7.30 (dd, J=8.7, 8.7 Hz, 2H), 7.15 (dd, J=8.7, 8.7 Hz, 2H), 4.96 (s, 2H), 4.57 (s, 2H), 2.22 (s, 3H); $^{13}$C NMR (75 MHz, DMSO-d$_6$) δ 163.7, 160.5, 150.2 (d, $^3J_{C-F}$=12 Hz), 143.2, 132.8 (d, $^3J_{C-F}$=11 Hz), 132.5, 130.7, 130.4 (d, $^3J_{C-F}$=33 Hz), 116.9 (d, $^3J_{C-F}$=86 Hz), 55.3, 48.1, 15.1; MS (ES+) m/z 321.2 (M+1).

Preparation 18

Preparation of 1-(5-acetyl-4-methylthiazol-2-yl)imidazolidin-2-one

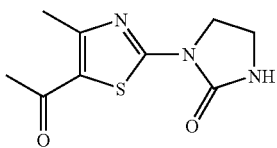

To a solution of 5-acetyl-2-amino-4-methylthiazole (5.50 g, 35.20 mmol) in tetrahydrofuran (200 mL) was added triethylamine (15.0 mL, 107.6 mmol) and 2-chloroethyl isocyanate (3.90 mL, 45.70 mmol). The reaction mixture was stirred at ambient temperature for 18 hours, and then heated to reflux for 27 hours. The solvent was removed in vacuo, and the residue was washed with water (200 mL) and ethyl acetate/hexanes (1/1, 50 mL) to afford the title compound in 99% yield (7.9 g): MS (ES+) m/z 226.1 (M+1).

Preparation 19

Preparation of 1-(5-acetyl-4-methylthiazol-2-yl)-3-(cyclopropylmethyl)imidazolidin-2-one

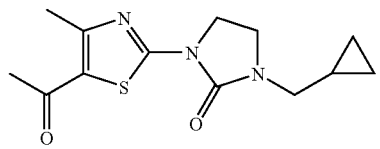

To a solution of 1-(5-acetyl-4-methylthiazol-2-yl)imidazolidin-2-one (2.25 g, 10.00 mmol), tetrabutylammonium iodide (0.10 g) and potassium carbonate (3.50 g, 25.27 mmol) in tetrahydrofuran (100 mL) was added cyclopropylmethyl bromide (2.0 mL, 20.88 mmol). The reaction mixture was heated to reflux for 50 hours. The solvent was removed in vacuo, and the residue was washed with water and hexanes to afford the title compound in 33% yield (0.94 g): mp 103-104° C. (ethyl acetate/hexanes); $^1$H NMR (300 MHz, CDCl$_3$) δ 4.14-4.05 (m, 2H), 3.72-3.69 (m, 2H), 3.19 (d, J=6.0 Hz, 2H), 2.57 (s, 3H), 2.44 (s, 3H), 0.99-0.89 (m, 1H), 0.59-0.55 (m, 2H), 0.27-0.22 (m, 2H); MS (ES+) m/z 280.2 (M+1).

Preparation 19.1

Preparation of 1-(5-acetyl-4-methylthiazol-2-yl)-3-(4-fluorobenzyl)imidazolidin-2-one

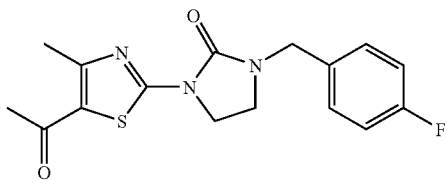

Following the procedure as describe in Preparation 19, making variations as required to replace cyclopropylmethyl bromide with 4-fluorobenzyl bromide to react with 1-(5-acetyl-4-methylthiazol-2-yl)imidazolidin-2-one, the title compound was obtained in 98% yield (3.27 g): $^1$H NMR (300 MHz, CDCl$_3$) δ 7.32-7.22 (m, 2H), 7.07-6.97 (m, 2H), 4.45 (s, 2H), 4.10-4.04 (m, 2H), 3.48-3.37 (m, 2H), 2.67 (s, 3H), 2.38 (s, 3H); MS (ES+) m/z 334.1 (M+1).

Preparation 20

Preparation of 2-(1-(4-fluorobenzyl)-5-oxo-1H-1,2,4-triazol-4(5H)-yl)-4-methylthiazole-5-carbonitrile

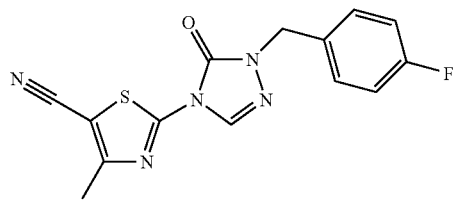

A mixture of 2-(1-(4-fluorobenzyl)-5-oxo-1H-1,2,4-triazol-4(5H)-yl)-4-methylthiazole-5-carboxamide (0.45 g, 1.35 mmol), pyridine (0.21 g, 2.71 mmol) and trifluoroacetic anhydride (0.57 g, 2.71 mmol) in dioxane (12.0 mL) was heated at reflux for 16 h and concentrated in vacuo to dryness. The residue was purified by column chromatography eluted with ethyl acetate in hexane (20%) to afford the title compound as a colourless solid (0.26 g, 63%): mp 190-192° C.; $^1$H NMR (300 MHz, DMSO-d$_6$) δ 8.80 (s, 1H), 7.38-7.33 (m, 2H), 7.18-7.12 (m, 2H), 4.97 (s, 2H), 2.49 (s, 3H); $^{13}$C NMR (75 MHz, DMSO-d$_6$) δ 162.2 (d), 161.3, 156.0, 150.3, 132.5, 132.4, 130.5 (d), 115.9 (d), 113.3, 97.5, 48.3, 17.2; MS (ES+) m/z 316.9 (M+1).

Preparation 20.1

Preparation of 2-(3-(4-fluorobenzyl)-2-oxoimidazolidin-1-yl)-4-methylthiazole-5-carbonitrile

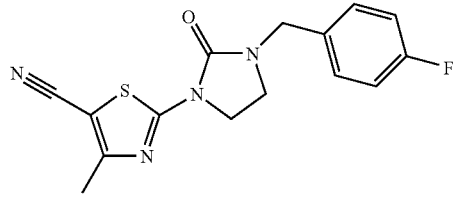

Following the procedure as describe in Preparation 20, making variations as required to replace 2-(1-(4-fluorobenzyl)-5-oxo-1H-1,2,4-triazol-4(5H)-yl)-4-methylthiazole-5-carboxamide with 2-(3-(4-fluorobenzyl)-2-oxoimidazolidin-1-yl)-4-methylthiazole-5-carboxamide, the title compound was obtained as a pale yellow solid in 68% yield: mp 136-139° C.; $^1$H NMR (300 MHz, DMSO-d$_6$) δ 7.35-7.31 (m, 2H), 7.18-7.13 (m, 2H), 4.41 (s, 2H), 4.00 (t, J=6.0 Hz, 2H), 3.46 (t, J=6.0 Hz, 2H) 2.37 (s, 3H); $^{13}$C NMR (75 MHz, DMSO-d$_6$) δ162.1 (d), 161.4, 161.1, 155.3, 150.3, 132.8 (d), 130.5 (d), 115.9 (d), 114.4, 92.4, 46.6, 42.7, 42.3, 17.3; MS (ES+) m/z 317.9 (M+1).

Example 1

Synthesis of 2-(1-(4-fluorobenzyl)-5-oxo-1H-1,2,4-triazol-4(5H)-yl)-4-methylthiazole-5-carboxamide

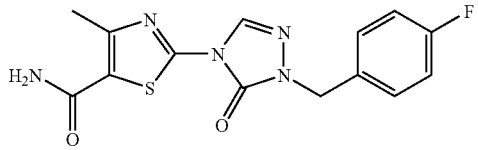

To a solution of 2-(1-(4-fluorobenzyl)-5-oxo-1H-1,2,4-triazol-4(5H)-yl)-4-methylthiazole-5-carboxylic acid (0.35 g, 1.05 mmol) in anhydrous N,N-dimethylformamide (10.0 mL) was added 1-hydroxybenzotriazole (0.28 g, 2.09 mmol), 2-(7-aza-1H-benzotriazole-1-yl)-1,1,3,3-tetramethyluronium hexafluorophosphate (HATU) (0.80 g, 2.09 mmol), N,N-diisopropylethylamine (1.09 mL, 6.28 mmol) and ammonium chloride (0.22 g, 4.19 mmol). The resulting solution was stirred at ambient temperature for 72 h and concentrated in vacuo. The residue was suspended in saturated aqueous sodium bicarbonate solution (100 mL). The crude product was filtered and washed with water (50 mL). The crude solid was recrystallized in ethanol to afford the title compound as an off-white solid (0.27 g, 73%): mp 232-233° C.; $^1$H NMR (300 MHz, DMSO-$d_6$) δ 8.75 (s, 1H), 7.64 (br, 2H), 7.40-7.36 (m, 2H), 7.22-7.16 (m, 2H), 5.00 (s, 2H), 2.55 (s, 3H); $^{13}$C NMR (75 MHz, DMSO-$d_6$) δ 162.7, 161.69 (d, $^1J_{C-F}$=243.5 Hz), 151.3, 150.9, 149.7, 132.2 (d, $^4J_{C-F}$=3.0 Hz), 132.0, 129.9 (d, $^3J_{C-F}$=8.4 Hz), 123.0, 115.4 (d, $^2J_{C-F}$=21.5 Hz), 47.7, 16.8; MS (ES+) m/z 334.3 (M+1).

Example 1.1

Synthesis of 2-[1-(cyclopropylmethyl)-5-oxo-1H-1,2,4-triazol-4(5H)-yl]-4-methylthiazole-5-carboxamide

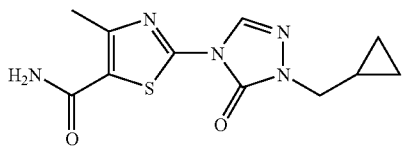

Following the procedure as described in Example 1, making variations as required to replace 2-(1-(4-fluorobenzyl)-5-oxo-1H-1,2,4-triazol-4(5H)-yl)-4-methylthiazole-5-carboxylic acid with 2-(1-(cyclopropylmethyl)-5-oxo-1H-1,2,4-triazol-4(5H)-yl)-4-methylthiazole-5-carboxylic acid, the title compound was obtained as an off-white solid in 43% yield: mp 180-181° C. (ethanol/water); $^1$H NMR (300 MHz, DMSO-$d_6$) δ 8.73 (s, 1H), 7.63 (br, 2H), 3.66 (d, J=7.0 Hz, 2H), 2.55 (s, 3H), 1.21-1.11 (m, 1H), 0.54-0.48 (m, 2H), 0.38-0.32 (m, 2H); $^{13}$C NMR (75 MHz, DMSO-$d_6$) δ 162.6, 151.3, 150.9, 149.5, 131.4, 122.9, 49.4, 16.8, 10.0, 3.3; MS (ES+) m/z 280.3 (M+1).

Example 1.2

Synthesis of 4-methyl-2-{2-oxo-3-[4-(trifluoromethyl)benzyl]imidazolidin-1-yl}thiazole-5-carboxamide

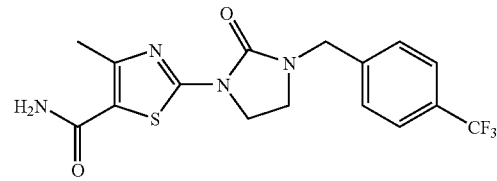

Following the procedure as described in Example 1, making variations as required to replace 2-(1-(4-fluorobenzyl)-5-oxo-1H-1,2,4-triazol-4(5H)-yl)-4-methylthiazole-5-carboxylic acid with 4-methyl-2-(2-oxo-3-(4-(trifluoromethyl)benzyl)-imidazolidin-1-yl)thiazole-5-carboxylic acid, the title compound was obtained as a colorless solid in 23% yield: mp 216-217° C. (hexanes/ethyl acetate); $^1$H NMR (300 MHz, DMSO-$d_6$) δ 7.74 (d, J=8.2 Hz, 2H), 7.55 (d, J=8.2 Hz, 2H), 7.32 (s, 2H), 4.54 (s, 2H), 4.02 (dd, J=9.0, 7.3 Hz, 2H), 3.49 (dd, J=9.0, 7.3 Hz, 2H), 2.46 (s, 3H); $^{13}$C NMR (75 MHz, DMSO-$d_6$) δ 163.5, 157.4, 155.2, 150.7, 141.5 (d, $J_{C-F}$=1.2 Hz), 128.5, 128.1 (q, $^2J_{C-F}$=31.6 Hz), 125.5 (q, $^3J_{C-F}$=3.8 Hz), 124.3 (q, $^1J_{C-F}$=272.2 Hz), 118.5, 46.5, 42.0, 41.8, 17.0; MS (ES+) m/z 384.9 (M+1).

Example 1.3

Synthesis of (S)-2-(3-(4-fluorobenzyl)-4-methyl-2-oxoimidazolidin-1-yl)-4-methylthiazole-5-carboxamide

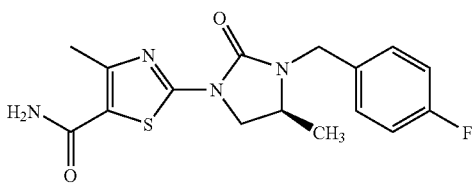

Following the procedure as described in Example 1, making variations as required to replace 2-(1-(4-fluorobenzyl)-5-oxo-1H-1,2,4-triazol-4(5H)-yl)-4-methylthiazole-5-carboxylic acid and 2-(1H-Benzotriazole-1-yl)-1,1,3,3-tetramethyluronium hexafluorophosphate (H BTU) with (S)-2-(3-(4-fluorobenzyl)-4-methyl-2-oxoimidazolidin-1-yl)-4-methylthiazole-5-carboxylic acid and 2-(1H-benzotriazole-1-yl)-1,1,3,3-tetramethyluronium tetrafluoroborate (TBTU), the title compound was obtained as a colorless solid in 67% yield: mp 192-194° C. (ethyl acetate/diethyl ether); $^1$H NMR (300 MHz, DMSO-$d_6$) δ 7.40-7.32 (m, 4H), 7.18 (dd, J=8.8, 8.8 Hz, 2H), 4.59 (d, J=15.6 Hz, 1H), 4.30 (d, J=15.6 Hz, 1H), 4.18 (dd, J=10.0, 9.1 Hz, 1H), 3.79-3.68 (m, 1H), 3.54 (dd, J=10.0, 6.8 Hz, 1H), 2.45 (s, 3H), 1.22 (d, J=6.2 Hz, 3H); $^{13}$C NMR (75 MHz, DMSO-$d_6$) δ 163.5, 161.5 (d, $^1J_{C-F}$=243 Hz), 157.3, 154.9, 150.7, 133.1 (d, $^4J_{C-F}$=3 Hz), 129.9 (d, $^3J_{C-F}$=8 Hz), 118.5, 115.4 (d, $^2J_{C-F}$=², Hz), 49.4, 48.6, 43.7, 18.4, 17.0; MS (ES+) m/z 348.8 (M+1).

Example 1.4

Synthesis of 4-methyl-2-(2-oxo-3-(4,4,4-trifluorobutyl)imidazolidin-1-yl)thiazole-5-carboxamide

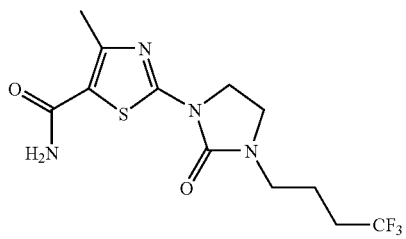

Following the procedure as described in Example 1, making variations as required to replace 2-(1-(4-fluorobenzyl)-5-oxo-1H-1,2,4-triazol-4(5H)-yl)-4-methylthiazole-5-carboxylic acid with 4-methyl-2-(2-oxo-3-(4,4,4-trifluorobutyl)-imidazolidin-1-yl)thiazole-5-carboxylic acid, the title compound was obtained as a colorless solid in 52% yield: $^1$H NMR (300 MHz, CDCl$_3$) δ 5.58 (s, 2H), 4.17-4.11 (m, 2H), 3.64-3.59 (m, 2H), 3.44-3.39 (m, 2H), 2.61 (s, 3H), 2.22-2.08 (m, 2H), 1.92-1.82 (m, 2H); $^{13}$C NMR (75 MHz, CDCl$_3$) δ164.3, 157.7, 155.6, 155.5, 153.8, 128.6, 124.9, 116.9, 42.9, 42.3, 42.0, 31.8, 31.4, 30.9, 30.6, 20.2, 20.1, 17.3; MS (ES+) m/z 336.8 (M+1).

Example 1.5

Synthesis of 2-(3-(cyclopropylmethyl)-2-oxoimidazolidin-1-yl)-4-methylthiazole-5-carboxamide

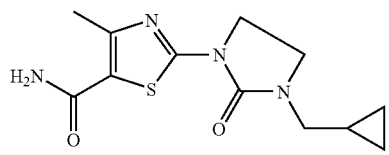

Following the procedure as described in Example 1, making variations as required to replace 2-(1-(4-fluorobenzyl)-5-oxo-1H-1,2,4-triazol-4(5H)-yl)-4-methylthiazole-5-carboxylic acid with 2-(3-(cyclopropylmethyl)-2-oxoimidazolidin-1-yl)-4-methylthiazole-5-carboxylic acid, the title compound was obtained as a colorless solid in 5% yield: mp 198-200° C. (methanol/hexanes); $^1$H NMR (300 MHz, DMSO-d$_6$) δ 7.29 (s, 2H), 4.02-3.97 (m, 2H), 3.67-3.62 (m, 2H), 3.10 (d, J=7.1 Hz, 2H), 2.45 (s, 3H), 0.99-0.90 (m, 1H), 0.52-0.46 (m, 2H), 0.25-0.20 (m, 2H); $^{13}$C NMR (75 MHz, DMSO-d$_6$) δ 163.5, 157.5, 154.7, 155.7, 118.2, 47.7, 41.9, 41.8 17.0, 8.8, 3.1; MS (ES+) m/z 281.1 (M+1).

Example 1.6

Synthesis of 2-(3-isobutyl-2-oxoimidazolidin-1-yl)-4-methylthiazole-5-carboxamide

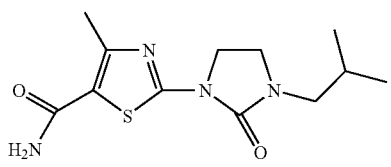

Following the procedure as described in Example 1, making variations as required to replace 2-(1-(4-fluorobenzyl)-5-oxo-1H-1,2,4-triazol-4(5H)-yl)-4-methylthiazole-5-carboxylic acid with 2-(3-isobutyl-2-oxoimidazolidin-1-yl)-4-methylthiazole-5-carboxylic acid, the title compound was obtained as a colorless solid in 54% yield: mp: 212-215° C. (methanol/hexanes); $^1$H NMR (300 MHz, CDCl$_3$) δ 5.69 (s, 2H), 4.13-4.08 (m, 2H), 3.61-3.56 (m, 2H), 3.12 (d, J=7.5 Hz, 2H), 2.60 (s, 3H); 1.97-1.88 (m, 1H), 0.94 (d, J=6.7 Hz, 6H); $^{13}$C NMR (75 MHz, CDCl$_3$) δ 165.5, 157.9, 155.6, 153.8, 116.6, 51.5, 42.8, 41.9, 26.7, 19.9, 17.2; MS (ES+) m/z 282.9 M+1).

Example 1.7

Synthesis of 2-(3-(3,4-difluorobenzyl)-2-oxoimidazolidin-1-yl)-4-methylthiazole-5-carboxamide

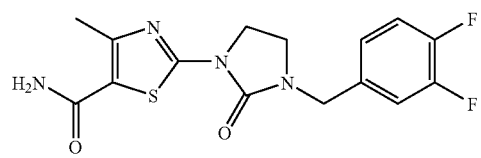

Following the procedure as described in Example 1, making variations as required to replace 2-(1-(4-fluorobenzyl)-5-oxo-1H-1,2,4-triazol-4(5H)-yl)-4-methylthiazole-5-carboxylic acid with 2-(3-(3,4-difluorobenzyl)-2-oxoimidazolidin-1-yl)-4-methylthiazole-5-carboxylic acid, the title compound was obtained as a colorless solid: mp 221-223° C.; $^1$H NMR (300 MHz, DMSO-d$_6$) δ 7.47-7.37 (m, 4H), 7.20-7.15 (m, 1H), 4.43 (s, 2H), 4.03-3.98 (m, 2H), 3.50-3.45 (m, 2H), 2.46 (s, 3H); MS (ES+) m/z 352.7 (M+1).

Example 1.8

Synthesis of 2-(3-(3,5-difluorobenzyl)-2-oxoimidazolidin-1-yl)-4-methylthiazole-5-carboxamide

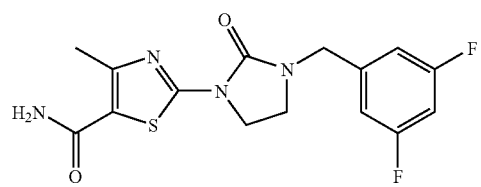

Following the procedure as described in Example 1, making variations as required to replace 2-(1-(4-fluorobenzyl)-5-oxo-1H-1,2,4-triazol-4(5H)-yl)-4-methylthiazole-5-carboxylic acid with 2-(3-(3,5-difluorobenzyl)-2-oxoimidazolidin-1-yl)-4-methylthiazole-5-carboxylic acid, the title compound was obtained as a colorless solid: mp >200° C.; $^1$H NMR (300 MHz, DMSO-d$_6$) δ 7.32 (br s, 2H), 7.21-7.04 (m, 3H), 4.47 (s, 2H), 4.05-4.00 (m, 2H), 3.54-3.48 (m, 2H), 2.47 (s, 3H); MS (ES+) m/z 352.8 (M+1).

Example 1.9

Synthesis of 4-methyl-2-(2-oxo-3-(4-(trifluoromethoxy)benzyl)imidazolidin-1-yl)thiazole-5-carboxamide

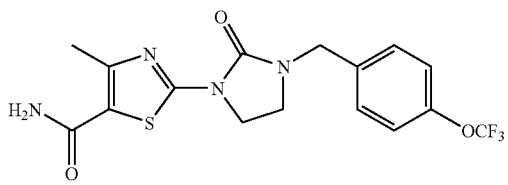

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with 4-methyl-2-(2-oxo-3-(4-(trifluoromethoxy)benzyl)-imidazolidin-1-yl)thiazole-5-carboxylic acid, the title compound was obtained as a colorless solid: mp 185-187° C.; $^1$H NMR (300 MHz, DMSO-d$_6$) δ 7.42 (d, J=8.7 Hz, 2H), 7.33 (d, J=8.2 Hz, 2H), 7.29 (br, 2H), 4.44 (s, 2H), 4.01 (t, J=7.3 Hz, 2H), 3.48 (t, J=7.3 Hz, 2H), 2.46 (s, 3H); MS (ES+) m/z 400.7 (M+1).

Example 1.10

Synthesis of 4-methyl-2-(2-oxo-3-((6-(trifluoromethyl)pyridine-3-yl)methyl)imidazolidin-1-yl)thiazole-5-carboxamide

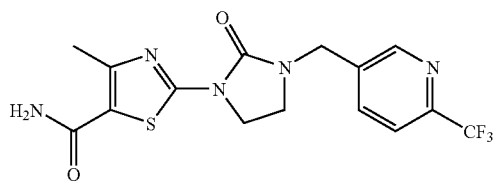

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with 4-methyl-2-(2-oxo-3-((6-(trifluoromethyl)pyridin-3-yl)methyl)imidazolidin-1-yl)thiazole-5-carboxylic acid, the title compound was obtained as a colorless solid: mp 225-228° C.; $^1$H NMR (300 MHz, DMSO-d$_6$) δ 8.75 (br, 2H), 8.04 (d, J=8.1 Hz, 1H), 7.92-7.89 (m, 2H), 4.61 (s, 2H), 4.06-3.99 (m, 2H), 3.58-3.53 (m, 2H), 2.50 (s, 3H); MS (ES+) m/z 386.2 (M+1).

Example 1.11

Synthesis of 2-(3-(3-fluoro-4-methoxybenzyl)-2-oxoimidazolidin-1-yl)-4-methylthiazole-5-carboxamide

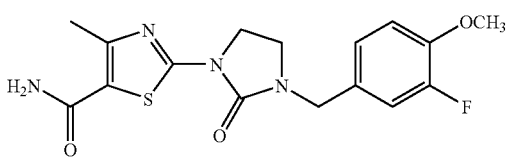

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with 2-(3-(3-fluoro-4-methoxybenzyl)-2-oxoimidazolidin-1-yl)-4-methylthiazole-5-carboxylic acid, the title compound was obtained as a colorless solid: mp 182-184° C.; $^1$H NMR (300 MHz, DMSO-d$_6$) δ 7.31 (br, 2H), 7.20-7.07 (m, 3H), 4.37 (s, 2H), 4.03-3.97 (m, 2H), 3.82 (s, 3H), 3.48-3.42 (m, 2H), 2.46 (s, 3H); MS (ES+) m/z 365.2 (M+1).

Example 1.12

Synthesis of (S)-2-(3-(4-fluorobenzyl)-5-methyl-2-oxoimidazolidin-1-yl)-4-methylthiazole-5-carboxamide

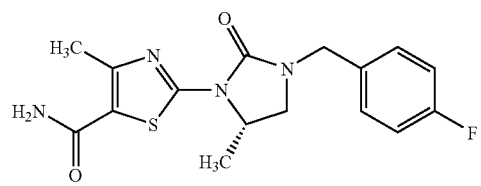

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with (S)-2-(3-(4-fluorobenzyl)-5-methyl-2-oxoimidazolidin-1-yl)-4-methylthiazole-5-carboxylic acid, the title compound was obtained as a colorless solid: mp 197-198° C.; $^1$H NMR (300 MHz, DMSO-d$_6$) δ 7.37-7.17 (m, 6H), 4.57-4.51 (m, 1H), 4.42 (d, J=5.4 Hz, 2H), 3.60 (dd, J=9.0, 9.0 Hz, 1H), 3.03 (dd, J=9.0, 3.4 Hz, 1H), 2.46 (s, 3H), 1.38 (d, J=6.2 Hz, 3H); MS (ES+) m/z 348.9 (M+1).

Example 1.13

Synthesis of 2-(3-(4-chlorobenzyl)-2-oxoimidazolidin-1-yl)-4-methylthiazole-5-carboxamide

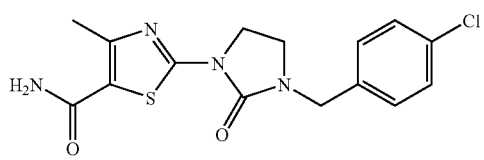

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with 2-(3-(4-chlorobenzyl)-2-oxoimidazolidin-1-yl)-4-methylthiazole-5-carboxylic acid, the title compound was obtained as a colorless solid: mp >200° C.; $^1$H NMR (300 MHz, DMSO-d$_6$) δ 7.46-7.37 (m, 6H), 4.47 (s, 2H), 4.03 (br s, 2H), 3.49-3.37 (m, 2H), 2.50 (s, 3H); MS (ES+) m/z 350.8 (M+1).

Example 1.14

Synthesis of (R)-2-(3-(3,5-difluorobenzyl)-4-methyl-2-oxoimidazolidin-1-yl)-4-methylthiazole-5-carboxamide

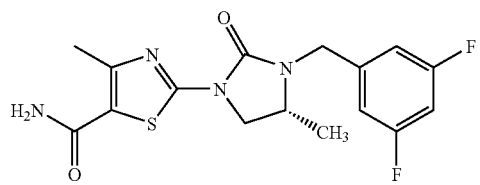

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with (R)-2-(3-(3,5-difluorobenzyl)-4-methyl-2-oxoimidazolidin-1-yl)-4-methylthiazole-5-carboxylic acid, the title compound was obtained as a colorless solid: mp 212-213° C.; $^1$H NMR (300 MHz, DMSO-$d_6$) δ 7.31 (br s, 2H), 7.18-7.07 (m, 3H), 4.57 (d, J=16.3 Hz, 1H), 4.39 (d, J=16.3 Hz, 1H), 4.22 (dd, J=10.0, 9.1 Hz, 1H), 3.87-3.79 (m, 1H), 3.58 (dd, J=10.0, 6.6 Hz, 1H), 2.46 (s, 3H), 1.22 (d, J=6.2 Hz, 3H); MS (ES+) m/z 366.9 (M+1).

Example 1.15

Synthesis of (R)-2-(3-(4-fluorobenzyl)-4-methyl-2-oxoimidazolidin-1-yl)-4-methylthiazole-5-carboxamide

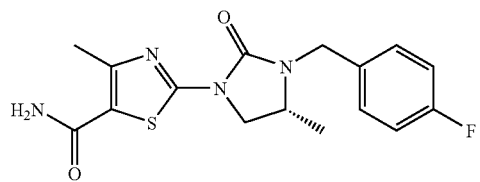

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with (R)-2-(3-(4-fluorobenzyl)-4-methyl-2-oxoimidazolidin-1-yl)-4-methylthiazole-5-carboxylic acid, the title compound was obtained as a colorless solid: mp 185-186° C.; $^1$H NMR (300 MHz, DMSO-$d_6$) δ 7.40-7.32 (m, 4H), 7.21-7.15 (m, 2H), 4.59 (d, J=15.6 Hz, 1H), 4.30 (d, J=15.6 Hz, 1H), 4.18 (dd, J=10.0, 9.1 Hz 1H), 3.77-3.70 (m, 1H), 3.54 (dd, J=10.1, 6.8 Hz, 1H), 2.45 (s, 3H), 1.22 (d, J=6.2 Hz, 3H); MS (ES+) m/z 348.9 (M+1).

Example 1.16

Synthesis of (R)-4-methyl-2-(4-methyl-2-oxo-3-(4-(trifluoromethyl)benzyl)imidazolidin-1-yl)thiazole-5-carboxamide

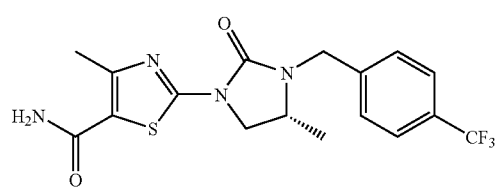

Following the procedure as described in Example 1, making variations as required to replace 2-(1-(4-fluorobenzyl)-5-oxo-1H-1,2,4-triazol-4(5H)-yl)-4-methyl-thiazole-5-carboxylic acid with (R)-4-methyl-2-(4-methyl-2-oxo-3-(4-(trifluoromethyl)-benzyl)imidazolidin-1-yl)thiazole-5-carboxylic acid, the title compound was obtained as a colorless solid: mp 110-112° C.; $^1$H NMR (300 MHz, DMSO-$d_6$) δ 7.73 (d, J=8.2 Hz, 2H), 7.56 (d, J=8.2 Hz, 2H), 7.32 (br, 2H), 4.66 (d, J=16.0 Hz, 1H), 4.45 (d, J=16.0 Hz, 1H), 4.21 (t, J=9.6 Hz, 1H), 3.83-3.76 (m, 1H), 3.57 (dd, J=10.2, 6.8 Hz, 1H), 2.46 (s, 3H), 1.22 (d, J=6.2 Hz, 3H); MS (ES+) m/z 399.0 (M+1).

Example 2

Synthesis of (S)-2-(3-(4-Fluorobenzyl)-4-methyl-2-oxoimidazolidin-1-yl)-4-methyl-N-(pyridin-3-ylmethyl)thiazole-5-carboxamide

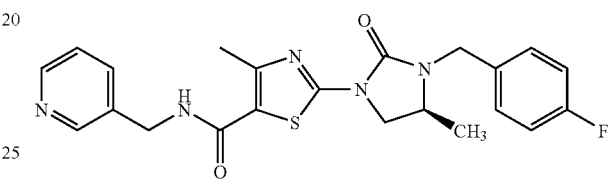

To a solution of (S)-2-(3-(4-fluorobenzyl)-4-methyl-2-oxoimidazolidin-1-yl)-4-methylthiazole-5-carboxylic acid (0.11 g, 0.30 mmol) in anhydrous tetrahydrofuran (3.0 mL) was added 1-hydroxybenzotriazole (HOBt) (0.08 g, 0.60 mmol), 2-(1H-benzotriazole-1-yl)-1,1,3,3-tetramethyluronium tetrafluoroborate (TBTU) (0.19 g, 0.60 mmol), N,N-diisopropylethylamine (0.23 g, 1.80 mmol) and pyridin-3-ylmethanamine (0.05 g, 0.45 mmol). The resulting mixture was stirred at ambient temperature for 16 h and concentrated in vacuo. The residue was diluted in ethyl acetate (100 mL), washed with saturated aqueous sodium bicarbonate solution (20 mL), dried over anhydrous sodium sulphate and filtered. The filtrate was concentrated in vacuo and the residue was purified by column chromatography eluted with 2-8% methanol in dichloromethane to afford the title compound as a colorless solid (0.09 g, 70%): mp 67-70° C. (hexanes/diethyl ether); $^1$H NMR (300 MHz, DMSO-$d_6$) δ 8.57 (t, J=5.9 Hz, 1H), 8.53 (d, J=1.9 Hz, 1H), 8.45 (dd, J=4.8, 1.5 Hz, 1H), 7.72-7.69 (m, 1H), 7.40-7.34 (m, 3H), 7.18 (dd, J=8.8, 8.8 Hz, 2H), 4.59 (d, J=15.6 Hz, 1H), 4.40 (d, J=5.9 Hz, 2H), 4.30 (d, J=15.6 Hz, 1H), 4.19 (dd, J=10.1, 9.1 Hz, 1H), 3.80-3.69 (m, 1H), 3.55 (dd, J=10.1, 6.2 Hz, 1H), 2.47 (s, 3H), 1.22 (d, J=6.2 Hz, 3H); $^{13}$C NMR (75 MHz, DMSO-$d_6$) δ161.5 (d, $^1J_{C\text{-}F}$=244 Hz), 161.8, 157.2, 154.9, 151.2, 148.8, 148.0, 135.1, 135.1, 133.1 (d, $^4J_{C\text{-}F}$=3 Hz), 130.0 (d, $^3J_{C\text{-}F}$=8 Hz), 123.5, 117.6, 115.4 (d, $^2J_{C\text{-}F}$=21 Hz), 49.4, 48.6, 43.7, 40.4, 18.4, 17.1; MS (ES+) m/z 439.9 (M+1).

Example 2.1

Synthesis of (S)—N-(3,4-difluorobenzyl)-2-(3-(4-fluorobenzyl)-4-methyl-2-oxoimidazolidin-1-yl)-4-methylthiazole-5-carboxamide

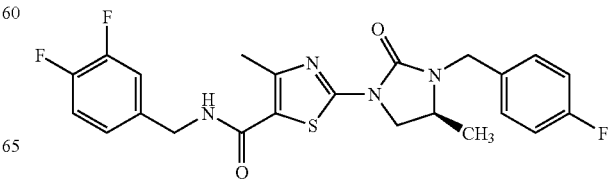

Following the procedure as described in Example 2, making variations as required to replace pyridin-3-ylmethanamine with 3,4-difluorobenzylamine to react with (S)-2-(3-(4-fluorobenzyl)-4-methyl-2-oxoimidazolidin-1-yl)-4-methylthiazole-5-carboxylic acid, the title compound was obtained as an off-white solid in 74% yield: mp 62-65° C. (diethyl ether); $^1$H NMR (300 MHz, DMSO-$d_6$) δ 8.54 (t, J=5.9 Hz, 1H), 7.44-7.30 (m, 4H), 7.21-7.12 (m, 3H), 4.60 (d, J=15.6 Hz, 1H), 4.35 (d, J=5.9 Hz, 2H), 4.30 (d, J=15.6 Hz, 1H), 4.19 (dd, J=10.0, 9.1 Hz, 1H), 3.80-3.69 (m, 1H), 3.55 (dd, J=10.0, 6.2 Hz, 1H), 2.47 (s, 3H), 1.22 (d, J=6.2 Hz, 3H); $^{13}$C NMR (75 MHz, DMSO-$d_6$) δ 161.8, 161.5 (d, $^1J_{C-F}$=244 Hz), 157.2, 154.9, 151.3, 150.4 (dd, $J_{C-F}$=66, 13 Hz), 147.1 (dd, $J_{C-F}$=66, 13 Hz), 137.6 (dd, $J_{C-F}$=5, 4 Hz), 133.1 (d, $^4J_{C-F}$=3 Hz), 130.0 (d, $^3J_{C-F}$=8 Hz), 124.0 (dd, $J_{C-F}$=7, 3 Hz), 117.6, 117.3 (d, $J_{C-F}$=17 Hz), 116.3 (d, $J_{C-F}$=17 Hz), 115.4 (d, $^2J_{C-F}$=21 Hz), 49.4, 48.6, 43.7, 41.7, 18.4, 17.1; MS (ES+) m/z 474.8 (M+1).

Example 2.2

Synthesis of 2-(3-(4-fluorobenzyl)-2-oxoimidazolidin-1-yl)-4-methyl-N-((3-methyl-1H-pyrazol-5-yl)methyl)thiazole-5-carboxamide

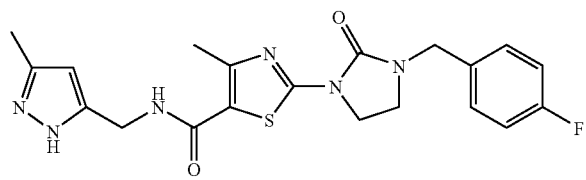

Following the procedure as described in Example 2, making variations as required to replace pyridin-3-ylmethanamine with (3-methyl-1H-pyrazol-5-yl)methanamine to react 2-(3-(4-fluorobenzyl)-2-oxoimidazolidin-1-yl)-4-methylthiazole-5-carboxylic acid instead of (S)-2-(3-(4-fluorobenzyl)-4-methyl-2-oxoimidazolidin-1-yl)-4-methylthiazole-5-carboxylic acid, the title compound was obtained as an off-white solid (0.04 g, 12%): mp 225-226° C. (ethyl acetate); $^1$H NMR (300 MHz, DMSO-$d_6$) δ 12.22 (s, 1H), 8.30 (t, J=5.0 Hz, 1H), 7.38-7.34 (m, 2H), 7.23-7.17 (m, 2H), 5.89 (s, 1H), 4.42 (s, 2H), 4.29 (d, J=5.7 Hz, 2H), 4.02-3.97 (m, 2H), 2.48-3.42 (m, 2H), 2.46 (s, 3H), 2.16 (s, 3H); $^{13}$C NMR (75 MHz, DMSO-$d_6$) δ 161.6, 161.5 (d, $^1J_{C-F}$=243 Hz), 157.3, 155.0, 150.5 (br), 132.6 (d, $^4J_{C-F}$=3 Hz), 129.9 (d, $^3J_{C-F}$=8 Hz), 118.2, 115.4 (d, $^2J_{C-F}$=21 Hz), 102.5, 46.1, 41.9, 41.5, 36.8 (br), 17.0, 10.6 (br); MS (ES+) m/z 428.9 (M+1).

Example 2.3

Synthesis of 2-(1-(4-Fluorobenzyl)-5-oxo-1H-1,2,4-triazol-4(5H)-yl)-4-methyl-N-((3-methyl-1H-pyrazol-5-yl)methyl)thiazole-5-carboxamide

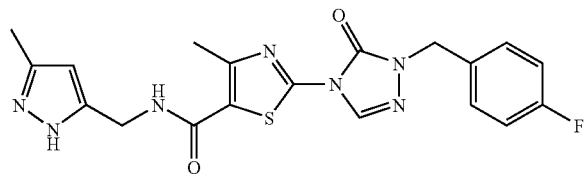

Following the procedure as described in Example 2, making variations as required to replace pyridin-3-ylmethanamine with (3-methyl-1H-pyrazol-5-yl)methanamine to react with 2-(1-(4-fluorobenzyl)-5-oxo-1H-1,2,4-triazol-4(5H)-yl)-4-methylthiazole-5-carboxylic acid instead of (S)-2-(3-(4-fluorobenzyl)-4-methyl-2-oxoimidazolidin-1-yl)-4-methylthiazole-5-carboxylic acid, the title compound was obtained as an off-white solid in 31% yield: mp 234-235° C. (diethyl ether); $^1$H NMR (300 MHz, DMSO-$d_6$) δ 12.25 (s, 1H), 8.76 (s, 1H), 8.67 (t, J=5.5 Hz, 1H), 7.41-7.36 (m, 2H), 7.27-7.16 (m, 2H), 5.91 (s, 1H), 5.00 (s, 2H), 4.37-4.31 (m, 2H), 2.55 (s, 3H), 2.19-2.12 (m, 3H); $^{13}$C NMR (75 MHz, DMSO-$d_6$) δ 161.7 (d, $^1J_{C-F}$=244 Hz), 160.7, 151.2, 150.5, 149.7, 149.6, 138.7, 132.2 (d, $^4J_{C-F}$=3 Hz), 132.1, 130.0 (d, $^3J_{C-F}$=8 Hz), 122.9, 115.4 (d, $^2J_{C-F}$=22 Hz), 102.3, 47.7, 37.3, 16.9, 10.4; MS (ES+) m/z 427.8 (M+1), MS (ES−) m/z 425.8 (M−1).

Example 2.4

Synthesis of 2-(3-(but-3-enyl)-2-oxoimidazolidin-1-yl)-4-methyl-N-(pyridin-3-ylmethyl)thiazole-5-carboxamide

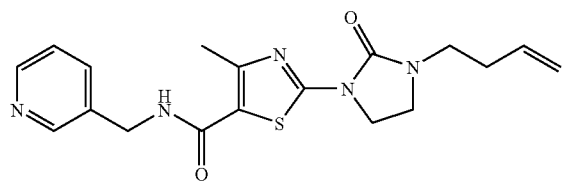

Following the procedure as described in Example 2, making variations as required to replace (S)-2-(3-(4-fluorobenzyl)-4-methyl-2-oxoimidazolidin-1-yl)-4-methylthiazole-5-carboxylic acid with 2-(3-(but-3-enyl)-2-oxoimidazolidin-1-yl)-4-methylthiazole-5-carboxylic acid to react with pyridin-3-ylmethanamine, the title compound was obtained as an off-white solid in 62% yield: mp 144-145° C. (ethyl acetate); $^1$H NMR (300 MHz, DMSO-$d_6$) δ 8.57-8.52 (m, 2H), 8.45 (d, J=3.8 Hz, 1H), 7.70 (ddd, J=7.8, 7.8, 1.8 Hz, 1H), 7.35 (dd, J=7.8, 4.8 Hz, 1H), 5.85-5.72 (m, 1H), 5.15-5.01 (m, 2H), 4.39 (d, J=5.8 Hz, 2H), 3.98 (d, J=9.0, 7.1 Hz, 2H), 3.59-3.54 (m, 2H), 3.31 (t, J=7.0 Hz, 2H), 2.47 (s, 3H), 2.32-2.25 (m, 2H); $^{13}$C NMR (75 MHz, DMSO-$d_6$) δ161.9, 157.4, 154.9, 151.2, 148.8, 148.0, 135.5, 135.1, 135.1, 123.4, 117.3, 116.8, 42.4, 41.9, 41.6, 40.4, 31.1, 17.1; MS (ES+) m/z 372.1 (M+1).

Example 2.5

Synthesis of (R)-2-(3-(4-fluorobenzyl)-4-methyl-2-oxoimidazolidin-1-yl)-4-methyl-N-(pyridin-2-ylmethyl)thiazole-5-carboxamide

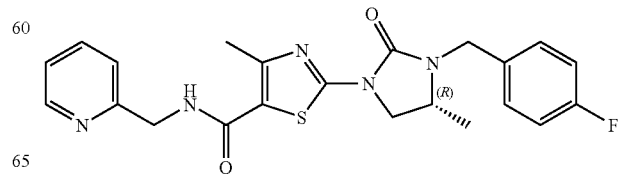

Following the procedure as described in Example 2, making variations as required to replace pyridin-3-ylmethanamine with pyridin-2-ylmethanamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-4-methyl-2-oxoimidazolidin-1-yl)-4-methylthiazole-5-carboxylic acid, the title compound was obtained as a white solid (48%): mp 118-119° C. (ethanol/water); $^1$H NMR (300 MHz, DMSO-d$_6$) δ 8.54-8.50 (m, 2H), 7.79-7.75 (m, 1H), 7.40-7.16 (m, 6H), 4.60 (d, J=15.6 Hz, 1H), 4.49 (d, J=5.8 Hz, 2H), 4.31 (d, J=15.6 Hz, 1H), 4.20 (dd, J=10.0, 9.2 Hz, 1H), 3.79-3.72 (m, 1H), 3.56 (dd, J=10.0, 6.8 Hz, 1H), 2.49 (s, 3H), 1.23 (d, J=6.1 Hz, 3H); MS (ES+) m/z 439.9 (M+1).

Example 2.6

Synthesis of (R)—N-(3,4-difluorobenzyl)-2-(3-(4-fluorobenzyl)-4-methyl-2-oxoimidazolidin-1-yl)-4-methylthiazole-5-carboxamide

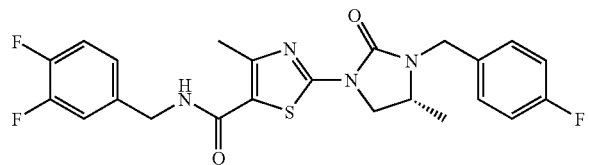

Following the procedure as described in Example 2, making variations as required to replace pyridin-3-ylmethanamine with 3,4-difluorobenzylamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-4-methyl-2-oxoimidazolidin-1-yl)-4-methylthiazole-5-carboxylic acid the title compound was obtained as a white solid: mp 134-135° C. (diethyl ether/hexanes); $^1$H NMR (300 MHz, DMSO-d$_6$) δ 8.54 (t, J=5.9 Hz, 1H), 7.44-7.30 (m, 4H), 7.21-7.12 (m, 3H), 4.60 (d, J=15.6 Hz, 1H), 4.35 (d, J=5.9 Hz, 2H), 4.30 (d, J=15.6 Hz, 1H), 4.19 (dd, J=10.0, 9.1 Hz, 1H), 3.80-3.69 (m, 1H), 3.55 (dd, J=10.0, 6.8 Hz, 1H), 2.47 (s, 3H), 1.22 (d, J=6.2 Hz, 3H); MS (ES+) m/z 475.0 (M+1).

Example 2.7

Synthesis of (R)-2-(3-(4-Fluorobenzyl)-4-methyl-2-oxoimidazolidin-1-yl)-4-methyl-N-(pyridin-3-ylmethyl)thiazole-5-carboxamide

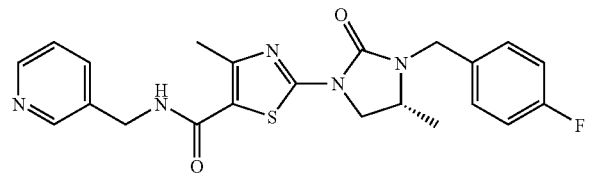

Following the procedure as described in Example 2, making variations as required to replace (S)-2-(3-(4-fluorobenzyl)-4-methyl-2-oxoimidazolidin-1-yl)-4-methylthiazole-5-carboxylic acid with (R)-2-(3-(4-fluorobenzyl)-4-methyl-2-oxoimidazolidin-1-yl)-4-methylthiazole-5-carboxylic acid the title compound was obtained as a white solid: mp 135-136° C. (diethyl ether/hexane); $^1$H NMR (300 MHz, DMSO-d$_6$) δ 8.57 (t, J=5.9 Hz, 1H), 8.53 (d, J=1.9 Hz, 1H), 8.45 (dd, J=4.8, 1.5 Hz, 1H), 7.73-7.68 (m, 1H), 7.40-7.34 (m, 3H), 7.21-7.15 (m, 2H), 4.59 (d, J=15.6 Hz, 1H), 4.40 (d, J=5.9 Hz, 2H), 4.30 (d, J=15.6 Hz, 1H), 4.19 (dd, J=10.1, 9.1 Hz, 1H), 3.80-3.69 (m, 1H), 3.55 (dd, J=10.1, 6.8 Hz, 1H), 2.47 (s, 3H), 1.22 (d, J=6.2 Hz, 3H); MS (ES+) m/z 440.2 (M+1).

Example 2.8

Synthesis of (R)-2-(3-(4-fluorobenzyl)-4-methyl-2-oxoimidazolidin-1-yl)-4-methyl-N-(thiazol-5-ylmethyl)thiazole-5-carboxamide

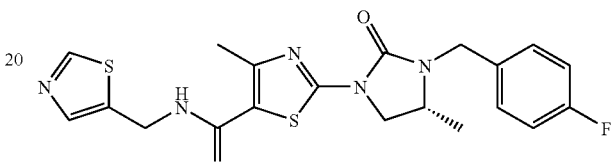

Following the procedure as described in Example 2, making variations as required to replace pyridin-3-ylmethanamine with thiazol-5-ylmethanamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-4-methyl-2-oxoimidazolidin-1-yl)-4-methylthiazole-5-carboxylic acid the title compound was obtained as a white solid: mp 66-69° C. (hexane); $^1$H NMR (300 MHz, DMSO-d$_6$) δ 8.93 (s, 1H), 8.62 (t, J=5.7 Hz, 1H), 7.75 (s, 1H), 7.36-7.31 (m, 2H), 7.17-7.12 (m, 2H), 4.58-4.53 (m, 3H), 4.26 (d, J=15.6 Hz, 1H), 4.15 (t, J=9.6 Hz, 1H), 3.74-3.67 (m, 1H), 3.51 (dd, J=10.1, 6.8 Hz, 1H), 2.43 (s, 3H), 1.22 (d, J=6.1 Hz, 3H); MS (ES+) m/z 445.6 (M+1).

Example 2.9

Synthesis of (R)-2-(3-(4-fluorobenzyl)-4-methyl-2-oxoimidazolidin-1-yl)-4-methyl-N-((3-methyl-1H-pyrazol-5-yl)methyl)thiazole-5-carboxamide

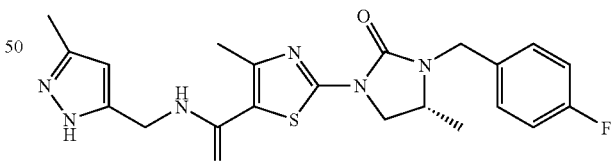

Following the procedure as described in Example 2, making variations as required to replace pyridin-3-ylmethanamine with (3-methyl-1H-pyrazol-5-yl)-methanamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-4-methyl-2-oxoimidazolidin-1-yl)-4-methylthiazole-5-carboxylic acid the title compound was obtained as a white solid: mp 215-216° C. (ethyl acetate); $^1$H NMR (300 MHz, DMSO-d$_6$) δ 12.22 (s, 1H), 8.31 (br, 1H), 7.40-7.35 (m, 2H), 7.22-7.16 (m, 2H), 5.89 (s, 1H), 4.59 (d, J=15.5 Hz, 1H), 4.33-4.16 (m, 4H), 3.78-3.71 (m, 1H), 3.55

(dd, J=10.1, 6.8 Hz, 1H), 2.46 (s, 3H), 2.17 (s, 3H), 1.22 (d, J=6.1 Hz, 3H); MS (ES+) m/z 442.9 (M+1).

Example 2.10

Synthesis of (R)—N-(3,5-difluorobenzyl)-2-(3-(4-fluorobenzyl)-4-methyl-2-oxoimidazolidin-1-yl)-4-methylthiazole-5-carboxamide

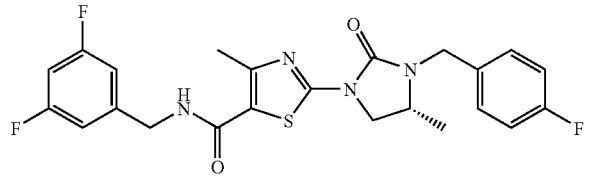

Following the procedure as described in Example 2, making variations as required to replace pyridin-3-ylmethanamine with (3,5-difluorophenyl)methanamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-4-methyl-2-oxoimidazolidin-1-yl)-4-methylthiazole-5-carboxylic acid the title compound was obtained as a white solid: mp 159-160° C. (ethyl acetate/hexane); $^1$H NMR (300 MHz, DMSO-$d_6$) δ 8.75 (t, J=5.6 Hz, 1H), 7.40-7.35 (m, 2H), 7.21-6.99 (m, 5H), 4.60 (d, J=15.6 Hz, 1H), 4.39 (d, J=5.6 Hz, 2H), 4.30 (d, J=15.6 Hz, 1H), 4.20 (dd, J=10.1, 9.1 Hz, 1H), 3.78-3.71 (m, 1H), 3.56 (dd, J=10.2, 6.8 Hz, 1H), 2.48 (s, 3H), 1.22 (d, J=6.1 Hz, 3H); MS (ES+) m/z 474.9 (M+1).

Example 2.11

Synthesis of (R)-2-(3-(4-fluorobenzyl)-4-methyl-2-oxoimidazolidin-1-yl)-4-methyl-N-((5-methylisoxazol-3-yl)methyl)thiazole-5-carboxamide

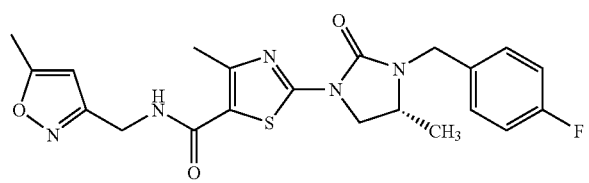

Following the procedure as described in Example 2, making variations as required to replace pyridin-3-ylmethanamine with (5-methylisoxazol-3-yl)methanamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-4-methyl-2-oxoimidazolidin-1-yl)-4-methylthiazole-5-carboxylic acid the title compound was obtained as a white solid: mp 139-140° C. (diethyl ether); $^1$H NMR (300 MHz, DMSO-$d_6$) δ 8.51 (t, J=5.8 Hz, 1H), 7.40-7.35 (m, 2H), 7.21-7.15 (m, 2H), 6.14 (d, J=0.4 Hz, 1H), 4.60 (d, J=15.6 Hz, 1H), 4.37-4.16 (m, 4H), 3.78-3.71 (m, 1H), 3.55 (dd, J=10.2, 6.8 Hz, 1H), 2.47 (s, 3H), 2.37 (s, 3H), 1.22 (d, J=6.2 Hz, 3H); MS (ES+) m/z 443.9 (M+1).

Example 2.12

Synthesis of (R)-2-(3-(3,5-difluorobenzyl)-4-methyl-2-oxoimidazolidin-1-yl)-4-methyl-N-(pyridin-2-ylmethyl)thiazole-5-carboxamide

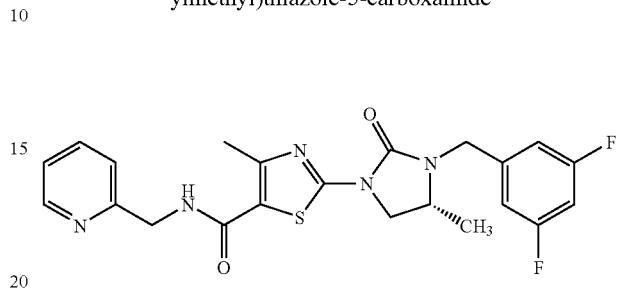

Following the procedure as described in Example 2, making variations as required to replace pyridin-3-ylmethanamine with pyridin-2-ylmethanamine and replace (S)-2-(3-(4-fluorobenzyl)-4-methyl-2-oxoimidazolidin-1-yl)-4-methylthiazole-5-carboxylic acid with (R)-2-(3-(3,5-difluorobenzyl)-4-methyl-2-oxoimidazolidin-1-yl)-4-methylthiazole-5-carboxylic acid, the title compound was obtained as a white solid: mp 147-148° C.; $^1$H NMR (300 MHz, DMSO-$d_6$) δ 8.55-8.50 (m, 2H), 7.79-7.73 (m, 1H), 7.31-7.24 (m, 2H), 7.19-7.08 (m, 3H), 4.60-4.37 (m, 4H), 4.27-4.20 (m, 1H), 3.88-3.81 (m, 1H), 3.60 (dd, J=10.1, 6.7 Hz, 1H), 2.50 (s, 3H), 1.23 (d, J=6.2 Hz, 3H); MS (ES+) m/z 458.0 (M+1).

Example 2.13

Synthesis of (R)-2-(3-(3,5-difluorobenzyl)-4-methyl-2-oxoimidazolidin-1-yl)-4-methyl-N-((5-methylpyrazin-2-yl)methyl)thiazole-5-carboxamide

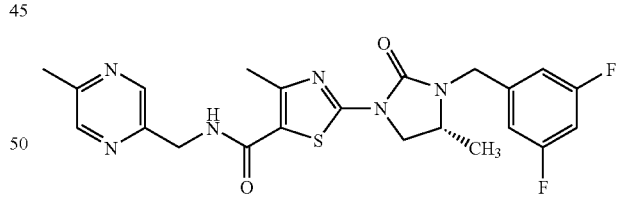

Following the procedure as described in Example 2, making variations as required to replace pyridin-3-ylmethanamine with (5-methylpyrazin-2-yl)methanamine and replace (S)-2-(3-(4-fluorobenzyl)-4-methyl-2-oxoimidazolidin-1-yl)-4-methylthiazole-5-carboxylic acid with (R)-2-(3-(3,5-difluorobenzyl)-4-methyl-2-oxoimidazolidin-1-yl)-4-methylthiazole-5-carboxylic acid, the title compound was obtained as a white solid: mp 131-132° C. (ethanol/water); $^1$H NMR (300 MHz, DMSO-$d_6$) δ 8.58 (t, J=5.7 Hz, 1H), 8.47-8.46 (m, 2H), 7.19-7.08 (m, 3H), 4.60-4.37 (m, 4H), 4.23 (t, J=9.6 Hz, 1H), 3.87-3.80 (m, 1H), 3.59 (dd, J=10.1, 6.7 Hz, 1H), 2.48 (s, 3H), 2.47 (s, 3H), 1.22 (d, J=6.2 Hz, 3H); MS (ES+) m/z 473.0 (M+1).

Example 2.14

Synthesis of (R)-2-(3-(3,5-difluorobenzyl)-4-methyl-2-oxoimidazolidin-1-yl)-4-methyl-N-((5-methylisoxazol-3-yl)methyl)thiazole-5-carboxamide

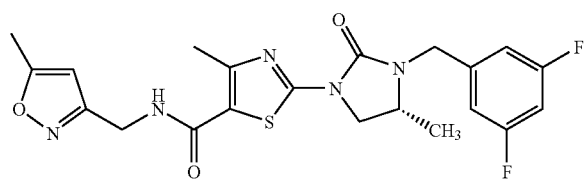

Following the procedure as described in Example 2, making variations as required to replace pyridin-3-ylmethanamine with (5-methylisoxazol-3-yl)methanamine and replace (S)-2-(3-(4-fluorobenzyl)-4-methyl-2-oxoimidazolidin-1-yl)-4-methylthiazole-5-carboxylic acid with (R)-2-(3-(3,5-difluorobenzyl)-4-methyl-2-oxoimidazolidin-1-yl)-4-methylthiazole-5-carboxylic acid, the title compound was obtained as a white solid: mp 63-66° C. (diethyl ether); $^1$H NMR (300 MHz, DMSO-$d_6$) δ 8.50 (t, J=5.4 Hz, 1H), 7.17-7.08 (m, 3H), 6.14 (s, 1H), 4.57 (d, J=16.2 Hz, 1H), 4.42-4.36 (m, 3H), 4.25-4.21 (m, 1H), 3.88-3.81 (m, 1H), 3.62-3.57 (m, 1H), 2.48 (s, 3H), 2.37 (s, 3H), 1.23 (d, J=5.9 Hz, 3H); MS (ES+) m/z 462.0 (M+1).

Example 2.15

Synthesis of (S)-2-(3-(4-fluorobenzyl)-5-methyl-2-oxoimidazolidin-1-yl)-4-methyl-N-(pyridin-2-ylmethyl)thiazole-5-carboxamide

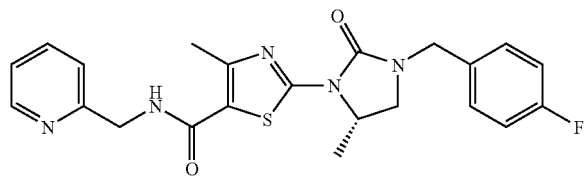

Following the procedure as described in Example 2, making variations as required to replace pyridin-3-ylmethanamine with pyridin-2-ylmethanamine and replace (S)-2-(3-(4-fluorobenzyl)-4-methyl-2-oxoimidazolidin-1-yl)-4-methylthiazole-5-carboxylic acid with (S)-2-(3-(4-fluorobenzyl)-5-methyl-2-oxoimidazolidin-1-yl)-4-methylthiazole-5-carboxylic acid, the title compound was obtained as a white solid (72%): mp 112-113° C. (diethyl ether/hexane); $^1$H NMR (300 MHz, DMSO-$d_6$) δ 8.50-8.46 (m, 2H), 7.75-7.70 (m, 1H), 7.34-7.14 (m, 6H), 4.56-4.51 (m, 1H), 4.46-4.39 (m, 4H), 3.56-3.50 (m, 1H), 3.01 (dd, J=9.1, 3.4 Hz, 1H), 2.46 (s, 3H), 1.36 (d, J=6.2 Hz, 3H); MS (ES+) m/z 439.9 (M+1).

Example 2.16

Synthesis of (S)-2-(3-(4-fluorobenzyl)-5-methyl-2-oxoimidazolidin-1-yl)-4-methyl-N-((1-methyl-1H-pyrazol-4-yl)methyl)thiazole-5-carboxamide

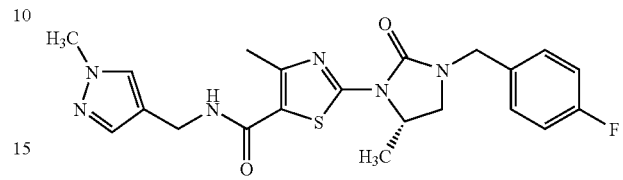

Following the procedure as described in Example 2, making variations as required to replace pyridin-3-ylmethanamine with (1-methyl-1H-pyrazol-4-yl)methanamine and replace (S)-2-(3-(4-fluorobenzyl)-4-methyl-2-oxoimidazolidin-1-yl)-4-methylthiazole-5-carboxylic acid with (S)-2-(3-(4-fluorobenzyl)-5-methyl-2-oxoimidazolidin-1-yl)-4-methylthiazole-5-carboxylic acid, the title compound was obtained as a white solid (70%): mp 176-177° C. (N,N-dimethylformamide/water); $^1$H NMR (300 MHz, DMSO-$d_6$) δ 8.28 (t, J=5.7 Hz, 1H), 7.56 (s, 1H), 7.36-7.32 (m, 3H), 7.23-7.17 (m, 2H), 4.57-4.50 (m, 1H), 4.42 (d, J=4.4 Hz, 2H), 4.19 (d, J=5.7 Hz, 2H), 3.78 (s, 3H), 3.63-3.57 (m, 1H), 3.03 (dd, J=9.0, 3.4 Hz, 1H), 2.46 (s, 3H), 1.38 (d, J=6.0 Hz, 3H); MS (ES+) m/z 443.1 (M+1).

Example 2.17

Synthesis of (S)-2-(3-(4-fluorobenzyl)-5-methyl-2-oxoimidazolidin-1-yl)-4-methyl-N-((5-methylisoxazol-3-yl)methyl)thiazole-5-carboxamide

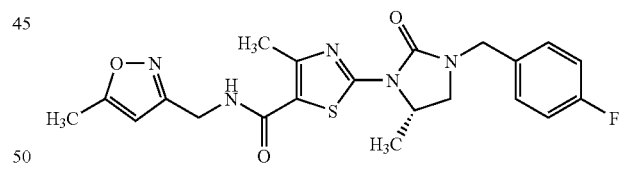

Following the procedure as described in Example 2, making variations as required to replace pyridin-3-ylmethanamine with (5-methylisoxazol-3-yl)methanamine and replace (S)-2-(3-(4-fluorobenzyl)-4-methyl-2-oxoimidazolidin-1-yl)-4-methylthiazole-5-carboxylic acid with (S)-2-(3-(4-fluorobenzyl)-5-methyl-2-oxoimidazolidin-1-yl)-4-methylthiazole-5-carboxylic acid, the title compound was obtained as a white solid (70%): mp 174-175° C. (N,N-dimethylformamide/water); $^1$H NMR (300 MHz, DMSO-$d_6$) δ 8.48 (t, J=5.8 Hz, 1H), 7.37-7.32 (m, 2H), 7.23-7.17 (m, 2H), 6.13 (d, J=0.7 Hz, 1H), 4.58-4.52 (m, 1H), 4.43 (d, J=4.3 Hz, 2H), 4.36 (d, J=5.8 Hz, 2H), 3.64-3.58 (m, 1H), 3.04 (dd, J=9.0, 3.4 Hz, 1H), 2.48 (s, 3H), 2.37 (d, J=0.7 Hz, 3H), 1.39 (d, J=6.0 Hz, 3H); MS (ES+) m/z 443.8 (M+1).

Example 2.18

Synthesis of (R)-2-(3-(4-fluorobenzyl)-5-methyl-2-oxoimidazolidin-1-yl)-4-methyl-N-(pyridin-2-ylmethyl)thiazole-5-carboxamide

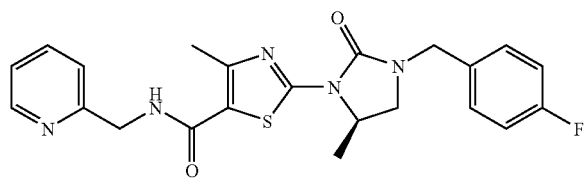

Following the procedure as described in Example 2, making variations as required to replace pyridin-3-ylmethanamine with pyridin-2-ylmethanamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-5-methyl-2-oxoimidazolidin-1-yl)-4-methylthiazole-5-carboxylic acid, the title compound was obtained as a white solid (68%): mp 55-57° C. (diethyl ether/hexane); $^1$H NMR (300 MHz, DMSO-$d_6$) δ 8.54-8.50 (m, 2H), 7.79-7.73 (m, 1H), 7.37-7.17 (m, 6H), 4.59-4.43 (m, 5H), 3.64-3.58 (m, 1H), 3.04 (dd, J=9.1, 3.2 Hz, 1H), 2.50 (s, 3H), 1.39 (d, J=6.2 Hz, 3H); MS (ES+) m/z 440.0 (M+1).

Example 2.19

Synthesis of (R)-2-(3-(4-fluorobenzyl)-5-methyl-2-oxoimidazolidin-1-yl)-4-methyl-N-(thiazol-5-ylmethyl)thiazole-5-carboxamide

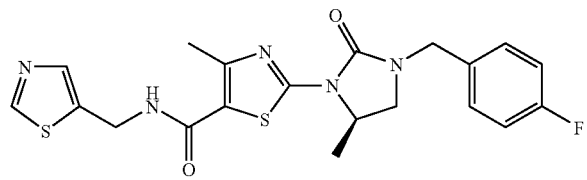

Following the procedure as described in Example 2, making variations as required to replace pyridin-3-ylmethanamine with thiazol-5-ylmethanamine and replace (S)-2-(3-(4-fluorobenzyl)-4-methyl-2-oxoimidazolidin-1-yl)-4-methylthiazole-5-carboxylic acid with (R)-2-(3-(4-fluorobenzyl)-5-methyl-2-oxoimidazolidin-1-yl)-4-methylthiazole-5-carboxylic acid, the title compound was obtained as a white solid (67%): mp 70-73° C. (diethyl ether/hexane); $^1$H NMR (300 MHz, DMSO-$d_6$) δ 8.93 (s, 1H), 8.62 (t, J=5.4 Hz, 1H), 7.76 (s, 1H), 7.33-7.28 (m, 2H), 7.18-7.13 (m, 2H), 4.56-4.39 (m, 5H), 3.59-3.56 (m, 1H), 3.00 (dd, J=9.0, 2.7 Hz, 1H), 2.45 (s, 3H), 1.35 (d, J=6.0 Hz, 3H); MS (ES+) m/z 445.7 (M+1).

Example 2.20

Synthesis of (R)-4-methyl-2-(4-methyl-2-oxo-3-(4-(trifluoromethyl)benzyl)imidazolidin-1-yl)-N-(pyridin-2-ylmethyl)thiazole-5-carboxamide

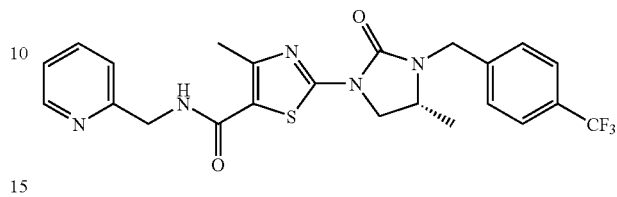

Following the procedure as described in Example 2, making variations as required to replace pyridin-3-ylmethanamine with pyridin-2-ylmethanamine and replace (S)-2-(3-(4-fluorobenzyl)-4-methyl-2-oxoimidazolidin-1-yl)-4-methylthiazole-5-carboxylic acid with (R)-4-methyl-2-(4-methyl-2-oxo-3-(4-(trifluoromethyl)benzyl)imidazolidin-1-yl)thiazole-5-carboxylic acid, the title compound was obtained as a solid (61%): mp 136-137° C. (ethyl acetate/hexane); $^1$H NMR (300 MHz, DMSO-$d_6$) δ 8.55-8.49 (m, 2H), 7.79-7.71 (m, 3H), 7.56 (d, J=8.1 Hz, 2H), 7.31-7.24 (m, 2H), 4.67 (d, J=16.1 Hz, 1H), 4.49-4.43 (m, 3H), 4.22 (dd, J=10.1, 9.1 Hz, 1H), 3.84-3.77 (m, 1H), 3.56 (dd, J=10.1, 6.8 Hz, 1H), 2.49 (s, 3H), 1.22 (d, J=6.2 Hz, 3H); MS (ES+) m/z 489.9 (M+1).

Example 3

Synthesis of 1-(4-methyl-5-(5-methyl-4H-1,2,4-triazol-3-yl)thiazol-2-yl)-3-(4-(trifluoromethyl)benzyl)imidazolidin-2-one

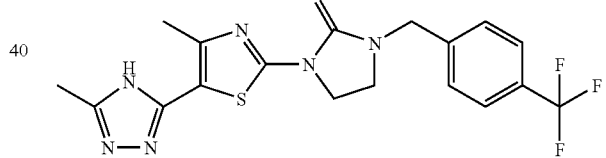

To a solution of 4-methyl-2-(2-oxo-3-(4-(trifluoromethyl)benzyl)imidazolidin-1-yl)thiazole-5-carboxamide (0.19 g, 0.50 mmol) in anhydrous 1,4-dioxane (5.0 mL) was added N,N-dimethylacetamide dimethylacetal (0.50 g, 3.50 mmol). The resulting mixture was refluxed for 16 h and concentrated in vacuo and acetic acid (5.0 mL) and hydrazine monohydrate (0.15 g, 3.00 mmol) was slowly added to the residue. The reaction mixture was stirred at 100° C. for 4 h and concentrated in vacuo. The residue was suspended in saturated aqueous sodium bicarbonate solution (150 mL) and extracted with ethyl acetate (3×80 mL). The organic layer was dried over anhydrous sodium sulphate and filtered. The filtrate was concentrated in vacuo and the residue was purified by column chromatography eluted with 2-10% methanol in dichloromethane to afford the title compound as a colorless solid (0.12 g, 58%): mp 273-274° C. (ethyl acetate); $^1$H NMR (300 MHz, DMSO-$d_6$) δ 13.64 (s, 1H), 7.74 (d, J=8.2 Hz, 2H), 7.55 (d, J=8.2 Hz, 2H), 4.55 (s, 2H), 4.06-4.00 (m, 2H), 3.52-3.47 (m, 2H), 2.57 (s, 3H), 2.38 (s, 3H); $^{13}$C NMR (75 MHz, DMSO-$d_6$) δ 156.4, 156.3, 155.3, 153.0, 145.0, 141.6 (d, $J_{C-F}$=1 Hz), 128.4, 128.1 (q, $^2J_{C-F}$=32 Hz), 125.5 (q, $^3J_{C-F}$=4 Hz), 124.3 (q, $^1J_{C-F}$=272 Hz), 115.3, 46.5, 42.0, 41.9, 16.7, 11.5; MS (ES+) m/z 422.9 (M+1).

Example 3.1

Synthesis of 1-(4-fluorobenzyl)-3-[4-methyl-5-(5-methyl-4H-1,2,4-triazol-3-yl)thiazol-2-yl]imidazolidin-2-one

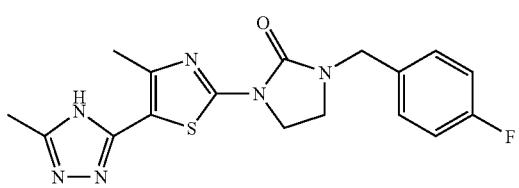

Following the procedure as described in Example 3, making variations as required to replace 4-methyl-2-(2-oxo-3-(4-(trifluoromethyl)benzyl)imidazolidin-1-yl)thiazole-5-carboxamide with 2-(3-(4-fluorobenzyl)-2-oxoimidazolidin-1-yl)-4-methylthiazole-5-carboxamide, the title compound was obtained as an off-white solid in 48% yield: mp 248-249° C. (DMF/Water); $^1$H NMR (300 MHz, DMSO-$d_6$) δ 13.65 (s, 1H), 7.37 (dd, J=8.5, 5.6 Hz, 2H), 7.20 (dd, J=8.8, 8.8 Hz, 2H), 4.43 (s, 2H), 4.00 (dd, J=9.0, 7.1 Hz, 2H), 3.44 (dd, J=9.0, 7.1 Hz, 2H), 2.56 (s, 3H), 2.38 (s, 3H); $^{13}$C NMR (75 MHz, DMSO-$d_6$) δ 161.6 (d, $^1J_{C-F}$=243 Hz), 156.5, 156.4, 155.2, 153.0, 145.0, 132.7 (d, $^4J_{C-F}$=3 Hz), 129.9 (d, $^3J_{C-F}$=8 Hz), 115.4 (d, $^2J_{C-F}$=21 Hz), 115.2, 46.2, 41.9, 41.6, 16.7, 11.5; MS (ES+) m/z 372.9 (M+1).

Example 4

Synthesis of 2-(3-(2-(4-fluorobenzylamino)-2-oxoethyl)-2-oxoimidazolidin-1-yl)-4-methyl-N-(pyridin-3-ylmethyl)thiazole-5-carboxamide

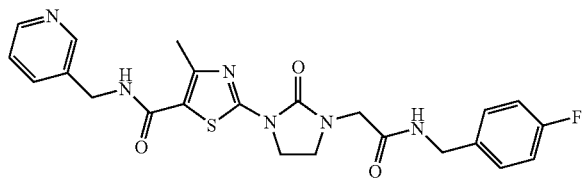

To a stirred mixture of crude 2-(3-(2-(4-fluorobenzylamino)-2-oxoethyl)-2-oxoimidazolidin-1-yl)-4-methylthiazole-5-carboxylic acid (0.18 g, 0.46 mmol), 1-hydroxybenzotriazole (0.09 g, 0.69 mmol) and 1-ethyl-3-(3-dimethylaminopropyl)-carbodiimide hydrochloride (0.13 g, 0.69 mmol) in N,N-dimethylformamide (2 mL) was added N,N-diisopropylethylamine (0.24 mL, 1.38 mmol) and 3-(aminomethyl)pyridine (0.05 mL, 0.46 mmol). The resulting reaction mixture was stirred for 18 h and diluted with ethyl acetate (75 mL). The organic layer was washed with saturated aqueous sodium bicarbonate solution (2×35 mL) and water (35 mL), dried over sodium sulfate, filtered and concentrated in vacuo. The residue was purified by column chromatography eluted with 5-15% methanol in dichloromethane to afford the title compound as a colorless foamy solid (0.06 g, 28%): $^1$H NMR (300 MHz, CDCl$_3$) δ 8.57-8.54 (m, 1H), 8.51-8.47 (m, 1H), 7.71-7.65 (m, 1H), 7.30-7.22 (m, 3H), 6.97-6.90 (m, 2H), 6.43 (br s, 1H), 6.05 (t, J=5.8 Hz, 1H), 4.55 (d, J=5.8 Hz, 2H), 4.51 (s, 2H), 4.01 (s, 2H), 3.63-3.53 (m, 4H), 2.39 (s, 3H); $^{13}$C NMR (75 MHz, CDCl$_3$) δ 169.5, 167.7, 162.4, 160.7, 157.1, 154.2, 149.1, 148.8, 135.7, 134.1, 131.6 (d, $J_{C-F}$=3.2 Hz), 130.4 (d, $J_{C-F}$=8.2 Hz), 123.6, 115.5 (d, $J_{C-F}$=21.5 Hz), 113.2, 50.3, 42.9, 42.6, 41.8, 41.3, 17.5; MS (ES+) m/z 483.2 (M+1).

Example 4.1

Synthesis of 4-methyl-2-(3-(2-(methylamino)-2-oxoethyl)-2-oxoimidazolidin-1-yl)-N-(pyridin-3-ylmethyl)thiazole-5-carboxamide

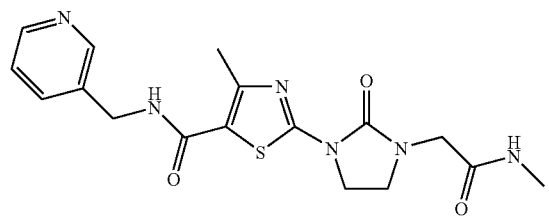

Following the procedure as described in Example 4, making variations as required to replace 2-(3-(2-(4-fluorobenzylamino)-2-oxoethyl)-2-oxoimidazolidin-1-yl)-4-methylthiazole-5-carboxylic acid with 4-methyl-2-(3-(2-(methylamino)-2-oxoethyl)-2-oxoimidazolidin-1-yl) thiazole-5-carboxylic acid, the title compound was obtained as a colorless gum in 12% yield: $^1$H NMR (300 MHz, CDCl$_3$) δ 8.55 (s, 1H), 8.49 (s, 1H), 7.67 (d, J=7.8 Hz, 1H), 7.29-7.23 (m, 1H), 6.60 (br s, 1H), 6.18 (t, J=5.8 Hz, 1H), 4.54 (d, J=5.8 Hz, 2H), 3.98 (s, 2H), 3.65-3.54 (m, 4H), 2.91 (s, 3H), 2.45 (s, 3H); $^{13}$C NMR (75 MHz, CDCl$_3$) δ 170.1, 167.9, 162.5, 157.4, 154.3, 148.9, 148.5, 135.7, 134.3, 123.6, 112.8, 50.3, 42.8, 42.4, 41.2, 24.8, 17.4; MS (ES+) m/z 389.2 (M+1).

Example 4.2

Synthesis of 4-methyl-2-(2-oxo-3-(2-oxo-2-(pyrrolidin-1-yl)ethyl)imidazolidin-1-yl)-N-(pyridin-3-ylmethyl)thiazole-5-carboxamide

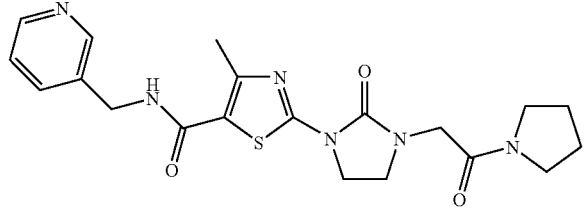

Following the procedure as described in Example 4, making variations as required to replace 2-(3-(2-(4-fluorobenzylamino)-2-oxoethyl)-2-oxoimidazolidin-1-yl)-4-methylthiazole-5-carboxylic acid with 4-methyl-2-(2-oxo-3-(2-oxo-2-(pyrrolidin-1-yl)ethyl)imidazolidin-1-yl)thiazole-5-carboxylic acid, the title compound was obtained as a colorless form in 69% yield: $^1$H NMR (300 MHz, CDCl$_3$) δ 8.58 (s, 1H), 8.54-8.49 (m, 1H), 7.72-7.65 (m, 1H), 7.30-7.22 (m, 1H), 6.12 (t, J=5.2 Hz, 1H), 4.58 (d, J=5.2 Hz, 2H), 4.19-4.09 (m, 2H), 4.03 (s, 2H), 3.83-3.74 (m, 2H), 3.51-3.40 (m, 4H), 2.61 (s, 3H), 2.05-1.93 (m, 2H), 1.92-1.80 (m, 2H); $^{13}$C NMR (75 MHz, CDCl$_3$) δ165.3, 162.7, 157.4, 155.9, 153.2, 149.1, 148.6, 135.6, 134.1, 123.5, 117.0, 45.9, 45.6, 43.1, 42.2, 41.2, 26.0, 23.9, 17.1; MS (ES+) m/z 429.3 (M+1).

Example 5

Synthesis of N-benzyl-2-(3-(4-fluorobenzyl)-2-oxo-2,3-dihydro-1H-benzo[d]imidazol-1-yl)-4-methylthiazole-5-carboxamide

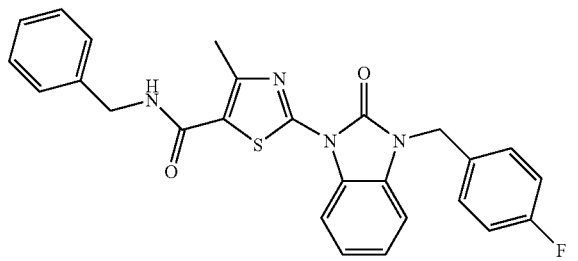

To a solution of 2-(3-(4-fluorobenzyl)-2-oxo-2,3-dihydro-1H-benzo[d]imidazol-1-yl)-4-methylthiazole-5-carboxylic acid in N,N-dimethylformamide is added N,N-diisopropylethylamine, followed by the addition of 1-hydroxybenzotriazole monohydrate and 1-(3-dimethylaminopropyl)-3-ethylcarbodiimide hydrochloride. The resulting mixture is stirred for 10 minutes and followed by the addition of benzylamine at ambient temperature. After stirred at ambient temperature for an additional 17 h, the mixture is concentrated in vacuo. The residue is poured into a saturated aqueous solution of sodium bicarbonate and then extracted with ethyl acetate. The organic layer is washed with saturated aqueous sodium bicarbonate solution, water and brine, dried over sodium sulfate, and filtered. The filtrate is concentrated and purified by column chromatography to afford the title compound.

Example 6

Synthesis of 1-(cyclopropylmethyl)-3-(4-methyl-5-(5-methyl-1H-pyrazol-3-yl)thiazol-2-yl)imidazolidin-2-one

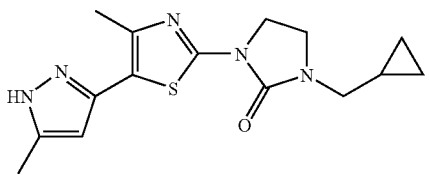

To a solution of 1-(5-acetyl-4-methylthiazol-2-yl)-3-(cyclopropylmethyl)-imidazolidin-2-one (0.28 g, 1.00 mmol) in N,N-dimethylacetamide (10 mL) was added N,N-dimethylacetamide dimethyl acetal (1.4 mL, 8.60 mmol). The reaction mixture was heated for 20 hours at 110° C., followed by the addition of hydrazine monohydrate (2.0 mL, 41.12 mmol). The reaction mixture was heated for another 10 minutes at 110° C. and concentrated in vacuo. The residue was washed with water and triturated with ethyl acetate and the title compound was obtained as a white solid in 71% yield (0.23 g): mp 231-233° C. (ethyl acetate); $^1$H NMR (300 MHz, DMSO-$d_6$) δ 12.5 (s, 1H), 6.15 (s, 1H), 3.98-3.92 (m, 2H), 3.62-3.57 (m, 2H), 3.05 (d, J=7.2 Hz, 2H), 2.33 (s, 3H), 2.21 (s, 3H), 0.95-0.84 (m, 1H), 0.49-0.43 (m, 2H), 0.21-0.17 (m, 2H); $^{13}$C NMR (75 MHz, DMSO-$d_6$) δ 155.8, 155.5, 144.4, 142.1, 139.9, 129.0, 102.5, 48.2, 42.5, 42.3, 16.9, 10.8, 9.3, 3.6; MS (ES+) m/z 318.2 (M+1).

Example 6.1

Synthesis of 1-(4-methyl-5-(5-methyl-1H-pyrazol-3-yl)thiazol-2-yl)-3-(3-(trifluoromethyl)benzyl)imidazolidin-2-one

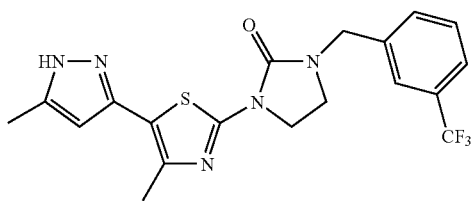

Following the procedure as describe in Example 6, making variations as required to replace 1-(5-acetyl-4-methylthiazol-2-yl)-3-(cyclopropylmethyl)-imidazolidin-2-one with 1-(5-acetyl-4-methylthiazol-2-yl)-3-(3-(trifluoromethyl)benzyl) imidazolidin-2-one, the title compound was obtained as a yellow solid in 22% yield: mp 163-164° C.; $^1$H NMR (300 MHz, DMSO-$d_6$) δ 12.59 (s, 1H), 7.69-7.61 (m, 4H), 6.20 (s, 1H), 4.54 (s, 2H), 4.02 (t, J=6.0 Hz, 2H), 3.49 (t, J=6.0 Hz, 2H), 2.38 (s, 3H), 2.25 (s, 3H); $^{13}$C NMR (75 MHz, DMSO-$d_6$) δ 155.9, 155.7, 142.1 (q, $^1J_{C-F}$=165 Hz), 138.7, 132.3, 130.3 (d, $^3J_{C-F}$=23 Hz), 130.2, 129.8 (d, $^3J_{C-F}$=30 Hz), 129.1, 126.4, 124.9-124.6 (m), 122.8, 118.6, 102.5, 47.0, 42.4, 42.3, 16.9, 10.8; MS (ES+) m/z 422.9 (M+1), 421.8 (M+1).

Example 6.2

Synthesis of 1-(4-fluorobenzyl)-3-(4-methyl-5-(5-methyl-1H-pyrazol-3-yl)thiazol-2-yl)imidazolidin-2-one

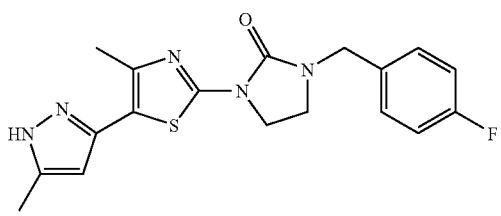

Following the procedure as describe in Example 6, making variations as required to replace 1-(5-acetyl-4-methylthiazol-2-yl)-3-(cyclopropylmethyl)imidazolidin-2-one with 1-(5-acetyl-4-methylthiazol-2-yl)-3-(4-fluorobenzyl)imidazolidin-2-one, the title compound was obtained in 46% yield: mp 218-221° C. (ethyl acetate); $^1$H NMR (300 MHz, CDCl$_3$) δ 7.28-7.23 (m, 2H), 7.05-6.97 (m, 2H), 6.15 (s, 1H), 4.44 (s, 2H), 4.09-4.02 (m, 2H), 3.43-3.38 (m, 2H), 2.52 (s, 3H), 2.24 (s, 3H); MS (ES+) m/z 372.2 (M+1).

Example 7

Synthesis of 1-(cyclopropylmethyl)-3-(4-methyl-5-(1H-pyrazol-3-yl)thiazol-2-yl)imidazolidin-2-one

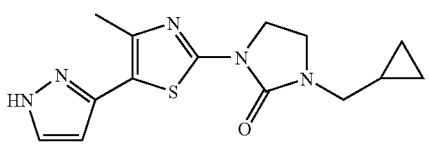

To a solution of 1-(5-acetyl-4-methylthiazol-2-yl)-3-(cyclopropylmethyl)-imidazolidin-2-one (0.24 g, 0.85 mmol) in N,N-dimethylformamide (10 mL) was added N,N-dimethylformamide dimethyl acetal (0.20 mL, 1.50 mmol). The reaction mixture was heated for 17 hours at 110° C., followed by the addition of hydrazine monohydrate (0.20 mL, 4.11 mmol). The reaction mixture was heated for another 10 minutes at 110° C. and concentrated in vacuo. The residue was washed with water and triturated with ethyl acetate and the title compound was obtained as a white solid in 76% yield (0.20 g): mp 169-171° C. (ethyl acetate); $^1$H NMR (300 MHz, DMSO-$d_6$) δ 12.8 (s, 1H), 7.74 (br s, 1H), 6.40 (d, J=3.0 Hz, 1H), 3.98-3.92 (m, 2H), 3.62-3.57 (m, 2H), 3.05 (d, J=7.2 Hz, 2H), 2.36 (s, 3H), 0.95-0.84 (m, 1H), 0.49-0.43 (m, 2H), 0.21-0.17 (m, 2H); $^1$H NMR (75 MHz, DMSO-$d_6$) δ 156.0, 155.5, 142.5, 103.3, 48.2, 42.5, 42.4, 16.9, 9.3, 3.6; MS (ES+) m/z 304.2 (M+1).

Example 8

Synthesis of 1-(2-cyclopropylethyl)-3-(4-methyl-5-(1H-pyrazol-3-yl)thiazol-2-yl)imidazolidin-2-one

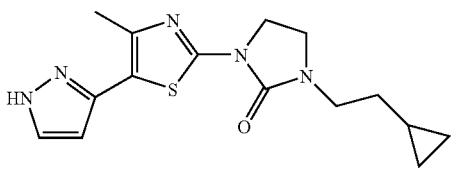

A. To a solution of 1-(5-acetyl-4-methylthiazol-2-yl)imidazolidin-2-one (4.50 g, 20.00 mmol), tetrabutylammonium iodide (0.10 g) and potassium carbonate (4.00 g, 28.92 mmol) in 1,4-dioxane (100 mL) was added 2-cyclopropylethyl-4-methylbenzenesulfonate (6.00 g, 24.96 mmol). The reaction mixture was heated to reflux for 37 h. The solvent was removed in vacuo. The residue was dissolved in water (50 mL) and extracted with ethyl acetate. The organic solution washed with water and brine and dried over anhydrous sodium sulfate and filtered. The filtrate was concentrated in vacuo and the residue was purified by column chromatography to afford 1-(5-acetyl-4-methylthiazol-2-yl)-3-(2-cyclopropylethyl)imidazolidin-2-one in 37% yield (2.20 g): mp 82-83° C. (ethyl acetate/hexanes); $^1$H NMR (300 MHz, CDCl$_3$) δ 4.12-4.06 (m, 2H), 3.63-3.57 (m, 2H), 3.40 (t, J=7.2 Hz, 2H), 2.60 (s, 3H), 2.44 (s, 3H), 1.51-1.44 (m, 2H), 0.71-0.62 (m, 1H), 0.49-0.43 (m, 2H), 0.09-0.04 (m, 2H); MS (ES+) m/z 294.2 (M+1).

B. To a solution of 1-(5-acetyl-4-methylthiazol-2-yl)-3-(2-cyclopropylethyl) imidazolidin-2-one (0.30 g, 1.00 mmol) in N,N-dimethylformamide (10 mL) was added N,N-dimethylformamide dimethyl acetal (0.30 mL, 2.25 mmol). The reaction mixture was heated for 23 hours at 110° C., followed by the addition of hydrazine monohydrate (0.30 mL, 6.16 mmol). The reaction mixture was heated for another 10 minutes at 110° C., and concentrated in vacuo. The residue was washed with water and triturated with ethyl acetate to afford the title compound as a white solid in 71% yield (0.23 g): mp 147-149° C. (ethyl acetate); $^1$H NMR (300 MHz, DMSO-$d_6$) δ 7.77-7.75 (m, 1H), 6.40 (d, J=1.2 Hz, 1H), 4.00-3.94 (m, 2H), 3.58-3.549 (m, 2H), 3.25 (t, J=6.9 Hz, 2H), 2.36 (s, 3H), 1.46-1.34 (m, 2H), 0.89-0.81 (m, 1H), 0.69-0.64 (m, 2H), 0.05-0.02 (m, 2H); $^{13}$C NMR (75 MHz, DMSO-$d_6$) δ 156.0, 155.5, 144.1, 142.3, 130.2, 117.9, 103.1, 43.8, 42.4, 42.3, 32.1, 16.9, 8.8, 4.5; MS (ES+) m/z 318.2 (M+1).

Example 9

Synthesis of 1-(4-fluorobenzyl)-3-(4-methyl-5-(1H-pyrazol-3-yl)thiazol-2-yl)imidazolidin-2-one

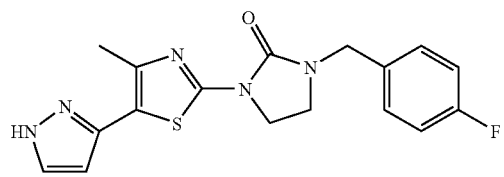

To a solution of 1-(5-acetyl-4-methylthiazol-2-yl)-3-(4-fluorobenzyl)-imidazolidin-2-one (0.33 g, 1.00 mmol) in N,N-dimethylformamide (10 mL) was added N,N-dimethylformamide dimethyl acetal (0.25 mL, 1.88 mmol). The reaction mixture was heated for 7 hours at 110° C., followed by the addition of hydrazine monohydrate (0.30 mL, 6.18 mmol). The reaction mixture was heated for another 10 minutes at 110° C., and concentrated in vacuo. The residue was washed with water and triturated with ethyl acetate to afford the title compound in 61% yield (0.22 g): mp 239-242° C. (ethyl acetate); $^1$H NMR (300 MHz, DMSO-$d_6$) δ 12.90 (br s, 1H), 7.76 (br s, 1H), 7.35-7.31 (m, 2H), 7.19-7.13 (m, 2H), 6.42 (d, J=2.1 Hz, 1H), 4.39 (s, 2H), 3.98-3.93 (m, 2H), 3.44-3.38 (m, 2H), 2.36 (s, 3H), 2.24 (s, 3H); $^{13}$C NMR (75 MHz, DMSO-$d_6$) δ 163.6, 160.4, 155.7, 144.0, 142.5, 133.2, 130.4, 118.1, 116.0, 115.7, 103.2, 46.6, 42.4, 42.0, 16.9; MS (ES+) m/z 358.2 (M+1).

Example 10

Synthesis of 2-(3-benzyl-2-oxoimidazolidin-1-yl)-4-methylthiazole-5-carboxamide

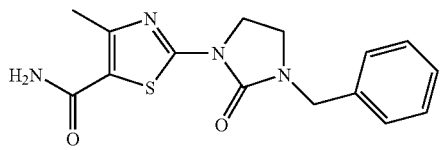

2-(3-Benzyl-2-oxoimidazolidin-1-yl)-4-methylthiazole-5-carboxylic acid (1.50 g, 4.72 mmol) and 4-methylmorpholine (0.60 mL, 5.45 mmol) in tetrahydrofuran (100 mL) was added isobutyl chloroformate (0.62 mL, 4.73 mmol) at 0° C. The resulting mixture was stirred at ambient temperature for 1 hour and followed by the addition of ammonia (7.0 N solution in methanol, 10 mL, 70 mmol). The reaction mixture was kept stirring at ambient temperature for 19 hours. The solvent was removed in vacuo and the residue was triturated with 10% sodium hydroxide solution. The solid was collected by filtration and washed with water to afford the title compound in 30% yield (0.47 g): mp 217-218° C. (water); $^1$H NMR (300 MHz, DMSO-$d_6$) δ 7.42-7.27 (m, 7H), 4.40 (s, 2H), 3.93-3.88 (m, 2H), 3.48-3.42 (m, 2H), 2.42 (s, 3H); MS (ES+) m/z 317.2 (M+1).

Example 11

Synthesis of 1-benzyl-3-(4-methyl-5-(5-methyl-4H-1,2,4-triazol-3-yl)thiazol-2-yl)imidazolidin-2-one

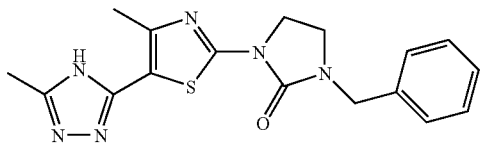

To a solution of 2-(3-benzyl-2-oxoimidazolidin-1-yl)-4-methylthiazole-5-carboxamide (0.20 g, 0.63 mmol) in 1,4 dioxane (10 mL) was added N,N-dimethylacetamide dimethyl acetal (1.0 mL, 6.80 mmol). The reaction mixture was heated to reflux for 5 hours and concentrated in vacuo. The residue was dissolved in acetic acid (10 mL) and hydrazine monohydrate (0.1 mL, 2.0 mmol) was added. The reaction mixture was heated for 3 hours at 90° C. and concentrated in vacuo. The residue was dissolved in saturated sodium bicarbonate (10 mL) and extracted with chloroform. The organic solution was washed with water and brine, dried over anhydrous sodium sulfate and filtered. The filtrate was concentrated in vacuo and the residue was triturated with ethyl acetate to afford the title in 65% yield (0.15 g): mp 284-287° C. (ethyl acetate); $^1$H NMR (300 MHz, DMSO-$d_6$) δ 13.6 (br s, 1H), 7.33-7.26 (m, 5H), 4.40 (s, 2H), 3.99-3.94 (m, 2H), 3.44-3.39 (m, 2H), 2.52 (s, 3H), 2.33 (s, 3H); $^{13}$C NMR (75 MHz, DMSO-$d_6$) δ 156.9, 155.7, 153.6, 145.6, 136.9, 129.1, 128.2, 127.9, 47.4, 42.4, 42.1, 17.1, 12.1; MS (ES+) m/z 355.2 (M+1).

Example 12

Synthesis of 2-(3-(cyclopropylmethyl)-2-oxoimidazolidin-1-yl)-N-((5-fluoropyridin-3-yl)methyl)-4-methylthiazole-5-carboxamide

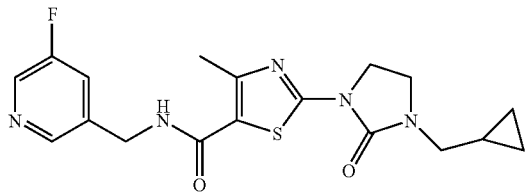

To a solution of 2-(3-(cyclopropylmethyl)-2-oxoimidazolidin-1-yl)-4-methylthiazole-5-carboxylic acid (1.00 g, 3.55 mmol), 2-(7-aza-1H-benzotriazole-1-yl)-1,1,3,3-tetramethyluronium hexafluorophosphate (HATU, 1.70 g, 4.47 mmol) and triethylamine (1.00 mL, 7.17 mmol) in N,N-dimethylformamide (15 mL) was added (5-fluoropyridin-3-yl)methanamine (0.55 g, 4.36 mmol). The reaction mixture was stirred at ambient temperature for 20 h, diluted with ethyl acetate (200 mL) and washed with water and brine. The organic solution was dried over anhydrous sodium sulfate and filtered. The filtrate was concentrated in vacuo and the residue was recrystallized from ethyl acetate to afford the title compound as a white powder in 47% yield (0.65 g): mp 144-145° C.; $^1$H NMR (300 MHz, DMSO-$d_6$) δ 8.53 (J=6.0 Hz, 1H), 8.43-8.38 (m, 2H), 7.59-7.56 (m, 1H), 4.39 (d, J=6.0 Hz, 2H), 4.00-3.95 (m, 2H), 3.64-3.59 (m, 2H), 3.06 (d, J=6.0 Hz, 2H), 2.44 (s, 3H), 0.95-0.87 (m, 1H), 0.48-0.42 (m, 2H), 0.20-0.16 (m, 2H); $^{13}$C NMR (75 MHz, DMSO-$d_6$) δ 162.4, 161.1, 157.9, 155.2, 145.5, 137.9, 136.6, 122.5, 122.3, 117.6, 48.2, 42.5, 42.3, 40.8, 17.6, 9.3, 3.6; MS (ES+) m/z 389.9 (M+1).

Example 12.1

Synthesis of 2-(3-(cyclopropylmethyl)-2-oxoimidazolidin-1-yl)-N-((3-fluoropyridin-2-yl)methyl)-4-methylthiazole-5-carboxamide

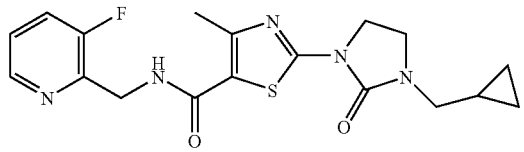

Following the procedure as describe in Example 12, making variations as required to replace (5-fluoropyridin-3-yl)methanamine with (3-fluoropyridin-2-yl)methanamine to react with 2-(3-(cyclopropylmethyl)-2-oxoimidazolidin-1-yl)-4-methylthiazole-5-carboxylic acid, the title compound was obtained as a white solid in 60% yield: mp 142-144° C.; $^1$H NMR (300 MHz, DMSO-$d_6$) δ 8.38-8.31 (m, 2H), 7.69-7.62 (m, 1H), 7.39-7.33 (m, 1H), 4.51-4.54 (m, 2H), 4.00-3.95 (m, 2H), 3.64-3.59 (m, 2H), 3.06 (d, J=6.0 Hz, 2H), 2.44 (s, 3H), 0.96-0.87 (m, 1H), 0.49-0.42 (m, 2H), 0.21-0.16 (m, 2H); $^{13}$C NMR (75 MHz, DMSO-$d_6$) δ 162.2, 159.1, 157.9, 155.7, 151.2, 146.2, 145.4, 124.5, 123.6, 118.2, 48.2, 42.5, 42.3, 40.8, 17.5, 9.3, 3.6; MS (ES+) m/z 389.9 (M+1).

Example 12.2

Synthesis of 4-methyl-2-(2-oxo-3-(4,4,4-trifluorobutyl)imidazolidin-1-yl)-N-(pyridin-2-ylmethyl)thiazole-5-carboxamide

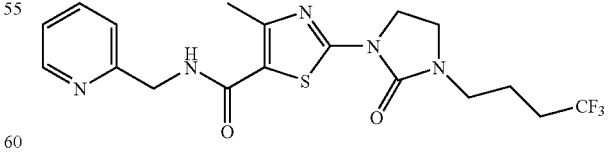

Following the procedure as describe in Example 12, making variations as required to replace (5-fluoropyridin-3-yl)methanamine with pyridin-2-ylmethanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 28% yield: $^1$H NMR (300 MHz, CDCl$_3$) δ 8.56-8.54 (m, 1H), 7.70-7.64 (m, 1H), 7.30-7.19 (m, 2H), 7.13-7.10 (m, 1H), 4.69 (d, J=4.6 Hz, 2H), 4.17-4.11 (m, 2H), 3.63-3.58 (m, 2H), 2.65 (s, 3H), 2.24-2.08 (m, 2H), 1.92-1.75 (m, 4H); $^{13}$C NMR (75 MHz, CDCl$_3$) δ 162.5, 157.5, 155.8, 155.6, 152.3, 148.9, 136.7, 122.4, 121.9, 118.2, 44.6, 42.9, 42.3, 42.0, 31.8, 31.4, 30.9, 30.6, 20.2, 20.1, 17.3; MS (ES+) m/z 427.9 (M+1).

Example 12.3

Synthesis of 4-methyl-2-(2-oxo-3-(4,4,4-trifluorobutyl)imidazolidin-1-yl)-N-(pyridin-3-ylmethyl)thiazole-5-carboxamide

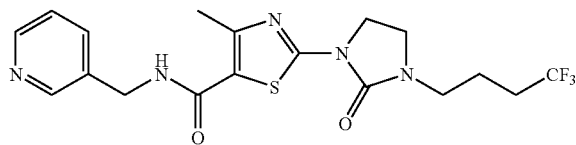

Following the procedure as describe in Example 12, making variations as required to replace (5-fluoropyridin-3-yl)methanamine with pyridin-3-ylmethanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 50% yield: mp 167-169° C. (dichloromethane/hexanes); $^1$H NMR (300 MHz, CDCl$_3$) δ 8.62-8.52 (m, 2H), 7.69-7.66 (m, 1H), 7.26-7.24 (m, 1H), 6.28-6.25 (m, 1H), 4.57 (d, J=5.9 Hz, 2H), 4.14-4.09 (m, 2H), 3.62-3.56 (m, 2H), 3.40-3.36 (m, 2H), 2.60 (s, 3H), 2.18-2.09 (m, 2H), 1.89-1.79 (m, 2H); MS (ES+) m/z 428.1 (M+1).

Example 12.4

Synthesis of 4-methyl-N-(oxazol-4-ylmethyl)-2-(2-oxo-3-(4,4,4-trifluorobutyl)imidazolidin-1-yl)thiazole-5-carboxamide

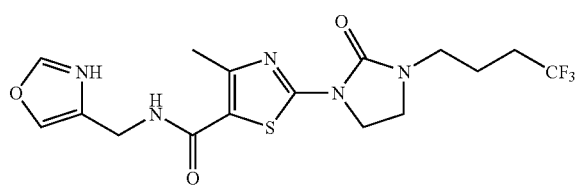

Following the procedure as describe in Example 12, making variations as required to replace (5-fluoropyridin-3-yl)methanamine with oxazol-4-ylmethanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 48% yield: $^1$H NMR (300 MHz, CDCl$_3$) δ 7.86 (s, 1H), 7.65 (s, 1H), 6.16-6.12 (m, 1H), 4.51 (d, J=5.4 Hz, 2H), 4.15-4.10 (m, 2H), 3.63-3.57 (m, 2H), 3.43-3.38 (m, 2H), 2.60 (s, 3H), 2.20-2.11 (m, 2H), 1.91-1.83 (m, 2H); $^{13}$C NMR (75 MHz, CDCl$_3$) δ 162.4, 157.3, 155.5, 152.8, 151.3, 151.2, 135.9, 135.8, 128.6, 124.9, 117.5, 42.9, 42.3, 41.9, 35.5, 31.7, 31.3, 30.9, 30.5, 20.2, 20.1, 17.2; MS (ES+) m/z 417.7 (M+1).

Example 12.5

Synthesis of 4-methyl-N-(oxazol-2-ylmethyl)-2-(2-oxo-3-(4,4,4-trifluorobutyl)imidazolidin-1-yl)thiazole-5-carboxamide

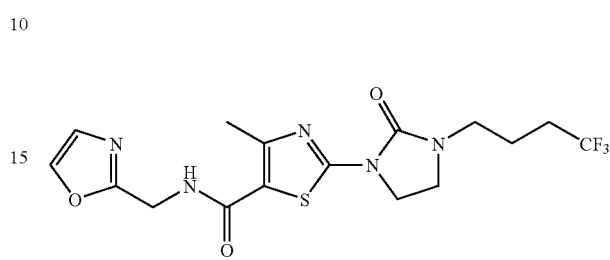

Following the procedure as describe in Example 12, making variations as required to replace (5-fluoropyridin-3-yl)methanamine with oxazol-2-ylmethanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 58% yield: $^1$H NMR (300 MHz, CDCl$_3$) δ 7.63 (s, 1H), 7.07 (s, 1H), 6.34-6.37 (m, 1H), 4.70 (d, J=5.3 Hz, 2H), 4.16-4.11 (m, 2H), 3.64-3.58 (m, 2H), 3.43-3.39 (m, 2H), 2.63 (s, 3H), 2.21-2.08 (m, 2H), 1.91-1.81 (m, 2H); $^{13}$C NMR (75 MHz, CDCl$_3$) δ 162.4, 160.6, 157.6, 155.6, 153.4, 139.2, 127.2, 117.2, 42.9, 42.3, 42.0, 37.2, 31.7, 31.3, 30.9, 30.6, 20.2, 17.3; MS (ES+) m/z 417.7 (M+1).

Example 12.6

Synthesis of 4-methyl-N-((6-methylpyrazin-2-yl)methyl)-2-(2-oxo-3-(4,4,4-trifluorobutyl)imidazolidin-1-yl)thiazole-5-carboxamide

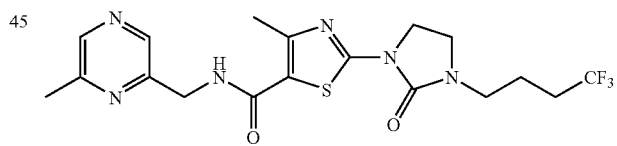

Following the procedure as describe in Example 12, making variations as required to replace (5-fluoropyridin-3-yl)methanamine with (6-methylpyrazin-2-yl)methanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 34% yield: mp 123-123° C. (dichloromethane/hexanes); $^1$H NMR (300 MHz, CDCl$_3$) δ 8.51 (s, 1H), 8.39 (s, 1H), 6.75-6.72 (m, 1H), 4.70 (d, J=4.9 Hz, 2H), 4.17-4.12 (m, 2H), 3.64-3.59 (m, 2H), 3.44-3.39 (m, 2H), 2.63 (s, 3H), 2.57 (s, 3H), 2.25-2.09 (m, 2H), 1.92-1.82 (m, 2H); $^{13}$C NMR (75 MHz, CDCl$_3$) δ 162.5, 157.4, 155.6, 152.9, 152.6, 148.7, 143.4, 142.7, 128.6, 124.9, 117.6, 42.9, 42.3, 42.0, 31.4, 30.9, 21.2, 20.2, 20.1, 17.3; MS (ES+) m/z 442.7 (M+1).

Example 12.7

Synthesis of 4-methyl-2-(2-oxo-3-(4,4,4-trifluorobutyl)imidazolidin-1-yl)-N-(pyridin-4-ylmethyl)thiazole-5-carboxamide

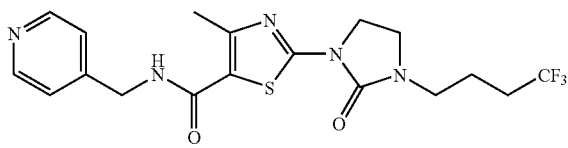

Following the procedure as describe in Example 12, making variations as required to replace (5-fluoropyridin-3-yl)methanamine with pyridin-4-ylmethanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 42% yield: mp 178-181° C. (dichloromethane/hexanes); $^1$H NMR (300 MHz, CDCl$_3$) δ 8.55 (s, 2H), 7.24-7.22 (m, 2H), 6.20-6.16 (m, 1H), 4.57 (d, J=5.9 Hz, 2H), 4.16-4.10 (m, 2H), 3.63-3.58 (m, 2H), 3.41-3.39 (m, 2H), 2.61 (s, 3H), 2.19-2.10 (m, 2H), 1.91-1.83 (m, 2H); MS (ES+) m/z 428.2 (M+1).

Example 12.8

Synthesis of N-((1H-pyrazol-4-yl)methyl)-4-methyl-2-(2-oxo-3-(4,4,4-trifluorobutyl)imidazolidin-1-yl)thiazole-5-carboxamide

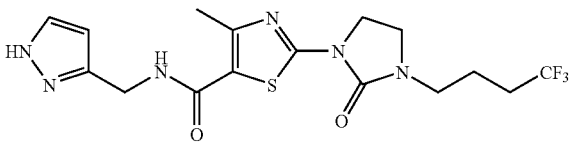

Following the procedure as describe in Example 12, making variations as required to replace (5-fluoropyridin-3-yl)methanamine with (1H-pyrazol-3-yl)methanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 3% yield: $^1$H NMR (300 MHz, DMSO-d$_6$) δ 12.58 (s, 1H), 8.34-8.32 (m, 1H), 7.58-7.57 (m, 1H), 6.14 (s, 1H), 4.37 (d, J=5.5 Hz, 2H), 4.02-3.96 (m, 2H), 3.59-3.53 (m, 2H), 3.33-3.28 (m, 2H), 2.46 (s, 3H), 2.32-2.26 (m, 2H), 1.76-1.71 (m, 2H); MS (ES+) m/z 416.7 (M+1).

Example 12.9

Synthesis of 4-methyl-N-((1-methyl-1H-pyrazol-4-yl)methyl)-2-(2-oxo-3-(4,4,4-trifluorobutyl)imidazolidin-1-yl)thiazole-5-carboxamide

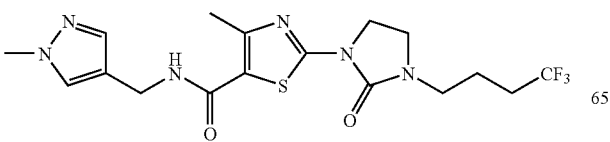

Following the procedure as describe in Example 12, making variations as required to replace (5-fluoropyridin-3-yl)methanamine with (1-methyl-1H-pyrazol-4-yl)methanamine to react with 4-methyl-2-(2-oxo-3-(4,4,4-trifluorobutyl)imidazolidin-1-yl)thiazole-5-carboxylic acid in place of 2-(3-(cyclopropylmethyl)-2-oxoimidazolidin-1-yl)-4-methylthiazole-5-carboxylic acid, the title compound was obtained as a colorless solid in 49% yield: $^1$H NMR (300 MHz, CDCl$_3$) δ 7.44 (s, 1H), 7.37 (s, 1H), 5.79-5.76 (m, 1H), 4.40 (d, J=5.3 Hz, 2H), 4.15-4.09 (m, 2H), 3.87 (s, 3H), 3.62-3.57 (m, 2H), 3.42-3.37 (m, 2H), 2.60 (s, 3H), 2.19-2.11 (m, 2H), 1.88-1.83 (m, 2H); $^{13}$C NMR (75 MHz, CDCl$_3$) δ 162.2, 157.1, 155.6, 152.8, 138.7, 129.4, 118.2, 117.4, 42.9, 42.3, 42.0, 38.9, 34.4, 31.4, 30.9, 20.2, 17.2; MS (ES+) m/z 430.9 (M+1).

Example 12.10

Synthesis of 2-(3-(cyclopropylmethyl)-2-oxoimidazolidin-1-yl)-4-methyl-N-(pyrimidin-4-ylmethyl)thiazole-5-carboxamide

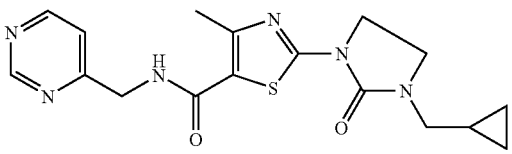

Following the procedure as describe in Example 12, making variations as required to replace (5-fluoropyridin-3-yl)methanamine with pyrimidin-4-ylmethanamine to react with 2-(3-(cyclopropylmethyl)-2-oxoimidazolidin-1-yl)-4-methylthiazole-5-carboxylic acid, the title compound was obtained as a colorless solid in 65% yield: mp 188-191° C. (dichloromethane/hexanes); $^1$H NMR (300 MHz, CDCl$_3$) δ 9.17 (s, 1H), 8.68 (d, J=5.1 Hz, 1H), 7.33 (d, J=4.9 Hz, 1H), 6.89-6.87 (m, 1H), 4.69 (d, J=5.0 Hz, 2H), 4.16-4.11 (m, 2H), 3.74-3.69 (m, 2H), 3.20 (d, J=7.1 Hz, 2H), 2.64 (s, 3H), 1.00-0.91 (m, 1H), 0.61-0.55 (m, 2H), 0.28-0.23 (m, 2H); $^{13}$C NMR (75 MHz, CDCl$_3$) δ 165.0, 162.8, 158.5, 157.9, 156.9, 155.2, 153.2, 119.1, 117.1, 48.6, 44.1, 42.2, 42.1, 17.3, 8.9, 3.5; MS (ES+) m/z 373.2 (M+1).

Example 12.11

Synthesis of 2-(3-(cyclopropylmethyl)-2-oxoimidazolidin-1-yl)-4-methyl-N-(pyrimidin-2-ylmethyl)thiazole-5-carboxamide

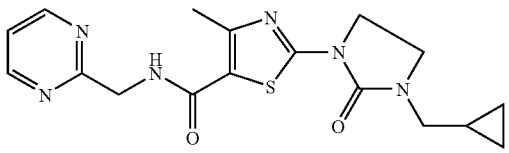

Following the procedure as describe in Example 12, making variations as required to replace (5-fluoropyridin-3-yl)methanamine with pyrimidin-2-ylmethanamine to react with 2-(3-(cyclopropylmethyl)-2-oxoimidazolidin-1-yl)-4-methylthiazole-5-carboxylic acid, the title compound was obtained as a colorless solid in 58% yield: mp 218-220° C. (dichloromethane/hexanes); $^1$H NMR (300 MHz, CDCl$_3$) δ 8.71 (d, J=4.9 Hz, 2H), 7.24-7.21 (m, 1H), 7.15-7.11 (m, 1H), 4.83 (d, J=4.4 Hz, 2H), 4.16-4.11 (m, 2H), 3.74-3.68 (m, 2H), 3.20 (d, J=7.1 Hz, 2H), 2.66 (s, 3H), 1.01-0.91 (m, 1H), 0.59-0.54 (m, 2H), 0.28-0.25 (m, 2H); $^{13}$C NMR (75 MHz, CDCl$_3$) δ 165.4, 162.5, 157.7, 157.1, 155.2, 152.7, 119.5, 117.6, 48.6, 45.5, 42.2, 42.1, 17.2, 8.9, 3.4; MS (ES+) m/z 373.3 (M+1).

Example 12.12

Synthesis of 2-(3-(cyclopropylmethyl)-2-oxoimidazolidin-1-yl)-4-methyl-N-(pyridazin-3-ylmethyl)thiazole-5-carboxamide

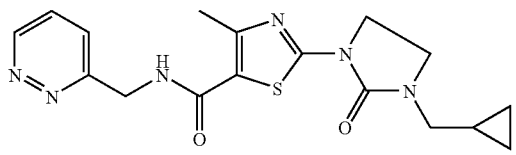

Following the procedure as describe in Example 12, making variations as required to replace (5-fluoropyridin-3-yl)methanamine with pyridazin-3-ylmethanamine to react with 2-(3-(cyclopropylmethyl)-2-oxoimidazolidin-1-yl)-4-methylthiazole-5-carboxylic acid, the title compound was obtained as a colorless solid in 17% yield: mp 187-189° C. (dichloromethane/hexanes); $^1$H NMR (300 MHz, CDCl$_3$) δ 9.11 (d, J=4.2 Hz, 1H), 7.59-7.56 (m, 1H), 7.49-7.45 (m, 1H), 7.03-7.00 (m, 1H), 4.88 (d, J=5.4 Hz, 2H), 4.14-4.09 (m, 2H), 3.73-3.67 (m, 2H), 3.19 (d, J=7.1 Hz, 2H), 2.62 (s, 3H), 0.97-0.92 (m, 1H), 0.60-0.54 (m, 2H), 0.27-0.22 (m, 2H); $^{13}$C NMR (75 MHz, CDCl$_3$) δ 163.0, 159.4, 158.1, 155.2, 152.8, 150.7, 126.9, 126.2, 117.4, 48.6, 43.7, 42.2, 42.1, 17.4, 8.9, 3.4; MS (ES+) m/z 373.2 (M+1).

Example 12.13

Synthesis of 2-(3-(cyclopropylmethyl)-2-oxoimidazolidin-1-yl)-4-methyl-N-(pyridin-4-ylmethyl)thiazole-5-carboxamide

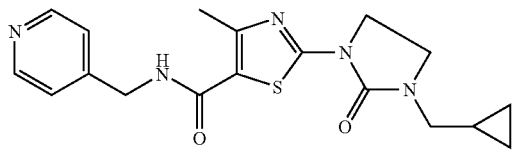

Following the procedure as describe in Example 12, making variations as required to replace (5-fluoropyridin-3-yl)methanamine with pyridin-4-ylmethanamine to react with 2-(3-(cyclopropylmethyl)-2-oxoimidazolidin-1-yl)-4-methylthiazole-5-carboxylic acid, the title compound was obtained as a colorless solid in 43% yield: mp >200° C. (dichloromethane/hexanes); $^1$H NMR (300 MHz, CDCl$_3$) δ 8.55-8.53 (m, 2H), 7.23 (d, J=6.0 Hz, 2H), 6.17-6.13 (m, 1H), 4.57 (d, J=6.0 Hz, 2H), 4.14-4.09 (m, 2H), 3.73-3.68 (m, 2H), 3.18 (d, J=7.1 Hz, 2H), 2.62 (s, 3H), 0.99-0.91 (m, 1H), 0.60-0.54 (m, 2H), 0.27-0.22 (m, 2H); $^{13}$C NMR (75 MHz, CDCl$_3$) δ 162.8, 157.5, 155.2, 153.9, 149.9, 147.5, 122.2, 116.4, 48.6, 42.6, 42.2, 42.1, 17.3, 8.9, 3.4; MS (ES+) m/z 372.2 (M+1).

Example 12.14

Synthesis of 2-(3-(cyclopropylmethyl)-2-oxoimidazolidin-1-yl)-4-methyl-N-((2-methylthiazol-5-yl)methyl)thiazole-5-carboxamide

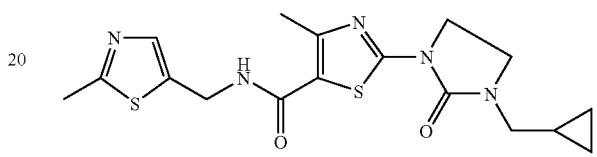

Following the procedure as describe in Example 12, making variations as required to replace (5-fluoropyridin-3-yl)methanamine with (2-methylthiazol-5-yl)methanamine to react with 2-(3-(cyclopropylmethyl)-2-oxoimidazolidin-1-yl)-4-methylthiazole-5-carboxylic acid, the title compound was obtained as a colorless solid in 65% yield: mp 165-167° C. (dichloromethane/hexanes); $^1$H NMR (300 MHz, CDCl$_3$) δ 7.00 (s, 1H), 6.30-6.27 (m, 1H), 4.60 (d, J=5.4 Hz, 2H), 4.13-4.08 (m, 2H), 3.72-3.66 (m, 2H), 3.18 (d, J=7.1 Hz, 2H), 2.69 (s, 3H), 2.60 (s, 3H), 0.97-0.92 (m, 1H), 0.60-0.53 (m, 2H), 0.27-0.22 (m, 2H); $^{13}$C NMR (75 MHz, CDCl$_3$) δ 166.6, 162.4, 157.6, 155.2, 152.9, 152.0, 117.2, 114.9, 48.6, 42.2, 42.1, 39.9, 19.1, 17.2, 8.9, 3.4; MS (ES+) m/z 392.0 (M+1).

Example 12.15

Synthesis of 2-(3-(cyclopropylmethyl)-2-oxoimidazolidin-1-yl)-4-methyl-N-(oxazol-2-ylmethyl)thiazole-5-carboxamide

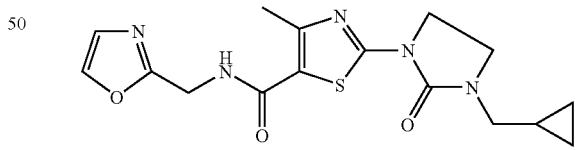

Following the procedure as describe in Example 12, making variations as required to replace (5-fluoropyridin-3-yl)methanamine with oxazol-2-ylmethanamine to react with 2-(3-(cyclopropylmethyl)-2-oxoimidazolidin-1-yl)-4-methylthiazole-5-carboxylic acid, the title compound was obtained as a colorless solid in 25% yield: mp 172-174° C. (dichloromethane/hexanes); $^1$H NMR (300 MHz, CD$_3$OD) δ 7.86 (s, 1H), 7.14-7.10 (m, 1H), 4.61 (s, 2H), 4.12-4.07 (m, 2H), 3.78-3.72 (m, 2H), 3.18 (d, J=7.1 Hz, 2H), 2.53 (s, 3H), 1.03-0.98 (m, 1H), 0.60-0.54 (m, 2H), 0.29-0.24 (m, 2H); MS (ES+) m/z 362.1 (M+1).

Example 12.16

Synthesis of 2-(3-(4-fluorobenzyl)-2-oxoimidazolidin-1-yl)-4-methyl-N-(oxazol-4-ylmethyl)thiazole-5-carboxamide

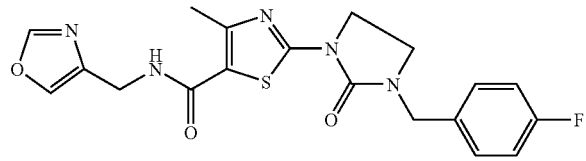

Following the procedure as describe in Example 12, making variations as required to replace (5-fluoropyridin-3-yl)methanamine with oxazol-4-ylmethanamine to react with 2-(3-(4-fluorobenzyl)-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 32% yield: mp 188-191° C. (dichloromethane/hexanes); $^1$H NMR (300 MHz, CDCl$_3$) δ 7.86 (s, 1H), 7.66 (s, 1H), 7.29-7.25 (m, 2H), 7.07-7.01 (m, 2H), 6.21-6.17 (m, 1H), 4.51 (d, J=5.8 Hz, 2H), 4.46 (s, 2H), 4.10-4.05 (m, 2H), 3.48-3.42 (m, 2H) 2.60 (s, 3H); $^{13}$C NMR (75 MHz, CDCl$_3$) δ 164.1, 162.4, 160.9, 157.5, 155.3, 152.9, 151.3, 136.8, 135.8, 131.4, 131.3, 130.1, 129.9, 117.5, 115.9, 115.7, 47.3, 41.9, 41.6, 35.6, 17.2; MS (ES+) m/z 416.1 (M+1).

Example 12.17

Synthesis of 2-(3-isobutyl-2-oxoimidazolidin-1-yl)-4-methyl-N-(pyridin-4-ylmethyl)thiazole-5-carboxamide

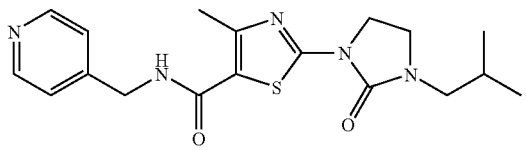

Following the procedure as describe in Example 12, making variations as required to replace (5-fluoropyridin-3-yl)methanamine with pyridin-4-ylmethanamine to react with 2-(3-isobutyl-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 48% yield: mp 185-187° C. (dichloromethane/hexanes); $^1$H NMR (300 MHz, CD$_3$OD) δ 8.49-8.47 (m, 2H), 7.40-7.38 (d, J=7.4 Hz, 1H), 4.55 (s, 2H), 4.14-4.07 (m, 2H), 3.68-3.63 (m, 2H), 3.12 (d, J=7.5 Hz, 2H), 2.55 (s, 3H), 2.02-1.93 (m, 1H), 0.95 (d, J=6.6 Hz, 6H); MS (ES+) m/z 373.8 (M+1).

Example 12.18

Synthesis of 2-(3-isobutyl-2-oxoimidazolidin-1-yl)-4-methyl-N-(pyridin-3-ylmethyl)thiazole-5-carboxamide

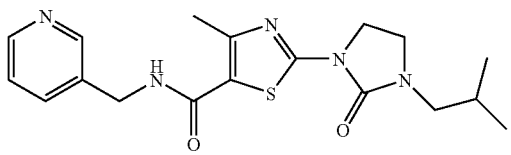

Following the procedure as describe in Example 12, making variations as required to replace (5-fluoropyridin-3-yl)methanamine with pyridin-3-ylmethanamine to react with 2-(3-isobutyl-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 40% yield: $^1$H NMR (300 MHz, CDCl$_3$) δ 8.58-8.52 (m, 2H), 7.69-7.66 (m, 1H), 7.28-7.23 (m, 1H), 6.20-6.17 (m, 1H), 4.57 (d, J=5.8 Hz, 2H), 4.12-4.07 (m, 2H), 3.61-3.55 (m, 2H), 3.10 (d, J=7.4 Hz, 2H), 2.61 (s, 3H), 1.96-1.87 (m, 1H), 0.92 (d, J=6.6 Hz, 6H); $^{13}$C NMR (75 MHz, CDCl$_3$) δ 162.7, 157.4, 155.6, 153.5, 149.1, 148.7, 135.5, 133.9, 123.5, 116.6, 51.5, 42.8, 41.9, 41.2, 26.7, 19.9, 17.2; MS (ES+) m/z 373.9 (M+1).

Example 12.19

Synthesis of 2-(3-isobutyl-2-oxoimidazolidin-1-yl)-4-methyl-N-(pyridin-2-ylmethyl)thiazole-5-carboxamide

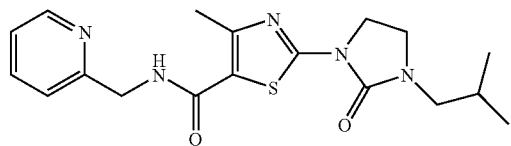

Following the procedure as describe in Example 12, making variations as required to replace (5-fluoropyridin-3-yl)methanamine with pyridin-2-ylmethanamine to react with 2-(3-isobutyl-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 46% yield: $^1$H NMR (300 MHz, CDCl$_3$) δ 8.52-8.50 (m, 1H), 7.65-7.60 (m, 1H), 7.26-7.23 (m, 1H), 7.18-7.14 (m, 1H), 7.11-7.06 (m, 1H), 4.66 (d, J=5.6 Hz, 2H), 4.10-4.05 (m, 2H), 3.58-3.53 (m, 2H), 3.09 (d, J=7.5 Hz, 2H), 2.61 (s, 3H), 1.94-1.85 (m, 1H), 0.91 (d, J=6.4 Hz, 6H); $^{13}$C NMR (75 MHz, CDCl$_3$) δ 162.5, 157.6, 155.8, 155.6, 152.3, 148.8, 136.5, 122.2, 121.7, 117.7, 51.4, 44.5, 42.7, 41.9, 26.6, 19.8, 17.1; MS (ES+) m/z 373.8 (M+1).

Example 12.20

Synthesis of 2-(3-isobutyl-2-oxoimidazolidin-1-yl)-4-methyl-N-((6-methylpyrazin-2-yl)methyl)thiazole-5-carboxamide

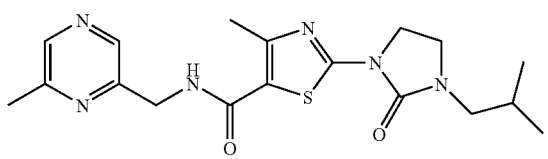

Following the procedure as describe in Example 12, making variations as required to replace (5-fluoropyridin-3-yl)methanamine with (6-methylpyrazin-2-yl)methanamine to react with 2-(3-isobutyl-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 46% yield: mp 139-142° C. (dichloromethane/hexanes); $^1$H NMR (300 MHz, CDCl$_3$) δ 8.50 (s, 1H), 8.38 (s, 1H), 6.75-6.72 (m, 1H), 4.69 (d, J=5.0 Hz, 2H), 4.14-4.08 (m, 2H), 3.62-3.56 (m, 2H), 3.13 (d, J=7.4 Hz, 2H), 2.62 (s, 3H), 2.56 (s, 3H), 1.98-1.88 (m, 1H), 0.94 (d, J=6.6 Hz, 6H); $^{13}$C NMR (75 MHz, CDCl$_3$) δ 162.6, 157.7, 155.7, 153.1, 152.5, 148.7, 143.4, 142.7, 117.1, 51.5, 42.9, 42.3, 42.0, 26.8, 21.2, 19.9, 17.2; MS (ES+) m/z 388.8 (M+1).

Example 12.21

Synthesis of 2-(3-isobutyl-2-oxoimidazolidin-1-yl)-4-methyl-N-((1-methyl-1H-pyrazol-4-yl)methyl)thiazole-5-carboxamide

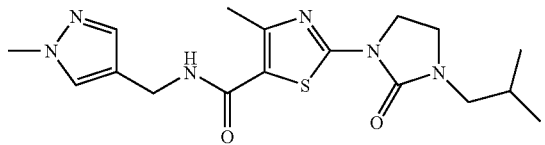

Following the procedure as describe in Example 12, making variations as required to replace (5-fluoropyridin-3-yl)methanamine with (1-methyl-1H-pyrazol-4-yl)methane to react with 2-(3-isobutyl-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 58% yield: mp 155-158° C. (dichloromethane/hexanes); $^1$H NMR (300 MHz, CDCl$_3$) δ 7.43 (s, 1H), 7.37 (s, 1H), 5.80-5.77 (m, 1H), 4.39 (d, J=5.3 Hz, 2H), 4.12-4.07 (m, 2H), 3.87 (s, 3H), 3.60-3.55 (m, 2H), 3.11 (d, J=7.4 Hz, 2H), 2.60 (s, 3H), 1.96-1.87 (m, 1H), 0.93 (d, J=7.4 Hz, 6H); $^{13}$C NMR (75 MHz, CDCl$_3$) δ162.3, 157.4, 155.6, 152.8 152.6, 138.6, 129.4, 118.3, 117.0, 51.5, 42.8, 41.9, 38.8, 34.3, 26.7, 19.9, 17.1; MS (ES+) m/z 377.1 (M+1).

Example 12.22

Synthesis of 2-(3-isobutyl-2-oxoimidazolidin-1-yl)-4-methyl-N-((1-methyl-1H-pyrazol-3-yl)methyl)thiazole-5-carboxamide

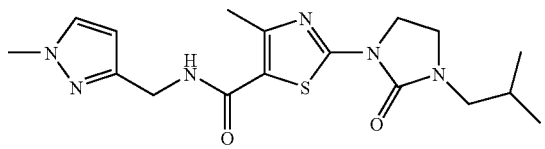

Following the procedure as describe in Example 12, making variations as required to replace (5-fluoropyridin-3-yl)methanamine with (1-methyl-1H-pyrazol-3-yl)methanamine to react with 2-(3-isobutyl-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 58% yield: mp 158-161° C. (dichloromethane/hexanes); $^1$H NMR (300 MHz, CDCl$_3$) δ 7.43 (s, 1H), 7.37 (s, 1H), 5.80-5.78 (m, 1H), 4.39 (d, J=5.3 Hz, 2H), 4.12-4.07 (m, 2H), 3.86 (s, 3H), 3.60-3.55 (m, 2H), 3.11 (d, J=7.4 Hz, 2H), 2.59 (s, 3H), 1.96-1.87 (m, 1H), 0.93 (d, J=7.4 Hz, 6H); $^{13}$C NMR (75 MHz, CDCl$_3$) δ 162.4, 157.4, 155.6, 152.9 152.6, 138.6, 129.5, 118.3, 117.0, 51.5, 42.8, 41.9, 38.8, 34.3, 26.7, 19.9, 17.1; MS (ES+) m/z 376.8 (M+1).

Example 12.23

Synthesis of 2-(3-isobutyl-2-oxoimidazolidin-1-yl)-4-methyl-N-(oxazol-4-ylmethyl)thiazole-5-carboxamide

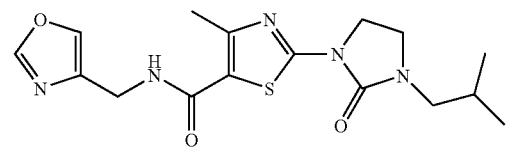

Following the procedure as describe in Example 12, making variations as required to replace (5-fluoropyridin-3-yl)methanamine with oxazol-4-ylmethanamine to react with 2-(3-isobutyl-2-oxoimidazolidin-1-yl)-4-methylthiazole-5-carboxylic acid in place of 2-(3-(cyclopropylmethyl)-2-oxoimidazolidin-1-yl)-4-methylthiazole-5-carboxylic acid, the title compound was obtained as a colorless solid in 17% yield: mp 115-118° C.; $^1$H NMR (300 MHz, CDCl$_3$) δ7.85 (s, 1H), 7.64 (s, 1H), 6.36-6.32 (m, 1H), 4.47 (d, J=5.5 Hz, 2H), 4.11-4.06 (m, 2H), 3.59-3.54 (m, 2H), 3.09 (d, J=7.4 Hz, 2H), 2.56 (s, 3H), 1.97-1.83 (m, 1H), 0.91 (d, J=7.4 Hz, 6H); MS (ES+) m/z 377.1 (M+1).

Example 13

Synthesis of 2-(1-(2-cyclopropylethyl)-5-oxo-1H-1,2,4-triazol-4(5H)-yl)-4-methyl-N-(pyridin-3-ylmethyl)thiazole-5-carboxamide

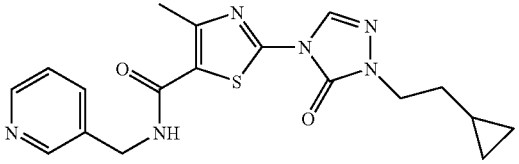

A. To a suspension of ethyl 4-methyl-2-(5-oxo-1H-1,2,4-triazol-4(5H)-yl)thiazole-5-carboxylate (0.25 g, 0.98 mmol) and potassium carbonate (0.20 g, 1.47 mmol) in acetone (20 mL) was added 2-cyclopropylethyl 4-methylbenzenesulfonate (0.28 g, 1.18 mmol). The reaction mixture was heated to reflux for 24 hours, cooled to ambient temperature and filtered. The filtrate was concentrated in vacuo to afford ethyl 2-(1-(2-cyclopropylethyl)-5-oxo-1H-1,2,4-triazol-4(5H)-yl)-4-methylthiazole-5-carboxylate in 63% yield (0.20 g): MS (ES+) m/z 323.3 (M+1).

B. To a solution of ethyl 2-(1-(2-cyclopropylethyl)-5-oxo-1H-1,2,4-triazol-4(5H)-yl)-4-methylthiazole-5-carboxylate (0.20 g, 2.78 mmol) in tetrahydrofuran (10 mL) and water (5 mL) was added lithium hydroxide monohydrate (0.15 g, 3.11 mmol) at ambient temperature. The resulting reaction mixture was heated to reflux for 20 hours. The solvent was removed in vacuo and the residue was neutralized to pH 4~5 with 10% hydrochloric acid. The resulting precipitate was collected by filtration and dried to afford 2-(1-(2-cyclopropylethyl)-5-oxo-1H-1,2,4-triazol-4(5H)-yl)-4-methylthiazole-5-carboxylic acid in 55% yield (0.10 g): MS (ES−) m/z 293.1 (M−1).

C. To a solution of 2-(1-(2-cyclopropylethyl)-5-oxo-1H-1,2,4-triazol-4(5H)-yl)-4-methylthiazole-5-carboxylic acid (0.07 g, 0.24 mmol) and 4-methylmorpholine (0.04 mL, 0.36 mmol) in tetrahydrofuran (10 mL) was added isobutyl chloroformate (0.04 mL, 0.30 mmol) at 0° C. The resulting mixture was stirred at ambient temperature for 1 hour and followed by the addition of 3-aminomethylpyridine (0.4 mL, 0.30 mmol). The reaction mixture was kept stirring at ambient temperature for 17 hours. The solvent was removed in vacuo and the residue was purified by column chromatography to afford N-ethyl-4-methyl-2-(2-oxo-3-(4-(trifluoromethoxy)benzyl)imidazolidin-1-yl)thiazole-5-carboxamide in 22% yield (0.02 g): mp 139-140° C.; (ethyl acetate/hexanes); $^1$H NMR (300 MHz, CDCl$_3$) δ 8.59-8.52 (m, 2H), 8.27 (s, 1H), 7.73-7.67 (m, 1H), 7.31-7.26 (m, 1H), 6.49 (t, J=5.8 Hz, 1H), 4.61 (d, J=5.8 Hz, 2H), 3.93 (t, J=7.0 Hz, 2H), 2.66 (s, 3H), 1.67 (q, J=7.0 Hz, 2H), 0.75-0.59 (m, 1H), 0.47-0.38 (m, 2H), 0.06-0.02 (m, 2H); MS (ES+) m/z 385.1 (M+1).

Example 14

Synthesis of 2-(1-(cyclopropylmethyl)-5-oxo-1H-1,2,4-triazol-4(5H)-yl)-4-methyl-N-(pyridin-4-ylmethyl)thiazole-5-carboxamide

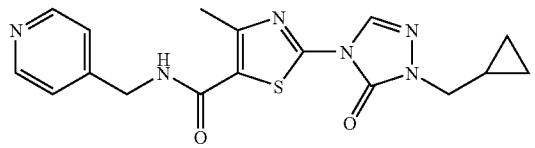

To a solution of 2-(1-(cyclopropylmethyl)-5-oxo-1H-1,2,4-triazol-4(5H)-yl)-4-methylthiazole-5-carboxylic acid (0.15 g, 0.53 mmol), 1-(3-dimethylaminopropyl)-3-ethylcarbodiimide hydrochloride (0.14 g, 0.69 mmol) and N,N-diisopropylethylamine (0.09 mL, 0.69 mmol) in N,N-dimethylformamide (10 mL) was added 1-hydroxybenzotriazole (0.09 g, 0.69 mmol). The resulting mixture was stirred at ambient temperature for 15 minutes, followed by the addition of 4-aminomethylpyridine (0.07 mL, 0.69 mmol). The reaction mixture was kept stirring at ambient temperature for 20 hours, diluted with ethyl acetate (200 mL) and washed with water and brine. The organic solution was dried over anhydrous sodium sulfate and filtered. The filtrate was concentrated in vacuo and the residue was purified by column chromatography to afford the title compound in 49% yield (0.10 g): mp 169-170° C.; $^1$H NMR (300 MHz, CDCl$_3$) δ 8.64-8.48 (m, 2H), 8.28-8.25 (m, 1H), 7.26-7.20 (m, 2H), 6.22 (t, J=5.8 Hz, 1H), 4.60 (d, J=5.8 Hz, 2H), 3.71 (d, J=7.2 Hz, 2H), 2.67 (s, 3H), 1.30-1.17 (m, 1H), 0.62-0.54 (m, 2H), 0.43-0.135 (m, 2H); MS (ES+) m/z 371.2 (M+1).

Example 14.1

Synthesis of N-((1H-pyrazol-3-yl)methyl)-2-(1-(cyclopropylmethyl)-5-oxo-1H-1,2,4-triazol-4(5H)-yl)-4-methylthiazole-5-carboxamide

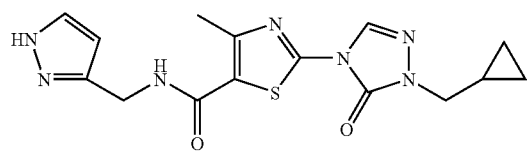

Following the procedure as describe in Example 14, making variations as required to replace 4-aminomethylpyridine with (1H-pyrazol-3-yl)methanamine, the title compound was obtained in 54% yield (0.11 g): mp 167-168° C.; $^1$H NMR (300 MHz, CDCl$_3$) δ 8.27-8.24 (m, 1H), 7.53 (d, J=2.1 Hz, 1H), 6.90 (t, J=5.5 Hz, 1H), 6.28 (d, J=2.1 Hz, 1H), 4.63 (d, J=5.5 Hz, 2H), 3.70 (d, J=7.2 Hz, 2H), 2.64 (s, 3H), 1.32-1.14 (m, 1H), 0.60-0.52 (m, 2H), 0.42-0.34 (m, 2H); MS (ES+) m/z 360.1 (M+1).

Example 14.2

Synthesis of 2-(1-(cyclopropylmethyl)-5-oxo-1H-1,2,4-triazol-4(5H)-yl)-4-methyl-N-(oxazol-4-ylmethyl)thiazole-5-carboxamide

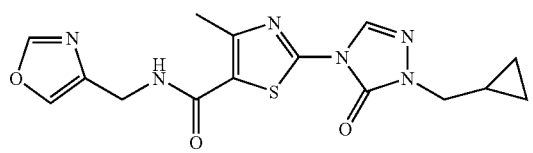

Following the procedure as describe in Example 14, making variations as required to replace 4-aminomethylpyridine with oxazol-4-ylmethanamine, the title compound was obtained in 48% yield (0.10 g): mp 157-158° C.; $^1$H NMR (300 MHz, CDCl$_3$) δ 8.26 (s, 1H), 7.86 (s, 1H), 7.68-7.63 (m, 1H), 6.34 (t, J=5.4 Hz, 1H), 4.51 (d, J=5.4 Hz, 2H), 3.71 (d, J=7.2 Hz, 2H), 2.64 (s, 3H), 1.32-1.14 (m, 1H), 0.65-0.52 (m, 2H), 0.43-7.34 (m, 2H); MS (ES+) m/z 361.0 (M+1).

Example 14.3

Synthesis of 2-(1-(Cyclopropylmethyl)-5-oxo-1H-1,2,4-triazol-4(5H)-yl)-4-methyl-N-(pyridin-2-ylmethyl)thiazole-5-carboxamide

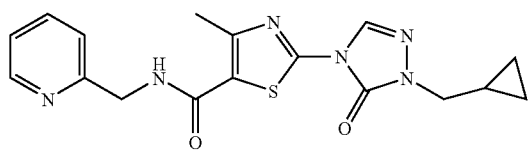

Following the procedure as describe in Example 14, making variations as required to replace 4-aminomethylpyridine with 2-aminomethylpyridine, the title compound was obtained in 52% yield (0.11 g): mp 160-161° C.; $^1$H NMR (300 MHz, CDCl$_3$) δ 8.59-8.49 (m, 1H), 8.30-8.27 (m, 1H), 7.75-7.63 (m, 1H), 7.39 (t, J=4.5 Hz, 1H), 7.30-7.25 (m, 1H), 7.24-7.18 (m, 1H), 4.70 (d, J=4.5 Hz, 2H), 3.72 (d, J=7.2 Hz, 2H), 2.69 (s, 3H), 1.36-1.14 (m, 1H), 0.67-0.49 (m, 2H), 0.43-0.34 (m, 2H); MS (ES+) m/z 371.1 (M+1).

Example 15

Synthesis of 2-(1-((2,2-difluorocyclopropyl)methyl)-5-oxo-1H-1,2,4-triazol-4(5H)-yl)-4-methyl-N-(pyridin-3-ylmethyl)thiazole-5-carboxamide

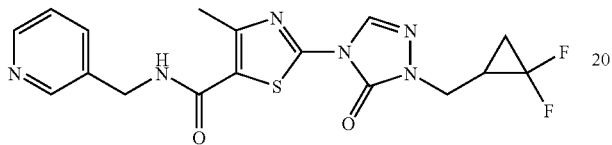

To a suspension of 4-methyl-2-(5-oxo-1H-1,2,4-triazol-4(5H)-yl)-N-(pyridin-3-ylmethyl)thiazole-5-carboxamide (0.15 g, 0.47 mmol) and potassium carbonate (0.10 g, 1.47 mmol) in N,N-dimethylformamide (2 mL) was added (2,2-difluorocyclopropyl)-methyl methanesulfonate (0.13 g, 0.70 mmol). The reaction mixture was kept stirring at ambient temperature for 20 hours, diluted with ethyl acetate (100 mL) and washed with water and brine. The organic solution was dried over anhydrous sodium sulfate and filtered. The filtrate was concentrated in vacuo and the residue was purified by column chromatography to afford the title compound in 41% yield (0.08 g): mp 160-161° C.; $^1$H NMR (300 MHz, CDCl$_3$) δ 8.53-8.41 (m, 2H), 8.24 (s, 1H), 7.69-7.62 (m, 1H), 7.27-7.16 (m, 2H), 4.54 (d, J=5.8 Hz, 2H), 4.00-3.81 (m, 2H), 2.58 (s, 3H), 2.08-1.91 (m, 1H), 1.56-1.41 (m, 1H), 1.40-1.10 (m, 1H); $^{13}$C NMR (75 MHz, CDCl$_3$) δ 161.8, 153.3, 150.9, 149.8, 149.1, 148.7, 135.8, 133.9, 131.1, 123.7, 121.8, 112.7, 43.2, 41.5, 20.8, 17.2, 15.4; MS (ES+) m/z 407.1 (M+1).

Example 16

Synthesis of 2-(3-((2,2-difluorocyclopropyl)methyl)-2-oxoimidazolidin-1-yl)-4-methyl-N-(pyridin-3-ylmethyl)thiazole-5-carboxamide

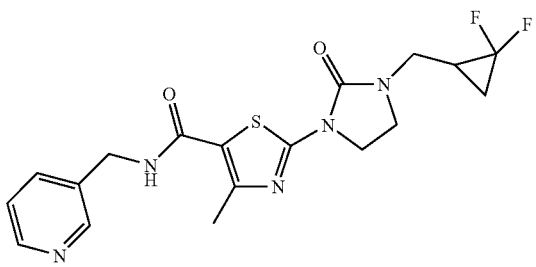

A mixture of 2-(3-((2,2-difluorocyclopropyl)methyl)-2-oxoimidazolidin-1-yl)-4-methylthiazole-5-carboxylic acid (0.11 g, 0.36 mmol), 2-(1H-benzotriazole-1-yl)-1,1,3,3-tetramethyluronium tetrafluoroborate (0.23 g, 0.73 mmol), N-hydroxybenzotriazole (0.20 g, 0.15 mmol) and N,N-diisopropylethylamine (0.09 g, 0.73 mmol) in anhydrous tetrahydrofuran (3.0 mL) was stirred at ambient temperature for 15 min, followed by the addition of 3-(aminomethyl)pyridine (0.08 g, 0.73 mmol) in anhydrous tetrahydrofuran (1.0 mL). The reaction mixture was stirred at ambient temperature for 16 h, followed by the addition of saturated sodium bicarbonate solution (2 mL). The mixture was extracted with ethyl acetate (3×3 mL). The combined organic layer was dried over anhydrous sodium sulfate and filtered. The filtrate was concentrated in vacuo to dryness. The solid was purified by flash chromatography eluted with dichloromethane in methanol (2%) to afford the title compound as a colourless solid (0.12 g, 81%): mp 169-171° C.; $^1$H NMR (300 MHz, DMSO-d$_6$) δ 8.52 (t, J=5.9 Hz, 1H), 8.49 (s, 1H), 8.42 (d, J=3.7 Hz, 1H), 7.67 (d, J=7.8 Hz, 1H), 7.32 (dd, J=7.8, 4.9 Hz, 1H), 4.35 (d, J=5.9 Hz, 2H), 3.99 (d, J=8.3 Hz, 1H), 3.61-3.47 (m, 3H), 3.20-3.12 (m, 1H), 2.44 (s, 3H), 2.05-1.88 (m, 1H), 1.67-1.55 (m, 1H), 1.37-1.27 (m, 1H); MS (ES+) m/z 409.0 (M+1).

Example 16.1

Synthesis of 2-(3-((2,2-difluorocyclopropyl)methyl)-2-oxoimidazolidin-1-yl)-4-methyl-N-(oxazol-2-ylmethyl)thiazole-5-carboxamide

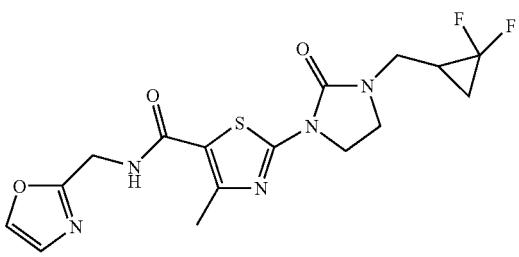

Following the procedure as describe in Example 16, making variations as required to replace 3-(aminomethyl)pyridine with (oxazol-2-yl)methylamine to react with 2-(3-((2,2-difluorocyclopropyl)methyl)-2-oxoimidazolidin-1-yl)-4-methylthiazole-5-carboxylic acid, the title compound was obtained as a colourless solid in 69% yield: mp 156-158° C.; $^1$H NMR (300 MHz, DMSO-d$_6$) δ 8.55 (t, J=5.7 Hz, 1H), 8.09 (s, 1H), 7.12 (s, 1H), 4.44 (d, J=5.7 Hz, 2H), 3.99 (t, J=8.4 Hz, 2H), 3.64-3.47 (m, 3H), 3.19-3.12 (m, 1H), 2.44 (s, 3H), 2.05-1.89 (m, 1H), 1.68-1.55 (m, 1H), 1.37-1.36 (m, 1H); $^{13}$C NMR (75 MHz, DMSO-d$_6$) δ 163.8, 163.1, 159.5, 156.8, 153.4, 141.5, 128.9, 119.2, 43.9, 43.6, 42.6, 42.6, 38.4, 21.8 5 (t, $^1J_{C\text{-}F}$=42 Hz), 19.0, 16.4 5 (t, $^1J_{C\text{-}F}$=42 Hz); MS (ES+) m/z 399.0 (M+1).

Example 16.2

Synthesis of 2-(3-((2,2-difluorocyclopropyl)methyl)-2-oxoimidazolidin-1-yl)-4-methyl-N-(thiazol-5-ylmethyl)thiazole-5-carboxamide

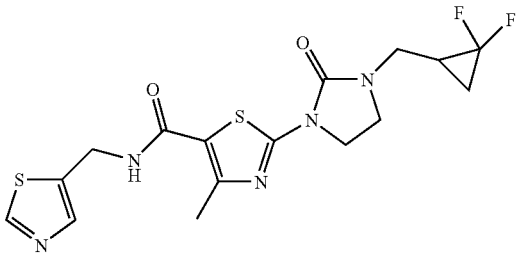

Following the procedure as describe in Example 16, making variations as required to replace 3-(aminomethyl)pyridine with (thiazole-5-yl)methylamine to react with 2-(3-((2,2-difluorocyclopropyl)methyl)-2-oxoimidazolidin-1-yl)-4-methylthiazole-5-carboxylic acid, the title compound was obtained as a colourless solid in 68% yield: mp 182-184° C.; $^1$H NMR (300 MHz, DMSO-d$_6$) δ 8.93 (s, 1H), 8.61 (t, J=6.0 Hz, 1H), 7.74 (s, 1H), 4.53 (d, J=6.0 Hz, 1H), 4.01-3.95 (m, 2H), 3.64-3.47 (m, 3H), 3.19-3.12 (m, 1H), 2.44 (s, 3H), 2.04-1.88 (m, 1H), 1.67-1.55 (m, 1H), 1.37-1.26 (m, 1H); MS (ES+) m/z 414.9 (M+1).

Example 16.3

Synthesis of 2-(3-((2,2-difluorocyclopropyl)methyl)-2-oxoimidazolidin-1-yl)-4-methyl-N-((4-methylthiazol-2-yl)methyl)thiazole-5-carboxamide

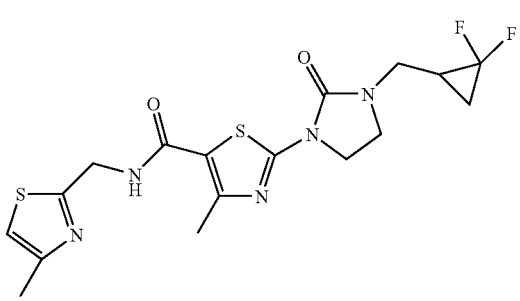

Following the procedure as describe in Example 16, making variations as required to replace 3-(aminomethyl)pyridine with 1-(4-methyl-1,3-thiazole-4-yl)methylamine to react with 2-(3-((2,2-difluorocyclopropyl)methyl)-2-oxoimidazolidin-1-yl)-4-methylthiazole-5-carboxylic acid, the title compound was obtained as a colourless solid in 77% yield: mp 157-159° C.; $^1$H NMR (300 MHz, DMSO-d$_6$) δ 8.42 (t, J=6.0 Hz, 1H), 7.11 (s, 1H), 4.36 (d, J=6.0 Hz, 1H), 4.02-3.96 (m, 2H), 3.64-3.47 (m, 3H), 3.20-3.12 (m, 1H), 2.59 (s, 3H), 2.44 (s, 3H), 2.04-1.89 (m, 1H), 1.68-1.55 (m, 1H), 1.37-1.26 (m, 1H); MS (ES+) m/z 428.9 (M+1).

Example 16.4

Synthesis of 2-(3-(4-fluorobenzyl)-2-oxoimidazolidin-1-yl)-N-((2-isopropylthiazol-4-yl)methyl)-4-methylthiazole-5-carboxamide

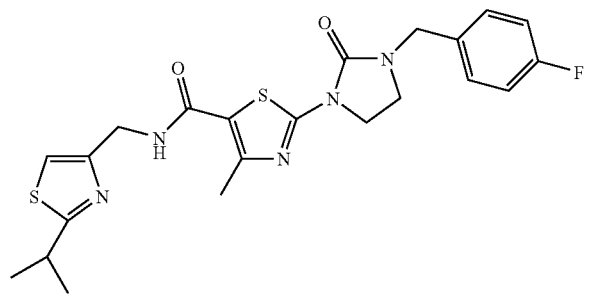

Following the procedure as describe in Example 16, making variations as required to replace 2-(3-((2,2-difluorocyclopropyl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with (2-isopropylthiazol-4-yl)methanamine, the title compound was obtained as a colourless solid in 68% yield: mp 170-172° C.; $^1$H NMR (300 MHz, DMSO-d$_6$) δ 8.45 (t, J=5.8 Hz, 1H), 7.35-7.30 (m, 2H), 7.19-7.14 (m, 3H), 4.41-4.39 (m, 4H), 3.97 (t, J=9.0 Hz, 2H), 3.42 (t, J=9.0 Hz, 2H), 3.26-3.15 (m, 1H), 2.44 (s, 3H), 1.28 (d, J=6.0 Hz, 6H); $^{13}$C NMR (75 MHz, DMSO-d$_6$) δ 177.2, 163.6, 162.2, 160.4, 157.9, 155.5, 154.0, 133.0 (d), 130.4 (d), 118.4, 115.9, 113.8, 46.6, 42.4, 42.0, 32.9, 23.3, 17.5; MS (ES+) m/z 474.0 (M+1).

Example 16.5

Synthesis of N-(3-(dimethylamino)benzyl)-2-(1-(4-fluorobenzyl)-5-oxo-1H-1,2,4-triazol-4(5H)-yl)-4-methylthiazole-5-carboxamide

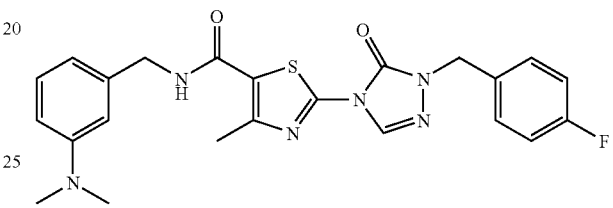

Following the procedure as describe in Example 16, making variations as required to replace 2-(3-((2,2-difluorocyclopropyl)methyl)-2-oxoimidazolidin-1-yl)-4-methylthiazole-5-carboxylic acid with 2-(1-(4-fluorobenzyl)-5-oxo-1H-1,2,4-triazol-4(5H)-yl)-4-methylthiazole-5-carboxylic acid to react with 3-(aminomethyl)-N,N-dimethylaniline, the title compound was obtained as a colourless solid in 50% yield: mp 149-151° C.; $^1$H NMR (300 MHz, DMSO-d$_6$) δ 8.78 (t, J=5.9 Hz, 1H), 8.71 (s, 1H), 7.35 (dd, J=8.5, 5.6 Hz, 1H), 7.15 (d, J=8.9 Hz, 1H), 7.09 (dd, J=7.9, 6.9 Hz, 2H), 6.66 (s, 1H), 6.58 (dd, J=7.7, 7.7 Hz, 2H), 4.96 (s, 2H), 4.35 (d, J=5.8 Hz, 2H), 2.83 (s, 6H); $^{13}$C NMR (75 MHz, DMSO-d$_6$) δ 163.7, 161.3, 160.5, 151.6, 151.2, 150.9, 150.1, 140.3, 132.7 (d, $^3J_{C-F}$=11 Hz), 132.4, 130.4 (d, $^2J_{C-F}$=33 Hz), 129.2, 123.1, 115.9 (d, $^1J_{C-F}$=86 Hz), 115.6, 111.7, 111.4, 48.2, 43.6, 40.5, 17.3; MS (ES+) m/z 467.16 (M+1).

Example 16.6

Synthesis of 2-(1-((2,2-difluorocyclopropyl)methyl)-5-oxo-1H-1,2,4-triazol-4(5H)-yl)-4-methylthiazole-5-carboxamide

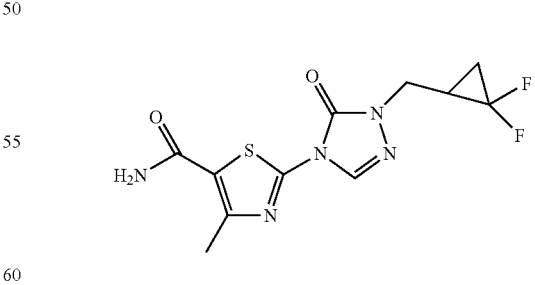

Following the procedure as describe in Example 16, making variations as required to replace 2-(3-((2,2-difluorocyclopropyl)methyl)-2-oxoimidazolidin-1-yl)-4-methylthiazole-5-carboxylic acid with 2-(1-((2,2-difluorocyclopropyl)methyl)-5-oxo-1H-1,2,4-triazol-4(5H)-yl)-4-methylthiazole-5-carboxylic acid to react with ammonium chloride, the title compound was obtained as a colourless solid in 62% yield: mp 273-275° C.; $^1$H NMR (300 MHz, DMSO-$d_6$) δ 8.74 (s, 1H), 7.60 (br, 2H), 4.02-3.79 (m, 2H), 2.52 (s, 3H), 2.20-2.05 (m, 1H), 1.72-1.60 (m, 1H), 1.48-1.37 (m, 1H); $^{13}$C NMR (75 MHz, DMSO-$d_6$) δ 163.1, 151.7, 151.4, 150.0, 132.4, 123.5, 114.4 (t), 42.7 (d), 20.8, 17.3, 14.9; MS (ES+) m/z 316.0 (M+1).

Example 16.7

Synthesis of N-((2-isopropylthiazol-4-yl)methyl)-4-methyl-2-(1-(4-methylbenzyl)-5-oxo-1H-1,2,4-triazol-4(5H)-yl)thiazole-5-carboxamide

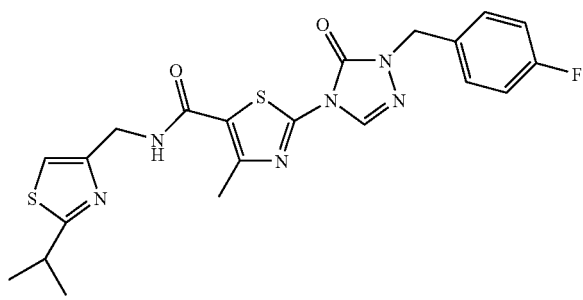

Following the procedure as describe in Example 16, making variations as required to replace 2-(3-((2,2-difluorocyclopropyl)methyl)-2-oxoimidazolidin-1-yl)-4-methylthiazole-5-carboxylic acid with 2-(1-(4-fluorobenzyl)-5-oxo-1H-1,2,4-triazol-4(5H)-yl)-4-methylthiazole-5-carboxylic acid to react with (2-isopropylthiazol-4-yl)methanamine, the title compound was obtained as a colourless solid in 61% yield: mp 151-153° C.; $^1$H NMR (300 MHz, DMSO-$d_6$) δ 8.81 (t, J=5.8 Hz, 1H), 8.73 (s, 1H), 7.33-7.30 (m, 2H), 7.20 (s, 1H), 7.19-7.13 (m, 2H), 4.97 (s, 2H), 4.44 (d, J=6.0 Hz, 2H), 3.63-3.53 (m, 1H), 2.54 (s, 3H), 1.28 (d, J=6.0 Hz, 6H); $^{13}$C NMR (75 MHz, DMSO-$d_6$) δ 177.3, 162.2 (d), 161.3, 153.6, 151.8, 151.4, 150.2, 132.7 (d), 132.5, 130.4 (d), 123.0, 115.9, 114.1, 48.2, 42.3, 32.9, 23.3, 17.4; MS (ES+) m/z 472.9 (M+1).

Example 17

Synthesis of 1-((2,2-difluorocyclopropyl)methyl)-3-(4-methyl-5-(1H-pyrazol-3-yl)thiazol-2-yl)imidazolidin-2-one

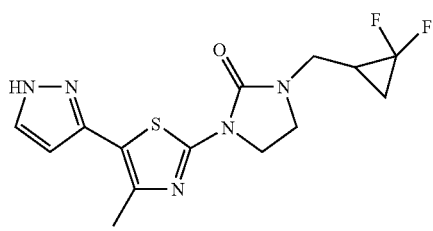

A mixture of 1-(5-acetyl-4-methylthiazol-2-yl)-3-((2,2-difluorocyclopropyl)-methyl)imidazolidin-2-one (0.32 g, 1.00 mmol) and N,N-dimethylformamidediemthyl acetal (0.24 g, 2.00 mmol) in anhydrous N,N-dimethylformamide (10.0 mL) was heated at 96° C. for 16 h and cooled to ambient temperature, followed by the addition of hydrazine monohydrate (1.0 mL). The mixture was heated at 96° C. for 0.5 h and cooled to ambient temperature, followed by the addition of water (20.0 mL). The pale yellow solid formed was collected by filtration and triturated with ethyl acetate and methanol to afford the title compound as a yellow solid (0.21 g, 90%): mp 227-230° C.; $^1$H NMR (300 MHz, DMSO-$d_6$) δ 12.89 (s, 1H), 7.76 (s, 1H), 6.41 (s, 1H), 3.97 (t, J=9.0 Hz, 2H), 3.63-3.47 (m, 3H), 3.18-3.10 (m, 1H), 2.37 (s, 3H), 2.03-1.88 (m, 1H), 1.67-1.55 (m, 1H), 1.36-1.25 (m, 1H); $^{13}$C NMR (75 MHz, DMSO-$d_6$) δ 155.8, 155.5, 144.0, 142.4, 130.3, 118.7, 114.9 (t), 103.2, 42.5, 42.2, 41.2 (d), 20.4 (t), 15.1 (t); MS (ES+) m/z 340.9 (M+1).

Example 17.1

Synthesis of 1-(4-methyl-5-(1H-pyrazol-3-yl)thiazol-2-yl)-3-(4,4,4-trifluorobutyl)imidazolidin-2-one

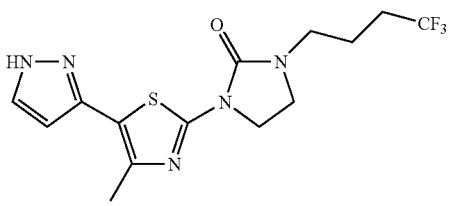

Following the procedure as describe in Example 17, making variations as required to replace 1-(5-acetyl-4-methylthiazol-2-yl)-3-((2,2-difluorocyclopropyl)methyl)-imidazolidin-2-one with 1-(5-acetyl-4-methylthiazol-2-yl)-3-(4,4,4-trifluorobutyl)-imidazolidin-2-one, the title compound was obtained as a yellow solid in 65% yield: mp 185-186° C.; $^1$H NMR (300 MHz, DMSO-$d_6$) δ12.88 (s, 1H), 7.77 (s, 1H), 6.41 (s, 1H), 3.95 (t, J=9.0 Hz, 2H), 3.52 (t, J=9.0 Hz, 2H), 3.30-3.24 (m, 2H), 2.37 (s, 3H), 2.32-2.19 (m, 2H), 1.76-1.66 (m, 2H); $^{13}$C NMR (75 MHz, DMSO-$d_6$) δ 155.9, 155.8, 144.1, 142.4, 130.3, 128.1 (q), 118.0, 103.2, 42.6, 42.5, 42.2, 30.4 (q), 20.2 (m), 17.0; MS (ES+) m/z 360.9 (M+1).

Example 17.2

Synthesis of 1-(4-methyl-5-(1H-pyrazol-3-yl)thiazol-2-yl)-3-(3-(trifluoromethyl)benzyl)imidazolidin-2-one

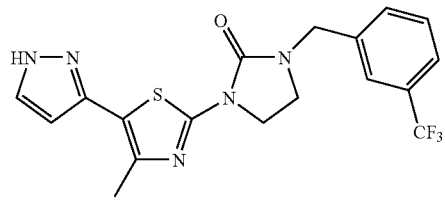

Following the procedure as describe in Example 17, making variations as required to replace 1-(5-acetyl-4-methylthiazol-2-yl)-3-((2,2-difluorocyclopropyl)methyl) imidazolidin-2-one with 1-(5-acetyl-4-methylthiazol-2-yl)-3-(3-(trifluoromethyl)benzyl)-imidazolidin-2-one, the title compound was obtained as a yellow solid in 38% yield: mp 209-214° C.; $^1$H NMR (300 MHz, DMSO-$d_6$) δ 7.70-7.58 (m, 4H), 4.55 (s, 2H), 4.04 (t, J=6.0 Hz, 2H), 3.51 (t, J=6.0 Hz, 2H), 2.51 (s, 3H), 2.45 (s, 3H); $^{13}$C NMR (75 MHz, DMSO-$d_6$) δ 155.9, 155.8, 144.0, 142.4, 138.8, 132.4, 130.2, 129.8

(q, $^3J_{CF}$=30 Hz), 126.4, 124.9-124.6 (m), 112.8, 118.2, 103.2, 49.1, 47.0, 42.5, 42.4, 16.9; MS (ES+) m/z 408.9 (M+1), 407.7 (M+1).

Example 18

Synthesis of 1-(4-fluorobenzyl)-4-(4-methyl-5-(2H-tetrazol-5-yl)thiazol-2-yl)-1H-1,2,4-triazol-5(4H)-one

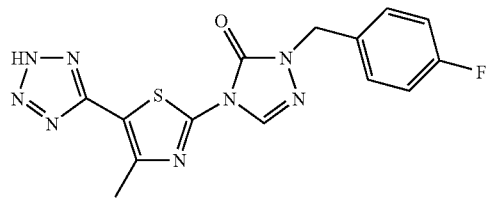

A. A mixture of 2-(1-(4-fluorobenzyl)-5-oxo-1H-1,2,4-triazol-4(5H)-yl)-4-methylthiazole-5-carboxamide (0.45 g, 1.35 mmol), pyridine (0.21 g, 2.71 mmol) and trifluoroacetic anhydride (0.57 g, 2.71 mmol) in dioxane (12.0 mL) was heated at reflux for 16 h and concentrated in vacuo to dryness. The residue was purified by flash column chromatography eluted with ethyl acetate in hexane (20%) to afford 2-(1-(4-fluorobenzyl)-5-oxo-1H-1,2,4-triazol-4(5H)-yl)-4-methylthiazole-5-carbonitrile as a colourless solid (0.26 g, 63%): mp 190-192° C.; $^1$H NMR (300 MHz, DMSO-$d_6$) δ 8.80 (s, 1H), 7.38-7.33 (m, 2H), 7.18-7.12 (m, 2H), 4.97 (s, 2H), 2.49 (s, 3H); $^{13}$C NMR (75 MHz, DMSO-$d_6$) δ 162.2 (d), 161.3, 156.0, 150.3, 132.5, 132.4, 130.5 (d), 115.9 (d), 113.3, 97.5, 48.3, 17.2; MS (ES+) m/z 316.9 (M+1).

B. A mixture of 2-(1-(4-fluorobenzyl)-5-oxo-1H-1,2,4-triazol-4(5H)-yl)-4-methylthiazole-5-carbonitrile (0.10 g, 0.31 mmol), sodium azide (0.08 g, 1.57 mmol) and ammonium chloride (0.07 g, 1.57 mmol) in anhydrous N,N-dimethylformamide (5.0 mL) was heated at 80° C. for 16 h. The reaction was quenched with the addition of water (2.0 mL) and the solvents were removed in vacuo. The residue was dissolved with ethyl acetate (10 mL), washed with water (2×2 mL), dried over anhydrous sodium sulfate and filtered. The filtrate was concentrated in vacuo to dryness. The residue was crystallized from methanol and ether to afford the title compound as a colourless solid (0.08 g, 72%): mp 136-139° C.; $^1$H NMR (300 MHz, DMSO-$d_6$) δ 8.80 (s, 1H), 7.42-7.37 (m, 2H), 7.23-7.17 (m, 2H), 6.17 (br, 1H), 5.02 (s, 2H), 2.75 (s, 3H); $^{13}$C NMR (75 MHz, DMSO-$d_6$) δ 161.6 (d), 158.7, 151.8, 149.7, 148.6, 132.1 (d), 132.0, 129.9 (d), 115.4 (d), 113.6, 47.7, 16.7; MS (ES−) m/z 356.9 (M−1).

Example 18.1

Synthesis of 1-(4-fluorobenzyl)-3-(4-methyl-5-(2H-tetrazol-5-yl)thiazol-2-yl)imidazolidin-2-one

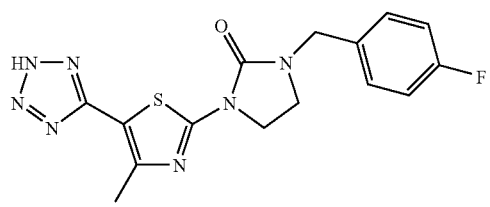

A. Following the procedure as describe in step A of Example 18, making variations as required to replace 2-(1-(4-fluorobenzyl)-5-oxo-1H-1,2,4-triazol-4(5H)-yl)-4-methylthiazole-5-carboxamide with 2-(3-(4-fluorobenzyl)-2-oxoimidazolidin-1-yl)-4-methylthiazole-5-carboxamide, 2-(3-(4-fluorobenzyl)-2-oxoimidazolidin-1-yl)-4-methylthiazole-5-carbonitrile was obtained as a pale yellow solid in 68% yield: mp 136-139° C.; $^1$H NMR (300 MHz, DMSO-$d_6$) δ 7.35-7.31 (m, 2H), 7.18-7.13 (m, 2H), 4.41 (s, 2H), 4.00 (t, J=6.0 Hz, 2H), 3.46 (t, J=6.0 Hz, 2H) 2.37 (s, 3H); $^{13}$C NMR (75 MHz, DMSO-$d_6$) δ 162.1 (d), 161.4, 161.1, 155.3, 150.3, 132.8 (d), 130.5 (d), 115.9 (d), 114.4, 92.4, 46.6, 42.7, 42.3, 17.3; MS (ES+) m/z 317.91 (M+1).

B. Following the procedure as describe in step B of Example 18, making variations as required to replace 2-(1-(4-fluorobenzyl)-5-oxo-1H-1,2,4-triazol-4(5H)-yl)-4-methylthiazole-5-carbonitrile with 2-(3-(4-fluorobenzyl)-2-oxoimidazolidin-1-yl)-4-methylthiazole-5-carbonitrile, the title compound was obtained as a colourless solid in 65% yield: mp 145-149° C.; $^1$H NMR (300 MHz, DMSO-$d_6$) δ 7.40-7.35 (m, 2H), 7.23-7.17 (m, 2H), 4.45 (s, 2H), 4.05 (t, J=9.0 Hz, 2H), 3.49 (t, J=9.0 Hz, 2H) 2.58 (s, 3H); $^{13}$C NMR (75 MHz, DMSO-$d_6$) δ 163.1, 159.9, 158.5, 155.0, 149.5, 132.5 (d), 129.9 (d), 115.5, 115.2, 46.1, 42.0, 41.6, 16.9; MS (ES+) m/z 359.9 (M+1).

Example 19

Synthesis of 2-(4-(4-fluorobenzyl)-3-oxo-2,4-diazabicyclo[3.1.0]hexan-2-yl)-4-methyl-N-(pyridin-3-ylmethyl)thiazole-5-carboxamide

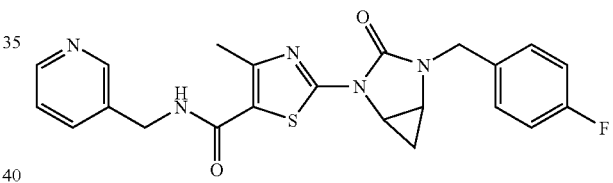

To a 25-mL two-neck round bottom flask under argon was charged with 2-(3-(4-fluorobenzyl)-2-oxo-2,3-dihydro-1H-imidazol-1-yl)-4-methyl-N-(pyridin-3-ylmethyl)thiazole-5-carboxamide (0.10 g, 0.24 mmol) and tetrahydrofuran (5 mL). Diethylzinc in hexanes (0.35 mL of 1 M solution, 0.35 mmol) was added slowly with a syringe. The solution was stirred and maintained at ambient temperature while diiodomethane (0.10 g, 0.35 mmol) was added slowly with a syringe. The reaction mixture was stirred at 60° C. for 8 hours and cooled in an ice-water bath, followed by the addition of saturated aqueous ammonium chloride (5 mL). The mixture was extracted with ethyl acetate (80 mL) and washed with saturated aqueous ammonium chloride (2×8 mL), water (3×8 mL), dried over sodium sulfate and filtered. The filtrate was concentrated and purified by preparative thin layer chromatography eluted with dichloromethane/methanol (20/1) to afford the title compound in 7% yield (7 mg). $^1$H NMR (300 MHz, CDCl$_3$) δ 8.57 (br, 2H), 7.66-7.63 (m, 1H), 7.35-7.26 (m, 2H), 7.20-7.18 (m, 1H), 7.06-7.00 (m, 2H), 6.31-6.29 (m, 1H), 4.87 (br s, 2H), 4.74 (br s, 2H), 3.00 (br s, 2H), 2.39 (s, 3H), 0.92-0.81 (m, 2H); MS (ES+) m/z 437.9 (M+1).

Example 20

The following compounds were prepared following the procedures as described in above examples or known by one skilled in the art:

| | Structure | Chemical Name | Characterization Data |
|---|---|---|---|
| 1 | 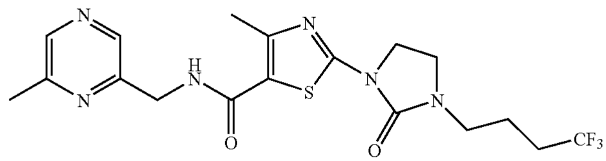 | 4-methyl-N-((6-methylpyrazin-2-yl)methyl)-2-(2-oxo-3-(4,4,4-trifluorobutyl)-imidazolidin-1-yl)-thiazole-5-carboxamide | mp 123° C.; $^1$H NMR (300 MHz, CDCl$_3$) δ 8.51 (s, 1H), 8.39 (s, 1H), 6.75-6.72 (m, 1H), 4.70 (d, J = 4.9 Hz, 2H), 4.17-4.12 (m, 2H), 3.64-3.59 (m, 2H), 3.44-3.39 (m, 2H), 2.63 (s, 3H), 2.57 (s, 3H), 2.25-2.09 (m, 2H), 1.92-1.82 (m, 2H); MS (ES+) m/z 442.7 (M + 1). |
| 2 | 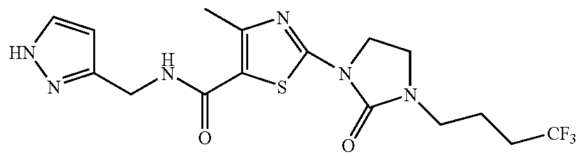 | N-((1H-pyrazol-4-yl)-methyl)-4-methyl-2-(2-oxo-3-(4,4,4-trifluorobutyl)-imidazolidin-1-yl)-thiazole-5-carboxamide | $^1$H NMR (300 MHz, DMSO-d$_6$) δ 12.58 (br s, 1H), 8.34-8.32 (m, 1H), 7.58-7.57 (m, 1H), 6.14 (s, 1H), 4.37 (d, J = 5.5 Hz, 2H), 4.02-3.96 (m, 2H), 3.59-3.53 (m, 2H), 3.33-3.28 (m, 2H), 2.46 (s, 3H), 2.32-2.26 (m, 2H), 1.76-1.71 (m, 2H); MS (ES+) m/z 416.7 (M + 1). |
| 3 | 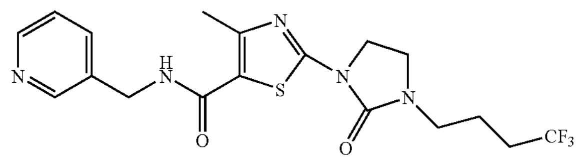 | 4-methyl-2-(2-oxo-3-(4,4,4-trifluorobutyl)-imidazolidin-1-yl)-N-(pyridin-3-ylmethyl)-thiazole-5-carboxamide | mp 167-169° C.; $^1$H NMR (300 MHz, CDCl$_3$) δ 8.62-8.52 (m, 2H), 7.69-7.66 (m, 1H), 7.26 7.24 (m, 1H), 6.28-6.25 (m, 1H), 4.57 (d, J = 5.9 Hz, 2H), 4.14-4.09 (m, 2H), 3.62-3.56 (m, 2H), 3.40-3.36 (m, 2H), 2.60 (s, 3H), 2.18-2.09 (m, 2H), 1.89-1.79 (m, 2H); MS (ES+) m/z 428.1 (M + 1). |
| 4 | 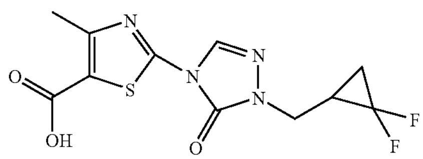 | 2-(1-((2,2-difluorocyclopropyl)-methyl)-5-oxo-1H-1,2,4-triazol-4(5H)-yl)-4-methylthiazole-5-carboxylic acid | mp 220-222° C.; $^1$H NMR (300 MHz, DMSO-d$_6$) δ 13.43 (br, 1H), 8.74 (s, 1H), 3.97-3.77 (m, 2H), 2.54 (s, 3H), 2.20-2.04 (m, 1H), 1.73-1.60 (m, 1H), 1.48-1.37 (m, 1H); MS (ES+) m/z 317.09 (M + 1). |
| 5 | 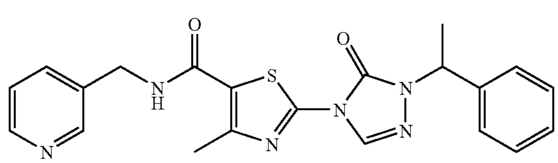 | 4-methyl-2-(5-oxo-1-(1-phenylethyl)-1H-1,2,4-triazol-4(5H)-yl)-N-(pyridin-3-ylmethyl)thiazole-5-carboxamide | mp 122-124° C.; $^1$H NMR (300 MHz, DMSO-d$_6$) δ 8.89 (t, J = 5.8 Hz, 1H), 8.79 (s, 1H), 8.55 (d, J = 1.8 Hz, 1H), 8.46 (dd J = 4.8, 1.6 Hz, 1H), 7.75-7.72 (m, 1H), 7.38-7.25 (m, 6H), 5.47 (q, J = 7.0 Hz, 1H), 4.44 (d, J = 5.8 Hz, 2H), 2.56 (s, 3H), 1.71 (d, J = 7.1 Hz, 3H); MS (ES+) m/z 421.0 (M + 1). |
| 6 | 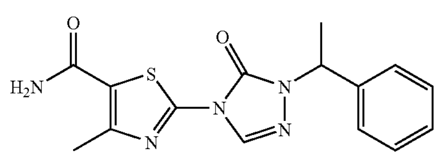 | 4-methyl-2-(5-oxo-1-(1-phenylethyl)-1H-1,2,4-triazol-4(5H)-yl)thiazole-5-carboxamide | mp 225-230° C.; $^1$H NMR (300 MHz, DMSO-d$_6$) δ 8.74 (s, 1H), 7.60 (br, 2H), 7.32 (d, J = 4.4 Hz, 4H), 7.29-7.21 (m, 1H), 5.47 (q, J = 7.0 Hz, 1H), 2.55 (s, 3H), 1.71 (d, J = 7.1 Hz, 3H); MS (ES+) m/z 330.0 M + 1). |
| 7 | 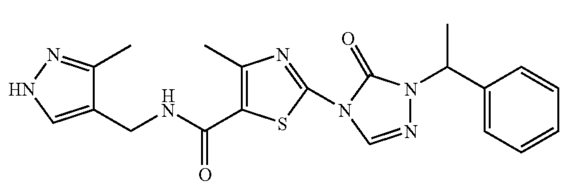 | 4-methyl-N-((3-methyl-1H-pyrazol-4-yl)methyl)-2-(5-oxo-1-(1-phenylethyl)-1H-1,2,4-triazol-4(5H)-yl)thiazole-5-carboxamide | mp 125-126° C.; $^1$H NMR (300 MHz, DMSO-d$_6$) δ 12.51 (s, 1H), 8.85 (t, J = 5.3 Hz, 1H), 8.83-8.79 (m, 2H), 7.44-7.28 (m, 5H), 5.49 (q, J = 7.0 Hz, 1H), 4.79 (d, J = 5.3 Hz, 2H), 2.76 (s, 3H), 2.59 (s, 3H), 1.73 (d, J = 6.9 Hz, 3H); MS (ES+) m/z 424.2 M + 1). |
| 8 | 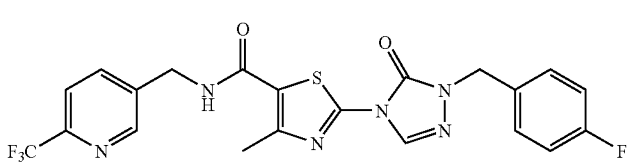 | 2-(1-(4-fluorobenzyl)-5-oxo-1H-1,2,4-triazol-4(5H)-yl)-4-methyl-N-((6-(trifluoromethyl)pyridin-3-yl)methyl)thiazole-5-carboxamide | mp 168-170° C.; $^1$H NMR (300 MHz, DMSO-d$_6$) δ , 8.78 (s, 1H), 8.74 (d, J = 1.3 Hz, 1H), 8.01 (dd, J = 8.1, 1.5 Hz, 1H), 7.90 (d, J = 8.1 Hz, 1H), 7.38 (dd, J = 8.6, 5.6 Hz, 2H), 7.19 (dd, J = 8.9, 5.9 Hz, 2H), 5.00 (s, 2H), 4.54 (d, J = 3.0 Hz, 2H), 2.57 (s, 3H); MS (ES+) m/z 492.9 (M + 1). |

-continued

| | Structure | Chemical Name | Characterization Data |
|---|---|---|---|
| 9 | 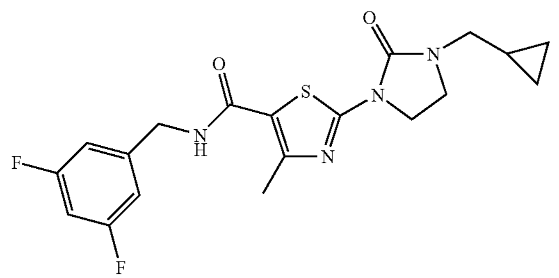 | 2-(3-(cyclopropylmethyl)-2-oxoimidazolidin-1-yl)-N-(3,5-difluorobenzyl)-4-methylthiazole-5-carboxamide | mp 163-165° C.; $^1$H NMR (300 MHz, DMSO-d$_6$) δ 8.54 (t, J = 6.0 Hz, 1H), 7.11-7.06 (m, 1H), 7.03-6.96 (m, 2H), 4.39 (d, J = 0.3 Hz, 2H), 4.04-3.99 (m, 2H), 3.68-3.63 (m, 2H), 3.10 (d, J = 6.0 Hz, 2H), 2.48 (s, 3H), 1.02-0.89 (m, 1H), 0.52-0.46 (m, 2H), 0.25-0.20 (m, 2H); MS (ES+) m/z 407.9 (M + 1), 406.9 (M + 1). |
| 10 | 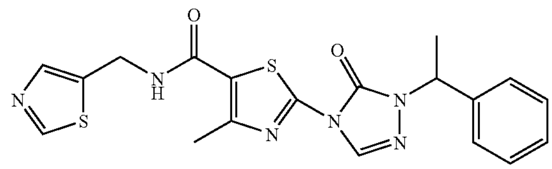 | 4-methyl-2-(5-oxo-1-(1-phenylethyl)-1H-1,2,4-triazol-4(5H)-yl)-N-(thiazol-5-ylmethyl)thiazole-5-carboxamide | mp 98-99° C.; $^1$H NMR (300 MHz, DMSO-d$_6$) δ 8.99 (t, J = 6.3 Hz, 1H), 8.90 (s, 1H), 8.79 (s, 1H), 7.81 (s, 1H), 7.37-7.35 (m, 4H), 7.33-7.26 (m, 1H), 5.48 (q, J = 7.0 Hz, 1H), 4.62 (d, J = 6.0 Hz, 1H), 2.56 (s, 3H), 1.71 (d, J = 7.0 Hz, 3H); MS (ES+) m/z 426.9 (M + 1). |
| 11 | 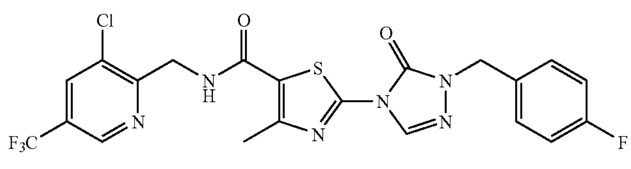 | N-((3-chloro-5-(trifluoromethyl)pyridin-2-yl)methyl)-2-(1-(4-fluorobenzyl)-5-oxo-1H-1,2,4-triazol-4(5H)-yl)-4-methylthiazole-5-carboxamide | mp 176-178° C.; $^1$H NMR (300 MHz, DMSO-d$_6$) δ 8.91 (t, J = 5.7 Hz, 1H), 8.80 (s, 1H), 8.74 (s, 1H), 8.45 (s, 1H), 7.35 (d, J = 8.6 Hz, 2H), 7.16 (d, J = 8.9 Hz, 2H), 4.97 (s, 2H), 4.68 (d, J = 5.8 Hz, 2H), 2.55 (s, 3H); MS (ES+) m/z 526.8 (M + 1). |
| 12 | 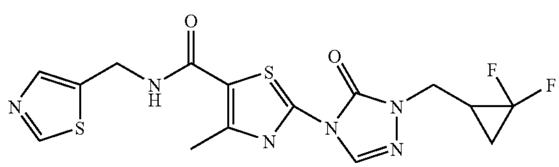 | 2-(1-((2,2-difluorocyclopropyl)methyl)-5-oxo-1H-1,2,4-triazol-4(5H)-yl)-4-methyl-N-(thiazol-5-ylmethyl)thiazole-5-carboxamide | mp 148-151° C.; $^1$H NMR (300 MHz, DMSO-d$_6$) δ 8.96 (t, J = 5.7 Hz, 1H), 8.79 (s, 1H), 8.75 (s, 1H), 7.78 (s, 1H), 4.59 (d, J = 5.7 Hz, 2H), 3.98-3.79 (m, 2H), 2.53 (s, 3H), 2.20-2.04 (m, 1H), 1.72-1.60 (m, 1H), 1.48-1.37 (m, 1H); MS (ES+) m/z 413.8 (M + 1), 412.7 (M + 1). |
| 13 | 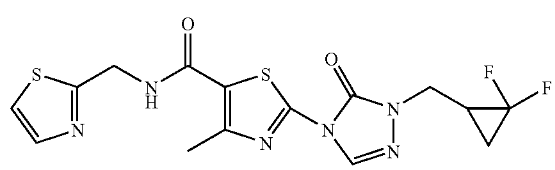 | 2-(1-((2,2-difluorocyclopropyl)methyl)-5-oxo-1H-1,2,4-triazol-4(5H)-yl)-4-methyl-N-(thiazol-2-ylmethyl)thiazole-5-carboxamide | mp 162-164° C.; $^1$H NMR (300 MHz, DMSO-d$_6$) δ 8.16 (t, J = 5.8 Hz, 1H), 8.77 (s, 1H), 7.71 (d, J = 3.3 Hz, 1H), 7.61 (d, J = 3.3 Hz, 1H), 4.67 (d, J = 5.9 Hz, 2H), 3.98-3.80 (m, 2H), 2.56 (s, 3H), 2.21-2.05 (m, 1H), 1.73-1.60 (m, 1H), 1.49-1.37 (m, 1H); MS (ES+) m/z 413.8 (M + 1), 412.9 (M + 1). |
| 14 | 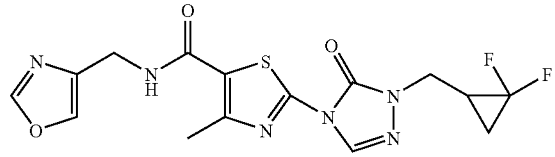 | 2-(1-((2,2-difluorocyclopropyl)methyl)-5-oxo-1H-1,2,4-triazol-4(5H)-yl)-4-methyl-N-(oxazol-4-ylmethyl)thiazole-5-carboxamide | mp 132-134° C.; $^1$H NMR (300 MHz, DMSO-d$_6$) δ 8.87 (t, J = 5.7 Hz, 1H), 8.78 (s, 1H), 8.75 (s, 1H), 7.78 (s, 1H), 4.59 (d, J = 5.7 Hz, 2H), 3.98-3.79 (m, 2H), 2.53 (s, 3H), 2.20-2.04 (m, 1H), 1.72-1.60 (m, 1H), 1.48-1.37 (m, 1H); MS (ES+) m/z 396.9 (M + 1). |
| 15 | 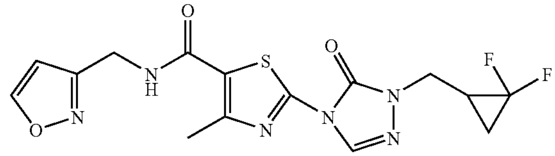 | 2-(1-((2,2-difluorocyclopropyl)methyl)-5-oxo-1H-1,2,4-triazol-4(5H)-yl)-N-(isoxazol-3-ylmethyl)-4-methylthiazole-5-carboxamide | mp 128-132° C.; $^1$H NMR (300 MHz, DMSO-d$_6$) δ 8.87 (t, J = 5.8 Hz, 1H), 8.82 (d, J = 3.4 Hz, 1H), 8.75 (s, 1H), 6.50 (d, J = 3.4 Hz, 1H), 4.47 (d, J = 5.9 Hz, 2H), 3.98-3.80 (m, 2H), 2.54 (s, 3H), 2.20-2.05 (m, 1H), 1.74-1.60 (m, 1H), 1.48-1.37 (m, 1H); MS (ES+) m/z 396.9 (M + 1). |

| | Structure | Chemical Name | Characterization Data |
|---|---|---|---|
| 16 | 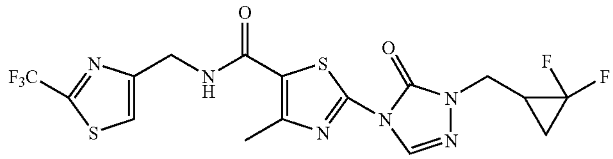 | 2-(1-((2,2-difluorocyclopropyl)-methyl)-5-oxo-1H-1,2,4-triazol-4(5H)-yl)-4-methyl-N-((2-(trifluoromethyl)thiazol-4-yl)methyl)thiazole-5-carboxamide | mp 159-161° C.; $^1$H NMR (300 MHz, DMSO-$d_6$) δ 8.99 (t, J = 5.6 Hz, 1H), 8.80 (s, 1H), 7.95 (s, 1H), 4.59 (d, J = 5.6 Hz, 2H), 4.03-3.89 (m, 2H), 2.58 (s, 3H), 2.24-2.08 (m, 1H), 1.76-1.64 (m, 1H), 1.52-1.41 (m, 1H); MS (ES+) m/z 480.6 (M + 1). |
| 17 | 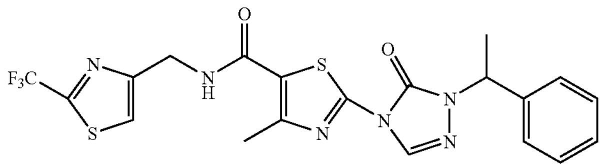 | 4-methyl-2-(5-oxo-1-(1-phenylethyl)-1H-1,2,4-triazol-4(5H)-yl)-N-((2-(trifluoromethyl)-thiazol-4-yl)-methyl)thiazole-5-carboxamide | mp 128-130° C.; $^1$H NMR (300 MHz, DMSO-$d_6$) δ 8.98 (br, 1H), 8.80 (s, 1H), 7.94 (s, 1H), 7.37-7.28 (m, 5H), 5.48 (q, J = 7.0 Hz, 2H), 4.59 (s, 2H), 2.57 (s, 3H), 1.72 (d, J = 7.1 Hz, 3H); MS (ES+) m/z 494.8 (M + 1). |
| 18 | 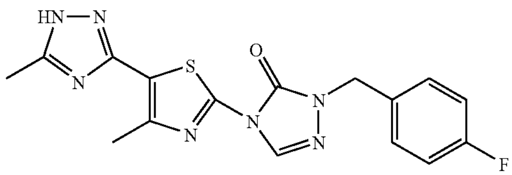 | 1-(4-fluorobenzyl)-4-(4-methyl-5-(5-methyl-1H-1,2,4-triazol-3-yl)thiazol-2-yl)-1H-1,2,4-triazol-5(4H)-one | mp 274-277° C.; $^1$H NMR (300 MHz, DMSO-$d_6$) δ 8.75 (s, 1H), 7.39 (dd, J = 8.7, 5.5 Hz, 2H), 7.20 (dd, J = 8.8, 5.6 Hz, 2H), 5.00 (s, 2H), 3.34 (br, 1H), 2.66 (s, 3H), 2.39 (s, 3H); MS (ES+) m/z 371.9 (M + 1). |
| 19 | 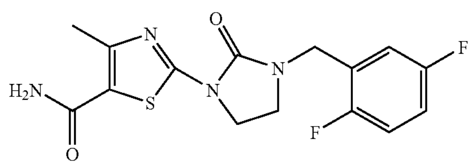 | 2-(3-(2,5-difluorobenzyl)-2-oxoimidazolidin-1-yl)-4-methylthiazole-5-carboxamide | $^1$H NMR (300 MHz, DMSO-$d_6$) δ 7.33-7.18 (m, 5H), 4.48 (s, 2H), 4.04-3.99 (m, 2H), 3.55-3.49 (m, 2H), 2.46 (s, 3H); MS (ES+) m/z 352.7 (M + 1). |
| 20 | 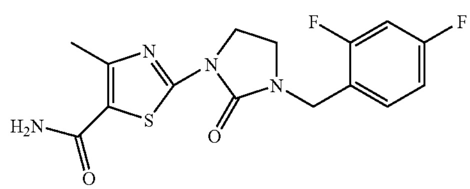 | 2-(3-(2,4-difluorobenzyl)-2-oxoimidazolidin-1-yl)-4-methylthiazole-5-carboxamide | $^1$H NMR (300 MHz, DMSO-$d_6$) δ 7.55-7.47 (m, 1H), 7.37-7.30 (m, 3H), 7.18-7.12 (m, 1H), 4.51 (s, 2H), 4.06-4.01 (m, 2H), 3.55-3.50 (m, 2H), 2.50 (s, 3H); MS (ES+) m/z 352.7 (M + 1). |
| 21 | 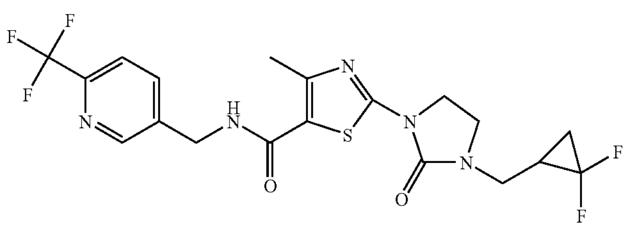 | 2-(3-((2,2-difluorocyclopropyl)-methyl)-2-oxoimidazolidin-1-yl)-4-methyl-N-((6-(trifluoromethyl)pyridin-3-yl)methyl)thiazole-5-carboxamide | mp 169-171° C.; $^1$H NMR (300 MHz, DMSO-$d_6$) δ 8.16 (t, J = 6.0 Hz, 1H), 7.89 (d, J = 8.3 Hz, 1H), 7.68 (d, J = 3.3 Hz, 1H), 7.54 (dd, J = 8.1, 3.6 Hz, 1H), 4.13 (t, J = 6.0 Hz, 2H), 3.73 (t, J = 6.0 Hz, 2H), 3.16 (d, J = 6.0 Hz, 2H), 2.63 (s, 3H), 1.06-0.93 (m, 1H), 0.55-0.49 (m, 2H), 0.28-0.23 (m, 2H); MS (ES+) m/z 439.9 (M + 1). |
| 22 | 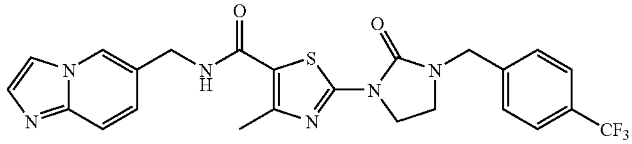 | N-(imidazo[1,2-a]pyridin-6-ylmethyl)-4-methyl-2-(2-oxo-3-(4-(trifluoromethyl)-benzyl)imidazolidin-1-yl)-thiazole-5-carboxamide | mp 155-158° C.; $^1$H NMR (300 MHz, DMSO-$d_6$) δ 8.54 (t, J = 5.8 Hz, 1H), 8.45 (s, 1H), 7.96 (s, 1H), 7.74 (d, J = 8.2 Hz, 2H), 7.58-7.50 (m, 4H), 7.22 (dd, J = 9.3, 1.5 Hz, 1H), 4.54 (s, 2H), 4.37 (d, J = 5.8 Hz, 2H), 4.05-4.00 (m, 2H), 3.52-3.47 (m, 2H), 2.49 (s, 3H); MS (ES+) m/z 515.2 (M + 1). |
| 23 | 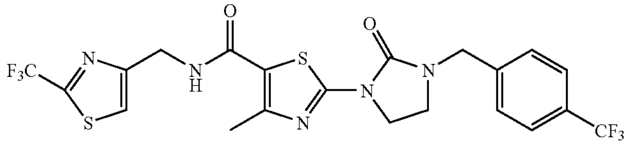 | 4-methyl-2-(2-oxo-3-(4-(trifluoromethyl)-benzyl)imidazolidin-1-yl)-N-((2-(trifluoromethyl)-thiazol-4-yl)-methyl)thiazole-5-carboxamide | $^1$H NMR (300 MHz, DMSO-$d_6$) δ 8.65 (t, J = 5.4 Hz, 1H), 7.90 (s, 1H), 7.74 (d, J = 8.2 Hz, 2H), 7.56 (d, J = 8.1 Hz, 2H), 4.57 (d, J = 5.4 Hz, 2H), 4.54 (s, 2H), 4.07-4.02 (m, 2H), 3.54-3.49 (m, 2H), 2.50 (s, 3H); MS (ES+) m/z 550.1 (M + 1). |

| | Structure | Chemical Name | Characterization Data |
|---|---|---|---|
| 24 | 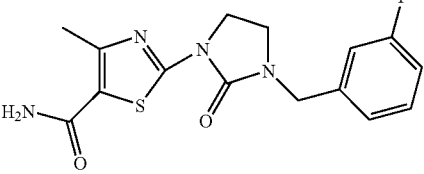 | 2-(3-(3-fluorobenzyl)-2-oxoimidazolidin-1-yl)-4-methylthiazole-5-carboxamide | $^1$H NMR (300 MHz, DMSO-d$_6$) δ 7.45-7.32 (m, 3H), 7.17-7.11 (m, 3H), 4.46 (s, 2H), 4.04-3.99 (m, 2H), 3.51-3.46 (m, 2H), 2.46 (s, 3H); MS (ES+) m/z 334.8 (M + 1). |
| 25 | 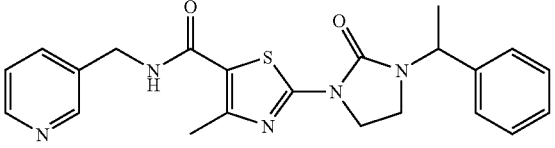 | 4-methyl-2-(2-oxo-3-(1-phenylethyl)-imidazolidin-1-yl)-N-(pyridin-3-yl-methyl)thiazole-5-carboxamide | mp 153-155° C.; $^1$H NMR (300 MHz, DMSO-d$_6$) δ 8.58-8.52 (m, 2H), 8.45 (dd, J = 4.7, 1.5 Hz, 1H), 7.79-7.74 (m, 1H), 7.45-7.27 (m, 6H), 5.14 (q, J = 7.0 Hz, 1H), 4.39 (d, J = 5.8 Hz, 2H), 4.04-3.93 (m, 2H), 3.66-3.58 (m, 1H), 3.27-3.18 (m, 1H), 2.46 (s, 3H), 1.55 (d, J = 7.1 Hz, 3H); MS (ES+) m/z 422.9 (M + 1). |
| 26 | 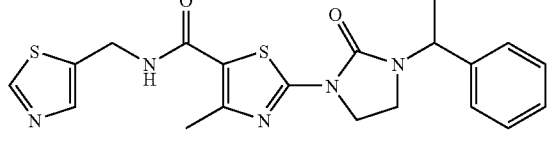 | 4-methyl-2-(2-oxo-3-(1-phenylethyl)-imidazolidin-1-yl)-N-(thiazol-5-yl-methyl)thiazole-5-carboxamide | mp 148-150° C.; $^1$H NMR (300 MHz, DMSO-d$_6$) δ 8.96 (s, 1H), 8.64 (t, J = 5.8 Hz, 1H), 7.78 (s, 1H), 7.43-7.34 (m, 4H), 7.32-7.28 (m, 1H), 5.14 (q, J = 7.0 Hz, 1H), 4.57 (d, J = 5.8 Hz, 2H), 3.98 (t, J = 8.2 Hz, 2H), 3.66-3.58 (m, 1H), 3.26-3.18 (m, 1H), 2.46 (s, 3H), 1.55 (d, J = 7.2 Hz, 3H); MS (ES+) m/z 428.9 (M + 1). |
| 27 | 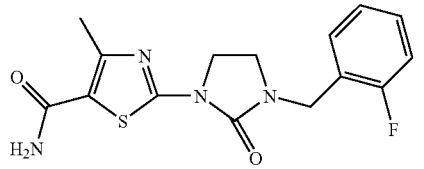 | 2-(3-(2-fluorobenzyl)-2-oxoimidazolidin-1-yl)-4-methylthiazole-5-carboxamide | $^1$H NMR (300 MHz, DMSO-d$_6$) δ 7.42-7.31 (m, 2H), 7.28-7.25 (br s, 2H), 7.24-7.19 (m, 2H), 4.50 (s, 2H), 4.02-3.97 (m, 2H), 3.52-3.46 (m, 2H), 2.46 (s, 3H); MS (ES+) m/z 334.8 (M + 1). |
| 28 | 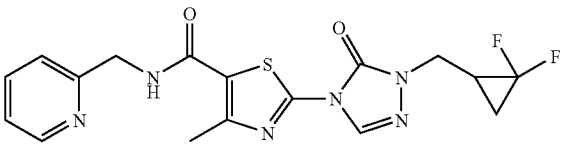 | 2-(1-((2,2-difluorocyclopropyl)-methyl)-5-oxo-1H-1,2,4-triazol-4(5H)-yl)-4-methyl-N-(pyridin-2-ylmethyl)thiazole-5-carboxamide | mp 168-169° C.; $^1$H NMR (300 MHz, DMSO-d$_6$) δ 8.88 (t, J = 5.8 Hz, 1H), 8.79 (s, 1H), 8.52 (d, J = 4.7 Hz, 1H), 7.81-7.74 (m, 1H), 7.34 (d, J = 7.9 Hz, 1H), 7.27 (d, J = 7.1, 5.1 Hz, 1H), 4.53 (d, J = 5.8 Hz, 2H), 4.02-3.84 (m, 2H), 2.59 (s, 3H), 2.24-2.09 (m, 1H), 1.76-1.64 (m, 1H), 1.52-1.41 (m, 1H); MS (ES+) m/z 407.1 (M + 1), 406.7 (M + 1); |
| 29 | 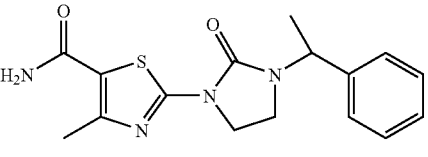 | 4-methyl-2-(2-oxo-3-(1-phenylethyl)-imidazolidin-1-yl)-thiazole-5-carboxamide | mp 212-215° C.; $^1$H NMR (300 MHz, DMSO-d$_6$) δ 7.41-7.34 (m, 4H), 7.32-7.27 (m, 3H), 5.14 (q, J = 7.0 Hz, 1H), 3.97 (t, J = 8.2 Hz, 2H), 3.66-3.57 (m, 1H), 3.26-3.18 (m, 1H), 2.45 (s, 3H), 1.55 (d, J = 7.2 Hz, 3H); MS (ES+) m/z 331.9 (M + 1). |
| 30 | 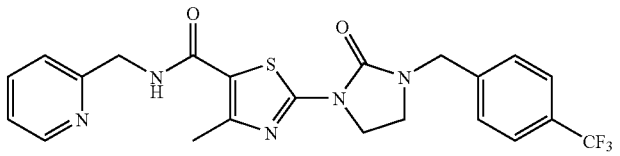 | 4-methyl-2-(2-oxo-3-(4-(trifluoromethyl)-benzyl)imidazolidin-1-yl)-N-(pyridin-2-ylmethyl)thiazole-5-carboxamide | mp 192-194° C.; $^1$H NMR (300 MHz, DMSO-d$_6$) δ 8.55-8.50 (m, 2H), 7.79-7.73 (m, 3H), 7.55 (d, J = 8.1 Hz, 2H), 7.30 (d, J = 7.9 Hz, 1H), 7.25 (d, J = 7.3 Hz, 1H), 4.55 (s, 2H), 4.49 (d, J = 5.7 Hz, 2H), 4.04 (t, J = 7.3 Hz, 2H), 3.50 (t, J = 7.3 Hz, 2H), 2.46 (s, 3H); MS (ES+) m/z 423.8 (M + 1), 422.8 (M + 1). |

| | Structure | Chemical Name | Characterization Data |
|---|---|---|---|
| 31 | 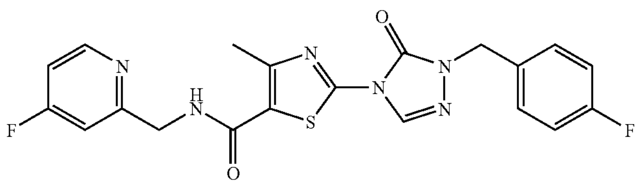 | 2-(1-(4-fluorobenzyl)-5-oxo-1H-1,2,4-triazol-4(5H)-yl)-N-((4-fluoropyridin-2-yl)methyl)-4-methylthiazole-5-carboxamide | mp 147-149° C.; $^1$H NMR (300 MHz, DMSO-d$_6$) δ 8.73 (s, 1H), 8.45 (d, J = 2.7 Hz, 1H), 8.30 (br, 1H), 7.61 (d, J = 9.1 Hz, 2H), 7.32-7.30 (m, 2H), 7.17-7.11 (m, 2H), 4.94 (s, 2H), 4.71 (s, 2H), 2.27 (s, 3H); MS (ES+) m/z 484.2 (M + 1). |
| 32 | 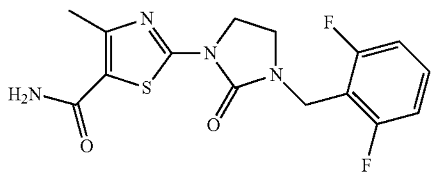 | 2-(3-(2,6-difluorobenzyl)-2-oxoimidazolidin-1-yl)-4-methylthiazole-5-carboxamide | $^1$H NMR (300 MHz, DMSO-d$_6$) δ 7.48-7.45 (m, 2H), 7.31 (br s, 2H), 7.16-7.14 (m, 1H), 4.53 (s, 2H), 3.96-3.94 (m, 2H), 3.47-3.45 (m, 2H), 2.45 (s, 3H); MS (ES+) m/z 352.8 (M + 1). |
| 33 | 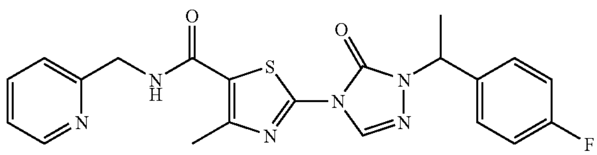 | 2-(1-(1-(4-fluorophenyl)ethyl)-5-oxo-1H-1,2,4-triazol-4(5H)-yl)-4-methyl-N-(pyridin-2-ylmethyl)thiazole-5-carboxamide | mp 169-170° C.; $^1$H NMR (300 MHz, DMSO-d$_6$) δ 8.87 (t, J = 5.8 Hz, 1H), 8.80 (s, 1H), 8.50 (d, J = 4.7 Hz, 1H), 7.79-7.74 (m, 1H), 7.43 (dd, J = 8.7, 5.5 Hz, 2H), 7.33 (d, J = 7.9 Hz, 2H), 7.27 (dd, J = 7.2, 5.0 Hz, 1H), 7.19 (dd, J = 8.9, 7.8 Hz, 2H), 5.50 (q, J = 6.9 Hz, 1H), 4.52 (d, J = 5.8 Hz, 2H), 2.59 (s, 3H), 1.70 (d, J = 7.1 Hz, 3H); MS (ES+) m/z 439.1 (M + 1). |
| 34 | 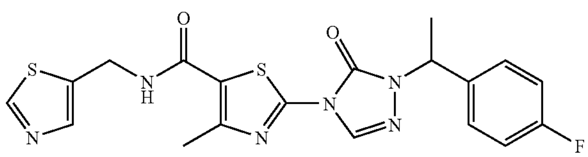 | 2-(1-(1-(4-fluorophenyl)ethyl)-5-oxo-1H-1,2,4-triazol-4(5H)-yl)-4-methyl-N-(thiazol-5-ylmethyl)thiazole-5-carboxamide | mp 137-139° C.; $^1$H NMR (300 MHz, DMSO-d$_6$) δ 8.89 (t, J = 5.8 Hz, 1H), 8.78 (s, 1H), 7.77 (s, 1H), 7.76 (s, 1H), 7.42 (d, J = 8.8 Hz, 2H), 7.18 (d, J = 8.8 Hz, 2H), 5.49 (q, J = 6.9 Hz, 1H), 4.53 (d, J = 5.7 Hz, 2H), 2.55 (s, 3H), 1.70 (d, J = 7.1 Hz, 3H); MS (ES+) m/z 445.2 (M + 1). |
| 35 | 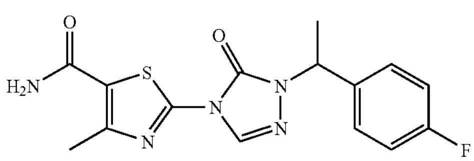 | 2-(1-(1-(4-fluorophenyl)ethyl)-5-oxo-1H-1,2,4-triazol-4(5H)-yl)-4-methylthiazole-5-carboxamide | mp 244-246° C.; $^1$H NMR (300 MHz, DMSO-d$_6$) δ 8.78 (s, 1H), 7.63 (br, 2H), 7.42 (dd, J = 8.8, 5.5 Hz, 2H), 7.18 (t, J = 8.8, 8.8 Hz, 2H), 5.49 (q, J = 6.9 Hz, 1H), 2.55 (s, 3H), 1.70 (d, J = 7.1 Hz, 3H); MS (ES+) m/z 347.9 (M + 1). |
| 36 | 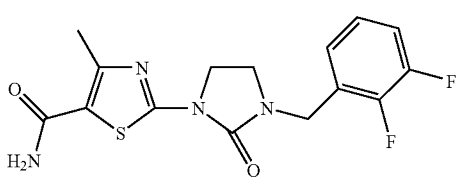 | 2-(3-(2,3-difluorobenzyl)-2-oxoimidazolidin-1-yl)-4-methylthiazole-5-carboxamide | $^1$H NMR (300 MHz, DMSO-d$_6$) δ 7.45-7.32 (m, 3H), 7.26-7.18 (m, 2H), 4.54 (s, 2H), 4.03-3.97 (m, 2H), 3.53-3.48 (m, 2H), 2.46 (s, 3H); MS (ES+) m/z 352.7 (M + 1). |
| 37 | 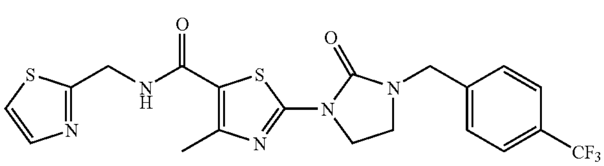 | 4-methyl-2-(2-oxo-3-(4-(trifluoromethyl)benzyl)imidazolidin-1-yl)-N-(thiazol-2-ylmethyl)thiazole-5-carboxamide | mp 135-137° C.; $^1$H NMR (300 MHz, DMSO-d$_6$) δ 8.55-8.50 (m, 1H), 7.79-7.73 (m, 2H), 7.55 (d, J = 8.1 Hz, 2H), 7.30 (d, J = 7.9 Hz, 1H), 7.25 (d, J = 7.3 Hz, 1H), 4.55 (s, 2H), 4.49 (d, J = 5.7 Hz, 2H), 4.04 (t, J = 7.3 Hz, 2H), 3.50 (t, J = 7.3 Hz, 2H), 2.46 (s, 3H); MS (ES+) m/z 481.9 (M + 1). |

| | Structure | Chemical Name | Characterization Data |
|---|---|---|---|
| 38 | 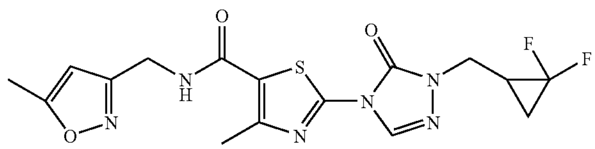 | 2-(1-((2,2-difluorocyclopropyl)-methyl)-5-oxo-1H-1,2,4-triazol-4(5H)-yl)-methylisoxazol-3-yl)methyl)thiazole-5-carboxamide | mp 120-122° C.; $^1$H NMR (300 MHz, DMSO-d$_6$) δ 8.87 (t, J = 5.8 Hz, 1H), 8.80 (s, 1H), 6.17 (s, 1H), 4.40 (d, J = 5.8 Hz, 2H), 4.02-3.83 (m, 2H), 2.57 (s, 3H), 2.37 (s, 3H), 2.24-2.08 (m, 1H), 1.76-1.64 (m, 1H), 1.52-1.41 (m, 1H); MS (ES+) m/z 410.9 (M + 1). |
| 39 | 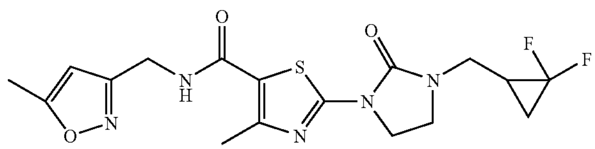 | 2-(3-((2,2-difluorocyclopropyl)-methyl)-2-oxoimidazolidin-1-yl)-4-methyl-N-((5-methylisoxazol-3-yl)methyl)thiazole-5-carboxamide | mp 140-142° C.; $^1$H NMR (300 MHz, DMSO-d$_6$) δ 8.50 (t, J = 5.8 Hz, 1H), 6.14 (s, 1H), 4.35 (d, J = 5.8 Hz, 2H), 4.02 (t, J = 8.3 Hz, 2H), 3.68-3.51 (m, 3H), 3.20 (dd, J = 14.6, 8.1 Hz, 1H), 2.47 (s, 3H), 2.36 (s, 3H), 2.08-1.92 (m, 1H), 1.71-1.59 (m, 1H), 1.41-1.30 (m, 1H); MS (ES+) m/z 411.9 (M + 1). |
| 40 | 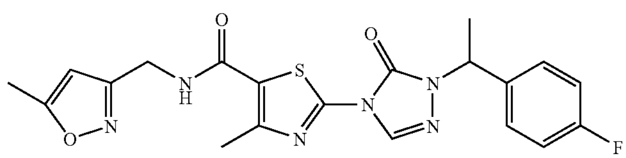 | 2-(1-(1-(4-fluorophenyl)ethyl)-5-oxo-1H-1,2,4-triazol-4(5H)-yl)-4-methyl-N-((5-methylisoxazol-3-yl)methyl)thiazole-5-carboxamide | mp 162-164° C.; $^1$H NMR (300 MHz, DMSO-d$_6$) δ 8.86 (br, 1H), 8.79 (s, 1H), 7.42 (dd, J = 8.8, 5.5 Hz, 2H), 7.18 (dd, J = 8.8, 8.8 Hz, 2H), 6.17 (d, J = 3.0 Hz, 1H), 5.49 (q, J = 6.9 Hz, 1H), 2.56 (s, 3H), 2.37 (s, 3H), 1.70 (d, J = 7.1 Hz, 3H); MS (ES+) m/z 464.9 (M + 23), 442.9 (M + 1). |
| 41 | 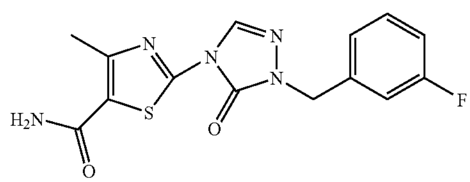 | 2-(1-(3-fluorobenzyl)-5-oxo-1H-1,2,4-triazol-4(5H)-yl)-4-methylthiazole-5-carboxamide | mp 202-204° C.; $^1$H NMR (300 MHz, DMSO-d$_6$) δ 8.77 (s, 1H), 7.64 (br, 2H), 7.45-7.37 (m, 2H), 7.19-7.12 (m, 2H), 5.04 (s, 2H), 2.56 (s, 3H); MS (ES+) m/z 333.9 (M + 1). |
| 42 | 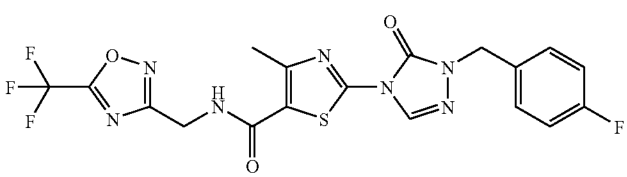 | 2-(1-(4-fluorobenzyl)-5-oxo-1H-1,2,4-triazol-4(5H)-yl)-4-methyl-N-((5-(trifluoromethyl)-1,2,4-oxadiazol-3-yl)methyl)thiazole-5-carboxamide | mp 180-182° C.; $^1$H NMR (300 MHz, DMSO-d$_6$) δ 9.01 (t, J = 5.6 Hz, 1H), 8.78 (s, 1H),7.43-7.34 (m, 2H), 7.22-7.17 (m, 2H), 5.01 (s, 2H) 4.68 (d, J = 5.6 Hz, 2H), 2.58 (s, 3H); MS (ES+) m/z 484.2 (M + 1). |
| 43 | 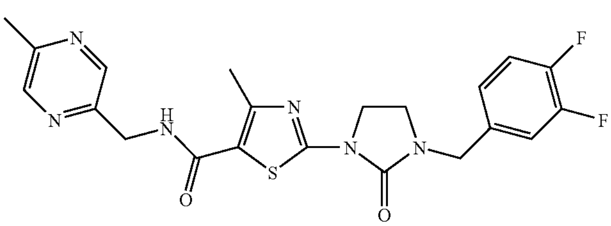 | 2-(3-(3,4-difluorobenzyl)-2-oxoimidazolidin-1-yl)-4-methyl-N-((6-methylpyrazin-2-yl)methyl)thiazole-5-carboxamide | mp 154-156° C.; $^1$H NMR (300 MHz, CDCl$_3$) δ 8.50 (s, 1H), 8.38 (s, 1H), 7.17-7.08 (m, 2H), 7.03-6.99 (m, 1H), 6.78-6.75 (t, J = 4.9 Hz, 1H), 4.68 (d, J = 4.9 Hz, 2H), 4.42 (s, 2H), 4.11-4.06 (m, 2H), 3.49-3.43 (m, 2H), 2.60 (s, 3H), 2.54 (s, 3H); MS (ES+) m/z 458.8 (M + 1). |
| 44 | 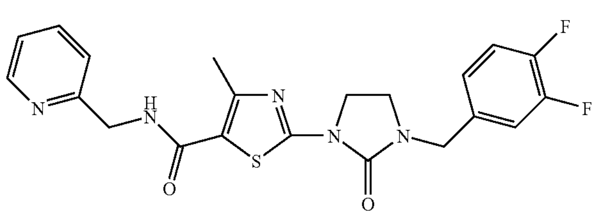 | 2-(3-(3,4-difluorobenzyl)-2-oxoimidazolidin-1-yl)-4-methyl-N-(pyridin-2-ylmethyl)thiazole-5-carboxamide | mp 150-153° C.; $^1$H NMR (300 MHz, CDCl$_3$) δ 8.57-8.55 (m, 1H), 7.70-7.65 (m, 1H), 7.31-7.28 (m, 1H), 7.23-7.17 (m, 1H), 7.13-7.11 (m, 3H), 7.06-7.01 (m, 1H), 4.71 (d, J = 4.7 Hz, 2H), 4.45 (s, 2H), 4.14-4.08 (m, 2H), 3.51-3.45 (m, 2H), 2.65 (s, 3H); MS (ES+) m/z 443.8 (M + 1). |

-continued

| | Structure | Chemical Name | Characterization Data |
|---|---|---|---|
| 45 | 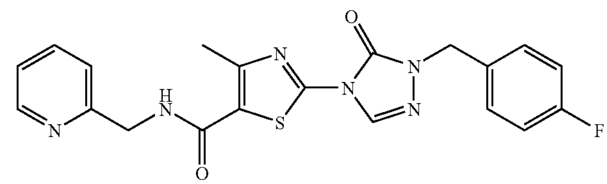 | 2-(1-(4-fluorobenzyl)-5-oxo-1H-1,2,4-triazol-4(5H)-yl)-4-methyl-N-(pyridin-2-ylmethyl)thiazole-5-carboxamide | mp 172-173° C.; $^1$H NMR (300 MHz, DMSO-d$_6$) δ 8.89 (t, J = 5.8 Hz, 1H), 8.78 (s, 1H), 8.53-8.51 (m, 1H), 7.79-7.75 (m, 1H), 7.41-7.16 (m, 6H), 5.01 (s, 2H), 4.53 (d, J = 5.8 Hz, 2H), 2.59 (s, 3H); MS (ES+) m/z 424.9 (M + 1). |
| 46 | 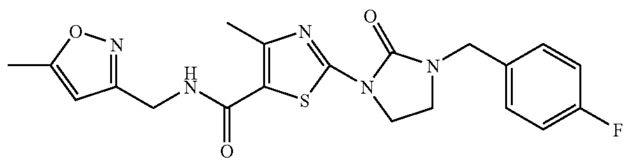 | 2-(3-(4-fluorobenzyl)-2-oxoimidazolidin-1-yl)-4-methyl-N-((5-methylisoxazol-3-yl)methyl)thiazole-5-carboxamide | mp 191-192° C.; $^1$H NMR (300 MHz, DMSO-d$_6$) δ 8.51 (t, J = 5.8 Hz, 1H), 7.39-7.34 (m, 2H), 7.23-7.17 (m, 2H), 6.14 (s, 1H), 4.43 (s, 2H), 4.36 (d, J = 5.8 Hz, 2H), 4.03-3.98 (m, 2H), 3.48-3.43 (m, 2H), 2.47 (s, 3H), 2.37 (s, 3H); MS (ES+) m/z 429.8 (M + 1). |
| 47 | 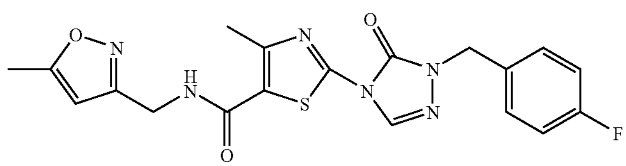 | 2-(1-(4-fluorobenzyl)-5-oxo-1H-1,2,4-triazol-4(5H)-yl)-4-methyl-N-((5-methylisoxazol-3-yl)methyl)thiazole-5-carboxamide | mp 164-165° C.; $^1$H NMR (300 MHz, DMSO-d$_6$) δ 8.87 (t, J = 5.8 Hz, 1H), 8.77 (s, 1H), 7.41-3.36 (m, 2H), 7.22-7.16 (m, 2H), 6.17 (s, 1H), 5.00 (s, 2H), 4.41 (d, J = 5.8 Hz, 2H), 2.57 (s, 3H), 2.37 (s, 3H); MS (ES+) m/z 428.8 (M + 1). |
| 48 | 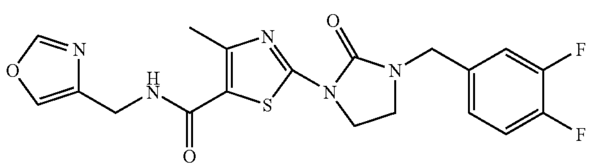 | 2-(3-(3,4-difluorobenzyl)-2-oxoimidazolidin-1-yl)-4-methyl-N-(oxazol-4-ylmethyl)thiazole-5-carboxamide | mp 117-119° C.; $^1$H NMR (300 MHz, DMSO-d$_6$) δ 8.39 (t, J = 5.6 Hz, 1H), 8.31 (s, 1H), 7.92 (s, 1H), 7.51-7.35 (m, 2H), 7.21-7.14 (m, 1H), 4.43 (s, 2H), 4.28 (d, J = 5.6 Hz, 2H), 4.07-3.95 (m, 2H), 3.53-3.44 (m, 2H), 2.47 (s, 3H); MS (ES+) m/z 456.2 (M + 23). |
| 49 | 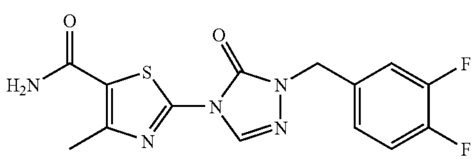 | 2-(1-(3,4-difluorobenzyl)-5-oxo-1H-1,2,4-triazol-4(5H)-yl)-4-methylthiazole-5-carboxamide | mp 238-240° C.; $^1$H NMR (300 MHz, DMSO-d$_6$) δ 8.76 (s, 1H), 7.64 (br, 2H), 7.47-7.38 (m, 2H), 7.21-7.17 (m, 1H), 5.01 (s, 2H), 2.56 (s, 3H); MS (ES+) m/z 351.8 (M + 1). |
| 50 | 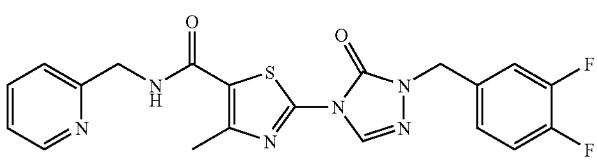 | 2-(1-(3,4-difluorobenzyl)-5-oxo-1H-1,2,4-triazol-4(5H)-yl)-4-methyl-N-(pyridin-2-ylmethyl)thiazole-5-carboxamide | mp 165-167° C.; $^1$H NMR (300 MHz, DMSO-d$_6$) δ 8.89 (t, J = 5.8 Hz, 1H), 8.80 (s, 1H), 8.52 (d, J = 4.2 Hz, 1H), 7.80-7.76 (m, 2H), 7.34 (d, J = 7.9 Hz, 1H), 7.27 (d, J = 7.0, 5.2 Hz, 1H), 7.23-7.16 (m, 1H), 7.09 (d, J = 6.4 Hz, 1H), 5.02 (s, 2H), 4.53 (d, J = 5.8 Hz, 2H), 2.59 (s, 3H); MS (ES+) m/z 442.8 (M + 1). |
| 51 | 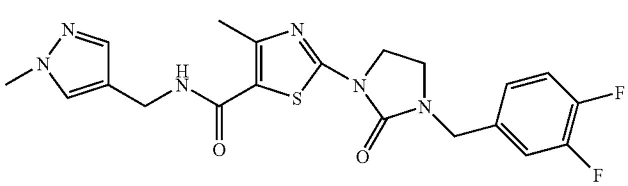 | 2-(3-(3,4-difluorobenzyl)-2-oxoimidazolidin-1-yl)-4-methyl-N-((1-methyl-1H-pyrazol-4-yl)methyl)thiazole-5-carboxamide | mp 175-177° C.; $^1$H NMR (300 MHz, CDCl$_3$) δ 7.44 (s, 1H), 7.39 (s, 1H), 7.19-7.08 (m, 2H), 7.04-7.00 (m, 1H), 5.83-5.80 (m, 1H), 4.43-4.40 (m, 5H), 4.11-4.06 (m, 2H), 3.87 (s, 2H), 3.50-3.44 (m, 2H), 2.59 (s, 3H); MS (ES+) m/z 446.9 (M + 1). |
| 52 | 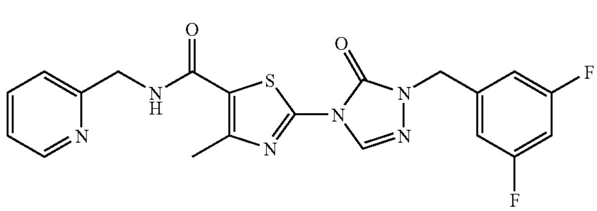 | 2-(1-(3,5-difluorobenzyl)-5-oxo-1H-1,2,4-triazol-4(5H)-yl)-4-methyl-N-(pyridin-2-ylmethyl)thiazole-5-carboxamide | mp 166-168° C.; $^1$H NMR (300 MHz, DMSO-d$_6$) δ 8.89 (t, J = 5.8 Hz, 1H), 8.80 (s, 1H), 8.52 (d, J = 4.2 Hz, 1H), 7.80-7.75 (m, 2H), 7.34 (d, J = 7.9 Hz, 1H), 7.27 (d, J = 7.0, 5.2 Hz, 1H), 7.22-7.15 (m, 1H), 7.09 (d, J = 6.4 Hz, 1H), 5.07 (s, 2H), 4.53 (d, J = 5.8 Hz, 2H), 2.60 (s, 3H); MS (ES+) m/z 444.9 (M + 1). |

| | Structure | Chemical Name | Characterization Data |
|---|---|---|---|
| 53 | 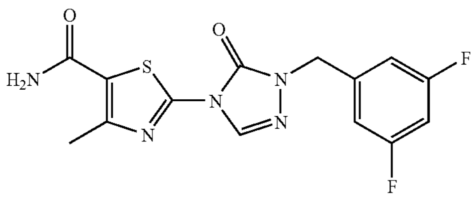 | 2-(1-(3,5-difluorobenzyl)-5-oxo-1H-1,2,4-triazol-4(5H)-yl)-4-methylthiazole-5-carboxamide | mp 193-195° C.; $^1$H NMR (300 MHz, DMSO-$d_6$) δ 8.74 (s, 1H), 7.61 (br, 2H), 7.19-7.13 (m, 1H), 7.04 (d, J = 6.4 Hz, 2H), 5.07 (s, 2H), 2.60 (s, 3H); MS (ES+) m/z 351.8 (M + 1). |
| 54 | 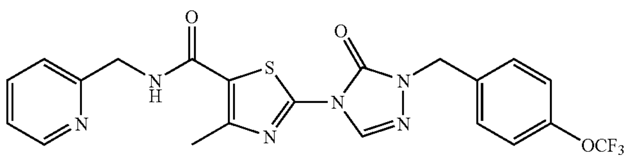 | 4-methyl-2-(5-oxo-1-(4-(trifluoromethoxy)-benzyl)-1H-1,2,4-triazol-4(5H)-yl)-N-(pyridin-2-ylmethyl)thiazole-5-carboxamide | mp 145-147° C.; $^1$H NMR (300 MHz, DMSO-$d_6$) δ 8.89 (t, J = 5.8 Hz, 1H), 8.80 (s, 1H), 8.52 (d, J = 8.7 Hz, 1H), 7.81-7.76 (m, 2H), 7.47 (d, J = 8.6 Hz, 1H), 7.37 (d, J = 8.2 Hz, 2H), 7.34 (d, J = 8.2 Hz, 1H), 7.27 (dd, J = 7.3, 4.9 Hz, 1H), 5.06 (s, 2H), 4.53 (d, J = 5.8 Hz, 2H), 2.59 (s, 3H); MS (ES+) m/z 490.7 (M + 1). |
| 55 | 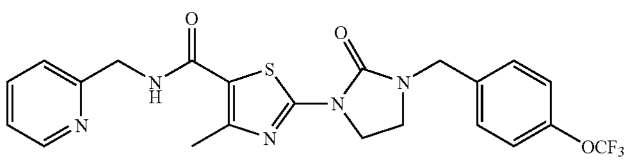 | 4-methyl-2-(2-oxo-3-(4-(trifluoromethoxy)-benzyl)imidazolidin-1-yl)-N-(pyridin-2-ylmethyl)thiazole-5-carboxamide | mp 194-195° C.; $^1$H NMR (300 MHz, DMSO-$d_6$) δ 8.53 (t, J = 5.8 Hz, 1H), 8.52 (d, J = 8.7 Hz, 1H), 7.80-7.74 (m, 1H), 7.46 (d, J = 8.7 Hz, 2H), 7.37 (d, J = 8.1 Hz, 2H), 7.30 (d, J = 7.9 Hz, 1H), 7.26 (dd, J = 7.5, 5.0 Hz, 1H), 4.50 (s, 2H), 4.48 (d, d, J = 5.7 Hz, 2H), 4.03 (t, J = 7.3 Hz, 2H), 3.49 (t, J = 7.3 Hz, 2H), 2.50 (s, 3H); MS (ES+) m/z 491.9 (M + 1). |
| 56 | 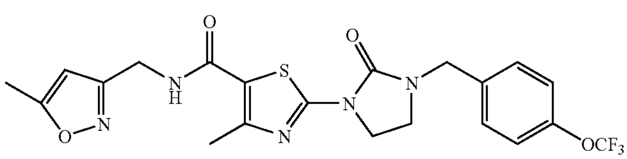 | 4-methyl-N-((5-methylisoxazol-3-yl)methyl)-2-(2-oxo-3-(4-(trifluoromethoxy)-benzyl)imidazolidin-1-yl)thiazole-5-carboxamide | mp 180-181° C.; $^1$H NMR (300 MHz, DMSO-$d_6$) δ 8.51 (t, J = 5.7 Hz, 1H), 7.45 (d, J = 8.7 Hz, 2H), 7.37 (d, J = 8.1 Hz, 2H), 6.14 (s, 1H), 4.48 (s, 2H), 4.36 (d, J = 5.7 Hz, 2H), 4.04-3.98 (m, 2H), 3.52-3.47 (m, 2H), 2.48 (s, 3H), 2.37 (s, 3H); MS (ES+) m/z 496.1 (M + 1). |
| 57 | 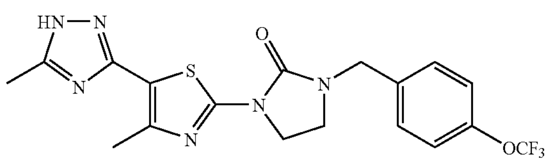 | 1-(4-methyl-5-(5-methyl-1H-1,2,4-triazol-3-yl)thiazol-2-yl)-3-(4-(trifluoromethoxy)-benzyl)imidazolidin-2-one | mp 172-178° C.; $^1$H NMR (300 MHz, DMSO-$d_6$) δ 13.64 (br, 1H), 7.45 (d, J = 8.7 Hz, 2H), 7.37 (d, J = 8.1 Hz, 2H), 4.47 (s, 2H), 4.04-3.98 (m, 2H), 3.48 (t, J = 7.3 Hz, 2H), 2.56 (s, 3H), 2.46 (s, 3H); MS (ES+) m/z 438.8 (M + 1). |
| 58 | 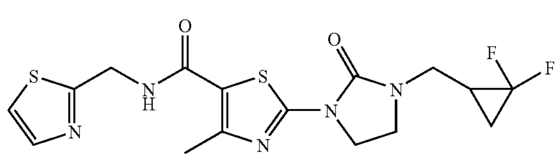 | 2-(3-((2,2-difluorocyclopropyl)-methyl)-2-oxoimidazolidin-1-yl)-4-methyl-N-(thiazol-2-ylmethyl)thiazole-5-carboxamide | mp 185-187° C.; $^1$H NMR (300 MHz, DMSO-$d_6$) δ 8.83 (t, J = 5.9 Hz, 1H), 7.72 (d, J = 3.3 Hz, 1H), 7.62 (d, J = 3.3 Hz, 1H), 4.65 (d, J = 5.9 Hz, 2H), 4.03 (t, J = 8.5 Hz, 2H), 3.68-3.52 (m, 3H), 3.24-3.16 (m, 1H), 2.50 (s, 3H), 2.08-1.92 (m, 1H), 1.78-1.59 (m, 1H), 1.40-1.30 (m, 1H); MS (ES+) m/z 413.9 (M + 1). |
| 59 | 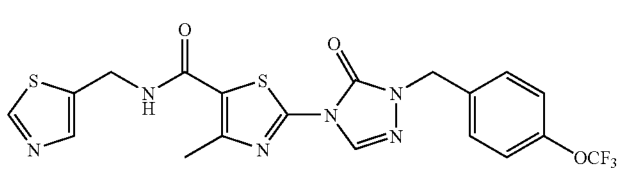 | 4-methyl-2-(5-oxo-1-(4-(trifluoromethoxy)-benzyl)-1H-1,2,4-triazol-4(5H)-yl)-N-(thiazol-5-yl-methyl)thiazole-5-carboxamide | mp 195-195° C.; $^1$H NMR (300 MHz, DMSO-$d_6$) δ 9.00 (br, 1H), 8.96 (s, 1H), 8.78 (s, 1H), 7.81 (s, 1H), 7.46 (d, J = 8.6 Hz, 2H), 7.36 (d, J = 8.1 Hz, 2H), 5.05 (s, 2H), 4.63 (d, J = 5.8 Hz, 2H), 2.56 (s, 3H); MS (ES+) m/z 496.9 (M + 1). |

-continued

| | Structure | Chemical Name | Characterization Data |
|---|---|---|---|
| 60 | 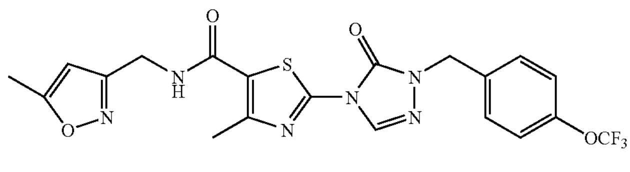 | 4-methyl-N-((5-methylisoxazol-3-yl)methyl)-2-(5-oxo-1-(4-(trifluoromethoxy)benzyl)-1H-1,2,4-triazol-4(5H)-yl)thiazole-5-carboxamide | mp 165-167° C.; $^1$H NMR (300 MHz, DMSO-$d_6$) δ 8.88 (br, 1H), 8.79 (s, 1H), 7.47 (d, J = 8.6 Hz, 2H), 7.37 (d, J = 8.6 Hz, 2H), 6.17 (s, 1H), 5.06 (s, 2H), 4.41 (br s, 2H), 2.57 (s, 3H), 2.37 (s, 3H); MS (ES+) m/z 494.9 (M + 1). |
| 61 | 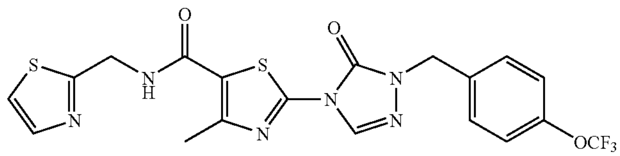 | 4-methyl-2-(5-oxo-1-(4-(trifluoromethoxy)benzyl)-1H-1,2,4-triazol-4(5H)-yl)-N-(thiazol-2-ylmethyl)thiazole-5-carboxamide | mp 170-172° C.; $^1$H NMR (300 MHz, DMSO-$d_6$) δ 9.21 (t, J = 5.8 Hz, 1H), 8.79 (s, 1H), 7.74 (d, J = 3.3 Hz, 1H), 7.64 (d, J = 3.3 Hz, 1H), 7.47 (d, J = 8.5 Hz, 2H), 7.36 (d, J = 8.5 Hz, 2H), 5.06 (s, 2H), 4.71 (d, J = 5.8 Hz, 2H), 2.59 (s, 3H); MS (ES+) m/z 496.9 (M + 1). |
| 62 | 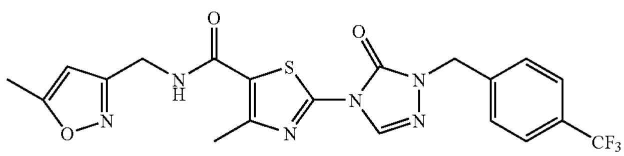 | 4-methyl-N-((5-methylisoxazol-3-yl)methyl)-2-(5-oxo-1-(4-(trifluoromethyl)benzyl)-1H-1,2,4-triazol-4(5H)-yl)thiazole-5-carboxamide | mp 172-174° C.; $^1$H NMR (300 MHz, DMSO-$d_6$) δ 8.88 (t, J = 5.8 Hz, 1H), 8.80 (s, 1H), 7.73 (d, J = 8.2 Hz, 2H), 7.55 (d, J = 8.1 Hz, 2H), 6.17 (s, 1H), 5.13 (s, 2H), 4.41 (d, J = 5.7 Hz, 2H), 2.57 (s, 3H), 2.37 (s, 3H); MS (ES+) m/z 478.9 (M + 1). |
| 63 | 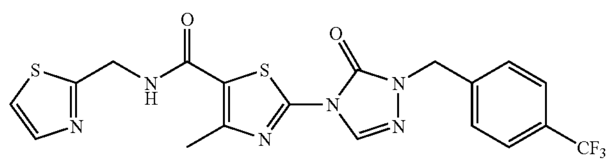 | 4-methyl-2-(5-oxo-1-(4-(trifluoromethyl)benzyl)-1H-1,2,4-triazol-4(5H)-yl)-N-(thiazol-2-ylmethyl)thiazole-5-carboxamide | mp 177-179° C.; $^1$H NMR (300 MHz, DMSO-$d_6$) δ 9.21 (t, J = 5.8 Hz, 1H), 8.79 (s, 1H), 7.74 (d, J = 3.3 Hz, 1H), 7.64 (d, J = 3.3 Hz, 1H), 7.47 (d, J = 8.7 Hz, 2H), 7.36 (d, J = 8.2 Hz, 2H), 5.06 (s, 2H), 4.71 (d, J = 5.9 Hz, 2H), 2.60 (s, 3H); MS (ES+) m/z 481.1 (M + 1). |
| 64 | 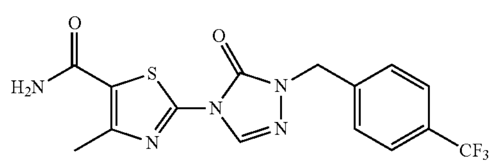 | 4-methyl-2-(5-oxo-1-(4-(trifluoromethyl)benzyl)-1H-1,2,4-triazol-4(5H)-yl)thiazole-5-carboxamide | mp 232-235° C.; $^1$H NMR (300 MHz, DMSO-$d_6$) δ 8.79 (s, 1H), 7.73 (d, J = 8.2 Hz, 2H), 7.65 (br, 2H), 7.55 (d, J = 8.1 Hz, 2H), 5.13 (s, 2H), 2.56 (s, 3H); MS (ES+) m/z 383.9 (M + 1). |
| 65 | 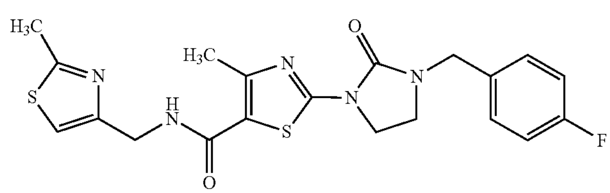 | 2-(3-(4-fluorobenzyl)-2-oxoimidazolidin-1-yl)-4-methyl-N-((2-methylthiazol-4-yl)methyl)thiazole-5-carboxamide | mp 231-232° C.; $^1$H NMR (300 MHz, DMSO-$d_6$) δ 8.46 (t, J = 5.7 Hz, 1H), 7.39-7.34 (m, 2H), 7.23-7.15 (m, 3H), 4.43-4.41 (m, 4H), 4.03-4.98 (m, 2H), 3.48-3.43 (m, 2H), 2.63 (s, 3H), 2.48 (s, 3H); MS (ES+) m/z 445.7 (M + 1). |
| 66 | 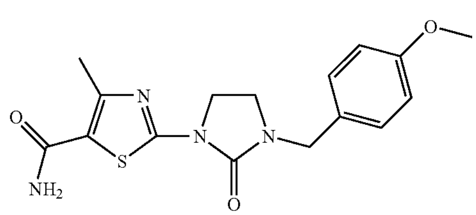 | 2-(3-(4-methoxybenzyl)-2-oxoimidazolidin-1-yl)-4-methylthiazole-5-carboxamide | mp 208-210° C.; $^1$H NMR (300 MHz, DMSO-$d_6$) δ 7.30 (br s, 2H), 7.23 (d, J = 8.6 Hz, 2H), 6.92 (d, J = 8.6 Hz, 2H), 4.36 (s, 2H), 4.00-3.94 (m, 2H), 3.74 (s, 3H), 3.44-3.39 (m, 2H), 2.45 (s, 3H); MS (ES+) m/z 346.8 (M + 1). |
| 67 | 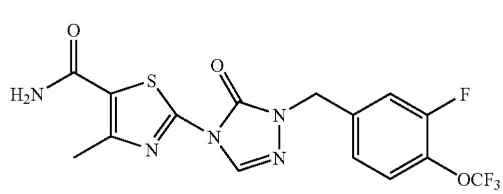 | 2-(1-(3-fluoro-4-(trifluoromethoxy)benzyl)-5-oxo-1H-1,2,4-triazol-4(5H)-yl)-4-methylthiazole-5-carboxamide | mp 192-193° C.; $^1$H NMR (300 MHz, DMSO-$d_6$) δ 8.78 (s, 1H), 7.64 (br, 2H), 7.57 (dd, J = 8.2, 2.2 Hz, 1H), 7.51 (dd, J = 11.3, 2.0 Hz, 1H), 7.28 (d, J = 8.5 Hz, 1H), 5.08 (s, 2H), 2.56 (s, 3H); MS (ES+) m/z 417.8 (M + 1). |

| | Chemical Name | Characterization Data |
|---|---|---|
| 68 | 2-(3-(3-fluoro-4-methoxybenzyl)-2-oxoimidazolidin-1-yl)-4-methyl-N-(pyridin-2-ylmethyl)thiazole-5-carboxamide | mp 168-170° C.; $^1$H NMR (300 MHz, DMSO-d$_6$) δ 8.55 (t, J = 5.8 Hz, 1H), 8.52-8.50 (m, 1H), 7.79-7.76 (m, 1H), 7.32-7.24 (m, 2H), 7.20-7.08 (m, 3H), 4.49 (d, J = 5.7 Hz, 2H), 4.38 (s, 2H), 4.04-3.98 (m, 2H), 3.82 (s, 3H), 3.49-3.43 (m, 2H), 2.49 (s, 3H); MS (ES+) m/z 455.9 (M + 1). |
| 69 | 4-methyl-2-(2-oxo-3-((6-(trifluoromethyl)-pyridin-3-yl)methyl)-imidazolidin-1-yl)-N-(pyridin-2-ylmethyl)-thiazole-5-carboxamide | mp 192-194° C.; $^1$H NMR (300 MHz, DMSO-d$_6$) δ 8.76 (t, J = 5.7 Hz, 1H), 8.55-8.49 (m, 2H), 8.05 (dd, J = 6.1, 1.6 Hz, 1H), 7.92 (d, J = 8.1 Hz, 1H), 7.80-7.76 (m, 1H), 7.30 (d, J = 8.9 Hz, 1H), 7.26 (dd, J = 6.6, 1.7 Hz, 1H), 4.61 (s, 2H), 4.49 (d, J = 5.7 Hz, 2H), 4.06-4.00 (m, 2H), 3.57-3.53 (m, 2H), 2.50 (s, 3H); MS (ES+) m/z 476.9 (M + 1). |
| 70 | 4-methyl-N-((5-methylisoxazol-3-yl)methyl)-2-(2-oxo-3-((6-(trifluoromethyl)-pyridin-3-yl)methyl)-imidazolidin-1-yl)-thiazole-5-carboxamide | mp 166-168° C.; $^1$H NMR (300 MHz, DMSO-d$_6$) δ 8.76 (d, J = 1.6 Hz, 1H), 8.52 (t, J = 5.8 Hz, 1H), 8.04 (dd, J = 8.1, 1.4 Hz, 1H), 7.91 (d, J = 8.1 Hz, 1H), 6.14 (s, 1H), 4.36 (d, J = 5.8 Hz, 2H), 4.06-3.99 (m, 2H), 3.57-3.53 (m, 2H), 2.48 (s, 3H), 2.37 (s, 3H); MS (ES+) m/z 480.9 (M + 1). |
| 71 | 4-methyl-2-(5-oxo-1-(4-(trifluoromethyl)-benzyl)-1H-1,2,4-triazol-4(5H)-yl)-N-(pyridine-2-ylmethyl)-thiazole-5-carboxamide | mp 168-169° C.; $^1$H NMR (300 MHz, DMSO-d$_6$) δ 8.89 (t, J = 5.8 Hz, 1H), 8.82 (s, 1H), 8.53-8.51 (m, 1H), 7.80-7.72 (m, 3H), 7.56 (d, J = 8.1 Hz, 2H), 7.34 (d, J = 7.8 Hz, 1H), 7.29-7.25 (m, 1H), 5.14 (s, 2H), 4.53 (d, J = 5.8 Hz, 2H), 2.60 (s, 3H); MS (ES+) m/z 474.8 (M + 1). |
| 72 | 4-methyl-N-((1-methyl-1H-pyrazol-4-yl)methyl)-2-(5-oxo-1-(4-(trifluoromethyl)benzyl)-1H-1,2,4-triazol-4(5H)-yl)thiazole-5-carboxamide | mp 161-163° C.; $^1$H NMR (300 MHz, DMSO-d$_6$) δ 8.79, (s, 1H), 8.66 (t, J = 5.8 Hz, 1H), 7.74 (d, J = 8.2 Hz, 1H), 7.60 (s, 1H), 7.55 (d, J = 8.1 Hz, 2H), 7.35 (s, 1H), 5.13 (s, 2H), 4.23 (d, J = 5.7 Hz, 2H), 3.78 (s, 3H), 2.55 (s, 3H); MS (ES+) m/z 477.9 (M + 1). |
| 73 | 4-methyl-N-((5-methylisoxazol-3-yl)methyl)-2-(2-oxo-3-(4-(trifluoromethyl)-benzyl)imidazolidin-1-yl)thiazole-5-carboxamide | mp 102-104° C.; $^1$H NMR (300 MHz, DMSO-d$_6$) δ 8.52 (t, J = 5.8 Hz, 1H), 7.74 (d, J = 8.2 Hz, 2H), 7.55 (d, J = 8.1 Hz, 2H), 6.14 (s, 1H), 4.55 (s, 2H), 4.36 (d, J = 5.7 Hz, 2H), 4.03 (t, J = 7.3 Hz, 2H), 3.52 (t, J = 7.3 Hz, 2H), 2.48 (s, 3H), 2.37 (s, 3H); MS (ES+) m/z 481.8 (M + 1). |
| 74 | 2-(3-(3-fluoro-4-methoxybenzyl)-2-oxoimidazolidin-1-yl)-4-methyl-N-((5-methylisoxazol-3-yl)methyl)thiazole-5-carboxamide | mp 170-172° C.; $^1$H NMR (300 MHz, DMSO-d$_6$) δ 8.51 (t, J = 5.8 Hz, 1H), 7.20-7.07 (m, 3H), 6.14 (s, 1H), 4.37 (s, 2H), 4.36 (d, J = 5.8 Hz, 2H), 4.05-4.00 (m, 2H), 3.82 (s, 3H), 3.52-3.47 (m, 2H), 2.48 (s, 3H), 2.37 (s, 3H); MS (ES+) m/z 459.9 (M + 1). |

| | Structure | Chemical Name | Characterization Data |
|---|---|---|---|
| 75 | 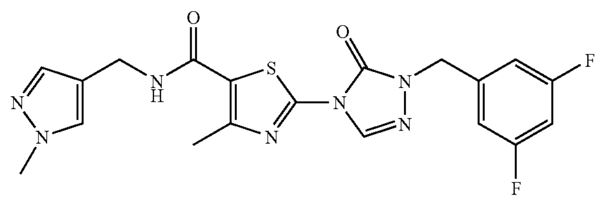 | 2-(1-(3,5-difluorobenzyl)-5-oxo-1H-1,2,4-triazol-4(5H)-yl)-4-methyl-N-((1-methyl-1H-pyrazol-3-yl)methyl)thiazole-5-carboxamide | mp 207-210° C.; $^1$H NMR (300 MHz, DMSO-d$_6$) δ 8.79 (s, 1H), 8.65 (t, J = 5.8 Hz, 1H), 7.60 (s, 1H), 7.35 (s, 1H), 7.22-7.16 (m, 1H), 7.11-7.05 (m, 2H), 5.06 (s, 2H), 4.23 (d, J = 5.8 Hz, 2H), 3.79 (s, 3H), 2.56 (s, 3H); MS (ES+) m/z 442.8 (M + 1). |
| 76 | 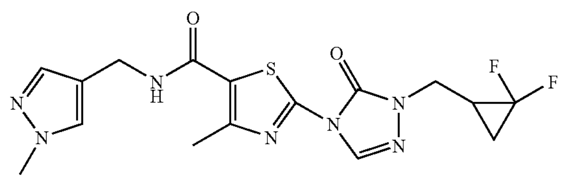 | 2-(1-((2,2-difluorocyclopropyl)methyl)-5-oxo-1H-1,2,4-triazol-4(5H)-yl)-4-methyl-N-((1-methyl-1H-pyrazol-4-yl)methyl)thiazole-5-carboxamide | mp 155-156° C.; $^1$H NMR (300 MHz, DMSO-d$_6$) δ 8.78 (s, 1H), 8.65 (t, J = 5.8 Hz, 1H), 7.60 (s, 1H), 7.35 (s, 1H), 4.23 (d, J = 5.9 Hz, 2H), 4.01-3.83 (m, 2H), 3.79 (s, 3H), 2.55 (s, 3H), 2.23-2.08 (m, 1H), 1.76-1.63 (m, 1H), 1.51-1.40 (m, 1H); MS (ES+) m/z 410.0 (M + 1). |
| 77 | 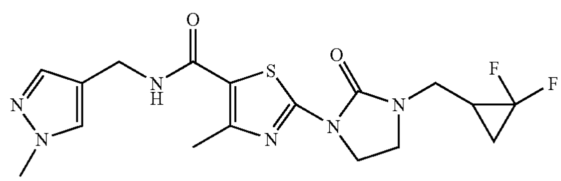 | 2-(3-((2,2-difluorocyclopropyl)methyl)-2-oxoimidazolidin-1-yl)-4-methyl-N-((1-methyl-1H-pyrazol-4-yl)methyl)thiazole-5-carboxamide | mp 152-154° C.; $^1$H NMR (300 MHz, DMSO-d$_6$) δ 8.29 (t, J = 5.9 Hz, 1H), 7.56 (s, 1H), 7.32 (s, 1H), 4.18 (d, J = 5.9 Hz, 2H), 4.01 (t, J = 8.5 Hz, 2H), 3.78 (s, 3H), 3.67-3.50 (m, 3H), 3.23-3.15 (m, 1H), 2.45 (s, 3H), 2.07-1.92 (m, 1H), 1.71-1.58 (m, 1H), 1.40-1.29 (m, 1H); MS (ES+) m/z 411.1 (M + 1). |
| 78 | 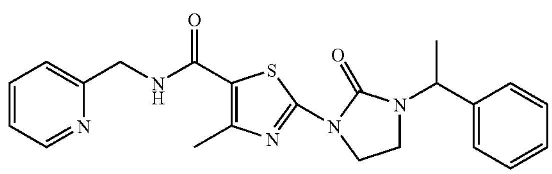 | 4-methyl-2-(2-oxo-3-(1-phenylethyl)imidazolidin-1-yl)-N-(pyridin-2-ylmethyl)thiazole-5-carboxamide | mp 144-146° C.; $^1$H NMR (300 MHz, DMSO-d$_6$) δ 8.53-8.50 (m, 2H), 7.80-7.76 (m, 1H), 7.43-7.35 (m, 4H), 7.24-7.23 (m, 3H), 5.15 (q, J = 7.1 Hz, 1H), 4.48 (d, J = 5.8 Hz, 2H), 4.01-3.97 (m, 2H), 3.65-3.62 (m, 1H), 3.25-3.22 (m, 1H), 2.49 (s, 3H), 1.55 (d, J = 7.1 Hz, 3H); MS (ES+) m/z 422.1 (M + 1). |
| 79 | 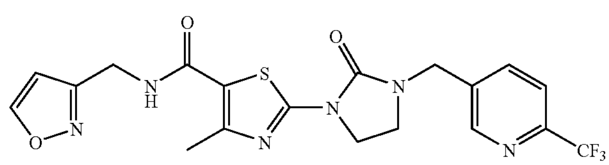 | N-(isoxazol-3-ylmethyl)-4-methyl-2-(2-oxo-3-((6-(trifluoromethyl)pyridin-3-yl)methyl)imidazolidin-1-yl)thiazole-5-carboxamide | mp 166-168° C.; $^1$H NMR (300 MHz, DMSO-d$_6$) δ 8.83 (d, J = 1.5 Hz, 1H), 8.76 (s, 1H), 8.55 (t, J = 5.8 Hz, 1H), 8.04 (dd, J = 8.1, 1.4 Hz, 1H), 7.92 (d, J = 8.1 Hz, 1H), 6.49 (d, J = 1.5 Hz, 1H), 4.61 (s, 2H), 4.45 (d, J = 5.8 Hz, 2H), 4.05-4.00 (m, 2H), 3.58-3.52 (m, 2H), 2.48 (s, 3H); MS (ES+) m/z 467.0 (M + 1). |
| 80 | 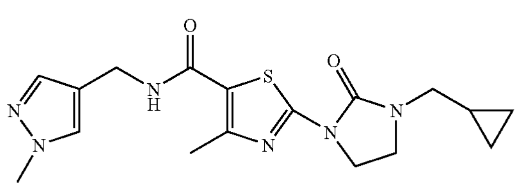 | 2-(3-(cyclopropylmethyl)-2-oxoimidazolidin-1-yl)-4-methyl-N-((1-methyl-1H-pyrazol-4-yl)methyl)thiazole-5-carboxamide | mp 203-205° C.; $^1$H NMR (300 MHz, DMSO-d$_6$) δ 8.27 (t, J = 5.8 Hz, 1H), 7.56 (s, 1H), 7.32 (s, 1H), 4.18 (d, J = 5.6 Hz, 2H), 4.02-3.98 (m, 2H), 3.78 (s, 3H), 3.66-3.58 (m, 2H), 3.09 (d, J = 7.1 Hz, 2H), 2.47 (s, 3H), 1.02-0.88 (m, 1H), 0.52-0.46 (m, 2H), 0.24-0.20 (m, 2H); MS (ES+) m/z 375.0 (M + 1). |
| 81 | 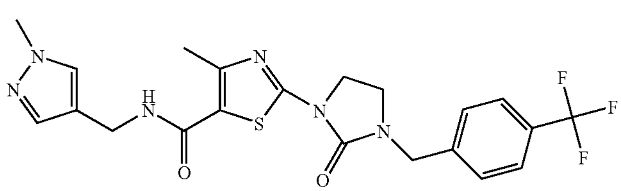 | 4-methyl-N-((1-methyl-1H-pyrazol-4-yl)methyl)-2-(2-oxo-3-(4-(trifluoromethyl)benzyl)imidazolidin-1-yl)thiazole-5-carboxamide | mp 205-208° C.; $^1$H NMR (300 MHz, DMSO-d$_6$) δ 8.79 (s, 1H), 8.66 (t, J = 5.8 Hz, 1H), 7.73 (d, J = 8.2 Hz, 2H), 7.60 (s, 1H), 7.55 (d, J = 8.1 Hz, 2H), 7.35 (s, 1H), 5.13 (s, 2H), 4.23 (d, J = 5.6 Hz, 2H), 3.79 (s, 3H), 2.55 (s, 3H); MS (ES+) m/z 478.1 (M + 1). |

| | Structure | Chemical Name | Characterization Data |
|---|---|---|---|
| 82 | 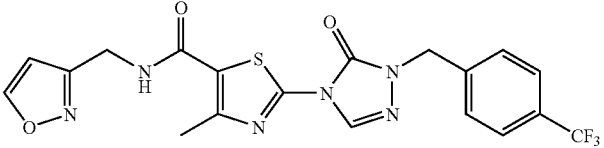 | N-(isoxazol-3-ylmethyl)-4-methyl-2-(5-oxo-1-(4-(trifluoromethyl)benzyl)-1H-1,2,4-triazol-4(5H)-yl)thiazole-5-carboxamide | mp 193-195° C.; $^1$H NMR (300 MHz, DMSO-d$_6$) δ 8.91 (t, J = 5.8 Hz, 1H), 8.86 (d, J = 1.6 Hz, 1H), 8.81 (s, 1H), 7.74 (d, J = 8.2 Hz, 2H), 7.55 (d, J = 8.1 Hz, 2H), 6.53 (d, J = 1.6 Hz, 1H), 5.13 (s, 2H), 4.50 (d, J = 5.8 Hz, 1H), 2.58 (s, 3H); MS (ES+) m/z 367.0 (M + 1). |
| 83 | 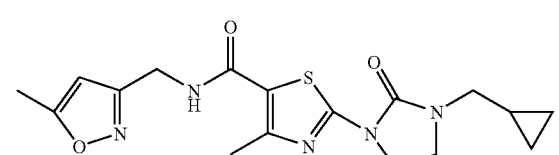 | 2-(3-(cyclopropylmethyl)-2-oxoimidazolidin-1-yl)-4-methyl-N-((5-methylisoxazol-3-yl)methyl)thiazole-5-carboxamide | mp 142-144° C.; $^1$H NMR (300 MHz, DMSO-d$_6$) δ 8.48 (t, J = 5.8 Hz, 1H), 6.14 (d, J = 3.0 Hz, 1H), 4.35 (d, J = 5.9 Hz, 2H), 4.03-3.96 (m, 2H), 3.67-3.63 (m, 2H), 3.10 (d, J = 7.1 Hz, 2H), 2.47 (s, 3H), 2.36 (s, 3H), 1.02-0.89 (m, 1H), 0.52-0.46 (m, 2H), 0.24-0.20 (m, 2H); MS (ES+) m/z 375.0 (M + 1). |
| 84 | 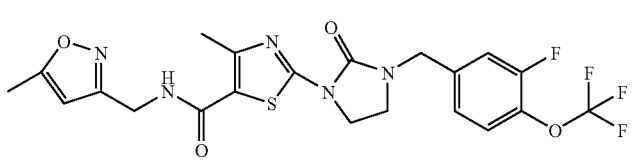 | 2-(3-(3-fluoro-4-(trifluoromethoxy)benzyl)-2-oxoimidazolidin-1-yl)-4-methyl-N-((5-methylisoxazol-3-yl)methyl)thiazole-5-carboxamide | mp 152-155° C.; $^1$H NMR (300 MHz, DMSO-d$_6$) δ 8.51 (t, J = 5.6 Hz, 1H), 7.60-7.54 (m, 1H), 7.51-7.49 (m, 1H), 7.28 (d, J = 8.0 Hz, 1H), 6.19 (s, 1H), 4.49 (s, 2H), 4.36 (d, J = 5.6 Hz, 2H), 4.06-4.01 (m, 2H), 3.54-3.48 (m, 2H), 2.48 (s, 3H), 2.37 (s, 3H); MS (ES+) m/z 513.1 (M + 1). |
| 85 | 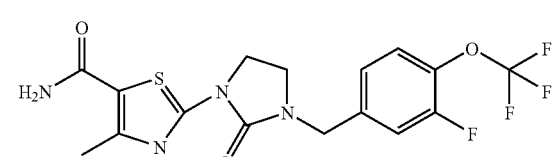 | 2-(3-(3-fluoro-4-(trifluoromethoxy)benzyl)-2-oxoimidazolidin-1-yl)-4-methylthiazole-5-carboxamide | mp 165-168° C.; $^1$H NMR (300 MHz, DMSO-d$_6$) δ 7.56-7.51 (m, 2H), 7.27 (br s, 2H), 7.24 (d, J = 8.4 Hz, 1H), 4.45 (s, 2H), 4.08-4.04 (m, 2H), 3.50-3.44 (m, 2H), 2.46 (s, 3H); MS (ES+) m/z 419.0 (M + 1). |
| 86 | 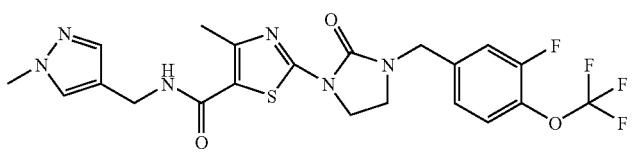 | 2-(3-(3-fluoro-4-(trifluoromethoxy)benzyl)-2-oxoimidazolidin-1-yl)-4-methyl-N-((1-methyl-1H-pyrazol-4-yl)methyl)thiazole-5-carboxamide | mp 128-130° C.; $^1$H NMR (300 MHz, DMSO-d$_6$) δ 8.29 (t, J = 5.5 Hz, 1H), 7.59-7.54 (m, 2H), 7.51-7.49 (m, 1H), 7.32 (s, 1H), 7.27 (d, J = 8.4 Hz, 1H), 4.48 (s, 2H), 4.19 (d, J = 5.6 Hz, 2H), 4.04-3.99 (m, 2H), 3.78 (s, 3H), 3.54-3.48 (m, 2H), 2.46 (s, 3H); MS (ES+) m/z 513.1 (M + 1). |
| 87 | 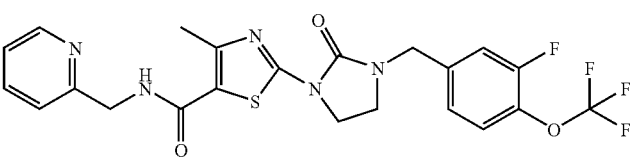 | 2-(3-(3-fluoro-4-(trifluoromethoxy)benzyl)-2-oxoimidazolidin-1-yl)-4-methyl-N-(pyridin-2-ylmethyl)thiazole-5-carboxamide | mp 189-190° C.; $^1$H NMR (300 MHz, DMSO-d$_6$) δ 8.55-8.50 (m, 2H), 7.76-7.74 (m, 1H), 7.56-7.51 (m, 1H), 7.51-7.49 (m, 1H), 7.31-7.28 (m, 3H), 4.49 (s, 2H), 4.48 (s, 2H), 4.06-4.00 (m, 2H), 3.49-3.45 (m, 2H), 2.50 (s, 3H); MS (ES+) m/z 510.1 (M + 1). |
| 88 | 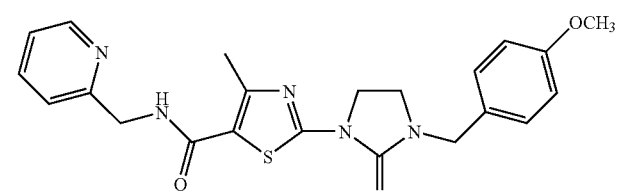 | 2-(3-(4-methoxybenzyl)-2-oxoimidazolidin-1-yl)-4-methyl-N-(pyridin-2-ylmethyl)thiazole-5-carboxamide | mp 162-165° C.; $^1$H NMR (300 MHz, CDCl$_3$) δ 8.60-8.55 (m, 1H), 7.72-7.66 (m, 1H), 7.32-7.22 (m, 4H), 7.13-7.12 (m, 1H), 6.93-6.86 (m, 2H), 4.71 (d, J = 4.6 Hz, 2H), 4.45 (s, 2H), 4.11-4.05 (m, 2H), 3.82 (s, 3H), 3.49-3.44 (m, 2H), 2.66 (s, 3H); MS (ES+) m/z 437.9 (M + 1). |
| 89 | 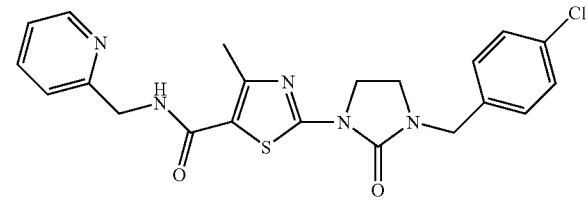 | 2-(3-(4-chlorobenzyl)-2-oxoimidazolidin-1-yl)-4-methyl-N-(pyridin-2-ylmethyl)thiazole-5-carboxamide | mp > 200° C.; $^1$H NMR (300 MHz, DMSO-d$_6$) δ 8.52-8.48 (m, 2H), 7.76-7.71 (m, 1H), 7.42-7.39 (m, 2H), 7.33-7.22 (m, 4H), 4.46-4.41 (m, 4H), 4.01-3.96 (m, 2H), 3.46-3.42 (m, 2H), 2.47 (s, 3H); MS (ES+) m/z 441.8 (M + 1). |

| | Structure | Chemical Name | Characterization Data |
|---|---|---|---|
| 90 | 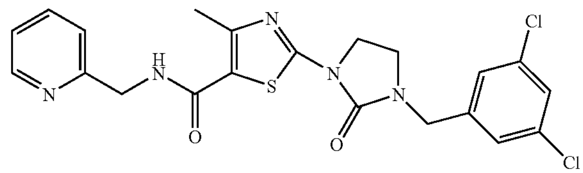 | 2-(3-(3,5-dichlorobenzyl)-2-oxoimidazolidin-1-yl)-4-methyl-N-(pyridin-2-ylmethyl)thiazole-5-carboxamide | mp 153-155° C.; $^1$H NMR (300 MHz, DMSO-d$_6$) δ 8.54-8.50 (m, 2H), 7.79-7.73 (m, 1H), 7.55-7.54 (m, 1H), 7.41-7.40 (m, 2H), 7.31-7.24 (m, 2H), 4.50-4.46 (m, 4H), 4.06-4.01 (m, 2H), 3.54-3.49 (m, 2H), 2.50 (s, 3H); MS (ES+) m/z 475.9 (M + 1). |
| 91 | 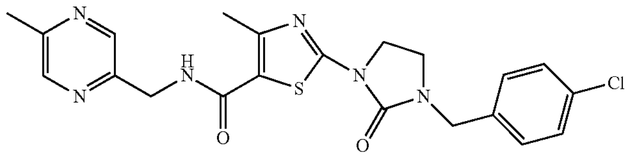 | 2-(3-(4-chlorobenzyl)-2-oxoimidazolidin-1-yl)-4-methyl-N-((5-methylpyrazin-2-yl)methyl)thiazole-5-carboxamide | mp 185-187° C.; $^1$H NMR (300 MHz, DMSO-d$_6$) δ 8.58 (t, J = 5.7 Hz, 1H), 8.47 (d, J = 3.0 Hz, 2H), 7.43 (d, J = 8.4 Hz, 2H), 7.34 (d, J = 8.4 Hz, 2H), 4.48 (d, J = 5.7 Hz, 2H), 4.44 (s, 2H), 4.04-3.98 (m, 2H), 3.49-3.44 (m, 2H), 2.48, (s, 3H), 2.47 (s, 3H); MS (ES+) m/z 456.9 (M + 1). |
| 92 | 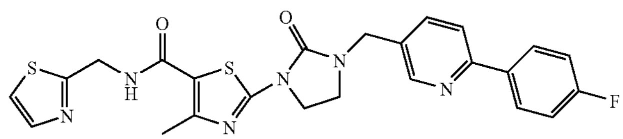 | 2-(3-((6-(4-fluorophenyl)pyridin-3-yl)methyl)-2-oxoimidazolidin-1-yl)-4-methyl-N-(thiazol-2-ylmethyl)thiazole-5-carboxamide | mp 180-182° C.; $^1$H NMR (300 MHz, DMSO-d$_6$) δ 8.83 (t, J = 5.8 Hz, 1H), 8.62 (d, J = 3.0 Hz, 1H), 8.13 (dd, J = 8.7, 5.6 Hz, 2H), 7.97 (d, J = 8.2 Hz, 2H), 7.82 (dd, J = 8.2, 2.1 Hz, 1H), 7.73 (d, J = 3.2 Hz, 1H), 7.62 (d, J = 3.2 Hz, 1H), 7.31 (t, J = 8.8, 8.8 Hz, 1H), 4.66 (d, J = 5.8 Hz, 2H), 4.53 (s, 2H), 4.03 (t, J = 7.3 Hz, 2H), 3.53 (t, J = 7.3 Hz, 2H), 2.50 (s, 3H); MS (ES+) m/z 509.2 (M + 1). |
| 93 | 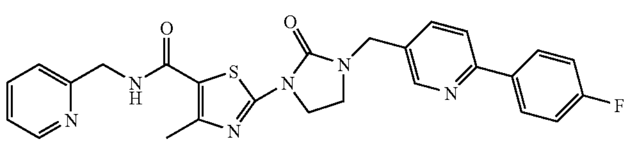 | 2-(3-((6-(4-fluorophenyl)pyridin-3-yl)methyl)-2-oxoimidazolidin-1-yl)-4-methyl-N-(pyridin-2-ylmethyl)thiazole-5-carboxamide | mp 188-189° C.; $^1$H NMR (300 MHz, DMSO-d$_6$) δ 8.83 (t, J = 5.8 Hz, 1H), 8.63 (d, J = 1.6 Hz, 1H), 8.15 (dd, J = 8.7, 5.6 Hz, 2H), 7.97 (d, J = 8.2 Hz, 2H), 7.83 (dd, J = 8.2, 2.1 Hz, 1H), 7.73 (d, J = 3.3 Hz, 1H), 7.62 (d, J = 3.3 Hz, 1H), 7.31 (t, J = 8.8, 8.8 Hz, 2H), 4.66 (d, J = 5.8 Hz, 2H), 4.53 (s, 2H), 4.04 (t, J = 7.3 Hz, 2H), 3.54 (t, J = 7.3 Hz, 2H), 2.50 (s, 3H); MS (ES+) m/z 503.2 (M + 1). |
| 94 | 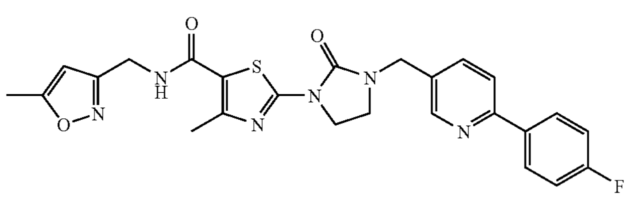 | 2-(3-((6-(4-fluorophenyl)pyridin-3-yl)methyl)-2-oxoimidazolidin-1-yl)-4-methyl-N-((5-methylisoxazol-3-yl)methyl)thiazole-5-carboxamide | mp 174-176° C.; $^1$H NMR (300 MHz, DMSO-d$_6$) δ 8.83 (t, J = 5.8 Hz, 1H), 8.62 (d, J = 3.0 Hz, 1H), 8.13 (dd, J = 8.7, 5.6 Hz, 1H), 7.97 (d, J = 8.2 Hz, 2H), 7.82 (dd, J = 8.2, 2.1 Hz, 1H), 7.73 (d, J = 3.2 Hz, 1H), 7.62 (d, J = 3.2 Hz, 1H), 7.32-7.26 (m, 1H), 4.66 (d, J = 5.8 Hz, 2H), 4.53 (s, 2H), 4.03 (t, J = 7.3 Hz, 2H), 3.53 (t, J = 7.3 Hz, 2H), 2.50 (s, 3H), 2.31 (s, 3H); MS (ES+) m/z 507.2 (M + 1). |
| 95 | 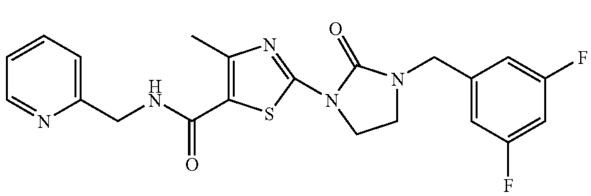 | 2-(3-(3,5-difluorobenzyl)-2-oxoimidazolidin-1-yl)-4-methyl-N-(pyridin-2-ylmethyl)thiazole-5-carboxamide | mp 163-164° C.; $^1$H NMR (300 MHz, DMSO-d$_6$) δ 8.56-8.50 (m, 2H), 7.79-7.75 (m, 1H), 7.32-7.02 (m, 5H), 4.50-4.48 (m, 4H), 4.08-4.03 (m, 2H), 3.55-3.50 (m, 2H), 2.51 (s, 3H); MS (ES+) m/z 457.9 (M + 1). |

| | Structure | Chemical Name | Characterization Data |
|---|---|---|---|
| 96 | 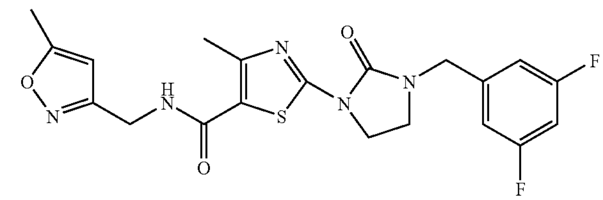 | 2-(3-(3,5-difluorobenzyl)-2-oxoimidazolidin-1-yl)-4-methyl-N-((5-methylisoxazol-3-yl)methyl)thiazole-5-carboxamide | mp 168-169° C.; $^1$H NMR (300 MHz, DMSO-d$_6$) δ 8.52 (t, J = 5.8 Hz, 1H), 7.20-7.06 (m, 3H), 6.14 (s, 1H), 4.47 (s, 2H), 4.36 (d, J = 5.8 Hz, 2H), 4.06-4.01 (m, 2H), 3.54-3.49 (m, 2H), 2.48 (s, 3H), 2.37 (s, 3H); MS (ES+) m/z 447.9 (M + 1). |
| 97 | 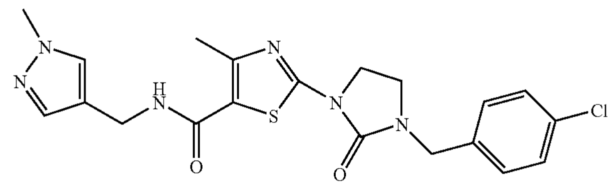 | 2-(3-(4-chlorobenzyl)-2-oxoimidazolidin-1-yl)-4-methyl-N-((1-methyl-1H-pyrazol-4-yl)methyl)thiazole-5-carboxamide | $^1$H NMR (300 MHz, CDCl$_3$) δ 7.45 (s, 1H), 7.39 (s, 1H), 7.34-7.32 (m, 2H), 7.26-7.21 (m, 2H), 5.80-5.77 (m, 1H), 4.45 (s, 2H), 4.41 (d, J = 5.3 Hz, 2H), 4.10-4.05 (m, 2H), 3.88 (s, 3H), 3.48-3.43 (m, 2H), 2.60 (s, 3H); MS (ES+) m/z 444.9 (M + 1), 446.8 (M + 2). |
| 98 | 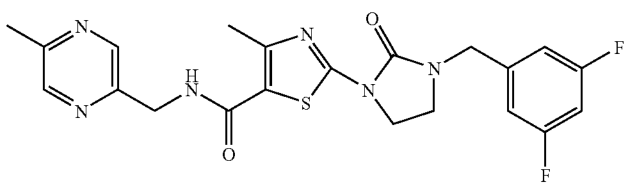 | 2-(3-(3,5-difluorobenzyl)-2-oxoimidazolidin-1-yl)-4-methyl-N-((5-methylpyrazin-2-yl)methyl)thiazole-5-carboxamide | mp 186-187° C.; $^1$H NMR (300 MHz, DMSO-d$_6$) δ 8.58 (t, J = 5.7 Hz, 1H), 8.47-8.46 (m, 2H), 7.21-7.07 (m, 3H), 4.49-4.47 (m, 4H), 4.07-4.01 (m, 2H), 3.54-3.39 (m, 2H), 2.48 (s, 3H), 2.47 (s, 3H); MS (ES+) m/z 459.0 (M + 1). |
| 99 | 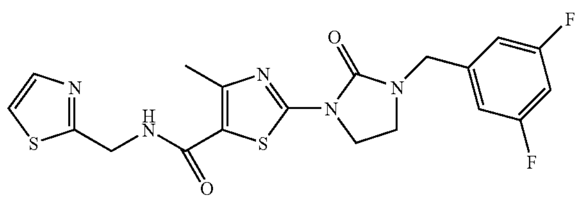 | 2-(3-(3,5-difluorobenzyl)-2-oxoimidazolidin-1-yl)-4-methyl-N-(thiazol-2-ylmethyl)thiazole-5-carboxamide | mp 127-128° C.; $^1$H NMR (300 MHz, DMSO-d$_6$) δ 8.84 (t, J = 5.7 Hz, 1H), 7.73 (d, J = 3.3 Hz, 1H), 7.62 (d, J = 3.3 Hz, 1H), 7.20-7.07 (m, 3H), 4.66 (d, J = 5.9 Hz, 2H), 4.48 (s, 2H), 4.07-4.01 (m, 2H), 3.55-3.50 (m, 2H), 2.51 (s, 3H); MS (ES+) m/z 459.0 (M + 1). |
| 100 | 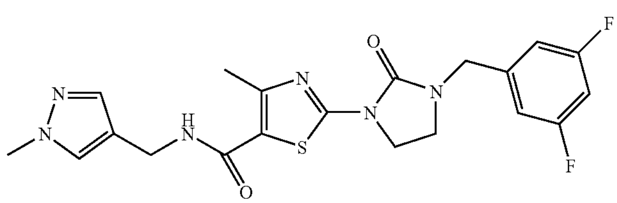 | 2-(3-(3,5-difluorobenzyl)-2-oxoimidazolidin-1-yl)-4-methyl-N-((1-methyl-1H-pyrazol-4-yl)methyl)thiazole-5-carboxamide | mp 158-159° C.; $^1$H NMR (300 MHz, DMSO-d$_6$) δ 8.29 (t, J = 5.7 Hz, 1H), 7.56 (s, 1H), 7.32 (s, 1H), 7.20-7.06 (m, 3H), 4.47 (s, 2H), 4.18 (d, J = 5.7 Hz, 2H), 4.05-4.00 (m, 2H), 3.78 (s, 3H), 3.54-3.48 (m, 2H), 2.46 (s, 3H); MS (ES+) m/z 447.0 (M + 1). |
| 101 | 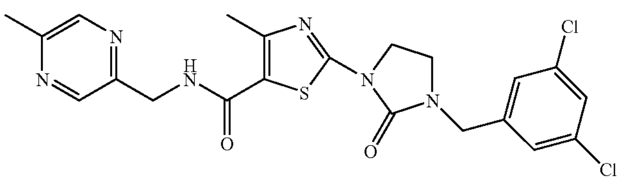 | 2-(3-(3,5-dichlorobenzyl)-2-oxoimidazolidin-1-yl)-4-methyl-N-((5-methylpyrazin-2-yl)methyl)thiazole-5-carboxamide | mp 175-178° C.; $^1$H NMR (300 MHz, DMS0-d$_6$) δ 8.58 (t, J = 5.7 Hz, 1H), 8.48-8.45 (m, 2H), 7.55 (t, J = 1.9 Hz, 1H), 7.41 (d, J = 1.8 Hz, 2H), 4.49-4.46 (m, 4H), 4.06-4.00 (m, 2H), 3.54-3.48 (m, 2H), 2.48 (s, 3H), 2.47 (s, 3H); MS (ES+) m/z 490.8 (M + 1), 492.8 (M + 2). |
| 102 | 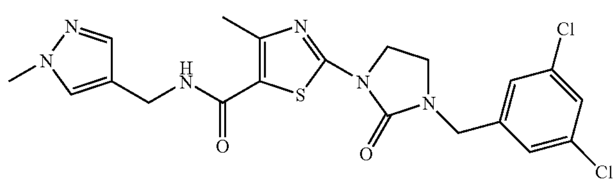 | 2-(3-(3,5-dichlorobenzyl)-2-oxoimidazolidin-1-yl)-4-methyl-N-((1-methyl-1H-pyrazol-4-yl)methyl)thiazole-5-carboxamide | mp 208-211° C. (methanol); $^1$H NMR (300 MHz, DMSO-d$_6$) δ 8.30 (t, J = 5.7 Hz, 1H), 7.57-7.55 (m, 2H), 7.41-7.40 (m, 2H), 7.32 (s, 1H), 4.45 (s, 2H), 4.18 (d, J = 5.7 Hz, 2H), 4.04-3.99 (m, 2H), 3.78 (s, 3H), 3.53-3.47 (m, 2H), 2.46 (s, 3H); MS (ES+) m/z 478.8 (M + 1), 480.8 (M + 2). |

| | Structure | Chemical Name | Characterization Data |
|---|---|---|---|
| 103 | 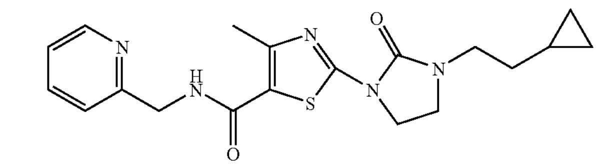 | 2-(3-(2-cyclopropylethyl)-2-oxoimidazolidin-1-yl)-4-methyl-N-(pyridin-2-ylmethyl)thiazole-5-carboxamide | mp 130-132° C.; $^1$H NMR (300 MHz, DMSO-d$_6$) δ 8.52 (s, 1H), 8.51 (t, J = 5.8 Hz, 1H), 7.77-7.75 (m, 1H), 7.31 (d, J = 8.7 Hz, 1H), 7.28-7.26 (m, 1H), 4.49 (d, J = 5.9 Hz, 2H), 4.04-3.98 (m, 2H), 3.61-3.56 (m, 2H), 3.31 (t, J = 7.1 Hz, 2H), 2.50 (s, 3H), 1.43 (q, J = 7.1 Hz, 2H), 0.72-0.62 (m, 1H), 0.44-0.38 (m, 2H), 0.10-0.05 (m, 2H); MS (ES+) m/z 386.1 (M + 1). |
| 104 | 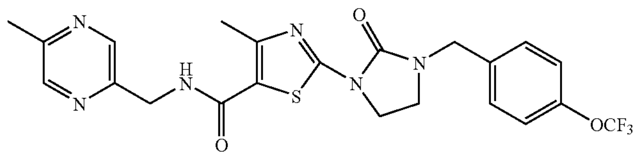 | 4-methyl-N-((5-methylpyrazin-2-yl)methyl)-2-(2-oxo-3-(4-(trifluoromethoxy)benzyl)imidazolidin-1-yl)thiazole-5-carboxamide | mp 183-184° C.; $^1$H NMR (300 MHz, DMSO-d$_6$) δ 8.58 (t, J = 5.8 Hz, 1H), 8.47-8.46 (m, 2H), 7.47-4.44 (m, 2H), 7.38-7.36 (m, 2H), 4.49-4.48 (m, 4H), 4.05-3.99 (m, 2H), 3.51-3.46 (m, 2H), 2.49 (s, 3H), 2.48 (s, 3H); MS (ES+) m/z 507.0 (M + 1). |
| 105 | 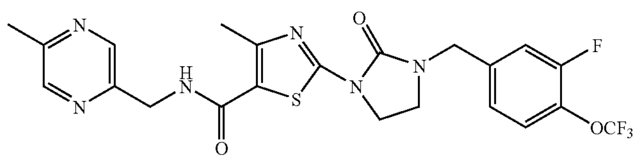 | 2-(3-(3-fluoro-4-methoxybenzyl)-2-oxoimidazolidin-1-yl)-4-methyl-N-((5-methylpyrazin-2-yl)methyl)thiazole-5-carboxamide | mp 190-191° C.; $^1$H NMR (300 MHz, DMSO-d$_6$) δ 8.57 (t, J = 5.7 Hz, 1H), 8.47-8.46 (m, 2H), 7.20-7.07 (m, 3H), 4.48 (d, J = 5.7 Hz, 2H), 4.37 (s, 2H), 4.03-3.97 (m, 2H), 3.82 (s, 3H), 3.48-3.42 (m, 2H), 3.47 (br s, 6H); MS (ES+) m/z 471.0 (M + 1). |
| 106 | 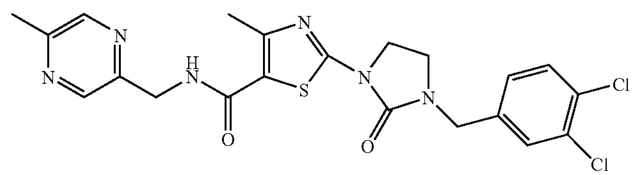 | 2-(3-(3,4-dichlorobenzyl)-2-oxoimidazolidin-1-yl)-4-methyl-N-((5-methylpyrazin-2-yl)methyl)thiazole-5-carboxamide | mp 148-151° C.; $^1$H NMR (300 MHz, CDCl$_3$) δ 8.51 (s, 1H), 8.39 (s, 1H), 7.44-7.38 (m, 2H), 7.16-7.13 (m, 1H), 6.80-6.77 (m, 1H), 4.70 (d, J = 4.9 Hz, 2H), 4.44 (s, 2H), 4.13-4.08 (m, 2H), 3.51-3.45 (m, 2H), 2.62 (s, 3H), 2.56 (s, 3H); MS (ES+) m/z 490.9 (M + 1), 492.8 (M + 2). |
| 107 | 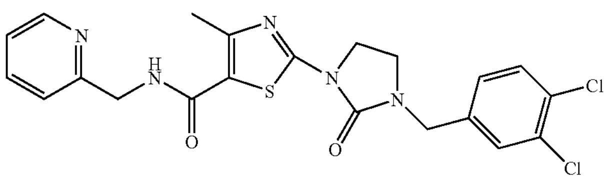 | 2-(3-(3,4-dichlorobenzyl)-2-oxoimidazolidin-1-yl)-4-methyl-N-(pyridine-2-ylmethyl)thiazole-5-carboxamide | mp 168-171° C.; $^1$H NMR (300 MHz, CDCl$_3$) δ 8.56-8.55 (m, 1H), 7.70-7.64 (m, 1H), 7.44-7.39 (m, 2H), 7.30-7.26 (m, 1H), 7.21-7.14 (m, 3H), 4.70 (d, J = 4.8 Hz, 2H), 4.45 (s, 2H), 4.14-4.08 (m, 2H), 3.51-3.45 (m, 2H), 2.64 (s, 3H); MS (ES+) m/z 475.8 (M + 1), 477.8 (M + 2). |
| 108 | 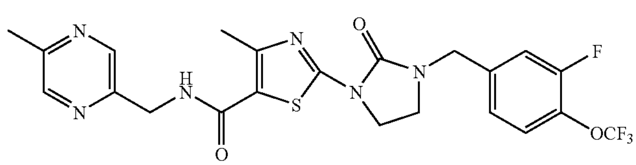 | 2-(3-(3-fluoro-4-(trifluoromethoxy)benzyl)-2-oxoimidazolidin-1-yl)-4-methyl-N-((5-methylpyrazin-2-yl)methyl)thiazole-5-carboxamide | mp 188-189° C.; $^1$H NMR (300 MHz, DMSO-d$_6$) δ 8.58 (t, J = 5.7 Hz, 1H), 8.47-8.46 (m, 2H), 7.57 (dd, J = 8.2, 8.2 Hz, 1H), 7.50 (dd, J = 11.3, 1.9 Hz, 1H), 7.28 (d, J = 8.5 Hz, 1H), 4.49-4.47 (m, 4H), 4.06-4.01 (m, 2H), 3.54-3.49 (m, 2H), 2.48 (s, 3H), 2.47 (s, 3H); MS (ES+) m/z 524.9 (M + 1). |
| 109 | 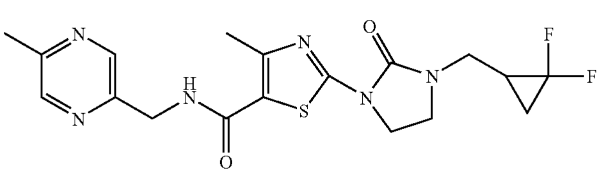 | 2-(3-((2,2-difluorocyclopropyl)methyl)-2-oxoimidazolidin-1-yl)-4-methyl-N-((5-methylpyrazin-2-yl)methyl)thiazole-5-carboxamide | mp 146-147° C.; $^1$H NMR (300 MHz, DMSO-d$_6$) δ 8.55 (t, J = 5.7 Hz, 1H), 8.47-8.46 (m, 2H), 4.48 (d, J = 5.7 Hz, 2H), 4.05-4.00 (m, 2H), 3.65-3.51 (m, 3H), 3.20 (dd, J = 14.6, 8.0 Hz, 1H), 2.48 (s, 3H), 2.47 (s, 3H), 2.08-1.92 (m, 1H), 1.71-1.59 (m, 1H), 1.41-1.30 (m, 1H); MS (ES+) m/z 422.9 (M + 1). |

| | Structure | Chemical Name | Characterization Data |
|---|---|---|---|
| 110 | 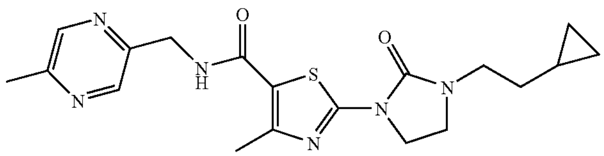 | 2-(3-(2-cyclopropylethyl)-2-oxoimidazolidin-1-yl)-4-methyl-N-((5-methylpyrazin-2-yl)methyl)thiazole-5-carboxamide | mp 148-150° C.; $^1$H NMR (300 MHz, DMSO-d$_6$) δ 8.52 (s, 1H), 8.46 (s, 1H), 8.45 (s, 1H), 4.48 (d, J = 5.9 Hz, 2H), 4.03-3.97 (m, 2H), 3.60-3.55 (m, 2H), 3.30 (t, J = 7.1 Hz, 2H), 2.47 (s, 6H), 1.42 (q, J = 7.1 Hz, 2H), 0.75-0.61 (m, 1H), 0.43-0.37 (m, 2H), 0.08-0.04 (m, 2H); MS (ES+) m/z 401.2 (M + 1), |
| 111 | 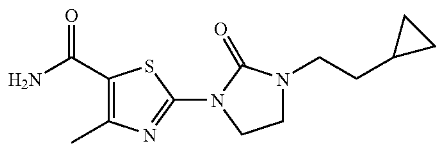 | 2-(3-(2-cyclopropylethyl)-2-oxoimidazolidin-1-yl)-4-methylthiazole-5-carboxamide | mp 172-175° C.; $^1$H NMR (300 MHz, DMSO-d$_6$) δ 7.27 (s, 2H), 4.04-3.96 (m, 2H), 3.60-3.54 (m, 2H), 3.29 (t, J = 7.1 Hz, 2H), 2.45 (s, 3H), 1.42 (q, J = 7.1 Hz, 2H), 0.74-0.60 (m, 1H), 0.43-0.37 (m, 2H), 0.08-0.04 (m, 2H); MS (ES+) m/z 295.1 (M + 1). |
| 112 | 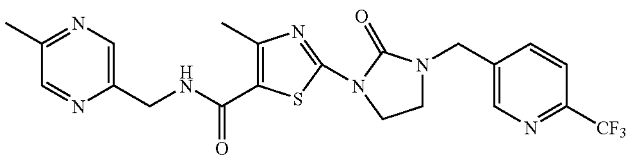 | 4-methyl-N-((5-methylpyrazin-2-yl)methyl)-2-(2-oxo-3-((6-(trifluoromethyl)pyridin-3-yl)methyl)-imidazolidin-1-yl)-thiazole-5-carboxamide | mp 185-186° C.; $^1$H NMR (300 MHz, DMSO-d$_6$) δ 8.75 (d, J = 1.5 Hz, 1H), 8.57 (t, J = 5.7 Hz, 1H), 8.47-8.46 (m, 2H), 8.04 (dd, J = 8.1, 1.5 Hz, 1H), 7.92 (d, J = 8.1 Hz, 1H), 4.61 (s, 2H), 4.48 (d, J = 5.7 Hz, 2H), 4.06-4.01 (m, 2H), 3.57- 3.52 (m, 2H), 2.48, (s, 3H), 2.47 (s, 3H); MS (ES+) m/z 492.0 (M + 1). |
| 113 | 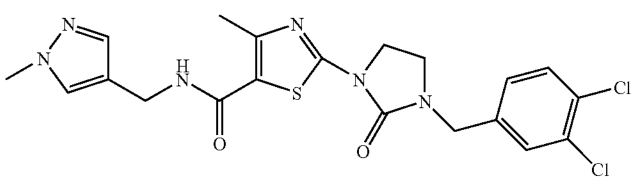 | 2-(3-(3,4-dichlorobenzyl)-2-oxoimidazolidin-1-yl)-4-methyl-N-((1-methyl-1H-pyrazol-4-yl)methyl)thiazole-5-carboxamide | mp 158-161° C.; $^1$H NMR (300 MHz, CDCl$_3$) δ 7.29-7.23 (m, 4H), 7.00-6.97 (m, 1H), 5.72-5.69 (m, 1H), 4.28-4.25 (m, 4H), 3.97-3.91 (m, 2H), 3.72 (s, 3H), 3.35-3.30 (m, 2H), 2.44 (s, 3H); MS (ES+) m/z 478.8 (M + 1), 480.8 (M + 2). |
| 114 | 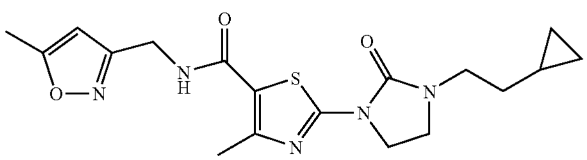 | 2-(3-(2-cyclopropylethyl)-2-oxoimidazolidin-1-yl)-4-methyl-N-((5-methylisoxazol-3-yl)methyl)thiazole-5-carboxamide | mp 144-146° C.; $^1$H NMR (300 MHz, DMSO-d$_6$) δ 8.45 (t, J = 5.8 Hz, 1H), 6.10 (s, 1H), 4.35 (d, J = 5.8 Hz, 2H), 4.03-3.97 (m, 2H), 3.60-3.55 (m, 2H), 3.29 (t, J = 7.1 Hz, 2H), 2.47 (s, 3H), 2.36 (s, 3H), 1.42 (q, J = 7.1 Hz, 2H), 0.74-0.57 (m, 1H), 0.43-0.37 (m, 2H), 0.08-0.04 (m, 2H); MS (ES+) m/z 390.1 (M + 1). |
| 115 | 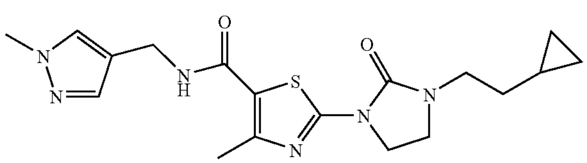 | 2-(3-(2-cyclopropylethyl)-2-oxoimidazolidin-1-yl)-4-methyl-N-((1-methyl-1H-pyrazol-4-yl)methyl)thiazole-5-carboxamide | mp 191-192° C.; $^1$H NMR (300 MHz, DMSO-d$_6$) δ 8.26 (t, J = 5.8 Hz, 1H), 7.56 (s, 1H), 7.32 (s, 1H), 4.18 (d, J = 5.8 Hz, 2H), 4.04-3.96 (m, 2H), 3.78 (s, 3H), 3.59-3.55 (m, 2H), 3.29 (t J = 7.1 Hz, 2H), 2.45 (s, 3H), 1.41 (q, J = 7.1 Hz, 2H), 0.74-0.61 (m, 1H), 0.43- 0.37 (m, 2H), 0.08-0.03 (m, 2H); MS (ES+) m/z 390.1 (M + 1). |
| 116 | 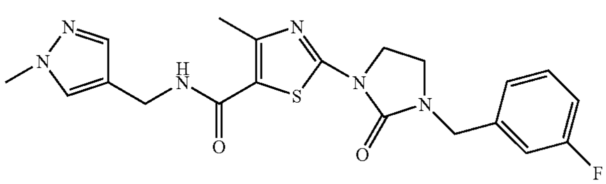 | 2-(3-(3-fluorobenzyl)-2-oxoimidazolidin-1-yl)-4-methyl-N-((1-methyl-1H-pyrazol-4-yl)methyl)thiazole-5-carboxamide | mp 157-159° C.; $^1$H NMR (300 MHz, CDCl$_3$) δ 7.44 (s, 1H), 7.35 (s, 1H), 7.33-7.26 (m, 1H), 7.07-6.97 (m, 3H), 5.87-5.84 (m, 1H), 4.46 (s, 2H), 4.40 (d, J = 5.3 Hz, 2H), 4.11-4.39 (m, 2H), 3.87 (s, 3H), 3.50-3.44 (m, 2H), 2.59 (s, 3H); MS (ES+) m/z 429.0 (M + 1). |

-continued

| | Structure | Chemical Name | Characterization Data |
|---|---|---|---|
| 117 | 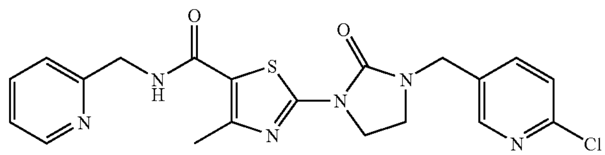 | 2-(3-((6-chloropyridin-3-yl)methyl)-2-oxoimidazolidin-1-yl)-4-methyl-N-(pyridin-2-ylmethyl)thiazole-5-carboxamide | mp 161-162° C.; $^1$H NMR (300 MHz, DMSO-d$_6$) δ 8.52-8.47 (s, 2H), 8.37 (d, J = 2.3 Hz, 1H), 7.81-7.70 (m, 2H), 7.50 (d, J = 8.2 Hz, 1H), 7.28-7.21 (m, 2H), 4.44 (s, 2H), 4.45 (d, J = 5.6 Hz, 2H), 4.01-3.96 (m, 2H), 3.50-3.45 (m, 2H), 2.46 (s, 3H); MS (ES+) m/z 352.1 (M + 1). |
| 118 | 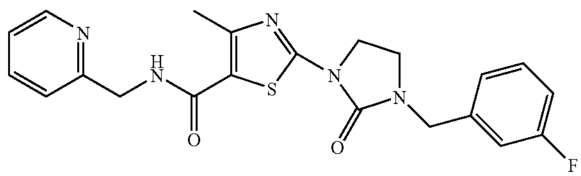 | 2-(3-(3-fluorobenzyl)-2-oxoimidazolidin-1-yl)-4-methyl-N-(pyridin-2-ylmethyl)thiazole-5-carboxamide | mp 137-140° C.; $^1$H NMR (300 MHz, CDCl$_3$) δ 8.57-8.55 (m, 1H), 7.70-7.64 (m, 1H), 7.37-7.28 (m, 2H), 7.26-7.12 (m, 1H), 7.10-6.99 (m, 4H), 4.70 (d, J = 4.9 Hz, 2H), 4.49 (s, 2H), 4.13-4.08 (m, 2H), 3.51-3.46 (m, 2H), 2.65 (s, 3H); MS (ES+) m/z 428.8 (M + 1). |
| 119 | 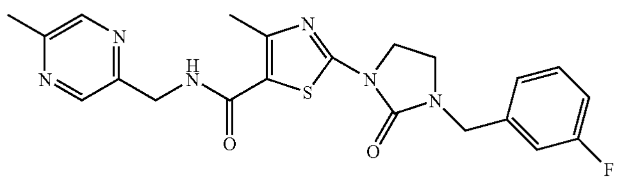 | 2-(3-(3-fluorobenzyl)-2-oxoimidazolidin-1-yl)-4-methyl-N-((5-methylpyrazin-2-yl)methyl)thiazole-5-carboxamide | mp 138-141° C.; $^1$H NMR (300 MHz, CDCl$_3$) δ 8.51 (s, 1H), 8.38 (s, 1H), 7.35-7.26 (m, 1H), 7.08-6.97 (m, 3H), 6.82-6.79 (m, 1H), 4.70 (d, J = 4.9 Hz, 2H), 4.47 (s, 2H), 4.12-4.06 (m, 2H), 3.50-3.45 (m, 2H), 2.61 (s, 3H), 2.55 (s, 3H); MS (ES+) m/z 440.9 (M + 1). |
| 120 | 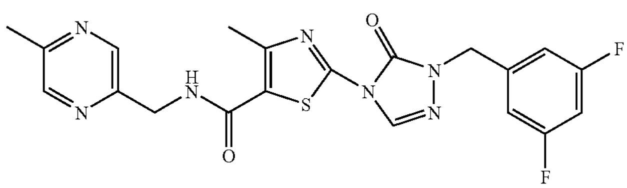 | 2-(1-(3,5-difluorobenzyl)-5-oxo-1H-1,2,4-triazol-4(5H)-yl)-4-methyl-N-((5-methylpyrazin-2-yl)methyl)thiazole-5-carboxamide | mp 177-179° C.; $^1$H NMR (300 MHz, DMSO-d$_6$) δ 8.92 (t, J = 5.7 Hz, 1H), 8.79 (s, 1H), 8.49-8.48 (m, 2H), 7.23-7.07 (s, 3H), 5.06 (s, 2H), 4.53 (d, J = 5.7 Hz, 2H), 2.58 (s, 3H), 2.47 (s, 3H); MS (ES+) m/z 457.9 (M + 1). |
| 121 | 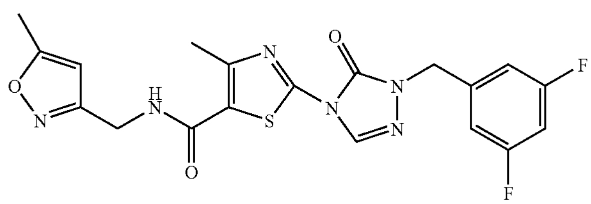 | 2-(1-(3,5-difluorobenzyl)-5-oxo-1H-1,2,4-triazol-4(5H)-yl)-4-methyl-N-((5-methylisoxazol-3-yl)methyl)thiazole-5-carboxamide | mp 159-160° C.; $^1$H NMR (300 MHz, DMSO-d$_6$) δ 8.87 (t, J = 5.8 Hz, 1H), 8.79 (s, 1H), 7.23-7.07 (s, 3H), 6.17 (s, 1H), 5.06 (s, 2H), 4.41 (d, J = 5.8 Hz, 2H), 2.58 (s, 3H), 2.37 (s, 3H); MS (ES+) m/z 446.8 (M + 1). |
| 122 | 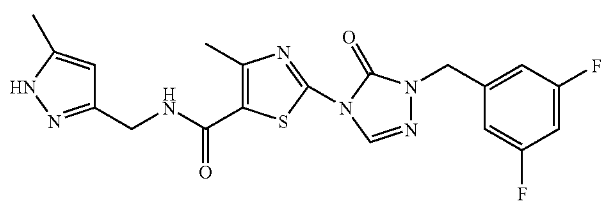 | 2-(1-(3,5-difluorobenzyl)-5-oxo-1H-1,2,4-triazol-4(5H)-yl)-4-methyl-N-((5-methyl-1H-pyrazol-3-yl)methyl)thiazole-5-carboxamide | mp 248-249° C.; $^1$H NMR (300 MHz, DMSO-d$_6$) δ 12.24 (s, 1H), 8.78 (s, 1H), 8.67 (br, 1H), 7.23-7.07 (m, 3H), 5.91 (s, 1H), 5.06 (s, 2H), 4.33 (br, 2H), 2.56 (s, 3H), 2.18 (s, 3H); MS (ES+) m/z 445.9 (M + 1). |
| 123 | 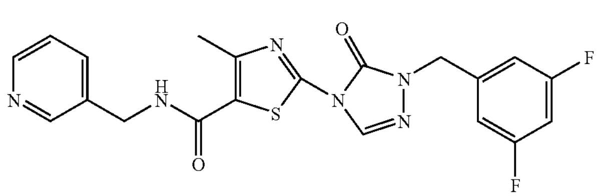 | 2-(1-(3,5-difluorobenzyl)-5-oxo-1H-1,2,4-triazol-4(5H)-yl)-4-methyl-N-(pyridin-3-ylmethyl)thiazole-5-carboxamide | mp 194-196° C.; $^1$H NMR (300 MHz, DMSO-d$_6$) δ 8.91 (dd, J = 5.8 Hz, 1H), 8.79 (s, 1H), 8.55 (d, J = 1.9 Hz, 1H), 8.91 (dd, J = 4.7 Hz, 1.4 Hz, 1H), 7.75-7.71 (m, 1.7 Hz, 1H), 7.37 (dd, J = 7.8 Hz, 4.7 Hz, 1H), 7.23-7.07 (m, 3H), 5.06 (s, 2H), 4.44 (d, J = 5.8 Hz, 2H), 2.58 (s, 3H); MS (ES+) m/z 442.8 (M + 1). |

| | Structure | Chemical Name | Characterization Data |
|---|---|---|---|
| 124 | 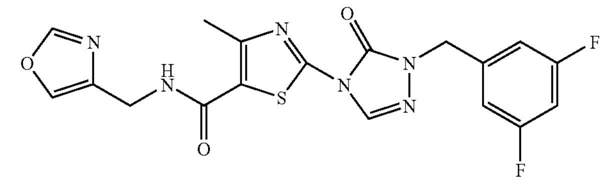 | 2-(1-(3,5-difluorobenzyl)-5-oxo-1H-1,2,4-triazol-4(5H)-yl)-4-methyl-N-(oxazol-4-ylmethyl)-thiazole-5-carboxamide | mp 171-174° C.; $^1$H NMR (300 MHz, DMSO-d$_6$) δ 8.78-8.74 (m, 2H), 8.33 (s, 1H), 7.97 (s, 1H), 7.22-7.07 (m, 3H), 5.06 (s, 2H), 4.33 (d, J = 5.5 Hz, 2H), 2.57 (s, 3H); MS (ES+) m/z 432.8 (M + 1). |
| 125 | 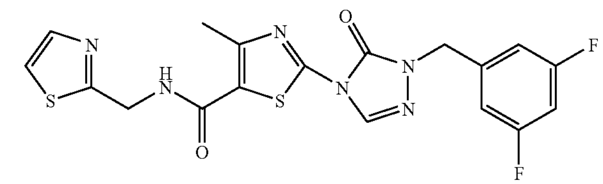 | 2-(1-(3,5-difluorobenzyl)-5-oxo-1H-1,2,4-triazol-4(5H)-yl)-4-methyl-N-(thiazol-2-ylmethyl)-thiazole-5-carboxamide | mp 189-190° C.; $^1$H NMR (300 MHz, DMSO-d$_6$) δ 9.20 (t, J = 5.8 Hz, 1H), 8.80 (s, 1H), 7.74 (d, J = 3.3 Hz, 1H), 7.64 (d, J = 3.3 Hz, 1H), 7.22-7.08 (m, 3H), 5.07 (s, 2H), 4.71 (d, J = 5.8 Hz, 2H), 2.60 (s, 3H); MS (ES+) m/z 448.8 (M + 1). |
| 126 | 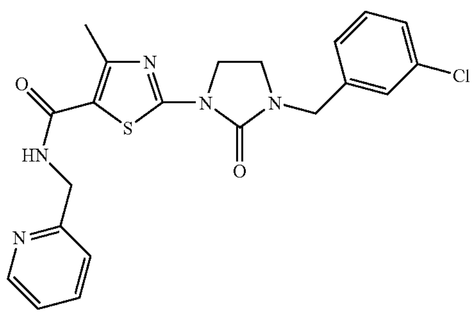 | 2-(3-(3-chlorobenzyl)-2-oxoimidazolidin-1-yl)-4-methyl-N-(pyridin-2-ylmethyl)-thiazole-5-carboxamide | $^1$H NMR (300 MHz, CDCl$_3$) δ 8.56 (d, J = 4.6 Hz, 1H), 7.70-7.64 (m, 1H), 7.30-7.19 (m, 6H), 7.13-7.10 (m, 1H), 4.71 (d, J = 4.6 Hz, 2H), 4.47 (s, 2H), 4.14-4.08 (m, 2H), 3.51-3.45 (m, 2H), 2.65 (s, 3H); MS (ES+) m/z 441.8 (M + 1), 443.8 (M + 2). |
| 127 | 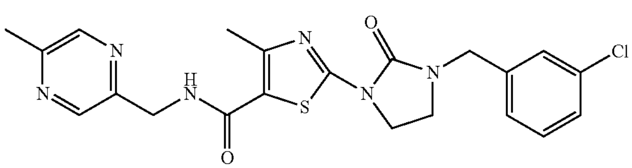 | 2-(3-(3-chlorobenzyl)-2-oxoimidazolidin-1-yl)-4-methyl-N-((5-methylpyrazin-2-yl)methyl)thiazole-5-carboxamide | mp 98-100° C.; $^1$H NMR (300 MHz, DMSO-d$_6$) δ 8.57 (t, J = 5.7 Hz, 1H), 8.47 (s, 1H), 8.46 (s, 1H), 7.45-7.25 (m, 4H), 4.48 (d, J = 5.7 Hz, 2H), 4.45 (s, 2H), 4.07-3.98 (m, 2H), 3.54-3.45 (m, 2H), 2.48 (s, 3H), 2.47 (s, 3H); MS (ES+) m/z 479.1 (M + 1), |
| 128 | 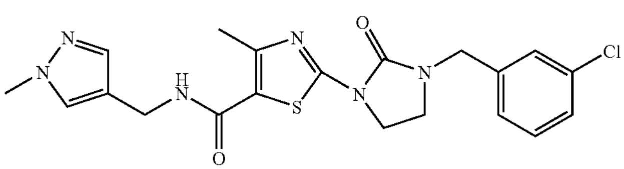 | 2-(3-(3-chlorobenzyl)-2-oxoimidazolidin-1-yl)-4-methyl-N-((1-methyl-1H-pyrazol-4-yl)methyl)thiazole-5-carboxamide | $^1$H NMR (300 MHz, DMSO-d$_6$) δ 8.31 (t, J = 5.6 Hz, 1H), 7.58 (s, 1H), 7.43-7.25 (m, 5H), 4.44 (s, 2H), 4.19 (d, J = 5.6 Hz, 2H), 4.05-3.97 (m, 2H), 3.78 (s, 3H), 3.53-3.43 (m, 2H), 2.46 (s, 3H), MS (ES+) m/z 445.1 (M + 1), 447.1 (M + 1). |
| 129 | 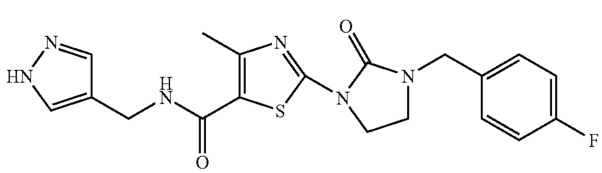 | N-((1H-pyrazol-4-yl)methyl)-2-(3-fluorobenzyl)-2-oxoimidazolidin-1-yl)-4-methylthiazole-5-carboxamide | mp 185-188° C.; $^1$H NMR (300 MHz, DMSO-d$_6$) δ 12.63 (br, 1H), 8.28 (t, J = 5.7 Hz, 1H), 7.60-7.33 (m, 4H), 7.22-7.16 (m, 2H), 4.42 (s, 2H), 4.23 (d, J = 5.7 Hz, 2H), 4.02-3.96 (m, 2H), 3.47-3.42 (m, 2H), 2.45 (s, 3H); MS (ES+) m/z 415.1 (M + 1). |
| 130 | 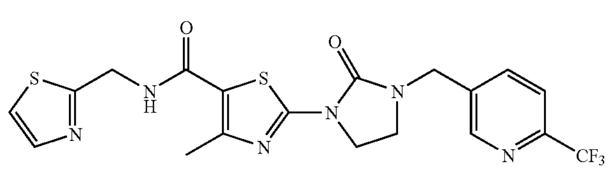 | 4-methyl-2-(2-oxo-3-((6-(trifluoromethyl)-pyridin-3-yl)methyl)imidazolidin-1-yl)-N-(thiazol-2-ylmethyl)-thiazole-5-carboxamide | mp 202-204° C.; $^1$H NMR (300 MHz, DMSO-d$_6$) δ 8.83 (t, J = 5.9 Hz, 1H), 8.75 (s, 1H), 8.04 (dd, J = 8.1, 1.1 Hz, 1H), 7.91 (d, J = 8.1 Hz, 1H), 7.72 (d, J = 3.2 Hz, 1H), 7.61 (d, J = 3.2 Hz, 1H), 4.66 (d, J = 5.7 Hz, 2H), 4.61 (s, 2H), 4.06-4.00 (m, 2H), 3.55-3.49 (m, 2H), 3.20 (s, 3H), 2.50 (s, 3H); MS (ES+) m/z 483.1 (M + 1). |

| | Structure | Chemical Name | Characterization Data |
|---|---|---|---|
| 131 | 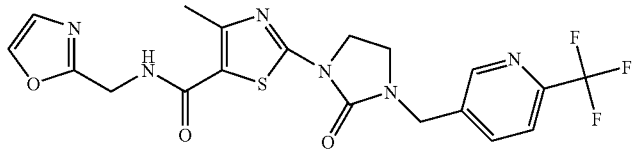 | 4-methyl-N-(oxazol-2-ylmethyl)-2-(2-oxo-3-((6-(trifluoromethyl)-pyridin-3-yl)methyl)-imidazolidin-1-yl)thiazole-5-carboxamide | mp 136-138° C.; $^1$H NMR (300 MHz, DMSO-d$_6$) δ 8.76 (d, J = 0.9 Hz, 1H), 8.60 (t, J = 5.6 Hz, 1H), 8.06-8.03 (m, 2H), 7.91 (d, J = 8.1 Hz, 1H), 7.16 (s, 1H), 4.61 (s, 2H), 4.49 (d, J = 5.7 Hz, 2H), 4.06-3.99 (m, 2H), 3.58-3.53 (m, 2H), 3.34 (s, 3H), 2.48 (s, 3H); MS (ES+) m/z 467.2 (M + 1). |
| 132 | 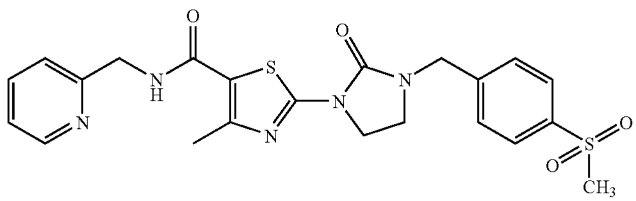 | 4-methyl-2-(3-(4-(methylsulfonyl)benzyl)-2-oxoimidazolidin-1-yl)-N-(pyridin-2-ylmethyl)thiazole-5-carboxamide | mp 198-199° C.; $^1$H NMR (300 MHz, DMSO-d$_6$) δ 8.55-8.50 (m, 2H), 7.93 (d, J = 8.3 Hz, 2H), 7.77 (t, J = 7.7 Hz, 1H), 7.59 (d, J = 8.2 Hz, 2H), 7.31-7.24 (m, 2H), 4.57 (s, 2H), 4.49 (d, J = 5.7 Hz, 2H), 4.06-4.00 (m, 2H), 3.55-3.49 (m, 2H), 3.21 (s, 3H), 2.50 (s, 3H); MS (ES+) m/z 486.1 (M + 1). |
| 133 | 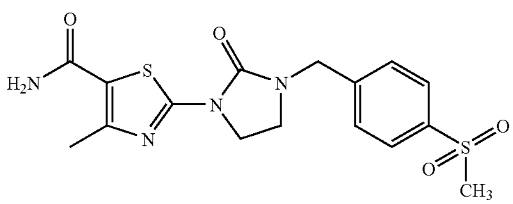 | 4-methyl-2-(3-(4-(methylsulfonyl)benzyl)-2-oxoimidazolidin-1-yl)thiazole-5-carboxamide | mp 253-256° C.; $^1$H NMR (300 MHz, DMSO-d$_6$) δ 12.32 (br s, 2H), 7.93 (d, J = 8.3 Hz, 2H), 7.59 (d, J = 8.4 Hz, 2H), 4.56 (s, 2H), 4.06-4.00 (m, 2H), 3.55-3.49 (m, 2H), 3.21 (s, 3H), 2.46 (s, 3H); MS (ES+) m/z 395.1 (M + 1). |
| 134 | 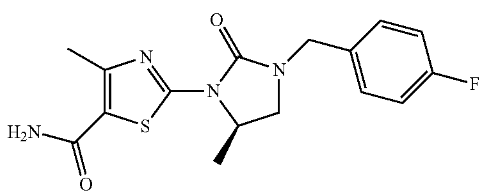 | (R)-2-(3-(4-fluorobenzyl)-5-methyl-2-oxoimidazolidin-1-yl)-4-methylthiazole-5-carboxamide | mp 195-196° C.; $^1$H NMR (300 MHz, DMSO-d$_6$) δ 7.37-7.32 (m, 4H), 7.23-7.11 (m, 2H), 4.58-4.51 (m, 1H), 4.42 (d, J = 5.3 Hz, 2H), 3.60 (t, J = 9.0 Hz, 1H), 3.03 (dd, J = 9.1, 3.4 Hz, 1H), 2.46 (s, 3H), 1.38 (d, J = 6.2 Hz, 3H); MS (ES+) m/z 348.8 (M + 1). |
| 135 | 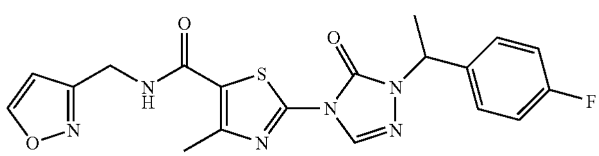 | 2-(1-(1-(4-fluorophenyl)ethyl)-5-oxo-1H-1,2,4-triazol-4(5H)-yl)-N-(isoxazol-3-ylmethyl)-4-methylthiazole-5-carboxamide | mp 130-131° C.; $^1$H NMR (300 MHz, DMSO-d$_6$) δ 8.89 (t, J = 5.8 Hz, 1H), 8.85 (d, J = 1.6 Hz, 1H), 8.79 (s, 1H), 7.43 (dd, J = 8.7, 5.5 Hz, 2H), 7.18 (dd, J = 8.9, 8.9 Hz, 2H), 6.52 (d, J = 1.6 Hz, 1H), 5.50 (q, J = 7.0 Hz, 1H), 4.50 (d, J = 5.8 Hz, 2H), 2.57 (s, 3H), 1.70 (d, J = 7.1 Hz, 3H); MS (ES+) m/z 429.0 (M + 1). |
| 136 | 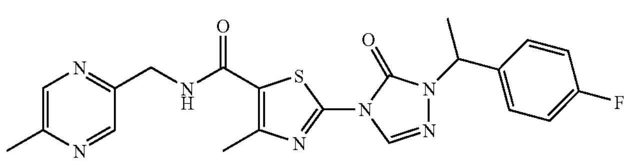 | 2-(1-(1-(4-fluorophenyl)ethyl)-5-oxo-1H-1,2,4-triazol-4(5H)-yl)-4-methyl-N-((5-methylpyrazin-2-yl)methyl)thiazole-5-carboxamide | mp 142-144° C.; $^1$H NMR (300 MHz, DMSO-d$_6$) δ 8.91 (t, J = 5.7 Hz, 1H), 8.80 (s, 1H), 8.49 (d, J = 1.9 Hz, 2H), 7.43 (dd, J = 8.7, 5.5 Hz, 2H), 7.18 (dd, J = 8.9, 8.9 Hz, 2H), 5.50 (q, J = 7.0 Hz, 1H), 4.52 (d, J = 5.7 Hz, 2H), 2.57 (s, 3H), 2.48 (s, 3H), 1.71 (d, J = 7.1 Hz, 3H); MS (ES+) m/z 454.1 (M + 1). |
| 137 | 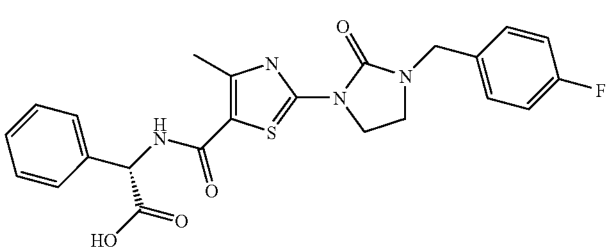 | (S)-2-(2-(3-(4-fluorobenzyl)-2-oxoimidazolidin-1-yl)-4-methylthiazole-5-carboxamido)-2-phenylacetic acid | mp 218-220° C.; $^1$H NMR (300 MHz, DMSO-d$_6$) δ 12.96 (s, 1H), 8.57 (d, J = 7.1 Hz, 1H), 7.48-7.46 (m, 2H), 7.40-7.32 (m, 5H), 7.22-7.16 (m, 2H), 5.48 (d, J = 7.1 Hz, 1H), 4.42 (s, 2H), 4.03-3.98 (m, 2H), 3.48-3.43 (m, 2H), 2.47 (s, 3H); MS (ES+) m/z 468.9 (M + 1). |

Example 21

Measuring Stearoyl-CoA Desaturase Inhibition Activity of a Test Compound Using Mouse Liver Microsomes The identification of compounds of the invention as SCD inhibitors was readily accomplished using the SCD microsomal assay procedure described in Shanklin J. and Summerville C., *Proc. Natl. Acad. Sci. USA* (1991), Vol. 88, pp. 2510-2514.

Preparation of Mouse Liver Microsomes:

Male ICR outbread mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1/3 w/v) containing 0.25 M sucrose, 62 mM potassium phosphate buffer (pH 7.0), 0.15 M KCl, 15 mM N-acetylcysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Desaturase activity is measured as the release of $^3H_2O$ from [9,10-$^3$H]stearoyl-CoA. Reactions per assay point conditions are as follows: 2 µL 1.5 mM stearoyl-CoA, 0.25 µL 1 mCi/mL $^3$H stearoyl CoA, 10 µL 20 mM NADH, 36.75 µL 0.1 M PK buffer ($K_2HPO_4/NaH_2PO_4$, pH 7.2). The test compound or control solution is added in a 1 µL volume. Reactions are started by adding 50 µL of microsomes (1.25 mg/mL). The plates are mixed and after 15 min incubation on a heating block (25° C.), the reactions are stopped by the addition of 10 µL 60% PCA. An aliquot of 100 µL is then transferred to a filter plate pretreated with charcoal and the plate centrifuged at 4000 rpm for 1 minute. The flow through containing the $^3H_2O$ released by the SCD1 desaturation reaction is added to scintillation fluid and the radioactivity measured in a Packard TopCount. The data is analysed to identify the $IC_{50}$ for test compounds and reference compounds.

Representative compounds of the invention showed activity as inhibitors of SCD when tested in this assay. The activity was defined in terms of % SCD enzyme activity remaining at the desired concentration of the test compound or as the $IC_{50}$ concentration. The $IC_{50}$ (affinity) of the example compounds toward the stearoyl-CoA desaturase is comprised between around 20 mM and 0.0001 µM or between around 5 µM and 0.0001 µM or between around 1 µM and 0.0001 µM.

The following Table provides data that exemplifies representative compounds and their Microsomal $IC_{50}$ (µM) data.

Example ACTIVITY DATA

| Example | Compound name | Microsomal $IC_{50}$ (µM) |
|---|---|---|
| 2.7 | (R)-2-(3-(4-fluorobenzyl)-4-methyl-2-oxoimidazolidin-1-yl)-4-methyl-N-(pyridin-3-ylmethyl)thiazole-5-carboxamide | 0.036 |
| 12.8 | N-((1H-pyrazol-4-yl)methyl)-4-methyl-2-(2-oxo-3-(4,4,4-trifluorobutyl)imidazolidin-1-yl)thiazole-5-carboxamide | 0.066 |
| 12.18 | 2-(3-isobutyl-2-oxoimidazolidin-1-yl)-4-methyl-N-(pyridin-3-ylmethyl)thiazole-5-carboxamide | 0.156 |
| 17.2 | 1-(4-methyl-5-(1H-pyrazol-3-yl)thiazol-2-yl)-3-(3-(trifluoromethyl)benzyl)imidazolidin-2-one | 0.186 |
| 19 | 2-(4-(4-Fluorobenzyl)-3-oxo-2,4-diazabicyclo[3.1.0]hexan-2-yl)-4-methyl-N-(pyridin-3-ylmethyl)thiazole-5-carboxamide | 1.209 |
| 20-5 | 4-methyl-2-(5-oxo-1-(1-phenylethyl)-1H-1,2,4-triazol-4(5H)-yl)-N-(pyridin-3-ylmethyl)thiazole-5-carboxamide | 0.098 |
| 20-6 | 4-methyl-2-(5-oxo-1-(1-phenylethyl)-1H-1,2,4-triazol-4(5H)-yl)thiazole-5-carboxamide | 0.080 |
| 20-8 | 2-(1-(4-fluorobenzyl)-5-oxo-1H-1,2,4-triazol-4(5H)-yl)-4-methyl-N-((6-(trifluoromethyl)pyridin-3-yl)methyl)thiazole-5-carboxamide | 1.722 |
| 20-10 | 4-methyl-2-(5-oxo-1-(1-phenylethyl)-1H-1,2,4-triazol-4(5H)-yl)-N-(thiazol-5-ylmethyl)thiazole-5-carboxamide | 0.008 |
| 20-12 | 2-(1-((2,2-difluorocyclopropyl)methyl)-5-oxo-1H-1,2,4-triazol-4(5H)-yl)-4-methyl-N-(thiazol-5-ylmethyl)thiazole-5-carboxamide | 0.018 |
| 20-17 | 4-methyl-2-(5-oxo-1-(1-phenylethyl)-1H-1,2,4-triazol-4(5H)-yl)-N-((2-(trifluoromethyl)-thiazol-4-yl)-methyl)thiazole-5-carboxamide | 0.208 |
| 20-22 | N-(imidazo[1,2-a]pyridin-6-ylmethyl)-4-methyl-2-(2-oxo-3-(4-(trifluoromethyl)benzyl)imidazolidin-1-yl)-thiazole-5-carboxamide | 0.709 |
| 20-24 | 2-(3-(3-fluorobenzyl)-2-oxoimidazolidin-1-yl)-4-methylthiazole-5-carboxamide | 0.040 |
| 20-26 | 4-methyl-2-(2-oxo-3-(1-phenylethyl)-imidazolidin-1-yl)-N-(thiazol-5-yl-methyl)thiazole-5-carboxamide | 0.011 |
| 20-28 | 2-(1-((2,2-difluorocyclopropyl)methyl)-5-oxo-1H-1,2,4-triazol-4(5H)-yl)-4-methyl-N-(pyridin-2-ylmethyl)thiazole-5-carboxamide | 0.088 |
| 20-52 | 2-(1-(3,5-difluorobenzyl)-5-oxo-1H-1,2,4-triazol-4(5H)-yl)-4-methyl-N-(pyridin-2-ylmethyl)-thiazole-5-carboxamide | 0.013 |
| 20-54 | 4-methyl-2-(5-oxo-1-(4-(trifluoromethoxy)-benzyl)-1H-1,2,4-triazol-4(5H)-yl)-N-(pyridin-2-ylmethyl)-thiazole-5-carboxamide | 0.020 |
| 20-57 | 1-(4-methyl-5-(5-methyl-1H-1,2,4-triazol-3-yl)thiazol-2-yl)-3-(4-(trifluoromethoxy)-benzyl)imidazolidin-2-one | 0.119 |
| 20-59 | 4-methyl-2-(5-oxo-1-(4-(trifluoromethoxy)-benzyl)-1H-1,2,4-triazol-4(5H)-yl)-N-(thiazol-5-yl-methyl)thiazole-5-carboxamide | 0.026 |
| 20-76 | 2-(1-((2,2-difluorocyclopropyl)methyl)-5-oxo-1H-1,2,4-triazol-4(5H)-yl)-4-methyl-N-((1-methyl-1H-pyrazol-4-yl)methyl)thiazole-5-carboxamide | 0.551 |
| 20-83 | 2-(3-(cyclopropylmethyl)-2-oxoimidazolidin-1-yl)-4-methyl-N-((5-methylisoxazol-3-yl)methyl)thiazole-5-carboxamide | 0.011 |
| 20-90 | 2-(3-(3,5-dichlorobenzyl)-2-oxoimidazolidin-1-yl)-4-methyl-N-(pyridin-2-ylmethyl)thiazole-5-carboxamide | 0.008 |
| 20-103 | 2-(3-(2-cyclopropylethyl)-2-oxoimidazolidin-1-yl)-4-methyl-N-(pyridin-2-ylmethyl)thiazole-5-carboxamide | 0.038 |
| 20-133 | 4-methyl-2-(3-(4-(methylsulfonyl)benzyl)-2-oxoimidazolidin-1-yl)thiazole-5-carboxamide | 0.527 |

Those skilled in the art are aware of a variety of modifications to this assay that can be useful for measuring inhibition of stearoyl-CoA desaturase activity in microsomes or in cells by test compounds.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:
1. A compound selected from the group consisting of:
4-methyl-2-{2-oxo-3-[4-(trifluoromethyl)benzyl]imidazolidin-1-yl}thiazole-5-carboxamide;
(S)-2-(3-(4-fluorobenzyl)-4-methyl-2-oxoimidazolidin-1-yl)-4-methylthiazole-5-carboxamide;
4-methyl-2-(2-oxo-3-(4,4,4-trifluorobutyl)imidazolidin-1-yl)thiazole-5-carboxamide;
2-(3-(cyclopropylmethyl)-2-oxoimidazolidin-1-yl)-4-methylthiazole-5-carboxamide;
2-(3-isobutyl-2-oxoimidazolidin-1-yl)-4-methylthiazole-5-carboxamide;
2-(3-(3,4-difluorobenzyl)-2-oxoimidazolidin-1-yl)-4-methylthiazole-5-carboxamide;
2-(3-(3,5-difluorobenzyl)-2-oxoimidazolidin-1-yl)-4-methylthiazole-5-carboxamide;
4-methyl-2-(2-oxo-3-(4-(trifluoromethoxy)benzyl)imidazolidin-1-yl)thiazole-5-carboxamide;
4-methyl-2-(2-oxo-3-((6-(trifluoromethyl)pyridine-3-yl)methyl)imidazolidin-1-yl)thiazole-5-carboxamide;
2-(3-(3-fluoro-4-methoxybenzyl)-2-oxoimidazolidin-1-yl)-4-methylthiazole-5-carboxamide;
(S)-2-(3-(4-fluorobenzyl)-5-methyl-2-oxoimidazolidin-1-yl)-4-methylthiazole-5-carboxamide;
2-(3-(4-chlorobenzyl)-2-oxoimidazolidin-1-yl)-4-methylthiazole-5-carboxamide;
(R)-2-(3-(3,5-difluorobenzyl)-4-methyl-2-oxoimidazolidin-1-yl)-4-methylthiazole-5-carboxamide;
(R)-2-(3-(4-fluorobenzyl)-4-methyl-2-oxoimidazolidin-1-yl)-4-methylthiazole-5-carboxamide;
(R)-4-methyl-2-(4-methyl-2-oxo-3-(4-(trifluoromethyl)benzypimidazolidin-1-yl)thiazole-5-carboxamide;
(S)-2-(3-(4-Fluorobenzyl)-4-methyl-2-oxoimidazolidin-1-yl)-4-methyl-N-(pyridin-3-ylmethyl)thiazole-5-carboxamide;
(S)—N-(3,4-difluorobenzyl)-2-(3-(4-fluorobenzyl)-4-methyl-2-oxoimidazolidin-1-yl)-4-methylthiazole-5-carboxamide;
2-(3-(4-fluorobenzyl)-2-oxoimidazolidin-1-yl)-4-methyl-N-((3-methyl-1 H-pyrazol-5-yl)methyl)thiazole-5-carboxamide;
2-(3-(but-3-enyl)-2-oxoimidazolidin-1-yl)-4-methyl-N-(pyridin-3-ylmethyl)thiazole-5-carboxamide;
(R)-2-(3-(4-fluorobenzyl)-4-methyl-2-oxoimidazolidin-1-yl)-4-methyl-N-(pyridin-2-ylmethyl)thiazole-5-carboxamide;
(R)—N-(3,4-difluorobenzyl)-2-(3-(4-fluorobenzyl)-4-methyl-2-oxoimidazolidin-1-yl)-4-methylthiazole-5-carboxamide;
(R)-2-(3-(4-Fluorobenzyl)-4-methyl-2-oxoimidazolidin-1-yl)-4-methyl-N-(pyridin-3-ylmethyl)thiazole-5-carboxamide;
(R)-2-(3-(4-fluorobenzyl)-4-methyl-2-oxoimidazolidin-1-yl)-4-methyl-N-(thiazol-5-ylmethyl)thiazole-5-carboxamide;
(R)-2-(3-(4-fluorobenzyl)-4-methyl-2-oxoimidazolidin-1-yl)-4-methyl-N-((3-methyl-1 H-pyrazol-5-yl)methyl)thiazole-5-carboxamide;
(R)—N-(3,5-difluorobenzyl)-2-(3-(4-fluorobenzyl)-4-methyl-2-oxoimidazolidin-1-yl)-4-methylthiazole-5-carboxamide;
(R)-2-(3-(4-fluorobenzyl)-4-methyl-2-oxoimidazolidin-1-yl)-4-methyl-N-((5-methylisoxazol-3-yl)methyl)thiazole-5-carboxamide;
(R)-2-(3-(3,5-difluorobenzyl)-4-methyl-2-oxoimidazolidin-1-yl)-4-methyl-N-(pyridin-2-ylmethyl)thiazole-5-carboxamide;
(R)-2-(3-(3,5-difluorobenzyl)-4-methyl-2-oxoimidazolidin-1-yl)-4-methyl-N-((5-methylpyrazin-2-yl)methyl)thiazole-5-carboxamide;
(R)-2-(3-(3,5-difluorobenzyl)-4-methyl-2-oxoimidazolidin-1-yl)-4-methyl-N-((5-methylisoxazol-3-yl)methyl)thiazole-5-carboxamide;
(S)-2-(3-(4-fluorobenzyl)-5-methyl-2-oxoimidazolidin-1-yl)-4-methyl-N-(pyridin-2-ylmethyl)thiazole-5-carboxamide;
(S)-2-(3-(4-fluorobenzyl)-5-methyl-2-oxoimidazolidin-1-yl)-4-methyl-N-((1-methyl-1 H-pyrazol-4-yl)methyl)thiazole-5-carboxamide;
(S)-2-(3-(4-fluorobenzyl)-5-methyl-2-oxoimidazolidin-1-yl)-4-methyl-N-((5-methylisoxazol-3-yl)methyl)thiazole-5-carboxamide;
(R)-2-(3-(4-fluorobenzyl)-5-methyl-2-oxoimidazolidin-1-yl)-4-methyl-N-(pyridin-2-ylmethyl)thiazole-5-carboxamide;
(R)-2-(3-(4-fluorobenzyl)-5-methyl-2-oxoimidazolidin-1-yl)-4-methyl-N-(thiazol-5-yl)methyl)thiazole-5-carboxamide;
(R)-4-methyl-2-(4-methyl-2-oxo-3-(4-(trifluoromethyl)benzyl)imidazolidin-1-yl)-N-(pyridin-2-ylmethyl)thiazole-5-carboxamide;
2-(3-(2-(4-fluorobenzylamino)-2-oxoethyl)-2-oxoimidazolidin-1-yl)-4-methyl-N-(pyridin-3-ylmethyl)thiazole-5-carboxamide;
4-methyl-2-(3-(2-(methylamino)-2-oxoethyl)-2-oxoimidazolidin-1-yl)-N-(pyridin-3-ylmethyl)thiazole-5-carboxamide;
4-methyl-2-(2-oxo-3-(2-oxo-2-(pyrrolidin-1-yl)ethyl)imidazolidin-1-yl)-N-(pyridin-3-ylmethyl)thiazole-5-carboxamide;
2-(3-benzyl-2-oxoimidazolidin-1-yl)-4-methylthiazole-5-carboxamide;
2-(3-(cyclopropylmethyl)-2-oxoimidazolidin-1-yl)-N-((5-fluoropyridin-3-yl)methyl)-4-methylthiazole-5-carboxamide;
2-(3-(cyclopropylmethyl)-2-oxoimidazolidin-1-yl)-N-((3-fluoropyridin-2-yl)methyl)-4-methylthiazole-5-carboxamide;
4-methyl-2-(2-oxo-3-(4,4,4-trifluorobutyl)imidazolidin-1-yl)-N-(pyridin-2-ylmethyl)thiazole-5-carboxamide;
4-methyl-2-(2-oxo-3-(4,4,4-trifluorobutyl)imidazolidin-1-yl)-N-(pyridin-3-ylmethyl)thiazole-5-carboxamide;
4-methyl-N-(oxazol-4-ylmethyl)-2-(2-oxo-3-(4,4,4-trifluorobutyl)imidazolidin-1-yl)thiazole-5-carboxamide;
4-methyl-N-(oxazol-2-ylmethyl)-2-(2-oxo-3-(4,4,4-trifluorobutyl)imidazolidin-1-yl)thiazole-5-carboxamide;
4-methyl-N-((6-methylpyrazin-2-yl)methyl)-2-(2-oxo-3-(4,4,4-trifluorobutyl)imidazolidin-1-yl)thiazole-5-carboxamide;
4-methyl-2-(2-oxo-3-(4,4,4-trifluorobutyl)imidazolidin-1-yl)-N-(pyridin-4-ylmethyl)thiazole-5-carboxamide;

N-((1H-pyrazol-4-yl)methyl)-4-methyl-2-(2-oxo-3-(4,4,4-trifluorobutyl)imidazolidin-1-yl)thiazole-5-carboxamide;
4-methyl-N-((1-methyl 1 H-pyrazol-4-yl)methyl)-2-(2-oxo-3-(4,4,4-trifluorobutyl)imidazolidin-1-yl)thiazole-5-carboxamide;
2-(3-(cyclopropylmethyl)-2-oxoimidazolidin-1-yl)-4-methyl-N-(pyrimidin-4-ylmethyl)thiazole-5-carboxamide;
2-(3-(cyclopropylmethyl)-2-oxoimidazolidin-1-yl)-4-methyl-N-(pyrimidin-2-yl)methyl)thiazole-5-carboxamide;
2-(3-(cyclopropylmethyl)-2-oxoimidazolidin-1-yl)-4-methyl-N-(pyridazin-3-ylmethyl)thiazole-5-carboxamide;
2-(3-(cyclopropylmethyl)-2-oxoimidazolidin-1-yl)-4-methyl-N-(pyridin-4-ylmethyl)thiazole-5-carboxamide;
2-(3-(cyclopropylmethyl)-2-oxoimidazolidin-1-yl)-4-methyl-N-((2-methylthiazol-5-yl)methyl)thiazole-5-carboxamide;
2-(3-(cyclopropylmethyl)-2-oxoimidazolidin-1-yl)-4-methyl-N-(oxazol-2-yl)methyl)thiazole-5-carboxamide;
2-(3-(4-fluorobenzyl)-2-oxoimidazolidin-1-yl)-4-methyl-N-(oxazol-4-yl)methyl)thiazole-5-carboxamide;
2-(3-isobutyl-2-oxoimidazolidin-1-yl)-4-methyl-N-(pyridin-4-ylmethyl)thiazole-5-carboxamide;
2-(3-isobutyl-2-oxoimidazolidin-1-yl)-4-methyl-N-(pyridin-3-ylmethyl)thiazole-5-carboxamide;
2-(3-isobutyl-2-oxoimidazolidin-1-yl)-4-methyl-N-(pyridin-2-ylmethyl)thiazole-5-carboxamide;
2-(3-isobutyl-2-oxoimidazolidin-1-yl)-4-methyl-N-((6-methylpyrazin-2-yl)methyl)thiazole-5-carboxamide;
2-(3-isobutyl-2-oxoimidazolidin-1-yl)-4-methyl-N-((1-methyl-1 H-pyrazol-4-yl)methyl)thiazole-5-carboxamide;
2-(3-isobutyl-2-oxoimidazolidin-1-yl)-4-methyl-N-((1-methyl-1 H-pyrazol-3-yl)methyl)thiazole-5-carboxamide;
2-(3-isobutyl-2-oxoimidazolidin-1-yl)-4-methyl-N-(oxazol-4-ylmethyl)thiazole-5-carboxamide;
2-(3-((2,2-difluorocyclopropyl)methyl)-2-oxoimidazolidin-1-yl)-4-methyl-N-(pyridin-3-ylmethyl)thiazole-5-carboxamide;
2-(3-((2,2-difluorocyclopropyl)methyl)-2-oxoimidazolidin-1-yl)-4-methyl-N-(oxazol-2-ylmethyl)thiazole-5-carboxamide;
2-(3-((2,2-difluorocyclopropyl)methyl)-2-oxoimidazolidin-1-yl)-4-methyl-N-(thiazol-5-yl)methyl)thiazole-5-carboxamide;
2-(3-((2,2-difluorocyclopropyl)methyl)-2-oxoimidazolidin-1-yl)-4-methyl-N-((4-methylthiazol-2-yl)methyl)thiazole-5-carboxamide;
4-methyl-N-((6-methylpyrazin-2-yl)methyl)-2-(2-oxo-3-(4,4,4-trifluorobutyl)-imidazolidin-1-yl)-thiazole-5-carboxamide;
N-((1H-pyrazol-4-yl)-methyl)-4-methyl-2-(2-oxo-3-(4,4,4-trifluorobutyl)-imidazolidin-1-yl)-thiazole-5-carboxamide;
4-methyl-2-(2-oxo-3-(4,4,4-trifluorobutyl)-imidazolidin-1-yl)-N-(pyridin-3-ylmethyl)-thiazole-5-carboxamide;
2-(3-(cyclopropylmethyl)-2-oxoimidazolidin-1-yl)-N-(3,5-difluorobenzyl)-4-methylthiazole-5-carboxamide;
2-(3-(2,5-difluorobenzyl)-2-oxoimidazolidin-1-yl)-4-methylthiazole-5-carboxamide;
2-(3-(2,4-difluorobenzyl)-2-oxoimidazolidin-1-yl)-4-methylthiazole-5-carboxamide;
2-(3-((2,2-difluorocyclopropyl)methyl)-2-oxoimidazolidin-1-yl)-4-methyl-N-((6-(trifluoromethyl)pyridin-3-yl)methyl)thiazole-5-carboxamide;
N-(imidazo[1,2-a]pyridin-6-ylmethyl)-4-methyl-2-(2-oxo-3-(4-(trifluoromethyl)-benzyl)imidazolidin-1-yl)-thiazole-5-carboxamide;
4-methyl-2-(2-oxo-3-(4-(trifluoromethyl)-benzyl)imidazolidin-1-yl)-N-((2-(trifluoromethyl)-thiazol-4-yl)-methyl)thiazole-5-carboxamide;
2-(3-(3-fluorobenzyl)-2-oxoimidazolidin-1-yl)-4-methylthiazole-5-carboxamide;
4-methyl-2-(2-oxo-3-(1-phenylethyl)-imidazolidin-1-yl)-N-(pyridin-3-yl-methyl)thiazole-5-carboxamide;
4-methyl-2-(2-oxo-3-(1-phenylethyl)-imidazolidin-1-yl)-N-(thiazol-5-yl-methyl)thiazole-5-carboxamide;
2-(3-(2-fluorobenzyl)-2-oxoimidazolidin-1-yl)-4-methylthiazole-5-carboxamide;
4-methyl-2-(2-oxo-3-(1-phenylethyl)-imidazolidin-1-yl)-thiazole-5-carboxamide;
4-methyl-2-(2-oxo-3-(4-(trifluoromethyl)-benzypimidazolidin-1-yl)-N-(pyridin-2-ylmethyl)thiazole-5-carboxamide;
2-(3-(2,6-difluorobenzyl)-2-oxoimidazolidin-1-yl)-4-methylthiazole-5-carboxamide;
2-(3-(2,3-difluorobenzyl)-2-oxoimidazolidin-1-yl)-4-methylthiazole-5-carboxamide;
4-methyl-2-(2-oxo-3-(4-(trifluoromethyl)-benzypimidazolidin-1-yl)-N-(thiazol-2-ylmethyl)thiazole-5-carboxamide;
2-(3-((2,2-difluorocyclopropyl)-methyl)-2-oxoimidazolidin-1-yl)-4-methyl-N-((5-methylisoxazol-3-yl)methyl)thiazole-5-carboxamide;
2-(3-(3,4-difluorobenzyl)-2-oxoimidazolidin-1-yl)-4-methyl-N-((6-methylpyrazin-2-yl)-methyl)thiazole-5-carboxamide;
2-(3-(3,4-difluorobenzyl)-2-oxoimidazolidin-1-yl)-4-methyl-N-(pyridin-2-ylmethyl)thiazole-5-carboxamide;
2-(3-(4-fluorobenzyl)-2-oxoimidazolidin-yl)-4-methyl-N-((5-methylisoxazol-3-yl)methyl)thiazole-5-carboxamide;
2-(3-(3,4-difluorobenzyl)-2-oxoimidazolidin-1-yl)-4-methyl-N-(oxazol-4-yl)methyl)thiazole-5-carboxamide;
2-(3-(3,4-difluorobenzyl)-2-oxoimidazolidin-1-yl)-4-methyl-N-((1-methyl-1H-pyrazol-4-yl)methyl)thiazole-5-carboxamide;
4-methyl-2-(2-oxo-3-(4-(trifluoromethoxy)-benzyl)imidazolidin-1-yl)-N-(pyridin-2-ylmethyl)thiazole-5-carboxamide;
4-methyl-N-((5-methylisoxazol-3-yl)methyl)-2-(2-oxo-3-(4-(trifluoromethoxy)-benzyl)imidazolidin-1-yl)thiazole-5-carboxamide;
2-(3-((2,2-difluorocyclopropyl)-methyl)-2-oxoimidazolidin-1-yl)-4-methyl-N-(thiazol-2-ylmethyl)thiazole-5-carboxamide;
2-(3-(4-fluorobenzyl)-2-oxoimidazolidin-1-yl)-4-methyl-N-((2-methylthiazol-4-yl)methyl)thiazole-5-carboxamide;
2-(3-(4-methoxybenzyl)-2-oxoimidazolidin-1-yl)-4-methylthiazole-5-carboxamide;
2-(3-(3-fluoro-4-methoxybenzyl)-2-oxoimidazolidin-1-yl)-4-methyl-N-(pyridin-2-ylmethyl)thiazole-5-carboxamide;
4-methyl-2-(2-oxo-3-((6-(trifluoromethyl)-pyridin-3-yl)methyl)-imidazolidin-1-yl)-N-(pyridin-2-ylmethyl)-thiazole-5-carboxamide;

4-methyl-N-((5-methylisoxazol-3-yl)methyl)-2-(2-oxo-3-((6-(trifluoromethyl)-pyridin-3-yl)methyl)-imidazolidin-1-yl)-thiazole-5-carboxamide;

4-methyl-N-((5-methylisoxazol-3-yl)methyl)-2-(2-oxo-3-(4-(trifluoromethyl)-benzyl)imidazolidin-1-yl)thiazole-5-carboxamide;

2-(3-(3-fluoro-4-methoxybenzyl)-2-oxoimidazolidin-1-yl)-4-methyl-N-((5-methylisoxazol-3-yl)methyl)thiazole-5-carboxamide;

2-(3-((2,2-difluorocyclopropyl)methyl)-2-oxoimidazolidin-1-yl)-4-methyl-N-((1-methyl-1 H-pyrazol-4-yl)methyl)thiazole-5-carboxamide;

4-methyl-2-(2-oxo-3-(1-phenylethyl)-imidazolidin-1-yl)-N-(pyridin-2-ylmethyl)-thiazole-5-carboxamide;

N-(isoxazol-3-ylmethyl)-4-methyl-2-(2-oxo-3-((6-(trifluoromethyl)pyridin-3-yl)methyl)-imidazolidin-1-yl)thiazole-5-carboxamide;

2-(3-(cyclopropylmethyl)-2-oxoimidazolidin-1-yl)-4-methyl-N-((1-methyl-1 H-pyrazol-4-yl)methyl)thiazole-5-carboxamide;

4-methyl-N-((1-methyl-1 H-pyrazol-4-yl)methyl)-2-(2-oxo-3-(4-(trifluoromethyl)-benzyl)imidazolidin-1-yl)thiazole-5-carboxamide;

2-(3-(cyclopropylmethyl)-2-oxoimidazolidin-1-yl)-4-methyl-N-((5-methylisoxazol-3-yl)methyl)thiazole-5-carboxamide;

2-(3-(3-fluoro-4-(trifluoromethoxy)-benzyl)-2-oxoimidazolidin-1-yl)-4-methyl-N-((5-methylisoxazol-3-yl)-methyl)thiazole-5-carboxamide;

2-(3-(3-fluoro-4-(trifluoromethoxy)-benzyl)-2-oxoimidazolidin-1-yl)-4-methylthiazole-5-carboxamide;

2-(3-(3-fluoro-4-(trifluoromethoxy)-benzyl)-2-oxoimidazolidin-1-yl)-4-methyl-N-((1-methyl-1 H-pyrazol-4-yl)methyl)thiazole-5-carboxamide;

2-(3-(3-fluoro-4-(trifluoromethoxy)-benzyl)-2-oxoimidazolidin-1-yl)-4-methyl-N-(pyridin-2-ylmethyl)thiazole-5-carboxamide;

2-(3-(4-methoxybenzyl)-2-oxoimidazolidin-1-yl)-4-methyl-N-(pyridin-2-ylmethyl)thiazole-5-carboxamide;

2-(3-(4-chlorobenzyl)-2-oxoimidazolidin-1-yl)-4-methyl-N-(pyridin-2-ylmethyl)-thiazole-5-carboxamide;

2-(3-(3,5-dichlorobenzyl)-2-oxoimidazolidin-1-yl)-4-methyl-N-(pyridin-2-yl)methyl)thiazole-5-carboxamide;

2-(3-(4-chlorobenzyl)-2-oxoimidazolidin-1-yl)-4-methyl-N-((5-methylpyrazin-2-yl)methyl)thiazole-5-carboxamide;

2-(3-((6-(4-fluorophenyl)pyridin-3-yl)methyl)-2-oxoimidazolidin-1-yl)-4-methyl-N-(thiazol-2-yl)methyl)thiazole-5-carboxamide;

2-(3-((6-(4-fluorophenyl)pyridin-3-yl)methyl)-2-oxoimidazolidin-1-yl)-4-methyl-N-(pyridin-2-ylmethyl)thiazole-5-carboxamide;

2-(3-((6-(4-fluorophenyl)pyridin-3-yl)methyl)-2-oxoimidazolidin-1-yl)-4-methyl-N-((5-methylisoxazol-3-yl)methyl)thiazole-5-carboxamide;

2-(3-(3,5-difluorobenzyl)-2-oxoimidazolidin-1-yl)-4-methyl-N-(pyridin-2-ylmethyl)thiazole-5-carboxamide;

2-(3-(3,5-difluorobenzyl)-2-oxoimidazolidin-1-yl)-4-methyl-N-((5-methylisoxazol-3-yl)methyl)thiazole-5-carboxamide;

2-(3-(4-chlorobenzyl)-2-oxoimidazolidin-1-yl)-4-methyl-N-((1-methyl-1 H-pyrazol-4-yl)methyl)thiazole-5-carboxamide;

2-(3-(3,5-difluorobenzyl)-2-oxoimidazolidin-1-yl)-4-methyl-N-((5-methylpyrazin-2-yl)methyl)thiazole-5-carboxamide;

2-(3-(3,5-difluorobenzyl)-2-oxoimidazolidin-1-yl)-4-methyl-N-(thiazol-2-yl)methyl)thiazole-5-carboxamide;

2-(3-(3,5-difluorobenzyl)-2-oxoimidazolidin-1-yl)-4-methyl-N-((1-methyl-1 H-pyrazol-4-yl)methyl)thiazole-5-carboxamide;

2-(3-(3,5-dichlorobenzyl)-2-oxoimidazolidin-1-yl)-4-methyl-N-((5-methylpyrazin-2-yl)methyl)thiazole-5-carboxamide;

2-(3-(3,5-dichlorobenzyl)-2-oxoimidazolidin-1-yl)-4-methyl-N-((1-methyl-1 H-pyrazol-4-yl)methyl)thiazole-5-carboxamide;

2-(3-(2-cyclopropylethyl)-2-oxoimidazolidin-1-yl)-4-methyl-N-(pyridin-2-ylmethyl)thiazole-5-carboxamide;

4-methyl-N-((5-methylpyrazin-2-yl)methyl)-2-(2-oxo-3-(4-(trifluoromethoxy)-benzyl)imidazolidin-1-yl)thiazole-5-carboxamide;

2-(3-(3-fluoro-4-methoxybenzyl)-2-oxoimidazolidin-1-yl)-4-methyl-N-((5-methylpyrazin-2-yl)methyl)thiazole-5-carboxamide;

2-(3-(3,4-dichlorobenzyl)-2-oxoimidazolidin-1-yl)-4-methyl-N-((5-methylpyrazin-2-yl)methyl)thiazole-5-carboxamide;

2-(3-(3,4-dichlorobenzyl)-2-oxoimidazolidin-1-yl)-4-methyl-N-(pyridine-2-yl)methyl)thiazole-5-carboxamide;

2-(3-(3-fluoro-4-(trifluoromethoxy)-benzyl)-2-oxoimidazolidin-1-yl)-4-methyl-N-((5-methylpyrazin-2-yl)methyl)thiazole-5-carboxamide;

2-(3-((2,2-difluorocyclopropyl)-methyl)-2-oxoimidazolidin-1-yl)-4-methyl-N-((5-methylpyrazin-2-yl)methyl)thiazole-5-carboxamide;

2-(3-(2-cyclopropylethyl)-2-oxoimidazolidin-1-yl)-4-methyl-N-((5-methylpyrazin-2-yl)methyl)thiazole-5-carboxamide;

2-(3-(2-cyclopropylethyl)-2-oxoimidazolidin-1-yl)-4-methylthiazole-5-carboxamide;

4-methyl-N-((5-methylpyrazin-2-yl)methyl)-2-(2-oxo-3-((6-(trifluoromethyl)-pyridin-3-yl)methyl)-imidazolidin-1-yl)-thiazole-5-carboxamide;

2-(3-(3,4-dichlorobenzyl)-2-oxoimidazolidin-1-yl)-4-methyl-N-a1-methyl-1 H-pyrazol-4-yl)methyl)thiazole-5-carboxamide;

2-(3-(2-cyclopropylethyl)-2-oxoimidazolidin-1-yl)-4-methyl-N-((5-methylisoxazol-3-yl)methyl)thiazole-5-carboxamide;

2-(3-(2-cyclopropylethyl)-2-oxoimidazolidin-1-yl)-4-methyl-N-((1-methyl-1 H-pyrazol-4-yl)methyl)thiazole-5-carboxamide;

2-(3-(3-fluorobenzyl)-2-oxoimidazolidin-1-yl)-4-methyl-N-((1-methyl-1 H-pyrazol-4-yl)methyl)thiazole-5-carboxamide;

2-(3-((6-chloropyridin-3-yl)methyl)-2-oxoimidazolidin-1-yl)-4-methyl-N-(pyridin-2-ylmethyl)thiazole-5-carboxamide;

2-(3-(3-fluorobenzyl)-2-oxoimidazolidin-1-yl)-4-methyl-N-(pyridin-2-ylmethyl)-thiazole-5-carboxamide;

2-(3-(3-fluorobenzyl)-2-oxoimidazolidin-1-yl)-4-methyl-N-((5-methylpyrazin-2-yl)methyl)thiazole-5-carboxamide;

2-(3-(3-chlorobenzyl)-2-oxoimidazolidin-1-yl)-4-methyl-N-(pyridin-2-ylmethyl)-thiazole-5-carboxamide;

2-(3-(3-chlorobenzyl)-2-oxoimidazolidin-1-yl)-4-methyl-N-((5-methylpyrazin-2-yl)methyl)thiazole-5-carboxamide;

2-(3-(3-chlorobenzyl)-2-oxoimidazolidin-1-yl)-4-methyl-N-((1-methyl-1 H-pyrazol-4-yl)methyl)thiazole-5-carboxamide;

N-((1H-pyrazol-4-yl)methyl)-2-(3-(4-fluorobenzyl)-2-oxoimidazolidin-1-yl)-4-methylthiazole-5-carboxamide;

4-methyl-2-(2-oxo-3-((6-(trifluoromethyl)-pyridin-3-yl)methyl)-imidazolidin-1-yl)-N-(thiazol-2-ylmethyl)-thiazole-5-carboxamide;

4-methyl-N-(oxazol-2-ylmethyl)-2-(2-oxo-3-((6-(trifluoromethyl)-pyridin-3-yl)methyl)-imidazolidin-1-yl)thiazole-5-carboxamide;

4-methyl-2-(3-(4-(methylsulfonyl)benzyl)-2-oxoimidazolidin-1-yl)-N-(pyridin-2-ylmethyl)thiazole-5-carboxamide;

4-methyl-2-(3-(4-(methylsulfonyl)benzyl)-2-oxoimidazolidin-1-yl)thiazole-5-carboxamide;

(R)-2-(3-(4-fluorobenzyl)-5-methyl-2-oxoimidazolidin-1-yl)-4-methylthiazole-5-carboxamide; and (S)-2-(2-(3-(4-fluorobenzyl)-2-oxoimidazolidin-1-yl)-4-methylthiazole-5-carboxamido)-2-phenylacetic acid; or a pharmaceutically acceptable salt thereof.

2. The compound according to claim 1, or a pharmaceutically acceptable salt thereof, wherein the compound is 2-(3-(3,5-difluorobenzyl)-2-oxoimidazolidin-1-yl)-4-methylthiazole-5-carboxamide.

3. The compound according to claim 1, or a pharmaceutically acceptable salt thereof, wherein the compound is (R)-2-(3-(4-fluorobenzyl)-4-methyl-2-oxoimidazolidin-1-yl)-4-methyl-N-(pyridin-2-ylmethyl)thiazole-5-carboxamide.

4. The compound according to claim 1, or a pharmaceutically acceptable salt thereof, wherein the compound is 4-methyl-2-(2-oxo-3-(1-phenylethyl)-imidazolidin-1-yl)-N-(thiazol-5-yl-methyl)thiazole-5-carboxamide.

5. The compound according to claim 1, or a pharmaceutically acceptable salt thereof, wherein the compound is 2-(3-(cyclopropylmethyl)-2-oxoimidazolidin-1-yl)-4-methyl-N-((5-methylisoxazol-3-yl)methyl)thiazole-5-carboxamide.

6. The compound according to claim 1, or a pharmaceutically acceptable salt thereof, wherein the compound is 2-(3-(3,5-dichlorobenzyl)-2-oxoimidazolidin-1-yl)-4-methyl-N-(pyridin-2-ylmethyl)thiazole-5-carboxamide.

7. A pharmaceutical composition, comprising:
a compound of Formula (I) according to claim 1, or a pharmaceutically acceptable salt thereof; and
a pharmaceutically acceptable excipient or carrier.

8. A method of treating a disease or condition mediated by stearoyl-CoA desaturase (SCD) in a mammal in need thereof, comprising:
identifying the mammal in need thereof; and
administering to the mammal in need thereof a therapeutically effective amount of a compound according to claim 1, or a pharmaceutically acceptable salt thereof, wherein the disease or condition is insulin resistance, decreased glucose tolerance, non-insulin-dependent diabetes mellitus, Type II diabetes, or obesity.

9. A method of treating a disease or condition mediated by stearoyl-CoA desaturase (SCD) in a mammal in need thereof, comprising:
identifying the mammal in need thereof; and
administering to the mammal in need thereof a therapeutically effective amount of a compound according to claim 1, or a pharmaceutically acceptable salt thereof, wherein the disease or disorder is eczema, acne, psoriasis, or keloid scar formation or prevention.

10. A pharmaceutical composition according to claim 7, wherein the compound is 2-(3-(3,5-difluorobenzyl)-2-oxoimidazolidin-1-yl)-4-methylthiazole-5-carboxamide, or a pharmaceutically acceptable salt thereof.

11. A pharmaceutical composition according to claim 7, wherein the compound is (R)-2-(3-(4-fluorobenzyl)-4-methyl-2-oxoimidazolidin-1-yl)-4-methyl-N-(pyridin-2-ylmethyl)thiazole-5-carboxamide, or a pharmaceutically acceptable salt thereof.

12. A pharmaceutical composition according to claim 7, wherein the compound is 4-methyl-2-(2-oxo-3-(1-phenylethyl)-imidazolidin-1-yl)-N-(thiazol-5-yl-methyl)thiazole-5-carboxamide, or a pharmaceutically acceptable salt thereof.

13. A pharmaceutical composition according to claim 7, wherein the compound is 2-(3-(cyclopropylmethyl)-2-oxoimidazolidin-1-yl)-4-methyl-N-((5-methylisoxazol-3-yl)methyl)thiazole-5-carboxamide, or a pharmaceutically acceptable salt thereof.

14. A pharmaceutical composition according to claim 7, wherein the compound is 2-(3-(3,5-dichlorobenzyl)-2-oxoimidazolidin-1-yl)-4-methyl-N-(pyridin-2-ylmethyl)thiazole-5-carboxamide, or a pharmaceutically acceptable salt thereof.

15. The method of claim 8, wherein the compound is 2-(3-(3,5-difluorobenzyl)-2-oxoimidazolidin-1-yl)-4-methylthiazole-5-carboxamide, or a pharmaceutically acceptable salt thereof.

16. The method of claim 8, wherein the compound is (R)-2-(3-(4-fluorobenzyl)-4-methyl-2-oxoimidazolidin-1-yl)-4-methyl-N-(pyridin-2-ylmethyl)thiazole-5-carboxamide, or a pharmaceutically acceptable salt thereof.

17. The method of claim 8, wherein the compound is 4-methyl-2-(2-oxo-3-(1-phenyl ethyl)-imidazolidin-1-yl)-N-(thiazol-5-yl-methyl)thiazole-5-carboxamide, or a pharmaceutically acceptable salt thereof.

18. The method of claim 8, wherein the compound is 2-(3-(cyclopropylmethyl)-2-oxoimidazolidin-1-yl)-4-methyl-N-((5-methyl isoxazol-3-yl)methyl)thiazol a-5-carboxamide, or a pharmaceutically acceptable salt thereof.

19. The method of claim 8, wherein the compound is 2-(3-(3,5-dichlorobenzyl)-2-oxoimidazolidin-1-yl)-4-methyl-N-(pyridin-2-ylmethyl)thiazole-5-carboxamide, or a pharmaceutically acceptable salt thereof.

* * * * *